US012376869B2

(12) United States Patent
Anderson et al.

(10) Patent No.: US 12,376,869 B2
(45) Date of Patent: *Aug. 5, 2025

(54) INTRAVASCULAR LITHOTRIPSY

(71) Applicant: FastWave Medical Inc., Dover, DE (US)

(72) Inventors: Edward Anderson, Maple Grove, MN (US); Randy Beyreis, Andover, MN (US); Scott Nelson, Mission Viejo, CA (US); JiChao Sun, Santa Rosa, CA (US); Brady Hatcher, Rogers, MN (US); Ae-Suk Pauling, St. Michael, MN (US); Daryl Kiefer, Howard Lake, MN (US); Dannah Dean, Minnetonka, MN (US); Curtis Goreham-Voss, Maple Grove, MN (US); Parker Hagen, Maple Grove, MN (US); Tristan Tieso, Minneapolis, MN (US); Lauren Eno, Minnetonka, MN (US)

(73) Assignee: FASTWAVE MEDICAL INC., Dover, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/916,404

(22) Filed: Oct. 15, 2024

(65) Prior Publication Data
US 2025/0032139 A1    Jan. 30, 2025

Related U.S. Application Data

(60) Continuation of application No. 18/443,267, filed on Feb. 15, 2024, now Pat. No. 12,156,668, which is a
(Continued)

(51) Int. Cl.
*A61B 17/22* (2006.01)
*A61M 25/10* (2013.01)
*A61B 17/00* (2006.01)

(52) U.S. Cl.
CPC .... *A61B 17/22022* (2013.01); *A61B 17/2202* (2013.01); *A61M 25/104* (2013.01); *A61B 2017/00557* (2013.01)

(58) Field of Classification Search
CPC ........... A61B 2017/22098; A61B 2017/22025; A61B 2017/2202; A61B 2017/00557; A61B 17/225; A61M 25/104
See application file for complete search history.

(56) References Cited

U.S. PATENT DOCUMENTS

| 4,587,975 A | 5/1986 | Salo et al. |
| 5,116,227 A | 5/1992 | Levy |

(Continued)

FOREIGN PATENT DOCUMENTS

| DE | 3038445 C2 | 6/1990 |
| EP | 0571306 A1 | 11/1993 |

(Continued)

OTHER PUBLICATIONS

Shockwave Medical—"Intravascular Lithotripsy (IVL)"—shockwavemedical.com [online]—Available at least as of Apr. 2022—Available from Internet <URL: https://shockwavemedical.com/technology/intravascular-lithotripsy-ivl/>.

(Continued)

*Primary Examiner* — Anh T Dang
(74) *Attorney, Agent, or Firm* — Gallium Law; Jacob Panangat; Justin Schwechter

(57) ABSTRACT

A medical device may include an elongated body, a balloon positioned at a distal portion of the elongated body, and one or more pressure-wave emitters positioned along a central longitudinal axis of the elongated body within the balloon. The one or more pressure-wave emitters may be configured to propagate pressure waves radially outward through the fluid to fragment a calcified lesion at the target treatment (Continued)

site. The at least one of the one or more pressure-wave emitters may comprise an electronic emitter including a first electrode and a second electrode. The first electrode and the second electrode may be arranged to define a spark gap between the first electrode and the second electrode, and the second electrode may comprise a portion of a hypotube.

20 Claims, 70 Drawing Sheets

Related U.S. Application Data continuation of application No. 18/367,811, filed on Sep. 13, 2023, now Pat. No. 11,944,331, which is a continuation-in-part of application No. 18/134,507, filed on Apr. 13, 2023, now Pat. No. 11,911,056, which is a continuation-in-part of application No. 17/861,137, filed on Jul. 8, 2022, now Pat. No. 11,633,200, which is a division of application No. 17/679,434, filed on Feb. 24, 2022, now Pat. No. 11,484,327.

(60) Provisional application No. 63/193,469, filed on May 26, 2021, provisional application No. 63/176,156, filed on Apr. 16, 2021.

(56) References Cited

U.S. PATENT DOCUMENTS

| | | |
|---|---|---|
| 5,536,252 A | 7/1996 | Imran et al. |
| 6,004,269 A | 12/1999 | Crowley et al. |
| 6,514,249 B1 | 2/2003 | Maguire et al. |
| 6,652,547 B2 | 11/2003 | Rabiner et al. |
| 6,692,484 B1 | 2/2004 | Karpiel et al. |
| 6,755,821 B1 | 6/2004 | Fry |
| 7,144,408 B2 | 12/2006 | Keegan et al. |
| 8,000,808 B2 | 8/2011 | Hegland et al. |
| 8,409,172 B2 | 4/2013 | Moll et al. |
| 8,419,613 B2 | 4/2013 | Saadat et al. |
| 8,439,890 B2 | 5/2013 | Beyar et al. |
| 8,657,814 B2 | 2/2014 | Werneth et al. |
| 8,728,091 B2 | 5/2014 | Hakala et al. |
| 8,747,416 B2 | 6/2014 | Hakala et al. |
| 8,888,788 B2 | 11/2014 | Hakala et al. |
| 8,956,371 B2 | 2/2015 | Hawkins et al. |
| 8,956,374 B2 | 2/2015 | Hawkins et al. |
| 9,005,216 B2 | 4/2015 | Hakala et al. |
| 9,011,462 B2 | 4/2015 | Adams et al. |
| 9,011,463 B2 | 4/2015 | Adams et al. |
| 9,072,534 B2 | 7/2015 | Adams et al. |
| 9,138,249 B2 | 9/2015 | Adams et al. |
| 9,289,596 B2 | 3/2016 | Leven |
| 9,333,000 B2 | 5/2016 | Hakala et al. |
| 9,370,644 B2 | 6/2016 | Rocha-Singh |
| 9,433,428 B2 | 9/2016 | Hakala et al. |
| 9,522,012 B2 | 12/2016 | Adams |
| 9,642,673 B2 | 5/2017 | Adams et al. |
| 9,867,629 B2 | 1/2018 | Hawkins |
| 10,039,561 B2 | 8/2018 | Adams et al. |
| 10,143,577 B2 | 12/2018 | Simpson |
| 10,159,505 B2 | 12/2018 | Hakala et al. |
| 10,201,387 B2 | 2/2019 | Grace et al. |
| 10,206,698 B2 | 2/2019 | Hakala et al. |
| 10,226,265 B2 | 3/2019 | Ku et al. |
| 10,357,264 B2 | 7/2019 | Kat-Kuoy et al. |
| 10,517,620 B2 | 12/2019 | Adams |
| 10,517,621 B1 | 12/2019 | Hakala et al. |
| 10,682,178 B2 | 6/2020 | Adams et al. |
| 10,702,293 B2 | 7/2020 | Adams et al. |
| 10,709,462 B2 | 7/2020 | Nguyen et al. |
| 10,786,267 B2 | 9/2020 | Wasdyke et al. |
| 10,786,661 B2 | 9/2020 | Grace |
| 10,842,567 B2 | 11/2020 | Grace et al. |
| 10,850,078 B2 | 12/2020 | Grace et al. |
| 10,898,213 B2 | 1/2021 | Grace et al. |
| 10,959,743 B2 | 3/2021 | Adams et al. |
| 10,966,737 B2 | 4/2021 | Nguyen |
| 10,973,538 B2 | 4/2021 | Hakala et al. |
| 11,058,492 B2 | 7/2021 | Grace et al. |
| 11,076,874 B2 | 8/2021 | Hakala et al. |
| 11,246,659 B2 | 2/2022 | Grace et al. |
| 11,266,817 B2 | 3/2022 | Cope et al. |
| 11,432,834 B2 | 9/2022 | Adams |
| 11,534,187 B2 | 12/2022 | Bonutti |
| 11,596,424 B2 | 3/2023 | Hakala et al. |
| 11,911,056 B2 | 2/2024 | Anderson et al. |
| 11,944,331 B2 | 4/2024 | Anderson et al. |
| 12,156,668 B2 | 12/2024 | Anderson et al. |
| 2002/0052621 A1 | 5/2002 | Fried |
| 2004/0015184 A1 | 1/2004 | Boyle |
| 2005/0251116 A1 | 11/2005 | Steinke et al. |
| 2006/0064082 A1 | 3/2006 | Bonutti |
| 2007/0179496 A1 | 8/2007 | Swoyer et al. |
| 2008/0109029 A1 | 5/2008 | Gurm |
| 2010/0036294 A1 | 2/2010 | Mantell et al. |
| 2014/0039513 A1 | 2/2014 | Hakala et al. |
| 2014/0288570 A1 | 9/2014 | Adams |
| 2015/0151113 A1 | 6/2015 | Govea et al. |
| 2016/0135828 A1 | 5/2016 | Hawkins |
| 2016/0183819 A1 | 6/2016 | Burnett et al. |
| 2016/0287323 A1 | 10/2016 | Yagi |
| 2016/0324571 A1 | 11/2016 | Beeckler |
| 2017/0135709 A1* | 5/2017 | Nguyen ........... A61B 17/22004 |
| 2017/0265942 A1 | 9/2017 | Grace et al. |
| 2018/0042661 A1 | 2/2018 | Long et al. |
| 2018/0153568 A1* | 6/2018 | Kat-Kuoy ........ A61B 17/22022 |
| 2019/0029703 A1 | 1/2019 | Wasdyke et al. |
| 2019/0104933 A1 | 4/2019 | Stern et al. |
| 2019/0150960 A1* | 5/2019 | Nguyen ........... A61B 17/22022 |
| 2019/0247680 A1 | 8/2019 | Mayer et al. |
| 2019/0388110 A1 | 12/2019 | Nguyen et al. |
| 2020/0000484 A1 | 1/2020 | Hawkins |
| 2020/0008856 A1 | 1/2020 | Harmouche et al. |
| 2020/0060704 A1 | 2/2020 | Ein-Gal |
| 2020/0085458 A1 | 3/2020 | Nguyen |
| 2020/0155818 A1 | 5/2020 | Yang |
| 2020/0297366 A1 | 9/2020 | Nguyen et al. |
| 2020/0383724 A1 | 12/2020 | Adams et al. |
| 2021/0085347 A1 | 3/2021 | Phan et al. |
| 2021/0085348 A1 | 3/2021 | Nguyen |
| 2021/0128241 A1 | 5/2021 | Schultheis |
| 2021/0282792 A1 | 9/2021 | Adams et al. |
| 2021/0290259 A1 | 9/2021 | Hakala et al. |
| 2021/0378743 A1 | 12/2021 | Massimini et al. |
| 2022/0071704 A1 | 3/2022 | Le |
| 2022/0183708 A1 | 6/2022 | Phan |
| 2022/0183738 A1 | 6/2022 | Flores et al. |
| 2022/0240958 A1 | 8/2022 | Nguyen |
| 2022/0249165 A1 | 8/2022 | Cook et al. |
| 2022/0249166 A1 | 8/2022 | Cook |
| 2022/0265295 A1 | 8/2022 | McCaffrey |
| 2022/0287730 A1 | 9/2022 | Chisena |
| 2022/0287732 A1 | 9/2022 | Anderson et al. |
| 2022/0313359 A1 | 10/2022 | Schultheis |
| 2022/0338890 A1 | 10/2022 | Anderson et al. |
| 2023/0037716 A1 | 2/2023 | Batchelder |
| 2023/0038308 A1 | 2/2023 | Batchelder |
| 2023/0038388 A1 | 2/2023 | Batchelder |
| 2023/0038663 A1 | 2/2023 | Batchelder |
| 2023/0040190 A1 | 2/2023 | Batchelder |
| 2023/0040420 A1 | 2/2023 | Batchelder |
| 2023/0041407 A1 | 2/2023 | Batchelder |
| 2023/0043475 A1 | 2/2023 | Adams |
| 2023/0044926 A1 | 2/2023 | Batchelder |
| 2023/0123003 A1 | 4/2023 | Vo |
| 2023/0248376 A1 | 8/2023 | Anderson et al. |

(56) References Cited

U.S. PATENT DOCUMENTS

| | | | |
|---|---|---|---|
| 2023/0414234 | A1 | 12/2023 | Anderson et al. |
| 2024/0252192 | A1 | 8/2024 | Anderson et al. |

FOREIGN PATENT DOCUMENTS

| | | | |
|---|---|---|---|
| EP | 3861942 | B1 | 8/2023 |
| JP | S62-275446 | A | 11/1987 |
| JP | 2004121859 | A | 4/2004 |
| JP | 2015522344 | A | 8/2015 |
| JP | 2015528327 | A | 9/2015 |
| JP | 2015531659 | A | 11/2015 |
| JP | 2021503344 | A | 2/2021 |
| WO | 2020141068 | A1 | 7/2020 |
| WO | 2020168213 | A1 | 8/2020 |
| WO | 2021162855 | A1 | 8/2021 |
| WO | 2021247685 | A1 | 12/2021 |
| WO | 2022055784 | A1 | 3/2022 |

OTHER PUBLICATIONS

Shockwave Medical—"Shockwave M5 IVL Catheter"—shockwavemedical.com [online]—Available at least as of Apr. 2022—Available from Internet <URL: https://shockwavemedical.com/clinicians/usa/peripheral/product-specs-resources/shockwave-m5/>.
Shockwave Medical—"Shockwave M5+"—shockwavemedical.com [online]—Available at least as of Apr. 2022—Available from Internet <URL: https://shockwavemedical.com/clinicians/usa/peripheral/product-specs-resources/shockwave-m5plus/>.
Shockwave Medical—"Shockwave S4 IVL Catheter"—shockwavemedical.com [online]—Available at least as of Apr. 2022—Available from Internet <URL: https://shockwavemedical.com/clinicians/usa/peripheral/shockwave-s4/>.
Marmur, Jonathan D.—"Carotid Artery Stenting"—marmur.com [online]—Available at least as of 2016—Available from Internet <URL: http://www.marmur.com/carotid-artery-stenting.html>.
Finol E.A., Siewiorek G.M., Scotti C.M., Wholey M.H., Wholey M.H.—"Wall Apposition Assessment and Performance Comparison of Distal Protection Filters"—Journal of Endovascular Therapy—May 2008—vol. 15, No. 2, p. 177-185—Available from Internet <URL: https://www.researchgate.net/publication/5427102_Wall_Apposition_Assessment_and_Performance_Comparison_of_Distal_Protection_Filters>.
Boston Scientific—"Peripheral Cutting Balloon™"—bostonscientific.com [online]—Available at least as of 2021—Available from Internet <URL: https://www.bostonscientific.com/en-us/products/catheters-balloon/peripheral-cutting-balloon.html>.
Philips—"AngioSculpt RX PTCA"—usa.philips.com [online]—Available at least as of 2021—Available from Internet <URL: https://www.usa.philips.com/healthcare/product/HCIGTDPTCARXSB/angiosculpt-rx-ptca-scoring-balloon-catheter>.
Cagent Vascular—"The Serration Balloon"—cagentvascular.com [online]—Available at least as of 2021—Available from Internet <URL: https://cagentvascular.com/information>.
Trireme Medical—"Chocolate® PTCA Balloon Catheter"—qtvascular.com [online]—Available at least as of 2021—Available from Internet <URL: https://qtvascular.com/us/products/chocolate-ptca/>.
BD (Becton, Dickinson and Company)—"Vascutrak™ PTA Dilatation Catheters"—bd.com [online]—Available at least as of 2021—Available from Internet <URL: https://www.bd.com/en-us/products-and-solutions/products/product-families/vascutrak-pta-dilatation-catheters>.
Boston Scientific—"FilterWire EZ™"—bostonscientific.com [online]—Available at least as of 2021—Available from Internet <URL: https://www.bostonscientific.com/en-us/products/embolic-protection/filterwire-ez-embolic-protection-system.html>.
Carefusion—"Introducing the AVAmax® vertebral balloon"—carefusion.com [online]—Available at least as of Apr. 1, 2010—Retrieved from Internet Archive Wayback Machine <URL: https://web.archive.org/web/20100401182423/http:/avamaxchoice.carefusion.com/>.
Abbott Laboratories—"Abbott Accunet—Model RX—Embolic Protection System"—medical-xprt.com [online]—Available at least as of 2021—Available from Internet <URL: https://www.medical-xprt.com/products/abbott-accunet-model-rx-embolic-protection-system-748573>.
Medtronic—"SpiderFX Embolic Protection Device"—medtronic.com [online]—Available at least as of 2021—Available from Internet <URL: https://www.medtronic.com/us-en/healthcare-professionals/products/cardiovascular/embolic-protection-devices/spiderfx.html>.
Contego Medical—"Corguard® Coronary Balloon Angioplasty System with Integrated Embolic Protection"—contegomedical.com [online]—Available at least as of 2021—Available from Internet <URL: https://contegomedical.com/coronary/>.
Contego Medical—"Paladin® Carotid PTA Balloon System with Integrated Embolic Protection"—contegomedical.com [online]—Available at least as of 2021—Available from Internet <URL: https://contegomedical.com/paladin-carotid-pta-balloon-system-u-s/>.

* cited by examiner

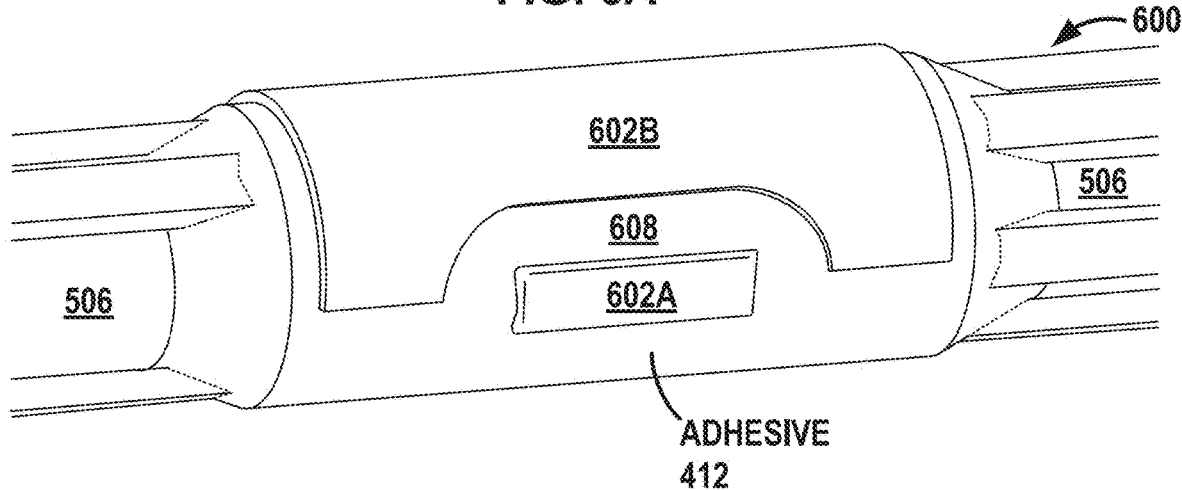
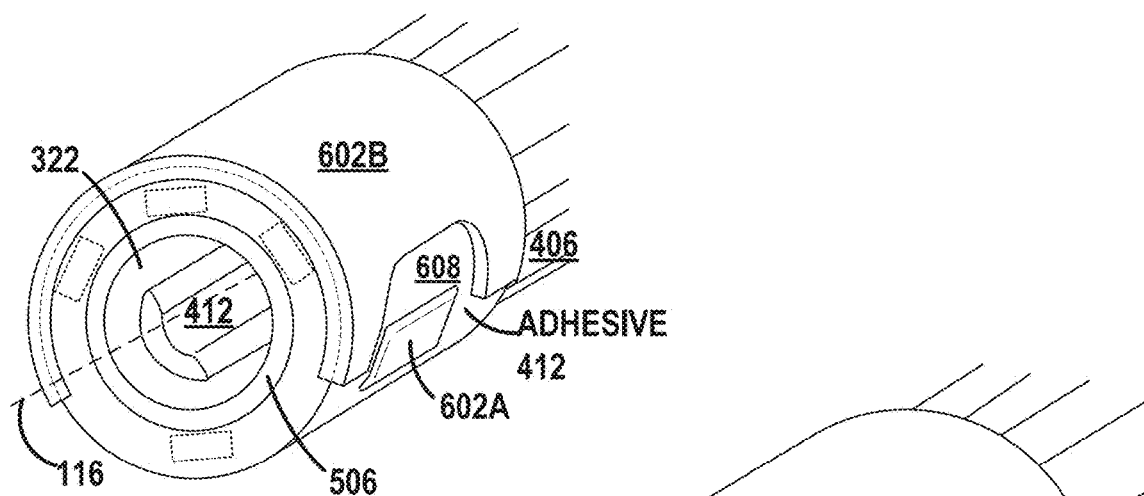
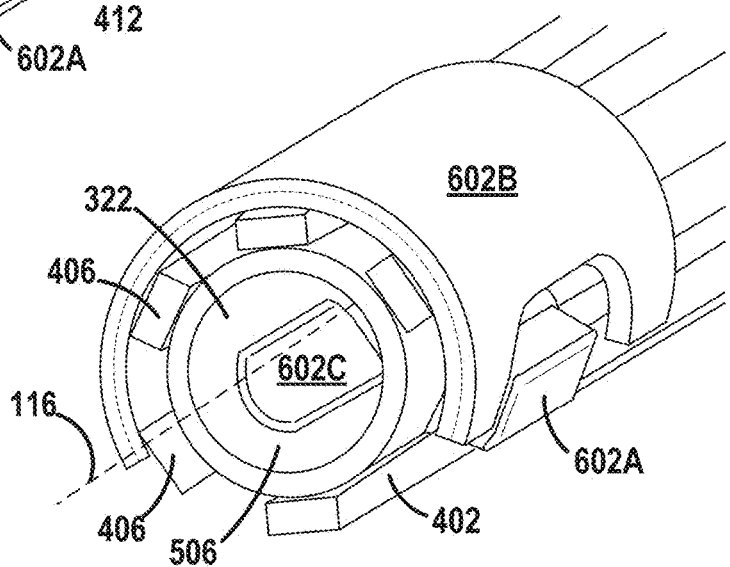

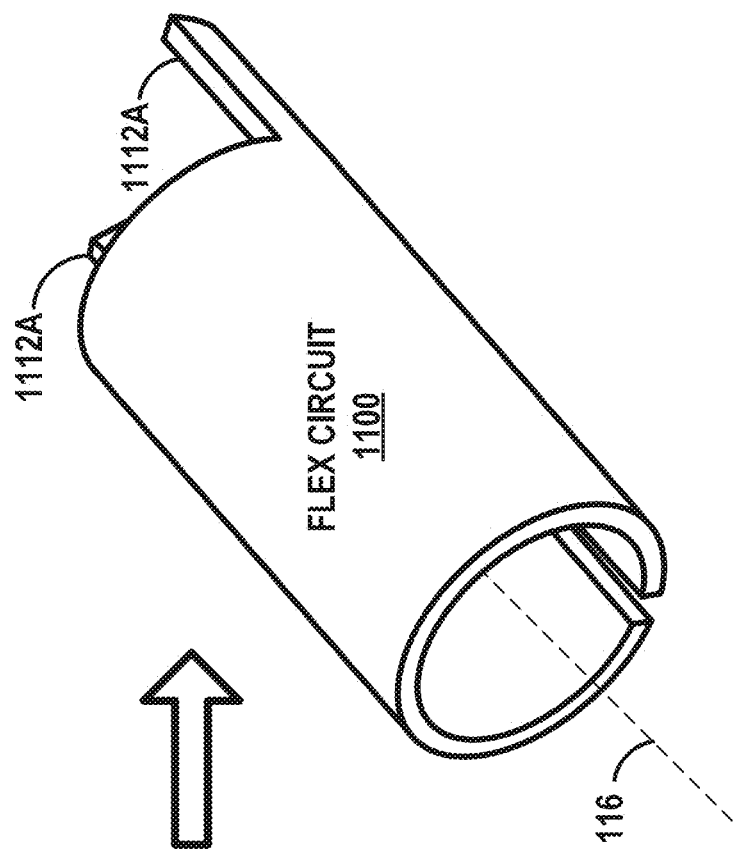
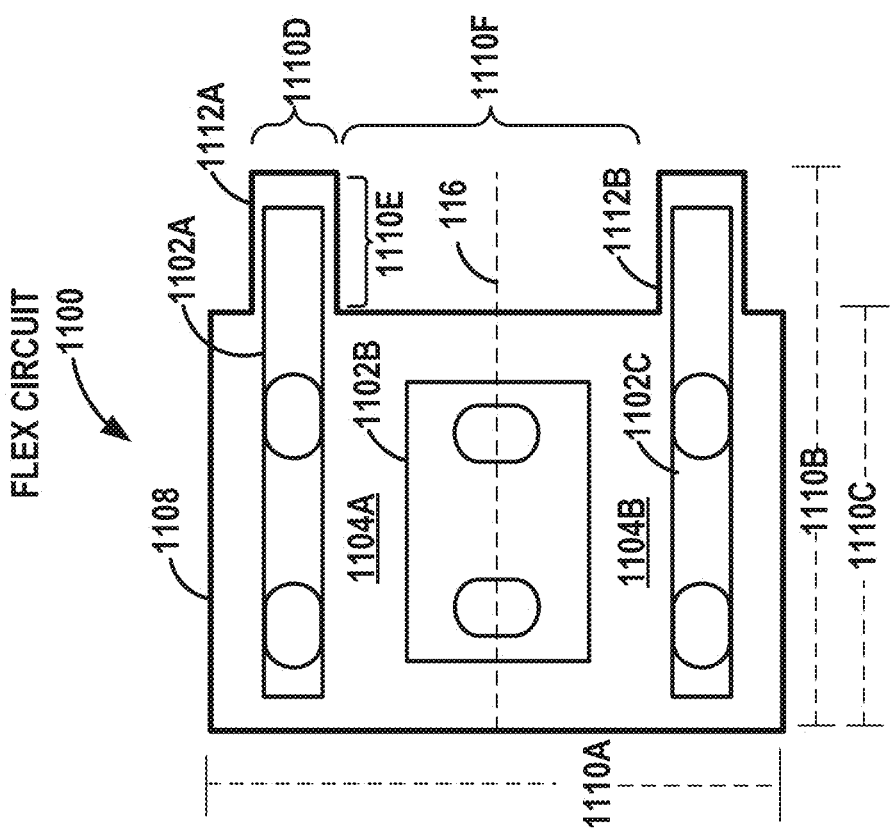
FIG. 11B
FIG. 11A

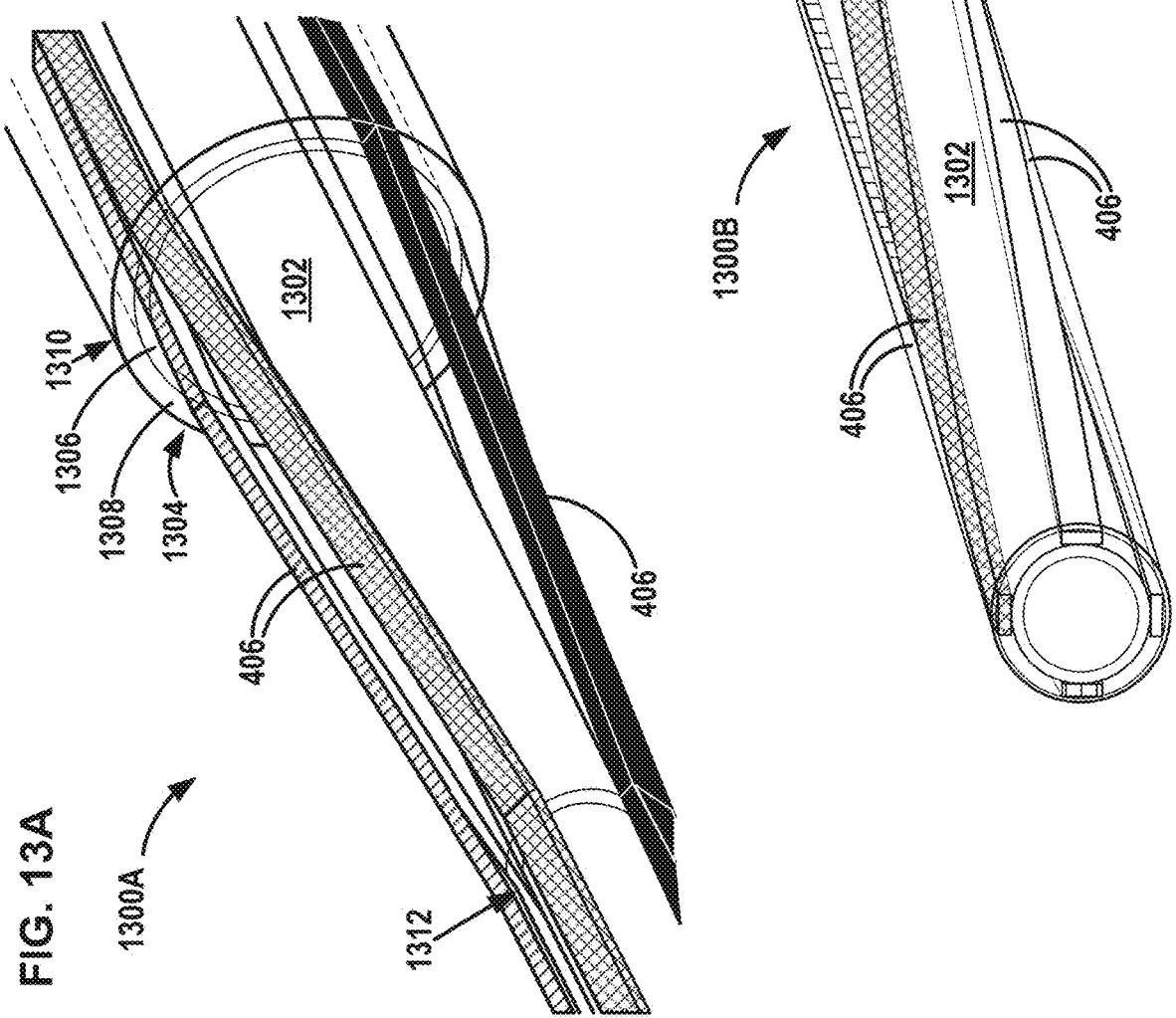

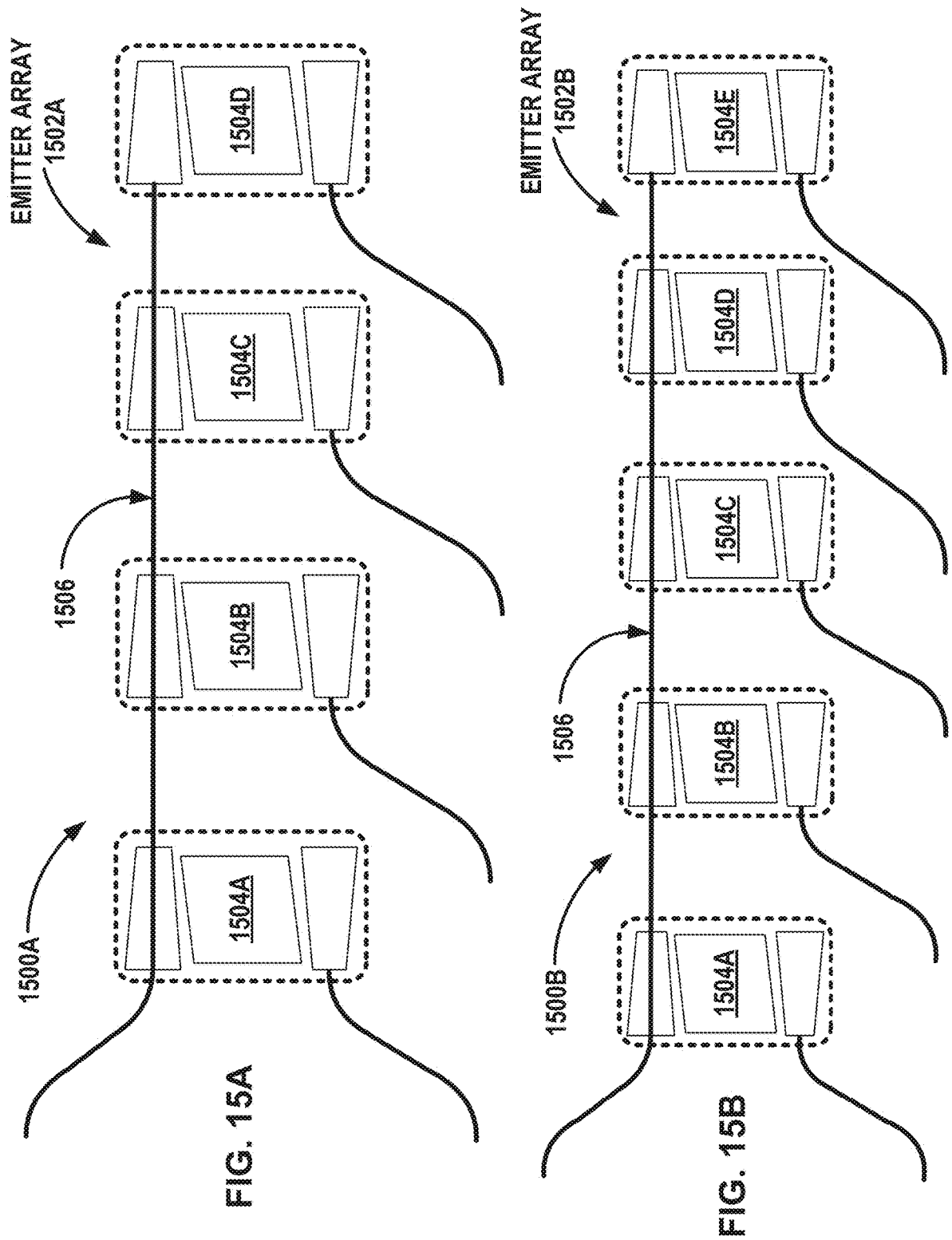

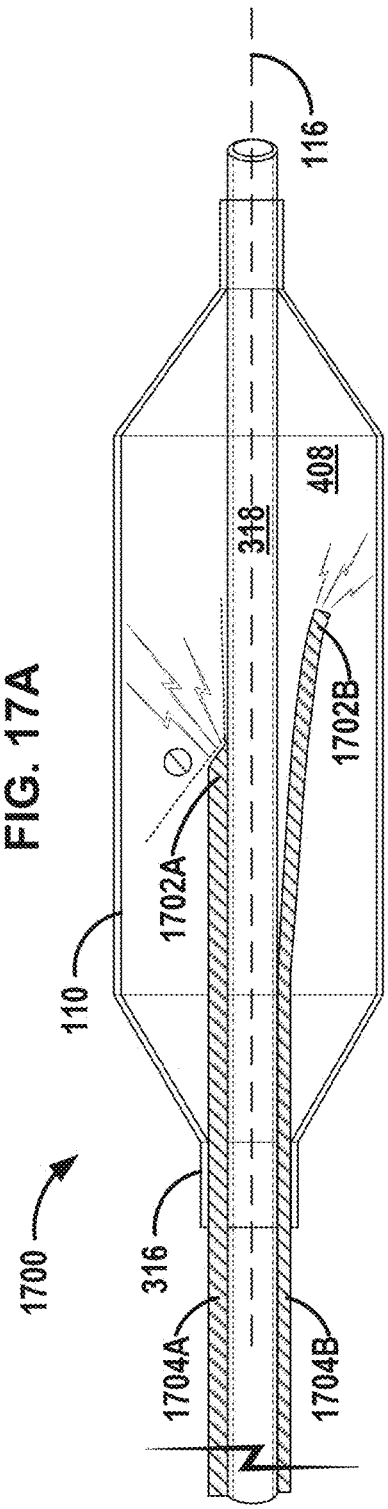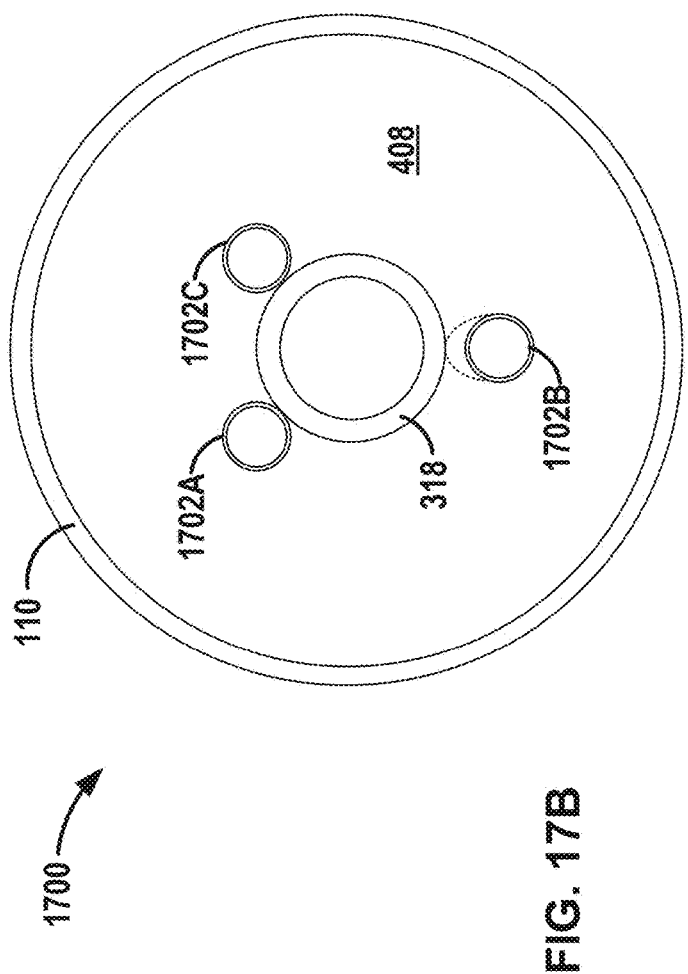

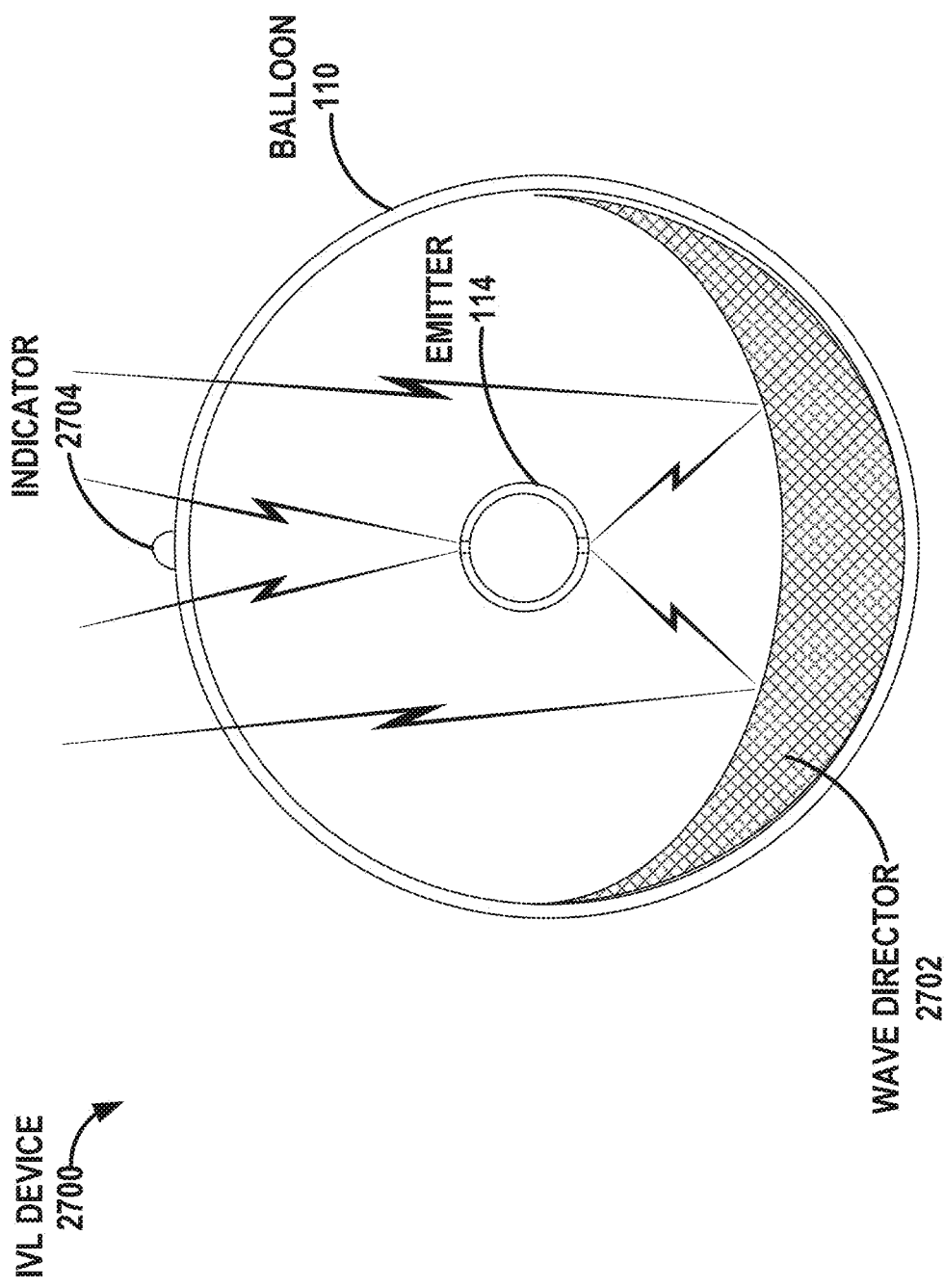

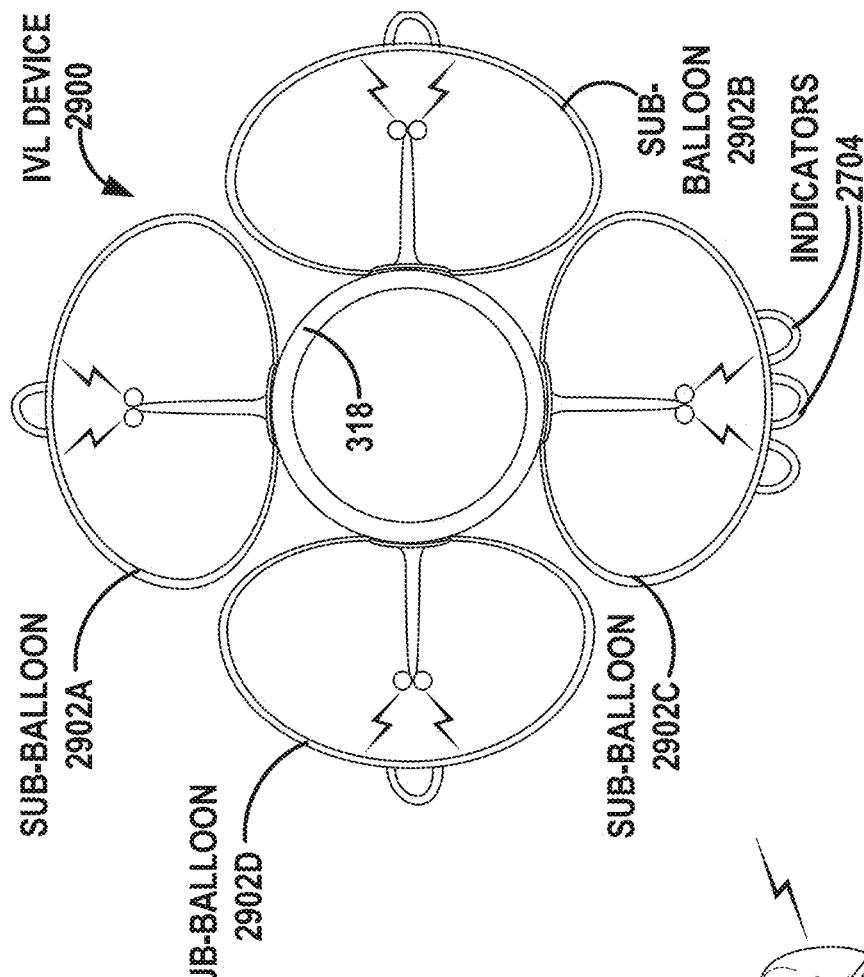
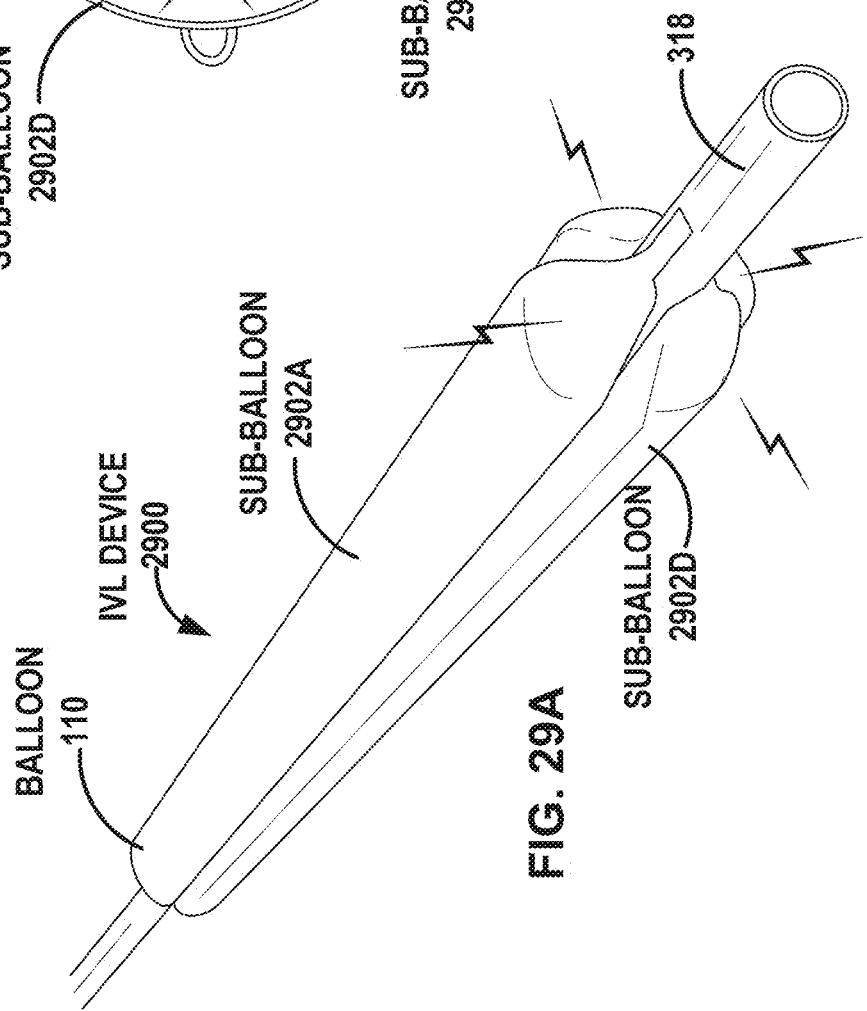
FIG. 29B
FIG. 29A

INTRAVASCULAR LITHOTRIPSY

CROSS-REFERENCE TO RELATED APPLICATIONS

The entire contents of the following application are incorporated herein by reference: U.S. Provisional Patent Application No. 63/154,603; filed Feb. 26, 2021; and entitled ENDOVASCULAR DEVICES AND METHODS.
The entire contents of the following application are incorporated herein by reference: U.S. Provisional Patent Application No. 63/169,091; filed Mar. 31, 2021; and entitled ENDOVASCULAR DEVICES AND METHODS.
The entire contents of the following application are incorporated herein by reference: U.S. Provisional Patent Application No. 63/176,156; filed Apr. 16, 2021; and entitled BALLOON CATHETER FOR DELIVERING A SHOCK WAVE TO VASCULATURE OR CORONARY VALVE.
The entire contents of the following application are incorporated herein by reference: U.S. Provisional Patent Application No. 63/193,469; filed May 26, 2021; and entitled BALLOON CATHETER FOR DELIVERING A SHOCK WAVE TO VASCULATURE OR CORONARY VALVE.
The entire contents of the following application are incorporated herein by reference: U.S. Non-Provisional patent application Ser. No. 17/679,434; filed Feb. 24, 2022; and entitled INTRAVASCULAR LITHOTRIPSY.
The entire contents of the following application are incorporated herein by reference: U.S. Non-Provisional patent application Ser. No. 17/861,137; filed Jul. 8, 2022; and entitled INTRAVASCULAR LITHOTRIPSY.
The entire contents of the following application are incorporated herein by reference: U.S. Non-Provisional patent application Ser. No. 18/134,507; filed Apr. 13, 2023; and entitled INTRAVASCULAR LITHOTRIPSY.
The entire contents of the following application are incorporated herein by reference: U.S. Non-Provisional patent application Ser. No. 18/367,811; filed Sep. 13, 2023; and entitled INTRAVASCULAR LITHOTRIPSY.
The entire contents of the following application are incorporated herein by reference: U.S. Non-Provisional patent application Ser. No. 18/443,267; filed Feb. 15, 2024; and entitled INTRAVASCULAR LITHOTRIPSY.

INTRODUCTION

Field

The present disclosure relates to treatments for a calcified-plaque lesion in a patient's vasculature.

Description of Related Art

During an intravascular lithotripsy (IVL) procedure, and more specifically, during an electrohydraulic lithotripsy (EHL) procedure, a clinician uses a catheter configured to emit high-energy pressure waves to break apart calcified-plaque lesions within a patient's vasculature.

SUMMARY

The present disclosure describes systems and techniques for producing and directing high-energy intravascular pressure waves for fragmentation and/or disintegration of calcified lesions within a vasculature of a patient. For purposes of illustration, the techniques herein are described primarily with respect to electrical-based systems and respective applications thereof, such as peripheral-vessel applications. However, it is to be understood that the techniques described herein may be assumed to be likewise applicable to similar systems based on other forms of energy, such as optical (e.g., laser) based systems and respective applications, such as coronary-treatment applications, except where explicitly noted below.

In general, the systems described herein include an energy generator removably coupled to a catheter having an array of pressure-wave emitters distributed within an interventional balloon. During a lesion-disintegration procedure, a clinician may advance the interventional balloon to a target treatment site within a patient's vasculature and inflate the balloon with an inflation fluid, such as a saline/contrast fluid mixture, until the balloon contacts at least a portion of the local vessel wall. The clinician may then actuate the energy generator, causing the catheter to generate a cavitation bubble within the fluid-filled balloon, propagating a high-energy pressure wave through the balloon and the calcified lesion. A secondary pressure wave can also result from the subsequent collapse of the fluid cavitation, further destabilizing the internal structure of the lesion.

In some examples, a medical device includes: an elongated body; a balloon positioned at a distal portion of the elongated body, the balloon configured to receive a fluid and thereby inflate such that an exterior surface of the balloon contacts an interior surface of a target treatment site within a vasculature of a patient; and one or more pressure-wave emitters positioned along a central longitudinal axis of the elongated body within the balloon, the one or more pressure-wave emitters configured to propagate pressure waves radially outward through the fluid to fragment a calcified lesion at the target treatment site, wherein at least one of the one or more pressure-wave emitters includes an electronic emitter including a first electrode and a second electrode, wherein the first electrode and the second electrode are arranged to define a spark gap between the first electrode and the second electrode, and wherein the second electrode includes a portion of a hypotube.

In some examples, the first electrode and the second electrode are embedded in an adhesive layer, and the electronic emitter further includes an elastomeric tube disposed radially between the elongated body and the second electrode. In some examples, the electronic emitter further includes a coil layer disposed radially between the elongated body and the elastomeric tube.

In some examples, the first electrode is oriented such that an exterior surface is non-parallel to the central longitudinal axis of the elongated body in the absence of external forces. In some examples, the first electrode is configured to move relative to the elongated body such that the exterior surface of the first electrode is oriented parallel to the central longitudinal axis during insertion and withdrawal of the medical device through the vasculature of the patient.

In some examples, the spark gap includes a first spark gap, the electronic emitter further includes a third electrode, and the third electrode is arranged so as to define a second spark gap between the second electrode and the third electrode. In some examples, the first electrode, the second electrode, and the third electrode are all portions of a common cylindrical surface of the hypotube. In some examples, the first electrode and the third electrode both define rounded triangular shapes, and the second electrode defines a parallelogram shape. In some examples, the first electrode, the second electrode, and the third electrode all define parallelogram shapes.

In some examples, the first electrode, the second electrode, and the third electrode all define rounded rectangular shapes. In some examples, the first electrode and the third electrode both define oval shapes, and the second electrode defines a semi-cylindrical shape. In some examples, the electronic emitter further includes a coupler layer positioned radially between the elongated body and the second electrode. In some examples, the coupler layer includes polyimide.

In some examples, the electronic emitter is wired such that the first electrode and the third electrode are independently actuatable. In some examples, the first electrode is ring-shaped; the second electrode is disc-shaped; and the first electrode is positioned around the second electrode.

In some examples, the electronic emitter further includes a third electrode and a fourth electrode; the third electrode is ring-shaped and the fourth electrode is disc-shaped; the third electrode is positioned around the fourth electrode; and the first, second, third, and fourth electrodes are all portions of a common cylindrical surface of the hypotube.

In some examples, the first electrode defines an inner radius of about 0.008 inches and an outer radius of about 0.0210 inches. In some examples, the hypotube defines a longitudinal length from about 0.080 inches to about 0.090 inches, and an outer circumference from about 0.10 inches to about 0.12 inches. In some examples, the hypotube defines an inner diameter of about 0.029 inches and an outer diameter of about 0.034 inches. In some examples, the first electrode is rectangular-prism shaped, and the first electrode extends at least partially radially inward through an outer surface of the elongated body.

In some examples, the first electrode extends radially inward through the elongated body and at least partially radially inward into an inner lumen of the elongated body. In some examples, the one or more pressure-wave emitters include five electronic emitters spaced longitudinally along the central longitudinal axis of the elongated body.

In some examples, an intravascular lithotripsy (IVL) system includes an energy generator; and a catheter, as referenced above.

In some examples, the energy generator is configured to control a treatment cycle by causing the electronic emitter to transmit a plurality of pressure-wave pulses, and the plurality of pressure-wave pulses includes about 80 pulses to about 300 pulses.

In some examples, a method of forming an electronic pressure-wave emitter of an intravascular lithotripsy (IVL) catheter includes: laser-cutting a hypotube to define at least a first electrode and a second electrode arranged to define a spark gap therebetween; inserting an elongated body through the laser-cut hypotube; flowing a potting material around the laser-cut hypotube; and removing obsolete support structures from the hypotube.

In some examples, the spark gap includes a first spark gap; and laser-cutting the hypotube further includes laser-cutting the hypotube to define a third electrode arranged so as to define a second spark gap between the second electrode and the third electrode.

In some examples, laser-cutting the hypotube includes laser-cutting the hypotube such that the first electrode and the third electrode both define rounded triangular shapes, and such that the second electrode defines a parallelogram shape. In some examples, laser-cutting the hypotube includes laser-cutting the hypotube such that the first electrode, the second electrode, and the third electrode all define parallelogram shapes.

In some examples, laser-cutting the hypotube includes laser-cutting the hypotube such that the first electrode, the second electrode, and the third electrode all define rounded rectangular shapes. In some examples, laser-cutting the hypotube includes laser-cutting the hypotube such that the first electrode and the third electrode both define oval shapes, and such that the second electrode defines a semi-cylindrical shape. In some examples, the method further includes wiring the first electrode and the third electrode so as to be independently actuatable.

In some examples, the spark gap includes a first spark gap; and laser-cutting the hypotube further includes laser-cutting the hypotube to define a third electrode and a fourth electrode arranged so as to define a second spark gap between the third electrode and the fourth electrode. In some examples, laser-cutting the hypotube further includes laser-cutting the hypotube such that: the first electrode and the third electrode are ring-shaped; the second electrode and the fourth electrode are disc-shaped; the first electrode is positioned around the second electrode; and the third electrode is positioned around the fourth electrode.

In some examples, a medical device includes an elongated body; a balloon positioned at a distal portion of the elongated body, the balloon configured to receive a fluid and thereby inflate such that an exterior surface of the balloon contacts an interior surface of a target treatment site within a vasculature of a patient; and one or more pressure-wave emitters positioned along a central longitudinal axis of the elongated body within the balloon, the one or more pressure-wave emitters configured to propagate pressure waves radially outward through the fluid to fragment a calcified lesion at the target treatment site, wherein at least one of the one or more pressure-wave emitters includes an electronic emitter including a first electrode, a second electrode, and a third electrode arranged to define a first spark gap between the first electrode and the second electrode, and a second spark gap between the second electrode and the third electrode, and wherein the first electrode, the second electrode, and the third electrode are portions of a common hypotube.

In some examples, the medical device includes a plurality of conductive wires configured to provide electrical energy to the emitter array, the plurality of conductive wires arranged according to a wiring configuration.

In some examples, the plurality of conductive wires extends generally parallel to the central longitudinal axis. In some examples, the wiring configuration includes a single-coil configuration such that the plurality of conductive wires coil helically around the elongated body, wherein adjacent coil turns of the plurality of conductive wires are spaced longitudinally along the central longitudinal axis. In some examples, the wiring configuration includes a double-coil configuration such that the plurality of conductive wires coil helically around the elongated body, wherein adjacent pairs of coil turns of the plurality of conductive wires are spaced longitudinally along the central longitudinal axis. In some examples, the wiring configuration includes a quadruple-coil configuration such that the plurality of conductive wires coil helically around the elongated body, wherein adjacent groups of four coil turns of the plurality of conductive wires are spaced longitudinally along the central longitudinal axis.

In some examples, the plurality of conductive wires includes a plurality of flat wires. In some examples, the plurality of conductive wires includes a plurality of round wires with flattened portions along the emitter array.

In some examples, the elongated body includes an inner body and an outer body; the outer body includes an inner layer and an outer layer; and the plurality of conductive wires coils around an exterior surface of the inner layer. In some examples, the outer layer of the outer body is flowed over the plurality of conductive wires such that the plurality of conductive wires is embedded in the outer layer. In some examples, the outer layer includes a potting layer or a heat-shrink tube. In some examples, the outer layer terminates proximally from the inner layer, such that a distal portion of the plurality of conductive wires is exposed to an interior of the balloon.

In some examples, the elongated body includes an inner body and an outer body, and the plurality of conductive wires coils around an exterior surface of the inner body such that the plurality of conductive wires forms a reinforcement layer for the elongated body.

In some examples, each of the plurality of emitters includes a respective voltage wire such that each of the plurality of emitters is independently actuatable. In some examples, the exterior surface of the balloon includes a polymer coating. In some examples, the exterior surface of the balloon includes a hydrophilic coating or a drug-based coating, such as an anti-thrombogenic coating or an anti-proliferative medication.

In some examples, the balloon includes two or more nested expandable substrates. In some examples, the two or more nested expandable substrates include at least an outer layer and an inner layer, wherein an interior surface of the outer layer is bonded to an exterior surface of the inner layer so as to form a single multi-layered extrusion. In some examples, the inner layer includes a high-pressure holding layer, and the outer layer includes a urethane layer.

In some examples, the balloon further includes a reinforcing structure. In some examples, the reinforcing structure includes a plurality of longitudinal fibers aligned parallel to the longitudinal axis of the balloon and a plurality of braided fibers. In some examples, the plurality of longitudinal fibers includes four to eight longitudinal fibers.

In some examples, the balloon includes an outer layer, an inner layer nested within the outer layer, and a cage structure nested between the outer layer and the inner layer, and the cage structure includes one or more longitudinal members oriented parallel to the longitudinal axis and one or more circumferential elements oriented perpendicular to the longitudinal axis.

In some examples, the medical device further includes a cage structure at least partially surrounding the exterior surface of the balloon. In some examples, the cage structure is rigidly coupled to the exterior surface of the balloon. In some examples, the cage structure includes a nitinol braid, metal wires, printed metals, radiopaque metal wires, or radiopaque printed metals. In some examples, the balloon includes a porous membrane configured to infuse a drug at the target treatment site.

In some examples, the balloon includes a plurality of longitudinal ribs configured to define folding guides as the balloon folds radially inward. In some examples, the plurality of longitudinal ribs includes an odd number of ribs. In some examples, the medical device includes a spring configured to longitudinally stretch the balloon in an absence of external forces.

In some examples, the medical device includes a fracturing member positioned on an external surface of the balloon. In some examples, the fracturing member includes a conductive wire running along the longitudinal axis of the balloon; and a plurality of piezo-elements positioned along the conductive wire, the plurality of piezo-elements configured to emit additional pressure waves against the calcified lesion. In some examples, the medical device includes a protective device positioned at the distal portion of the elongated body, and the protective device is configured to at least partially occlude the target treatment site and to collect fragmented lesion portions.

In some examples, the medical device includes a protective device positioned along the elongated body proximal to the balloon, and the protective device is configured to at least partially occlude the target treatment site and to collect fragmented lesion portions.

In some examples, the elongated body defines a lumen configured to receive a 0.0104" to 0.035" guidewire. In some examples, the medical device includes a handle positioned at a proximal end of the elongated body, wherein the handle includes an integral power supply for the emitter array. In some examples, the medical device includes a scoring member configured to contact and abrade the calcified lesion. In some examples, the scoring member defines a serrated exterior surface.

In some examples, the medical device includes means for controlling a primary direction of emission of the pressure waves. In some examples, the medical device includes a wave director positioned against an interior surface of the balloon and along only a portion of a circumference of the balloon, the wave director configured to absorb or reflect the pressure waves from the second portion of the circumference of the balloon. In some examples, the medical device includes a ceramic, porcelain, diamond, polyimide, or polyether ether ketone (PEEK). In some examples, the wave director defines a reflective-fluid pocket or an absorbent-fluid pocket.

In some examples, the medical device includes a radiopaque indicator positioned along the first portion of the circumference of the balloon, and the radiopaque indicator is configured to indicate an emitted direction of the pressure waves. In some examples, the radiopaque indicator includes a radiopaque wire positioned along the exterior surface of the balloon. In some examples, the radiopaque indicator includes a conductive wire of a fracturing element positioned along an exterior surface of the balloon, and the fracturing element further includes a plurality of piezoelectric elements configured to emit additional pressure waves through the calcified lesion.

In some examples, each of the one or more shockwave emitters defines a respective orientation, and the medical device further includes a user-input mechanism to modify the respective orientations of the one or more shockwave emitters. In some examples, each of the one or more shockwave emitters defines a respective fixed orientation, and the medical device further includes a user-input mechanism configured to independently actuate a first subset of the one or more shockwave emitters independently from a second subset of the one or more shockwave emitters. In some examples, the balloon includes two or more elongated sub-balloons oriented circumferentially around the central longitudinal axis, each sub-balloon including a respective subset of the one or more shockwave emitters.

In some examples, the system further includes a sensor configured to generate sensor data indicative of at least one parameter. In some such examples, the energy generator is configured to vary an amount of energy delivered based on the sensor data. In some examples, to vary the amount of energy, the energy generator is configured to vary a current level, a voltage level, a pulse duration, a pulse frequency, or a light intensity. In some examples, the sensor data includes fluid-pressure data, fluid-rate data, or temperature data. In some examples, the sensor includes an electrical-impedance monitor, an inflation-fluid flow-rate monitor, an inflation-fluid pressure monitor, a vessel-wall surface monitor, a vessel-diameter monitor, an interventional-balloon diameter monitor, or a plaque-fragmentation monitor. In some examples, the sensor includes a resonant-frequency sensor, and the energy monitor is configured to vary a pressure-wave frequency to approximate a resonant frequency of the calcified lesion. In some examples, the energy generator is configured to terminate an applied voltage based on the sensor data.

BRIEF DESCRIPTION OF THE DRAWINGS

These and other features, aspects, and advantages are described below with reference to the drawings, which are intended to illustrate, but not to limit, the invention. In the drawings, like characters denote corresponding features consistently throughout similar embodiments.

FIG. 6A illustrates a third example emitter assembly of the catheter of FIG. 1.

FIG. 6B is a cross-sectional diagram of the emitter assembly of FIG. 6A.

FIG. 6C is a cross-sectional diagram of the emitter assembly of FIG. 6A with a potting-material layer removed to illustrate the components embedded therein.

FIGS. 11A and 11B illustrate an example flex circuit for an emitter assembly of an IVL catheter.

FIGS. 13A and 13B illustrate two example wiring configurations for conductively wiring an electronic pressure-wave-emitter array.

FIG. 15A is a conceptual diagram illustrating an example wiring configuration for an electronic-emitter array having four emitter units.

FIG. 15B is a conceptual diagram illustrating an example wiring configuration for an electronic-emitter array having five emitter units.

FIG. 17A is a conceptual diagram illustrating an example IVL device having an optical-based emitter array.

FIG. 17B is a cross-sectional view through the IVL device of FIG. 17A.

FIG. 27 is a cross-sectional view through a first example directionally focused IVL device.

FIG. 29A is a perspective view, and FIG. 29B is a cross-sectional view of a third example directionally focused IVL device.

COMPONENT INDEX

Figure 1:
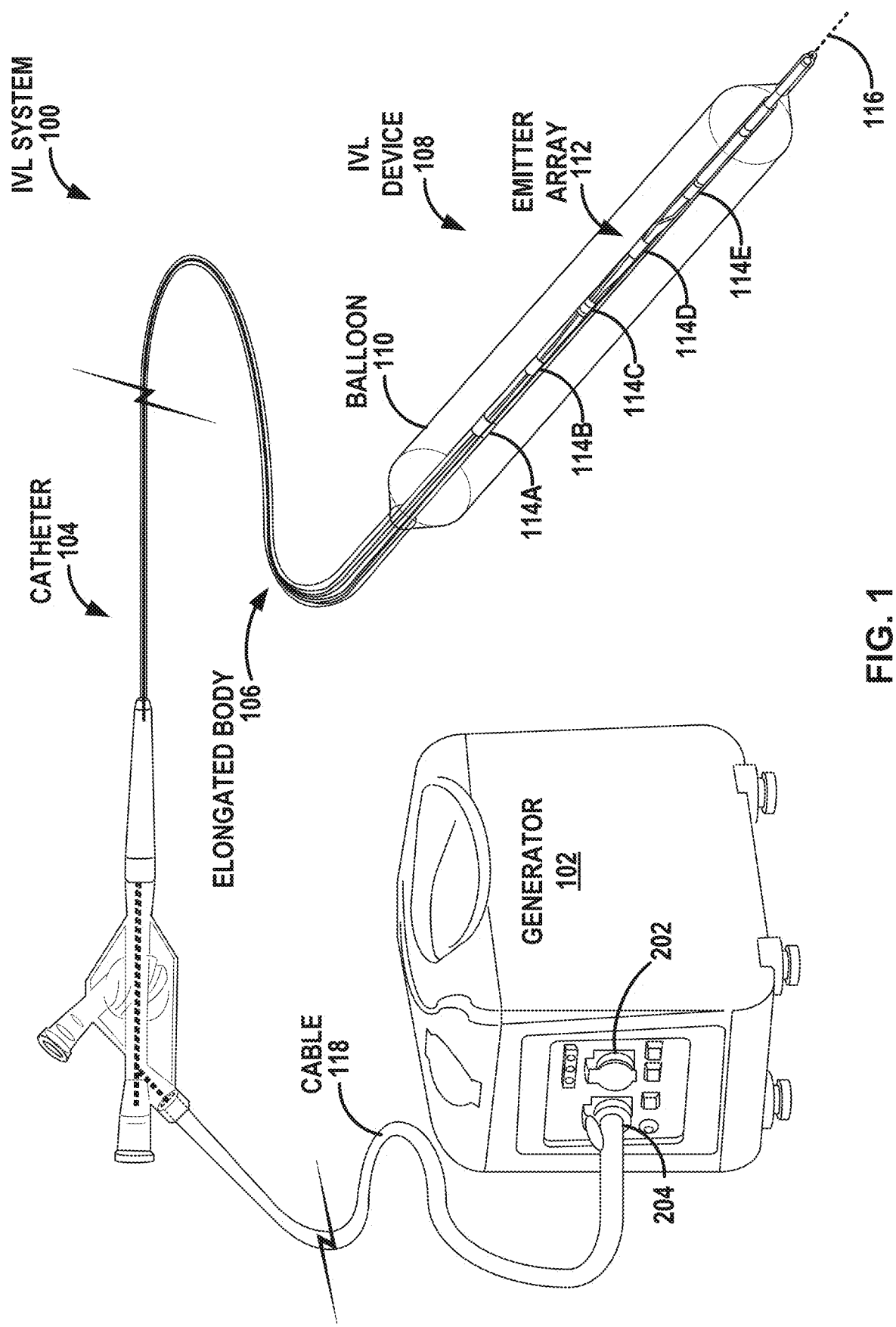
FIG. 1 is a conceptual diagram of an example intravascular lithotripsy (IVL) system, including an energy generator and a catheter having a pressure-wave-emitter array within an interventional balloon.

100—Intravascular Lithotripsy (IVL) System
102—Energy Generator
104—Catheter
106—Elongated Catheter Body
108—IVL Device
110—Interventional Balloon
112—Pressure-Wave-Emitter Array
114A—First Emitter
114B—Second Emitter
114C—Third Emitter
114D—Fourth Emitter
114E—Fifth Emitter 116—Central Longitudinal Axis
118—Removable Cable
202—Power-Input Connector
204—Catheter Connector
208—Internal Power Supplies
210—High-Voltage DC-DC Converter
212—High-Voltage Capacitor and Transistor Switch
216—Voltage-and-Current Measurement Unit
218—Processor 218
222—Device Identification Unit
224—Power Module
226—User-Interface (UI) Control Processor
234—User Interface
302—Proximal Catheter Portion
304—Distal Catheter Portion
306—Catheter Hub
308—Access Port
310—Inflation Port
312—Power Port
314—Strain Relief
316—Outer Elongated Structure
318—Inner Elongated Structure
320—Inflation Lumen
322—Guidewire Lumen
324—Distal Port
326—Exterior Balloon Coating
400—First Electric Emitter Assembly
402A—First Electrode
402B—Second Electrode
402C—Third Electrode
404A—First Spark Gap
404B—Second Spark Gap
406A—First Wire
406B—Second Wire
408—Inflation Fluid
410—Hypotube
412—Potting Material
414—Electrode Edges
416—Elastomeric Layer
418—Coils
420—Polymer Layer
500—Second Electric Emitter Assembly
502A—First Emitter Electrode
502B—Hypotube Electrode
502C—Second Emitter Electrode
504—Insulating Layer
506—Polyimide Inner Elongated Structure
508A, 508B—Spark Gaps
600—Third Electric Emitter Assembly
602A—First Emitter Electrode
602B—Hypotube Electrode
602C—Second Emitter Electrode
608—Spark Gap
700—First Hypotube Design
800—Second Hypotube Design
802A—First Electrode
802B—Second Electrode
802C—Third Electrode
804A—First Spark Gap
804B—Second Spark Gap
806—Support Structures
810A—Circumferential Length
810B—Longitudinal Length
810C—Electrode Edge Length
810D—Spark Gap Width
810E—Support Structure Width
812—Hypotube-Array Design
814—Coupling Supports
816—Removable Supports
900—Third Hypotube Design
902A—First Ring Electrode
902B—First Disc Electrode
902C—Second Ring Electrode
902D—Second Disc Electrode 904—Spark Gaps
906—Support Structures
910A—Circumferential Length
910B—Longitudinal Length
910C—Support Structure Width
1000—Assembly Technique
1002-1010—Assembly Steps
1100—Flex Circuit
1102A—First Electrode
1102B—Second Electrode
1102C—Third Electrode
1104—Spark Gaps
1108—Flexible Substrate
1110A—Circumferential Length
1110B—Flex Circuit Longitudinal Length
1110C—Rectangle Longitudinal Length
1110D—Prong Circumferential Width
1110E—Prong Longitudinal Length
1110F—Prong Gap Circumferential Length
1112—Prongs
1200A—First Flex-Circuit Wiring Configuration
1200B—Second Flex-Circuit Wiring Configuration
1202—Top Wire
1204—Bottom Wire
1206—Top Wire
1208—Middle Wire
1210—Bottom Wire
1300A—First Wiring Configuration
1300B—Second Wiring Configuration
1302—Inner Elongated Structure
1304—Outer Elongated Structure
1306—Outer Structure Inner Layer
1308—Outer Structure Outer Layer
1310—Outer Structure Outer Layer Termination Point
1312—Outer Structure Inner Layer Termination Point
1400A—D-Wiring Configurations
1402—Wire Loop-Back Point
1404—Distal Balloon Cone
1406—Emitters
1408—Exposed Wire Conductor Points
1500A—First Wiring Configuration
1500B—Second Wiring Configuration
1502A—Four-Emitter Array
1502B—Five-Emitter Array
1504—Electric Emitters
1506—Ground Wire
1600A—First Wiring Configuration
1600B—Second Wiring Configuration
1602—Emitter Array
1604—Emitters
1606—Conductive Wires
1700—IVL Device
1702—Optical Emitters
1704—Optical Fibers
1800—IVL Device
1802—Balloon Outer Layer
1804—Balloon Inner Layer
1806—Balloon Middle Layer
1810—Interventional Balloon
1900—Interventional Device
1902—First Protective Structure
1904—Longitudinal Members
1906—Circumferential Members
2000—IVL Device
2002—Second Protective Structure
2100—IVL Device
2102—Scoring Members
2200—IVL Device
2202—Fracturing Element
2204—Wire
2206—Piezoelectric Elements
2300—IVL Device
2302—Spring
2304A—Spring Proximal End
2304B—Spring Distal End
2400—IVL Device
2402—Distal Protective Device
2404—Elongated Element
2406—Expandable Basket Member
2502—Sensor
2600—Catheter Handle
2602—Integrated Power Supply
2700—IVL Device
2702—Wave Director
2704—Fluid Pocket
2704—Visual Direction Indicator
2800—IVL Device
2814—Emitter Assemblies
2816—Emitter Units
2900—IVL Device
2902—Sub-Balloons
3000—Hypotube
3002—Strut
3004—Spark gap
3006—Parallelogram
3100—Laser-cut elliptical hypotube
3102—Strut
3200—Laser-cut elliptical hypotube
3202—Strut
3204—Elongated body
3300—Electronic emitter
3302—First electrode
3304—Second electrode
3306—Longitudinal spark gap
3308—Elongated body
3310—First perimeter
3312—Second perimeter
3400—First electronic emitter
3402—First electrode
3404—Second electrode
3406—First longitudinal spark gap
3408—Elongated body
3410—First perimeter
3412—Second perimeter
3414—Second electronic emitter
3416—Third electrode
3418—Fourth electrode
3420—Second longitudinal spark gap
3422—Third perimeter
3424—Fourth perimeter
3500—Electronic emitter
3502—Adhesive
3504a—Copolymer
3504b—Polymer
3506a—Wire
3506b—Wire
3508—Reinforcement
3510—Polyimide
3512—Guide wire lumen
3700—Elliptical spark gap
3800A—First wiring configuration
3800B—Second wiring configuration
3802—Emitter array
3804—Electrode pair 3804A—First electrode pair
3804B—Second electrode pair
3804C—Third electrode pair
3804D—Fourth electrode pair
3806—Power wire
3806A—First ground wire
3806B—Second ground wire
3808—Power wire
3810A—First ground wire
3810B—Second ground wire
3810C—Power wire
3810D—First connecting wire
3810E—Second connecting wire
3900-3910—Assembly steps
4000-4004—Assembly steps
4100-4110—Assembly steps
4200-4204—Procedure steps
4300-4308—Procedure steps
4400-4404—Procedure steps
4502—First electrode
4504—Second electrode
4506—Strut
4506a—Strut
4506b—Strut
4506c—Strut
4506d—Strut
4508—Recess
4510a—Protrusion
4510b—Protrusion
4510c—Protrusion
4600—Emitter
4602—First electrode
4604—Second electrode
4606—First width
4608—Second width
4610—Spark gap
4612—Inner elongated structure
4700—Emitter
4702—First electrode
4704—Second electrode
4706—Protrusion
4708—Inner elongated structure
4802—First electrode
4804—Second electrode
4806—Third electrode
4808—Fourth electrode
4810—First spark gap
4812—Second spark gap
4814—Inner elongated structure
4900—Emitter
4902—First electrode
4904—Second electrode
4906—Third electrode
4908—First spark gap
4910—Second spark gap
4912—First width
4914—Second width
4916—Third width
4918—Inner elongated structure
5000—Emitter
5002—First electrode
5004—Second electrode
5006—Third electrode
5008—First spark gap
5010—Second spark gap
5012—First width
5014—Second width
5016—Third width
5018—Inner elongated structure
5100—Emitter
5102—First electrode
5104—Second electrode
5106—Third electrode
5108—Protrusion
5110—Inner elongated structure
5200—Emitter
5202—First electrode
5204—Second electrode
5206—Third electrode
5208—First spark gap 22
5210—Second spark gap
5212—Inner elongated structure
5302—First electrode
5304—Second electrode
5306—Third electrode
5308—Fourth electrode
5310—Fifth electrode
5312—Sixth electrode
5314—First spark gap
5316—Second spark gap
5318—Third spark gap
5320—Fourth spark gap
5322—Inner elongated structure
5402—First electrode
5404—Second electrode
5406—Third electrode
5408—Fourth electrode
5410—Fifth electrode
5412—Sixth electrode
5414—First spark gap
5416—Second spark gap
5418—Third spark gap
5420—Fourth spark gap
5422—Inner elongated structure
5500—Emitter
5502—First electrode
5504—Second electrode
5506—Third electrode
5508—First spark gap
5510—Second spark gap
5600—Emitter
5602—First electrode
5604—Second electrode
5606—Third electrode
5608—First spark gap
5610—Second spark gap
5700—Emitter
5702—First electrode
5704—Second electrode
5706—Third electrode
5708—Proximal first spark gap
5710—Proximal second spark gap
5712—Distal first spark gap
5714—Distal second spark gap
5800—Emitter
5802—First electrode
5804—Second electrode
5806—Third electrode
5808—First spark gap
5810—Second spark gap
5900—Emitter
5902—First electrode
5904—Second electrode
5906—Spark gap 6000—Emitter
6002—First electrode
6004—Second electrode
6006—Spark gap
6100a—Emitter
6100b—Emitter
6100c—Emitter
6100d—Emitter
6102—Wire
6104—Multifilar wire
6106—Inner elongated structure
6108—First electrode
6110—Second electrode
6112—Third electrode
6114—Fourth electrode

DETAILED DESCRIPTION

Although specific examples are disclosed below, inventive subject matter extends beyond the specifically disclosed examples to other alternative examples and/or uses and to modifications and equivalents thereof. Thus, the scope of the claims appended hereto is not limited by any of the particular examples described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain examples; however, the order of description should not be construed to imply that these operations are order-dependent. Additionally, the structures, systems, and/or devices described herein may be embodied as integrated components or as separate components.

For purposes of comparing various examples, certain aspects and advantages of these examples are described. Not necessarily all such aspects or advantages are achieved by any particular example. Thus, for example, various examples may be carried out in a manner that achieves or optimizes one advantage or group of advantages as taught herein without necessarily achieving other aspects or advantages as may also be taught or suggested herein.

During an intravascular lithotripsy (IVL) procedure, and more specifically, during an electrohydraulic lithotripsy (EHL) procedure, a clinician uses high-energy pressure waves to break apart calcified-plaque lesions within a patient's vasculature. Typical IVL systems suffer from a number of disadvantages that limit the efficacy of the treatment. For instance, IVL catheters typically emit pressure waves that propagate around the entire inner circumference of the vessel wall at a target treatment site. In instances in which the calcified lesion is limited to only a portion of the vessel-wall circumference, for example, eccentric, focal, and/or nodular-shaped lesions, pressure waves that propagate in all directions can present less-effective disintegration or a waste of applied energy. As a second example, in addition to directional limitations, typical IVL catheters are designed to deliver a fixed level of energy and/or power, regardless of the particular clinical need (e.g., lesion size and/or density) at the target treatment site, presenting a similar set of difficulties and/or effectiveness limitations.

As a third example, many IVL-catheter designs include a distal interventional balloon for distributing the pressure waves across the surrounding tissue. In some cases, these interventional balloons may rupture in response to an above-threshold wave pressure or when treating heavily calcified lesions. If the balloon tears around its entire circumference, the distal portion of the balloon may "bunch up" around the distal catheter tip, causing a more difficult and/or more complex withdrawal from the patient, e.g., by removing an outer sheath or other introducer in order to remove the balloon catheter. As a final example, certain features of typical interventional balloons can increase resistance against inserting the catheter into the introducer sheath at the beginning of the procedure, and/or withdrawing the catheter through the introducer sheath at the end of the procedure. For instance, bulky balloon "cones" and ineffective re-wrapping of balloon "pleats" can require the clinician to apply additional undue force to successfully perform the IVL procedure.

The present disclosure describes systems and techniques for producing and directing high-energy intravascular pressure waves for fragmentation and/or disintegration of calcified lesions within a vasculature of a patient. For illustration purposes, the techniques herein are described primarily with respect to electrical-based systems and respective applications thereof, such as peripheral-vessel applications. However, it is to be understood that the techniques described herein may be assumed to be likewise applicable to similar systems based on other forms of energy, such as optical (e.g., laser) based systems and respective applications, such as coronary-treatment applications, except where explicitly noted below.

In general, the systems described herein include an energy source and an IVL catheter having a distal IVL device, including an interventional balloon and a pressure-wave-emitter array. During a lesion-disintegration procedure, a clinician may advance the interventional balloon to a target treatment site within a patient's vasculature and inflate the balloon with an inflation fluid, such as a saline/contrast-fluid mixture, until the balloon contacts at least a portion of the local vessel wall. The clinician may then actuate the energy generator, causing the catheter to generate a cavitation bubble within the fluid-filled balloon, propagating a high-energy pressure wave through the balloon and the calcified lesion. A secondary pressure wave can also result from the subsequent collapse of the fluid cavitation, further destabilizing the internal structure of the lesion.

FIG. 1 is a conceptual diagram illustrating an example IVL system 100. As shown in FIG. 1, IVL system 100 includes at least an energy generator 102 and an IVL catheter 104 removably coupled to energy generator 102, such as via a catheter-connector interface 204. In some examples, a removable cable 118 may be connected between generator 102 and catheter 104 to provide energy to catheter 104. As detailed further below, an energy source (e.g., a battery, capacitor, etc.) may additionally or alternatively be integrated into catheter 104. Catheter 102 includes an elongated body 106 and an IVL device 108 positioned at a distal portion of elongated body 106. Elongated body 106 is configured to navigate a tortuous vasculature of a patient toward a target treatment site, e.g., a calcified-plaque lesion within a vessel.

As shown in FIG. 1, IVL device 108 includes a fluid-inflatable interventional balloon 110 and a pressure-wave-emitter array 112 positioned within balloon 110. Emitter array 112 includes one or more individual emitter units 114A-114E. For instance, interventional balloon 110, or a distal portion of elongated body 106 passing therethrough, may define a central longitudinal axis 116, and emitter units 114A-114E may be distributed longitudinally along central longitudinal axis 116. It is to be noted that individual emitter units 114A-114E are also referred to throughout this disclosure as "emitters" (e.g., in reference to an emitter unit as a whole), as well as "emitter assemblies" (e.g., in reference to a particular arrangement of sub-components collectively forming the emitter unit).

In particular, the example emitter array 112 shown in FIG. 1 includes a first emitter unit 114A, a second emitter unit 114B, a third emitter unit 114C, a fourth emitter unit 114D, and a fifth emitter unit 114E. While five emitter units 114 are illustrated in FIG. 1, emitter array 112 of IVL device 108 may include as few as one individual emitter unit and up to as many emitter units as could reasonably fit within balloon 110. Each emitter unit 114 is configured to receive energy from energy generator 102 and use the received energy to generate and transmit high-energy pressure waves through balloon 110 and across the target treatment site. As detailed further below, energy generator 102 may generate and transmit energy in the form of electrical energy, optical energy, or a combination thereof. For instance, emitter units 114 may use the received energy to generate a cavitation within the fluid inside balloon 110, propagating one or more high-energy pressure waves radially outward through balloon 110 and the calcified lesion. In some cases, but not all cases, a secondary set of high-energy pressure waves can subsequently result from the collapse of the fluid cavitation, further destabilizing the internal structure of the calcified-plaque lesion. In some examples, one or more of emitters 114 can include an electrical-based emitter configured to receive electrical energy from generator 102, such as via one or more conductive wires, and generate a spark between a pair of electrodes, thereby triggering the initial cavitation. Additionally, or alternatively, one or more of emitters 114 can include an optical-based emitter configured to receive a high-energy optical (e.g., light) signal from generator 102, such as via one or more fiber-optic wires or tubes and direct the optical signal to trigger the initial cavitation.

Figure 2:
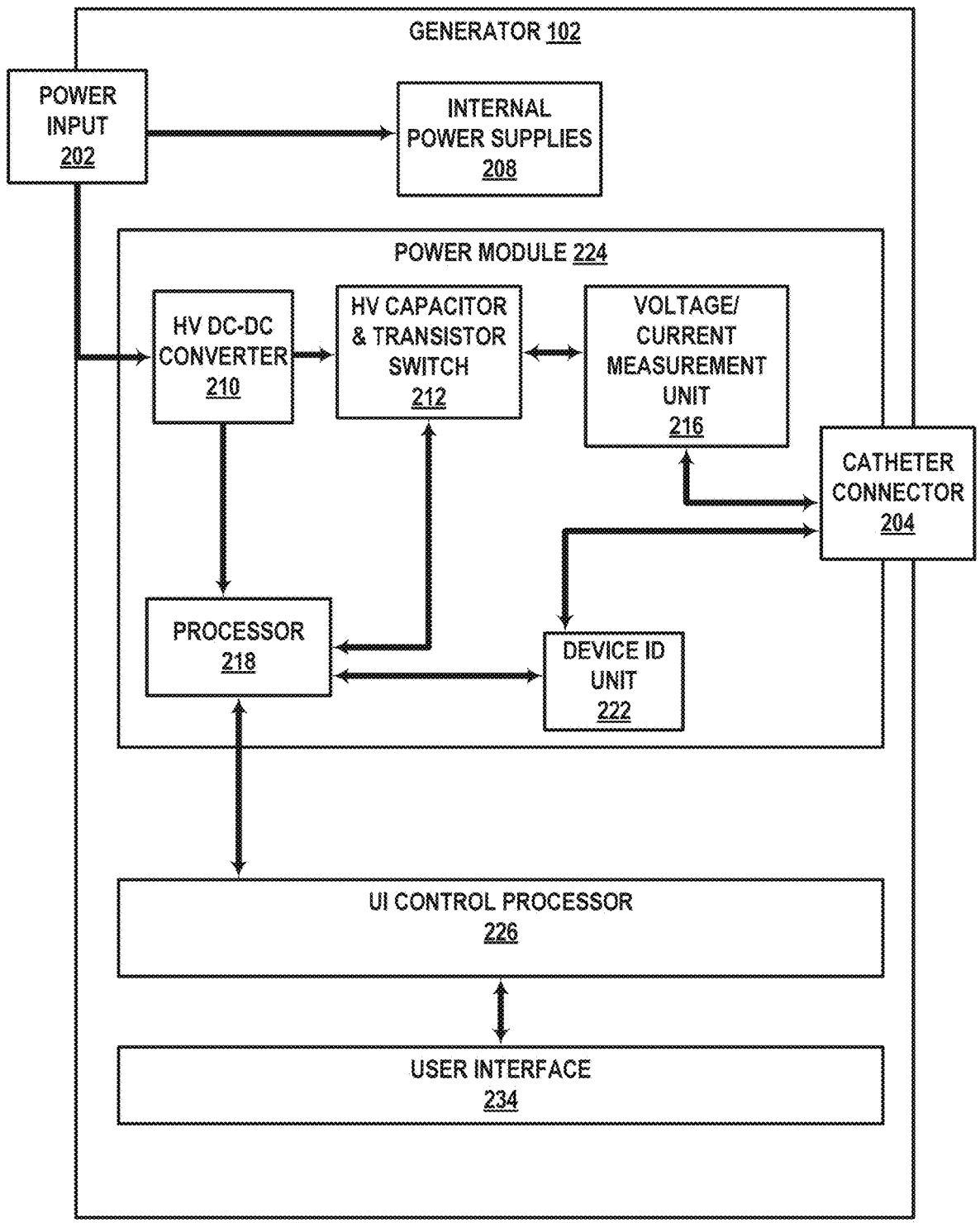
FIG. 2 is a conceptual block diagram illustrating some example components of the energy generator of FIG. 1.

FIG. 2 is a block diagram illustrating some example components of energy generator 102 of FIG. 1. A power input 202 (e.g., for conductively coupling to a wall port or another electricity source) connects to power module 224 and an internal power supply 208. As shown in FIG. 2, power module 224 can include, as various, non-limiting examples, a high-voltage DC-DC converter 210, a high-voltage capacitor and transistor switch 212, a voltage and/or current measurement unit 216, and a device identification unit 222, configured to determine whether catheter 104 is an authorized device while catheter 104 is connected via catheter connector 204. For instance, energy generator 102 may be configured to disable energy output to catheter connector 204 when an unidentified device is connected.

Generator 102 can include a memory and one or more processors, such as processor 218 and/or user-interface-control processor 226. UI control processor 226 is configured to provide functionality for the user interface 234 of energy generator 102, such as a display screen, touch screen, buttons, or other manual controls enabling a user (e.g., a clinician) to operate the energy generator 102.

Although not illustrated in FIG. 2, additionally or alternatively to electrical-energy-based components, in some examples, energy generator 102 includes an optical signal unit configured to convert electrical power (e.g., from power input 202) into a beam of light, such as a laser beam. The optical signal unit may then direct the optical signal into a carrying cable, such as an optical fiber, either coupled to catheter 104 (FIG. 1) or integrated as part of catheter 104.

Figure 3:
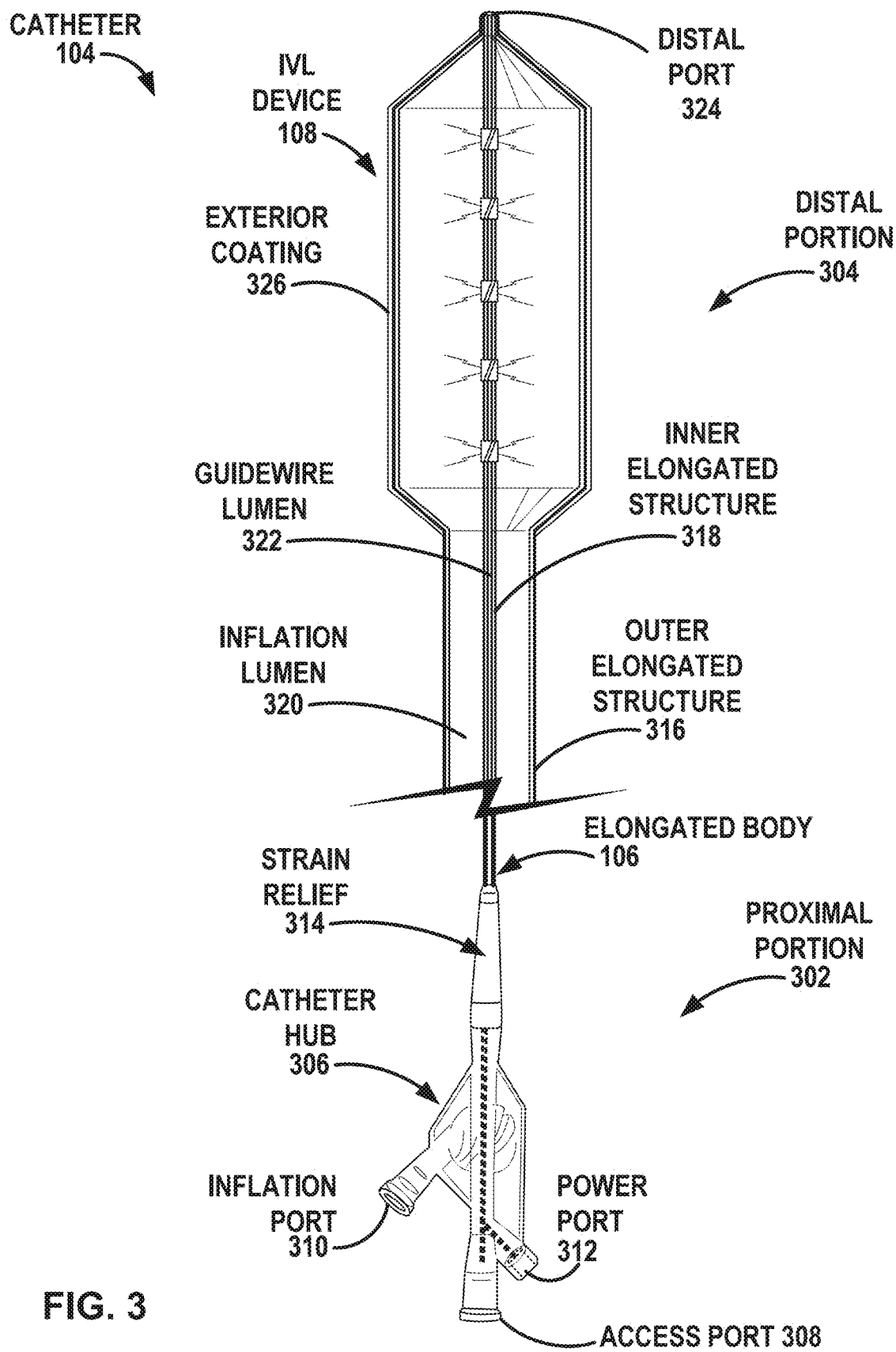
FIG. 3 is a conceptual diagram illustrating some example components of the catheter of FIG. 1.

FIG. 3 is a conceptual diagram showing some example components of catheter 104 of FIG. 1. As shown in FIG. 3, catheter 104 includes a proximal portion 302 and a distal portion 304 opposite the proximal portion. The proximal portion 302 may include a catheter hub 306 and/or a handle (as detailed further below). Catheter hub 306 defines an access port 308, an inflation port 310, and a power port 312. Access port 308 enables the clinician to manipulate (e.g., maneuver, actuate, etc.) the distal portion 304, including IVL device 108. The clinician may use inflation port 310 to inject an inflation fluid, such as a saline/contrast-fluid solution to inflate interventional balloon 110 to an expanded or inflated state, in which an exterior surface of balloon 110 contacts an interior surface of the vessel wall at the target treatment site. Power port 312 is configured to interconnect with a power cable (not shown) to conductively couple catheter 104 to energy generator 102 (FIGS. 1 and 2). Catheter hub 306 may also include a strain relief portion 314 to reinforce elongated body 106 and reduce kinking.

As shown in FIG. 3, in some examples, but not all examples, elongated body 106 may include an outer elongated structure 316 and an inner elongated structure 318. For instance, outer elongated structure 316 may include a sheath or outer catheter defining an inflation lumen 320. In some examples, outer elongated structure 316 forms a proximal extension of interventional balloon 110, such that inflation lumen 320 fluidically couples inflation port 310 to the interior cavity of interventional balloon 110.

Inner elongated structure 318 may include an inner catheter or other inner structure, positioned within inflation lumen 320, configured to retain emitters 114 of emitter array 112. In some such examples, inner elongated structure 318 may itself define an inner lumen 322, e.g., configured to receive a guidewire via distal port 324. In other examples, such as depicted in subsequent figures, elongated body 106 includes just a single layer defining a single inner lumen.

As described above, catheter 104 is configured to advance through a patient's vasculature (e.g., through an arteriotomy) to position the balloon 110 adjacent to a calcium lesion located at a target treatment site. IVL device 108 may be configured to cause a first pressure-wave (or group of waves) by expanding a volume of liquid resulting from a phase change from a liquid into a liquid-vapor, which may cause a bubble to rapidly expand. A second pressure wave may occur as the bubble subsequently collapses. In some examples, the balloon 110 has an exterior coating 326, e.g., made from a polymer and/or other materials, as detailed further below. For instance, exterior coating 326 may include a hydrophilic coating to improve navigability through the patient's vasculature. Additionally, or alternatively, exterior coating 326 may include a drug coating, such as an anti-thrombogenic drug or an anti-proliferative medication, as well as an excipient to aid in drug transfer. As detailed further below, balloon 110 may be or be porous/semi-permeable (e.g., a "weeping" balloon) for the infusion of drugs into the vessel, as compared to being injected into the vessel through a lumen.

Figure 4A:
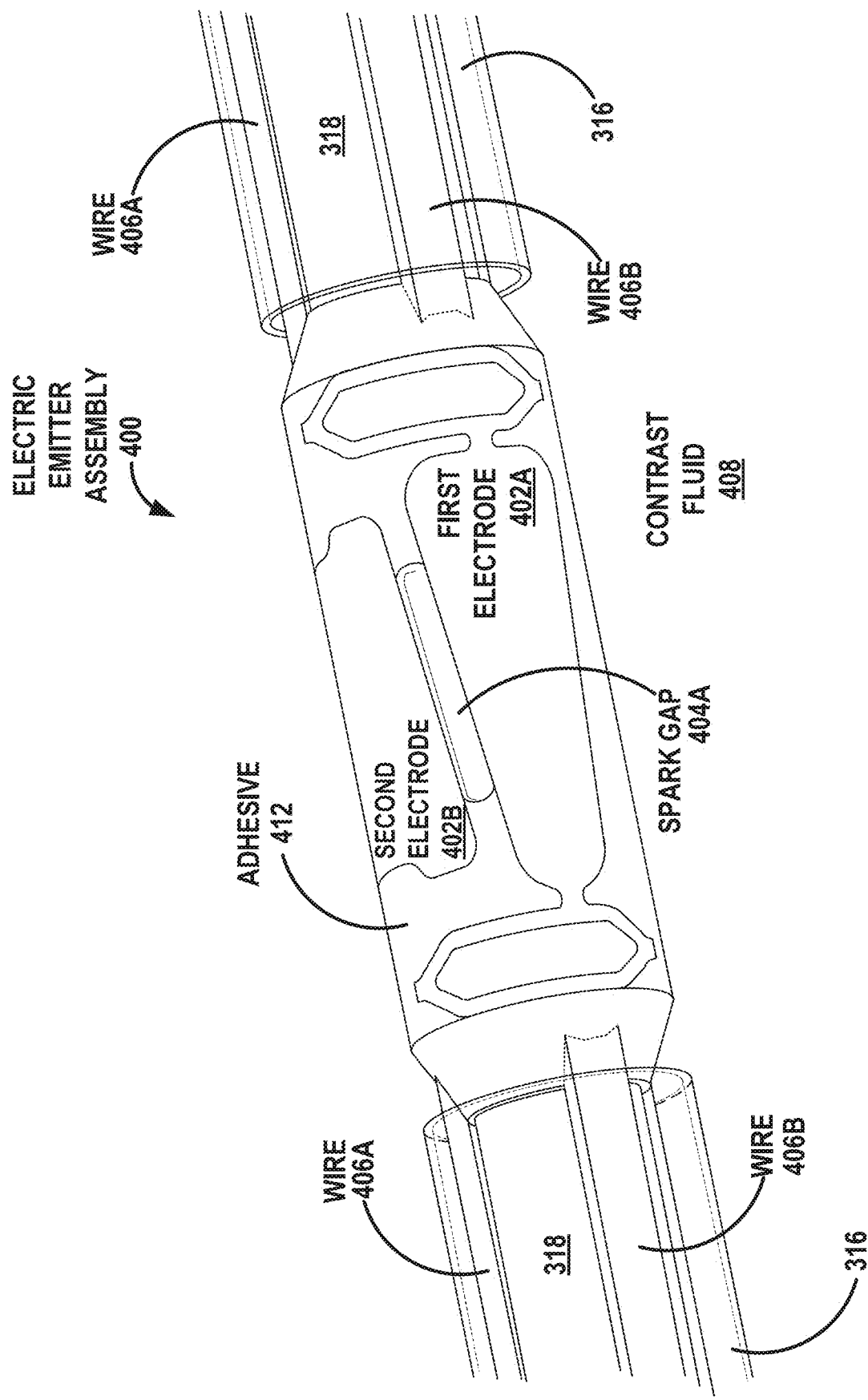
FIG. 4A is a perspective view of a first example emitter assembly of the catheter of FIG. 1.
Figure 4B:
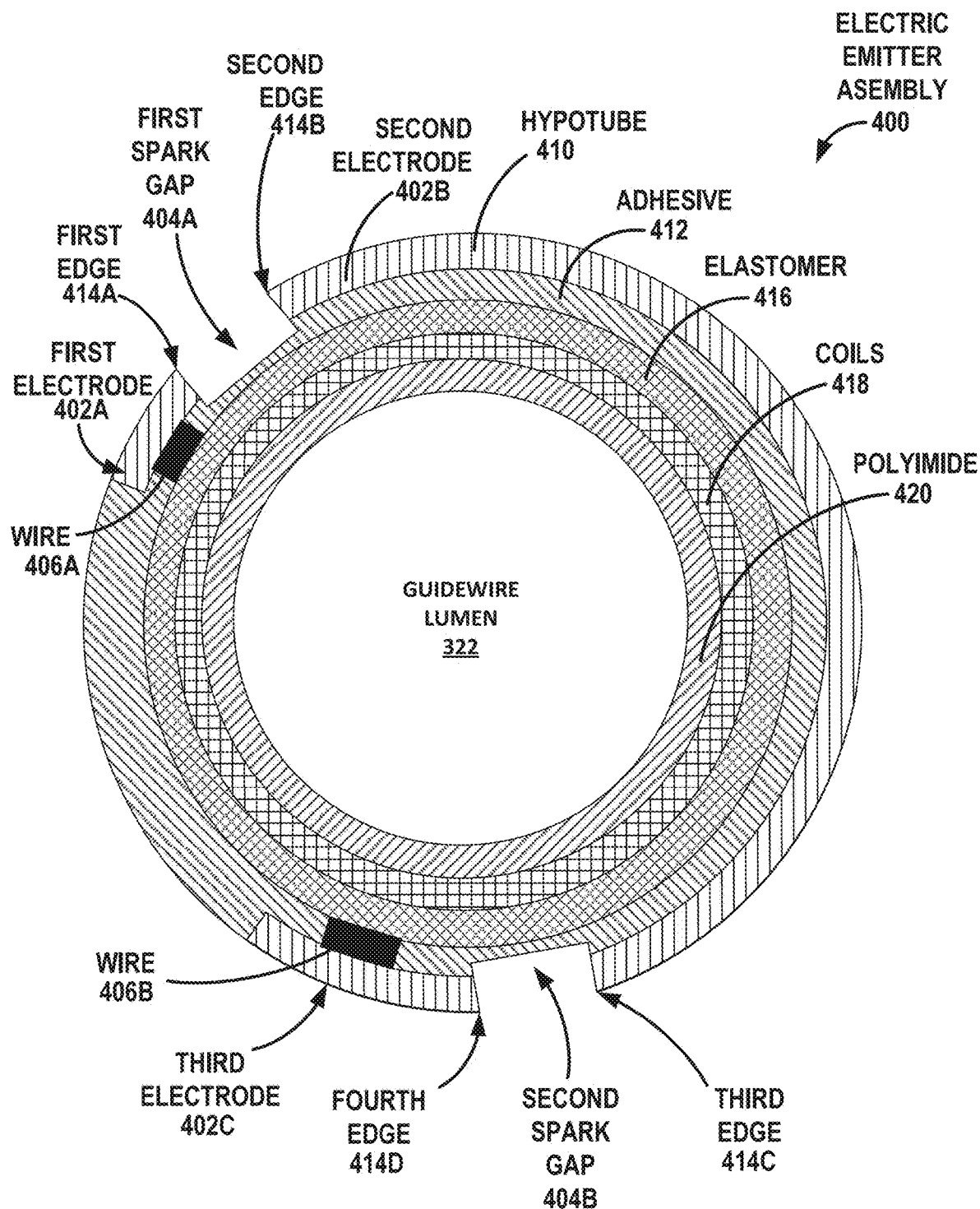
FIG. 4B is a cross-sectional diagram of the emitter assembly of FIG. 4A.

FIG. 4A is a perspective view of a first example emitter assembly 400 (e.g., emitter assembly 114A of FIG. 1) of catheter 104 of FIG. 1, and FIG. 4B is a cross-sectional diagram of emitter 400 of FIG. 4A. In particular, FIGS. 4A and 4B illustrate an electronic emitter 400, including a pair of conductive electrodes 402A, 402B defining a first spark gap 404A therebetween. In such examples, electrodes 402A, 402B are configured to receive electrical energy (e.g., an electric current) from energy generator 102 (FIGS. 1 and 2) via conductive wires 406A, 406B. The resulting spark across spark gap 404 is configured to cavitate the surrounding inflation fluid 408 to propagate high-energy pressure waves through inflation fluid 408.

In accordance with techniques of this disclosure, one or both electrodes 402A, 402B are subsections or portions of a cylindrical surface of a common hypotube 410. As used herein, a "hypotube" refers to a metallic tube with micro-engineered features along its length.

That is, particular sections of a cylindrical hypotube 410 may be removed (e.g., laser-cut) so as to form one or both electrodes 402A, 402B, and the spark gap 404A therebetween. In some such examples, a potting material 412, such as an adhesive layer, may be flowed overtop of the remaining portions of the cylindrical hypotube (e.g., electrodes 402A, 402B) and then either hardened, or allowed to harden, to retain the hypotube portions in place. Some examples of potting materials 412 include a polyurethane base, an acrylic base, a silicone base, or any other suitable material with sufficient dielectric strength. In some examples, but not all examples, excess potting material 412 may be subsequently removed (e.g., scored, ablated, or milled-out) from between electrodes 402A, 402B to re-establish spark gap 404A, as necessary.

As illustrated further in FIG. 4B, hypotube 410 of emitter assembly 400 includes two pairs of conductive electrodes and respective spark gaps therebetween-first pair of electrodes 402A, 402B (with spark gap 404A therebetween), and second pair of electrodes 402B, 402C (with spark gap 404B therebetween). That is, electrode 402B may be used as a common electrode for both of electrodes 402A, 402C, aligned relative to opposite edges of electrode 402B. Put explicitly, first edge 414A of first electrode 402A is aligned relative to second edge 414B of second electrode 402B to define first spark gap 404A. Additionally, third edge 414C of second electrode 402B is aligned relative to fourth edge 414D of third electrode 402C to define second spark gap 404B. In some examples, the two pairs of conductive electrodes may be wired to be simultaneously actuatable, or in other examples, may be wired to be separately actuatable, as detailed further below. Such wiring configurations enable the clinician to choose which emitter assemblies, or even particular electrode pairs, to activate for treatment of the calcified-plaque lesion. While a two-electrode-pair system is primarily shown and described herein, it should be noted that greater numbers of electrode pairs may also be incorporated into emitter assembly 400.

In some examples, hypotube 410 may similarly define a three-electrode system, but rather than defining two emitter-electrode pairs, the three electrodes may consist of a working electrode, a counter electrode, and a reference electrode. For instance, while the working electrode and the counter electrode are configured to create the pressure-wave, the reference electrode's role is to act as a reference in measuring and controlling the working-electrode potential without passing any current itself.

As further illustrated in FIG. 4B, electronic emitter assembly 400 includes a plurality of nested layers (e.g., to define elongated body 106 therein). For instance, within hypotube 410 and potting material 412, emitter assembly 400 includes an elastomeric layer 416, such as a thermoplastic elastomer. One such example includes polyether block amide (e.g., PEBAX® from Arkema S. A. of Colombes, France). In some examples, but not all examples, within elastomeric layer 416, emitter assembly 400 may include coils 418, e.g., coiled turns of conductive wires 408, or coils of a spring associated with interventional balloon 110 (FIG. 1), as detailed further below with respect to FIG. 23. Finally, the most internal layer of emitter assembly 400 is a secondary polymer layer 420, such as polyimide. Polymer layer 420 may be tubular-shaped, defining a portion of guidewire lumen 322 therein.

According to some examples, emitter assembly 400 is configured to implement a relatively high, redundant voltage. Accordingly, composing materials should be selected for low degradation, such that the IVL device 108 lasts the duration of the IVL treatment. In some examples, catheter 104 is configured to be single-use-only, while energy generator 102 is considered to be theoretically infinitely reusable. In some examples, the number of pressure-wave "cycles" of an IVL treatment may range from about 80 wave pulses to about 300 wave pulses, but treatments may include more or fewer wave pulses, depending on the unique clinical parameters presented.

In some examples, the electrode pairs 402A/402B and 402B/402C may be made of narrow copper strips that are fixated on inner elongated structure 318 inside of interventional balloon 110 (FIGS. 1, 3). In some examples, but not all examples, each electrode 402 may be cut, bent, or otherwise formed to define an angle relative to central longitudinal axis 116. That is, electrodes 402 may be configured to "tilt" away from central longitudinal axis 116 in the absence of outside forces. During delivery through the patient's vasculature, a radially inward compressive force from the deflated balloon 110 may cause the electrodes to "flatten" toward the central longitudinal axis 116.

Figure 5A:
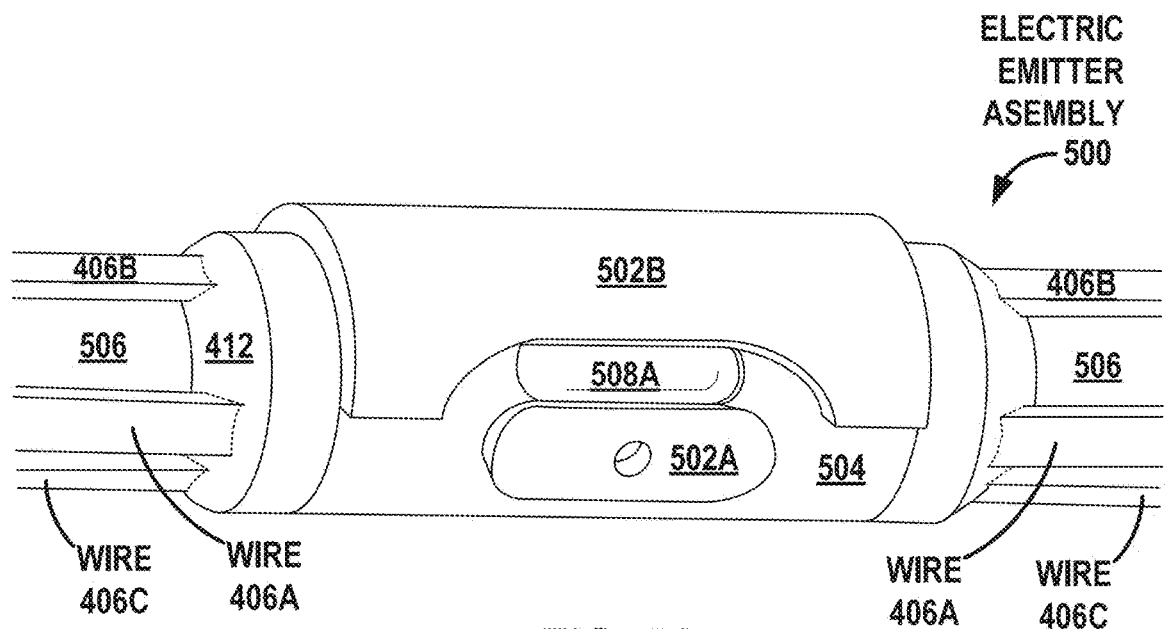
FIG. 5A is a perspective view of a second example emitter assembly of the catheter of FIG. 1.
Figure 5B:
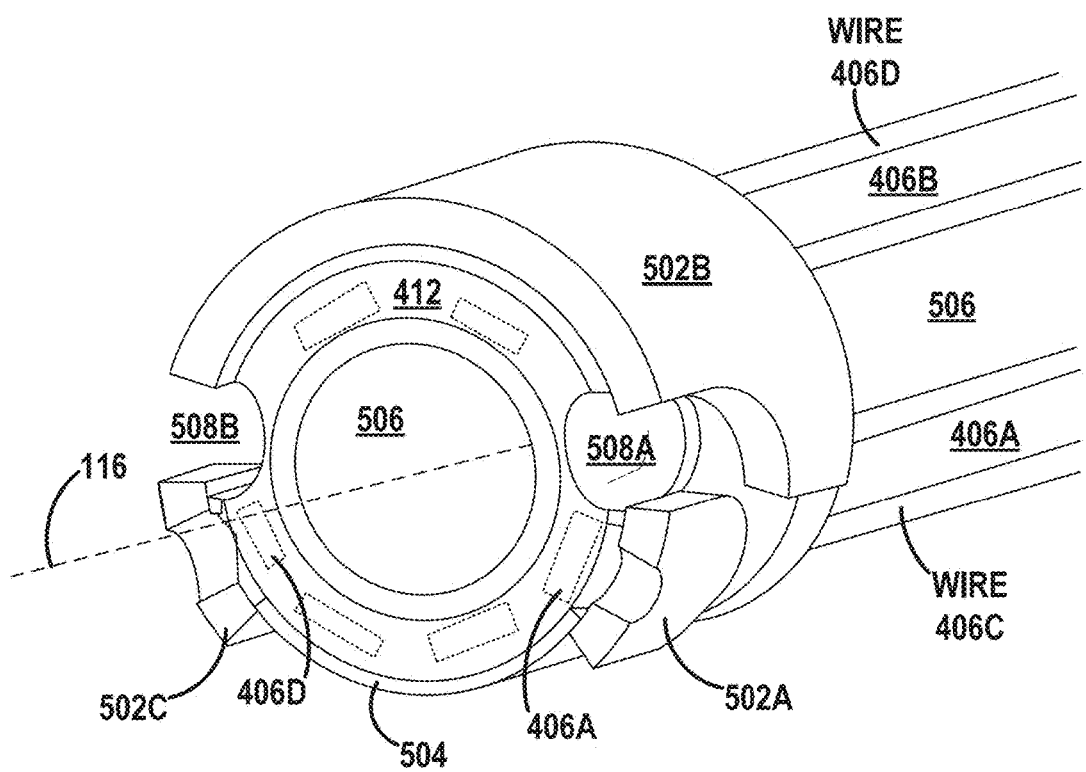
FIG. 5B is a cross-sectional diagram of the emitter assembly of FIG. 5A.

FIG. 5A is a perspective view of a second example electronic emitter assembly 500 of the catheter 104 of FIG. 1, and FIG. 5B is a cross-sectional diagram of the emitter assembly 500 of FIG. 5A. Specifically, the example emitter assembly 500 of FIGS. 5A and 5B includes two laser-cut "emitter" electrodes 502A, 502C welded to a laser-cut polyimide "coupler" layer 504. In this example, emitter electrodes 502A, 502C are shown to be generally oval-shaped, but other geometric shapes are contemplated.

A laser-cut "hypotube" electrode 502B is also attached to the coupler layer 504 in between emitter electrodes 502A, 502C, so as to define respective spark gaps 508A, 508B. In this example, hypotube-electrode 502B is shown to be generally semi-cylindrical-shaped, but other geometric shapes are contemplated. A series of flat wires 406A-406D may be utilized to deliver energy from the energy generator 102 (FIGS. 1 and 2) to the emitter electrodes 502A and 502C; from the emitter electrodes 502A, 502C to additional emitter units 114 (FIG. 1) within the IVL device 108; and from the additional emitter units 114 back to ground voltage.

As shown in FIGS. 5A and 5B, in this example, a polyimide inner elongated structure 506 extends distally through the core of the emitter assembly 500, as seen on the outside of the assembly in FIG. 5A, or at the innermost circle in FIG. 5B. The portion of the outermost concentric ring above central longitudinal axis 116 is a laser-cut-hypotube electrode 502B that passes energy to the opposing-side mirrored "emitter" electrodes 502A, 502C. The portion of the outermost concentric ring below central longitudinal axis 116 is another emitter electrode 502C welded to the wire 406D. The rectangular extensions about the longitudinal axis 116 that carry on away from the emitter assembly on both sides are additional flat wires 406 that lead to and away from the emitters to carry energy for producing the pressure waves and then leading the voltage back to ground. The outer portion of the emitter assembly 500 as seen in FIG. 5A, or the middle core as seen in FIG. 5B, is the first spark gap 508A at which the current from the emitter electrode 502A "jumps" to the hypotube electrode 502B.

In some examples, but not all examples, a reflective surface or coating may be applied to the surface within the spark gaps 508, in order to reflect the emitted pressure waves radially outward toward the interventional balloon 110 (FIG. 1). The reflective surface or coating may be, for instance, an acoustically opaque and non-conductive (e.g., insulative) material, such as a ceramic, porcelain, diamond, polyimide, polyether ether ketone (PEEK), another similar material, or any suitable combination thereof.

The penultimate core that lies just beneath both the laser-cut hypotube 502B and the emitter electrode 502A in FIG. 5A, and which can be seen wrapped around the middle core in FIG. 5B, is a coupler or insulating material 504 that creates space between the inner lumen and the emitter electrode 502A.

FIG. 6A illustrates a third example electronic emitter assembly 600 of catheter 104 of FIG. 1, FIG. 6B is a cross-sectional diagram of emitter assembly 600, and FIG. 6C is a cross-sectional diagram of emitter assembly 600 with potting material 412 removed to illustrate the components embedded therein. In particular, emitter assembly 600 includes two laser-cut "emitter" electrodes 602A, 602C positioned opposite a hypotube electrode 602B. As shown in FIG. 6C, in some examples, but not all examples, emitter electrodes 602A, 602C are configured to breach the exterior surface of inner elongated structure 506, e.g., to help retain the emitter electrodes 602A, 602B in place. In some such examples, emitter electrodes 602A, 602B extend radially inward through the entire wall of inner elongated structure 506 and extend partially radially inward into guidewire lumen 322. Emitter electrodes 602A, 602B may additionally be potted in place, e.g., embedded within potting material 412.

The third example emitter assembly 600 shown in FIGS. 6A, 6B, and 6C shares similarities with the second example emitter assembly 500 shown in FIGS. 5A and 5B, except for the differences noted herein. For instance, in both examples, a polyimide inner elongated structure 506 extends distally through the core of the emitter assembly, as seen on the outside of the assembly 600 in FIG. 6A, or at the radially innermost circle in FIGS. 6B and 6C.

The portion of the outermost concentric ring above central longitudinal axis 116 is a laser-cut hypotube electrode 602B that passes energy to the opposing-side emitter electrodes 602A, 602C. As described above, below the central longitudinal axis 116 in FIG. 6C are two emitter electrodes 602A, 602C that extend radially inward through both the outer surface and the inner surface of elongated structure 506. As shown particularly in FIG. 6C, a plurality of flat wires 406 are distributed circumferentially around longitudinal axis 116 that lead toward and away from the emitter electrodes 602A, 602C to carry energy for producing the high-energy pressure waves, and then leading proximally back to ground voltage. In FIG. 6B, these flat wires 406 are represented as dashed lines embedded within potting material 412, and as solid components in FIG. 6C, as the potting material 412 has been removed to facilitate visualization of the flat wires 406 in this space.

In the example of FIGS. 6A and 6B, the spark gap 608A (e.g., the site at which the electric current from the emitter electrode 602A "jumps" to the hypotube electrode 602B, is shown to be substantially filled with potting material 412. In other examples, the section of potting material 412 within spark gap 608A may be milled out or otherwise removed. The potting material 412, shown just beneath both the laser-cut hypotube 602B and the emitter 602A in FIG. 6A, and wrapped around inner elongated structure 506, can include any suitable adhesive or potting material, such as an ultraviolet adhesive, an epoxy, or a reflowing polymer.

In some examples, a pressure-reflective material may be appended within and/or around spark gap 608A, the reflective material configured to redirect the radially inward pressure waves to travel radially outward toward interventional balloon 110 (FIGS. 1, 3).

FIGS. 7A-9 illustrate three example electrode-design configurations for a laser-cut hypotube 410 (FIG. 4B) defining two or more conductive electrodes for an electronic emitter assembly 400 (FIG. 4). These hypotube designs may be cut (e.g., laser-cut) from a common 2-D surface. In some examples, the electrode designs may be cut from a planar 2-D surface, which may subsequently be formed into a cylindrical hypotube. In other examples, the electrode designs may be cut directly from a cylindrical hypotube.

Example materials that may be used to cut the conductive electrodes from the common planar surface or cylindrical hypotube include 304 SST, titanium, cobalt chromium, 316 SST, or a nickel-titanium alloy (e.g., Nitinol), though other options are suitable, as long as they have low degradation, low resistivity, ductility, and are machinable through use of a laser. Additionally, the electrodes may be cut directly out of stents, so a flat sheet of material is not strictly necessary. In some examples, all emitters 114 of emitter array 112 (FIG. 1) may be cut from a single continuous hypotube. This has the advantage of removing the need to weld individual emitters 114 to wires, thus facilitating the manufacturing process.

Figure 7A:
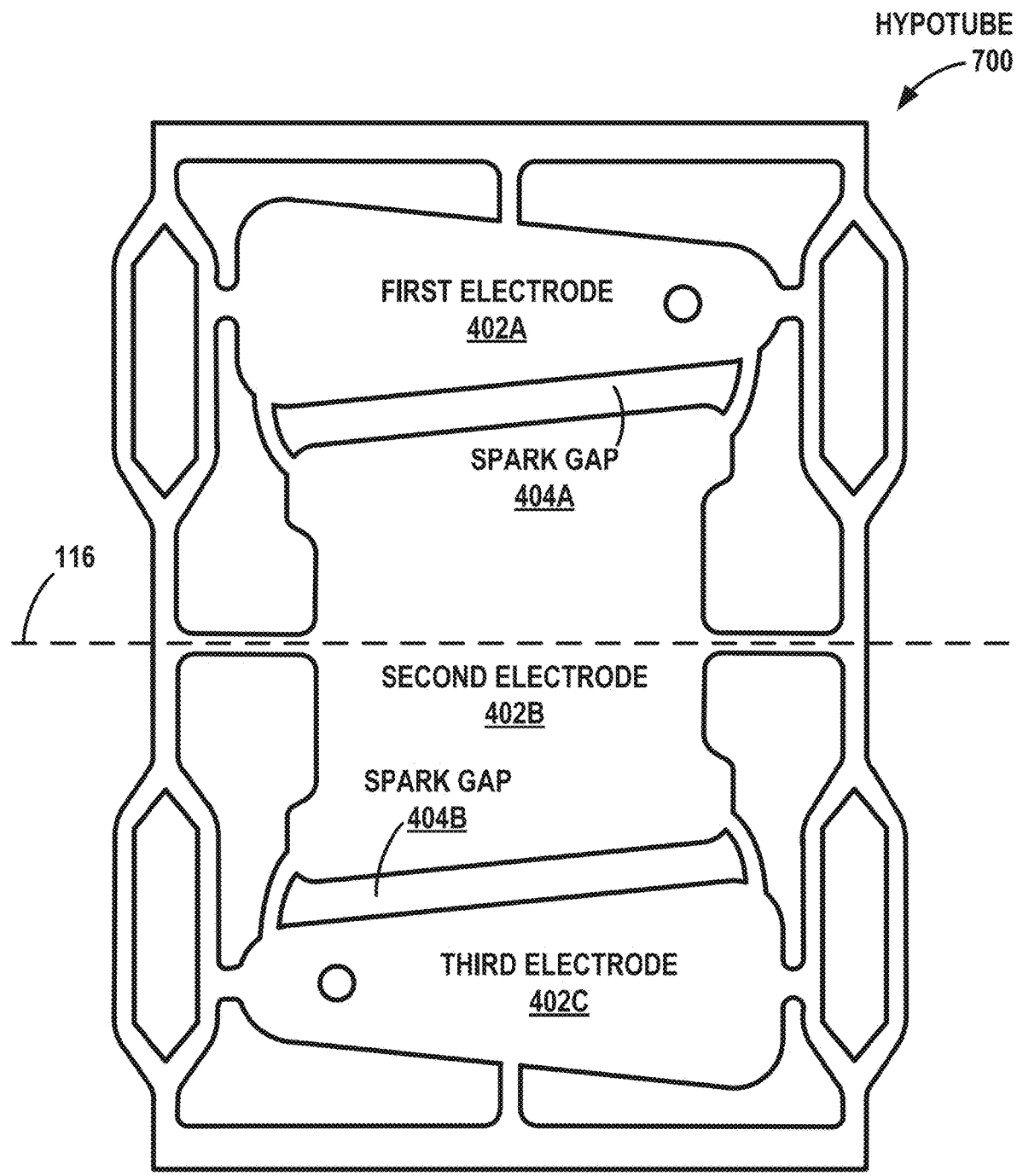
FIG. 7A is a 2-D representation of a first example design for a laser-cut hypotube of an emitter assembly, defining a non-orthogonal spark-gap orientation.
Figure 7B:
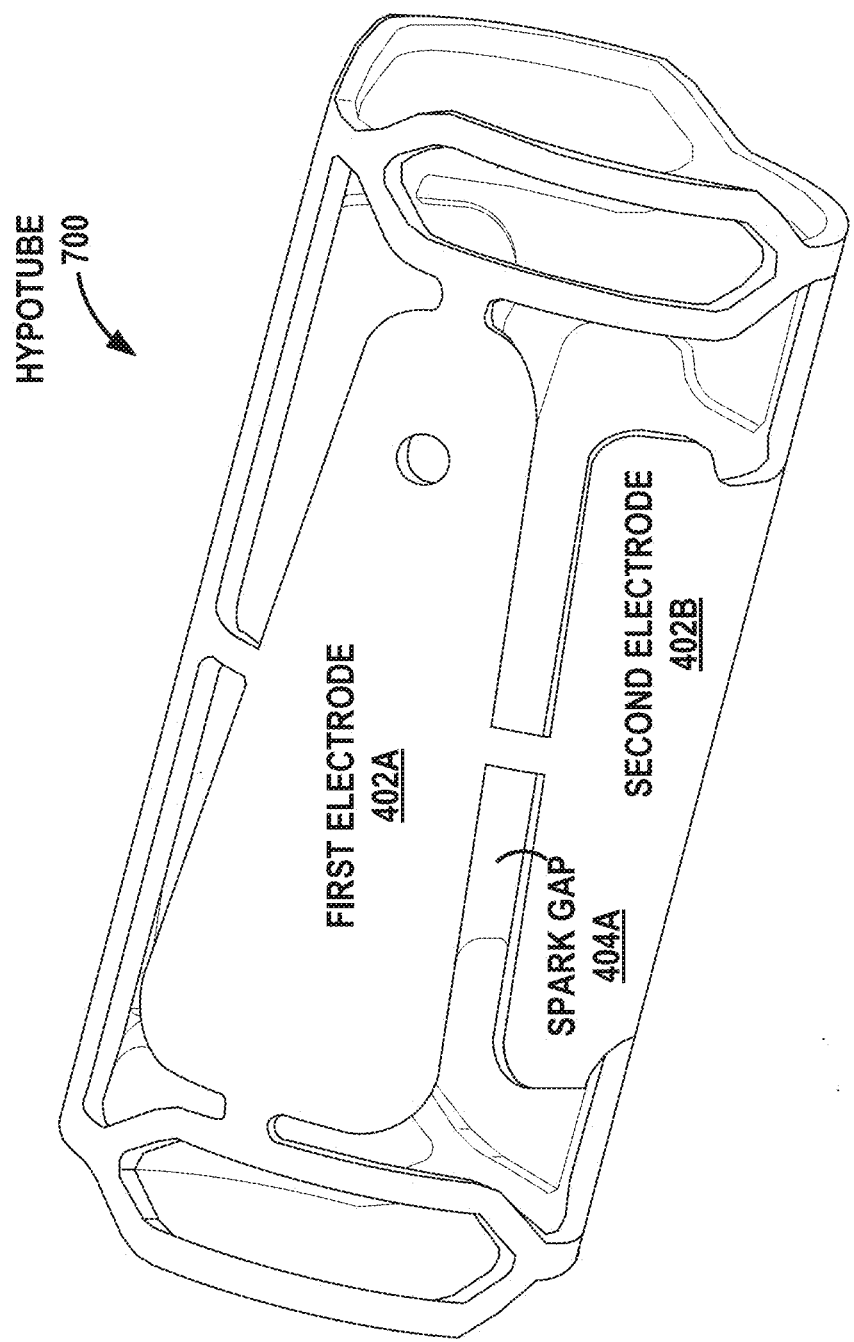
FIG. 7B is a 3-D representation of the first example hypotube design of FIG. 7A.

FIG. 7A is a 2-D representation of a first example design for a laser-cut hypotube 700 of an electronic emitter assembly 400 (FIG. 4), and FIG. 7B is a 3-D representation of the first example hypotube 400 of FIG. 7A. For instance, FIG. 7B illustrates what hypotube 400 of FIG. 7A would look like when rolled into its final tubular form. As one non-limiting, illustrative example, in the tubular form shown in FIG. 7B, cylindrical hypotube 700 may define an inner diameter of about 0.025 to about 0.035 (e.g., about 0.03 inches), and an outer diameter of about 0.03 inches to about 0.04 inches (e.g., about 0.035 inches).

The hypotube design 700 shown in FIGS. 7A and 7B largely corresponds to the hypotube design 410 shown in FIG. 4. For instance, hypotube 700 defines first electrode pair 402A/402B with spark gap 404A therebetween, and second electrode pair 402B/402C with spark gap 404B therebetween. FIGS. 7A and 7B. illustrate a generally non-orthogonal hypotube design, in which electrodes 402 are irregularly shaped, such that spark gaps 404A, 404B are not oriented parallel to central longitudinal axis 116. In particular, as shown in FIG. 7A, electrodes 402A and 402C are generally shaped as rounded triangles (e.g., three-sided shapes with rounded corners), and electrode 402B is generally shaped as a parallelogram. However, other configurations are contemplated, such as all three electrodes 402A-402C being shaped as parallelograms.

The relative angle between spark gaps 404A, 404B and central longitudinal axis 116 may be varied across different emitters 114 (FIG. 1) to provide differing directions of propagation of the emitted pressure waves. In some such examples, the clinician may independently actuate different emitters to control this aspect of the IVL treatment.

Figure 8A:
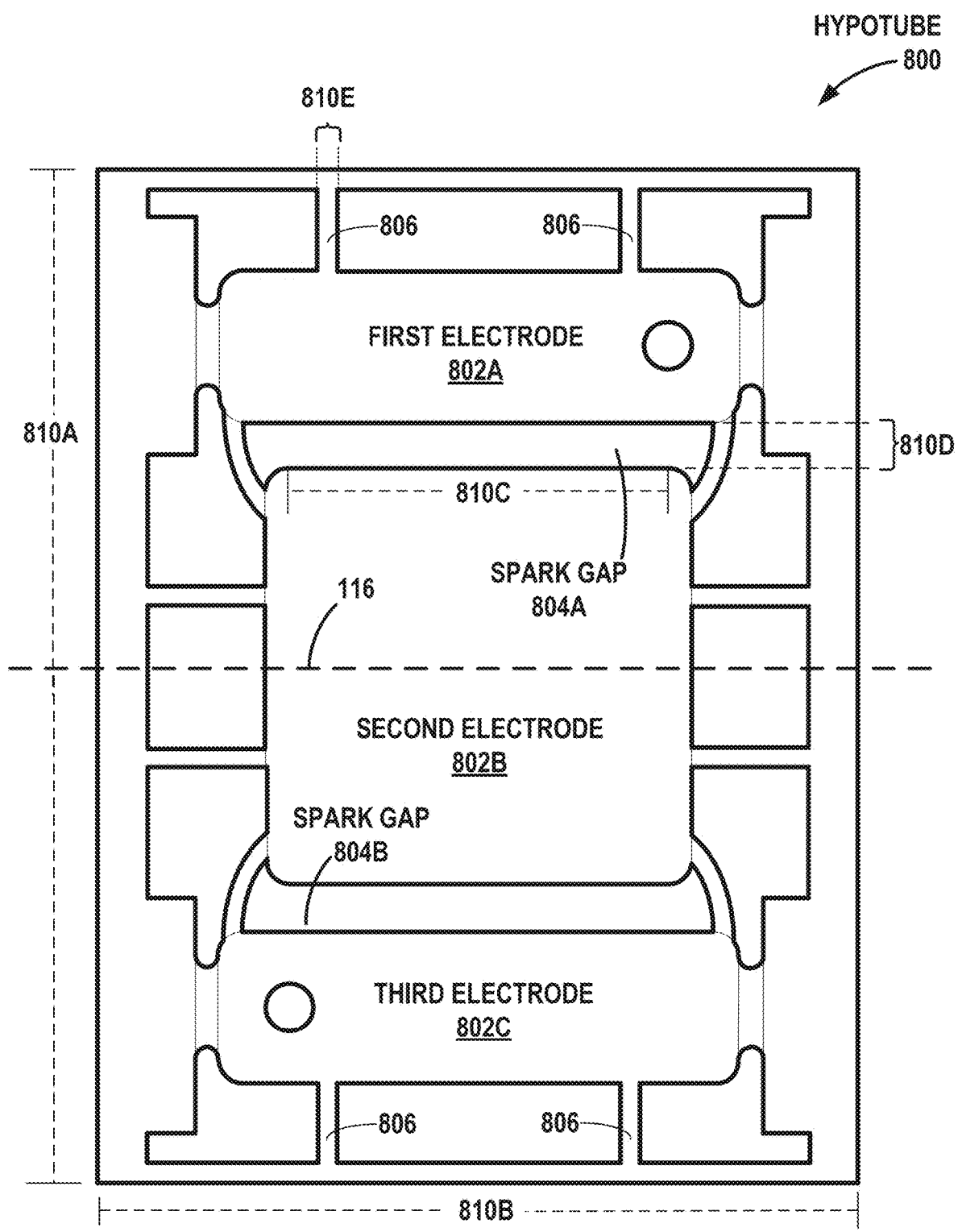
FIG. 8A is a 2-D representation of a second example design for a laser-cut hypotube of an emitter assembly, defining an orthogonal spark-gap orientation.

FIG. 8A is a 2-D representation of a second example design 800 for a laser-cut hypotube of an electronic emitter assembly 400 (FIG. 4). As compared to the hypotube 410 shown in FIGS. 7A and 7B, hypotube design 800 includes a more-orthogonal design, in which spark gaps 804A, 804B are oriented parallel to central longitudinal axis 116. For instance, electrodes 802A-802C are more-regularly shaped, such as substantially rectangular, such that spark gaps 804A, 804B are substantially parallel to longitudinal axis 116.

For purposes of illustration, some non-limiting examples of various dimensions of hypotube 800 are shown in FIG. 8. For instance, hypotube 800 (while in the flat configuration shown in FIG. 8) may define a rectangle having a circumferential length 810A of about 0.1 inch. The rectangular width 810B (e.g., the longitudinal length of hypotube 800 along longitudinal axis 116) can range from about 0.080 inches to about 0.090 inches.

Each of electrodes 802A, 802B, 802C may include emitting edges 414 (FIG. 4), e.g., defining spark gaps 804A, 804B therebetween, having lengths 810C of about 0.040 inches to about 0.055 inches. The resulting spark gaps, then, may define gap widths from about 0.0025 inches to about 0.0040 inches. Hypotube 800A may further include a plurality of support structures 806 configured to at least temporarily retain the primary structures (e.g., electrodes 802) in place during fabrication of the emitter assembly 114. These support structures 806 may be subsequently removed, e.g., after electrodes 802 are suspended in place via potting material 412 (FIG. 4). Support structures 806 may define widths 810E of about 0.0020 inches.

Figure 8B:
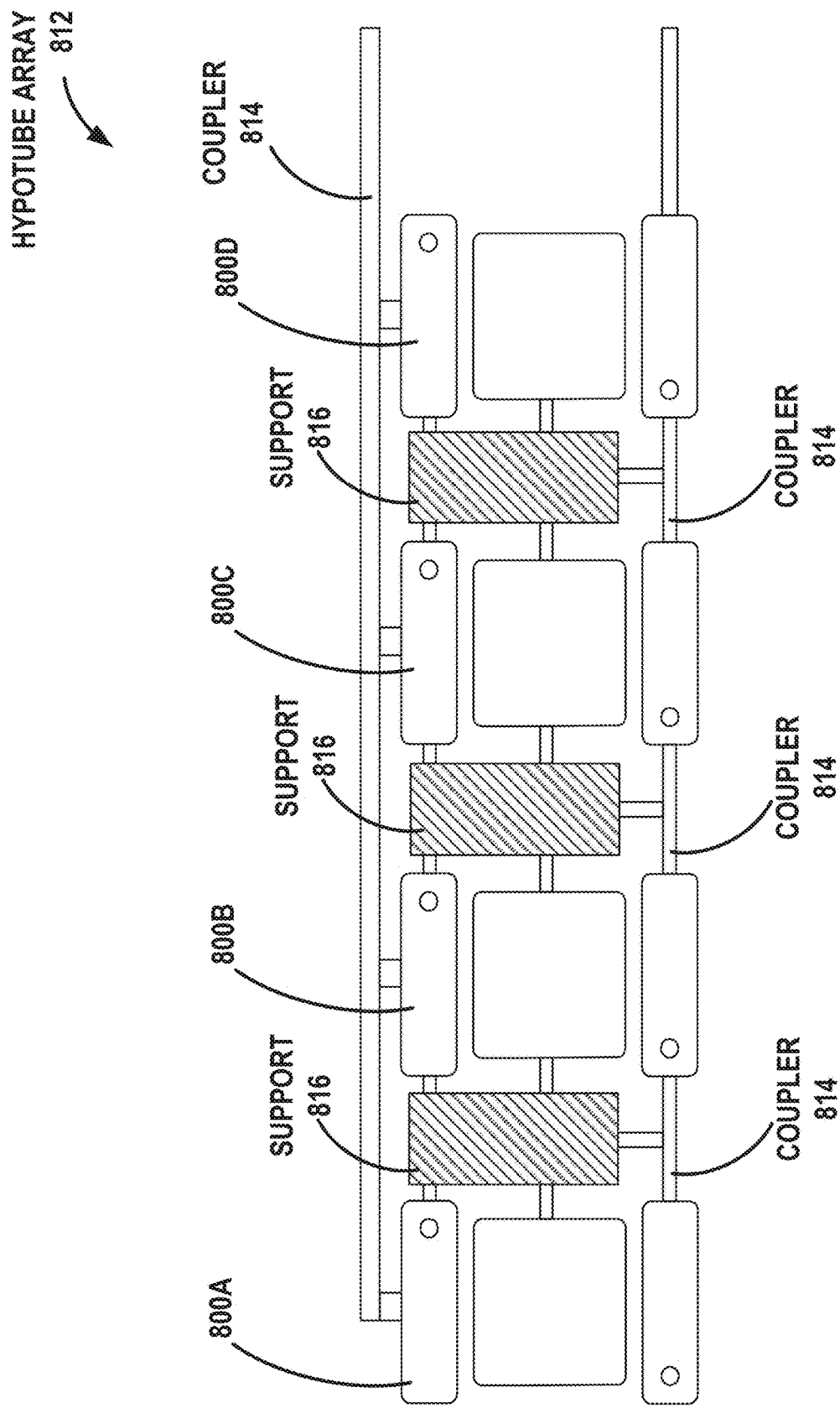
FIG. 8B is a 2-D representation of a laser-cut hypotube array that includes the second example hypotube design of FIG. 8A.

FIG. 8B is a 2-D representation of a hypotube-array design 812 that includes multiple instances 800A-800D of the second hypotube design 800 of FIG. 8A. As referenced above, in some examples, two or more emitter units 114 (FIG. 1) of an emitter array 112 may be cut from a single continuous hypotube, or alternatively, cut from a common planar surface and then formed into a cylindrical hypotube. This technique removes the need to weld individual emitters 114 to wires, thus facilitating the manufacturing process. That is, in place of conductively coupled wires 406 (FIG. 4), individual hypotubes 800A-800D may be conductively coupled via conductive-coupling supports 814 that are cut from the same substrate as the emitters. The example design 812 shown in FIG. 8B also includes a plurality of removable supports 816. Removable supports 816 may initially be cut into the common substrate with hypotubes 800A-800D and coupling supports 814 to help retain these components in place during fabrication, and then subsequently removed after hypotube array 812 is assembled into functioning emitter units.

Figure 9:
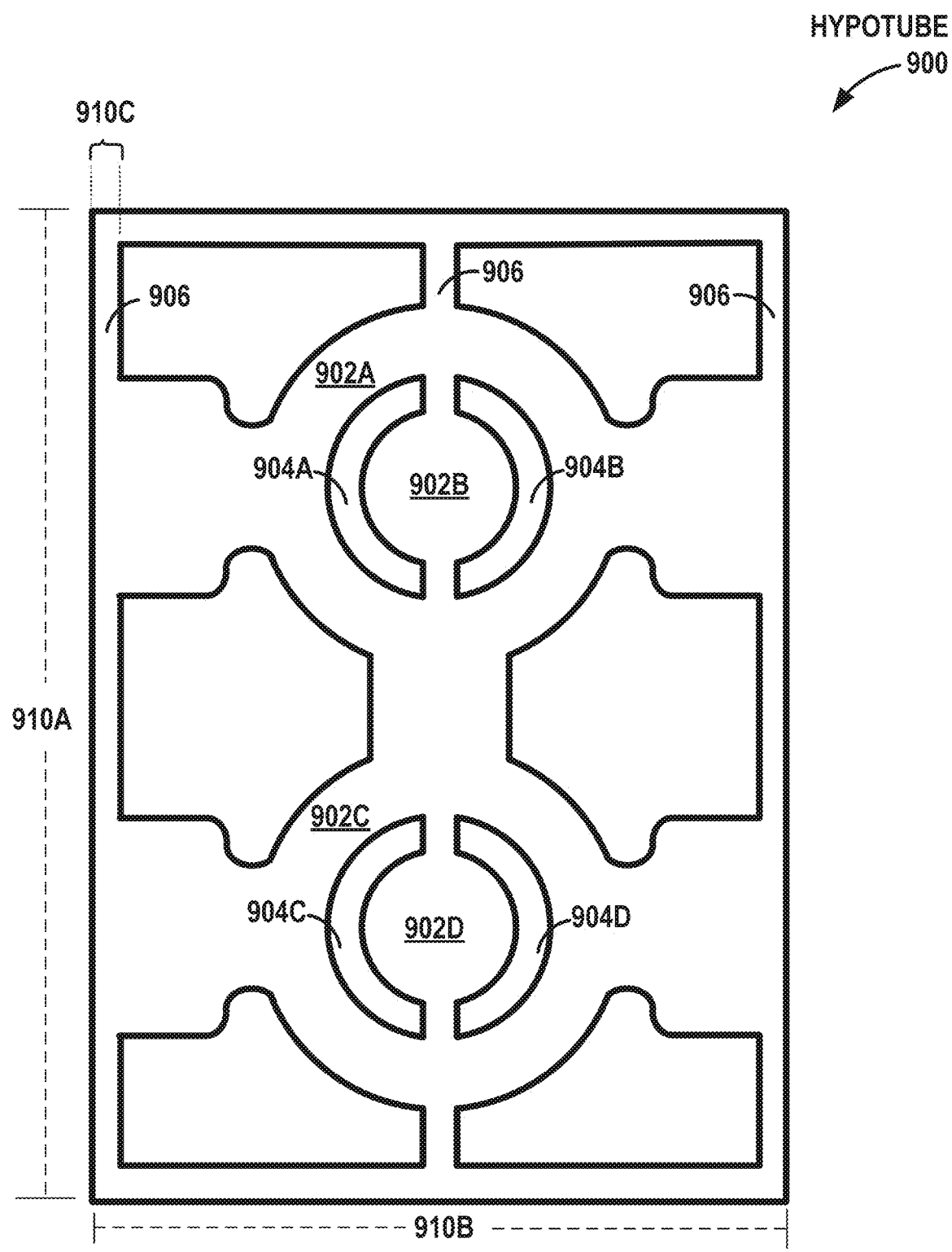
FIG. 9 is a 2-D representation of a third example design for a laser-cut hypotube of an emitter assembly, defining a circular spark-gap configuration.

FIG. 9 is a 2-D representation of a third example design 900 for a laser-cut hypotube 410 of an electronic emitter assembly 400 (FIG. 4). Similar to hypotube design 800 (FIG. 8), hypotube design 900 (while in the planar configuration shown in FIG. 9) may define a rectangle having a circumferential length 910A of about 0.1 inch. The rectangular width 910B (e.g., the longitudinal length of hypotube 900 along longitudinal axis 116) can range from about 0.080 inches to about 0.090 inches.

As compared to hypotube designs 700 (FIGS. 7A and 7B) and 800 (FIGS. 8A and 8B), both of which define generally linear spark-gap configurations, electrodes 902A-902D of hypotube design 900 are shaped and oriented so as to define substantially rounded or circular spark gaps 904A-904D. For instance, hypotube design 900 may include two substantially ring-like electrodes 902A, 902C, each defining an outer radius of about 0.0210 inches and an inner radius of about 0.013 inches. In the center of ring electrodes 902A, 902C are disc electrodes 902B, 902D, respectively. Disc electrodes 902B, 902D may define outer radii of about 0.0090 inches. Accordingly, electrode pairs 902A/902B and 902C/902D may define respective ring-shaped, or semi-ring-shaped spark gaps 904 therebetween, having a gap width of about 0.0040 inches. Similar to hypotube 800 (FIG. 8), hypotube 900 may initially include one or more vertical support structures 906, which may be removed once electrodes 902 are adhered in place. Support structures 906 may define widths 910C of about 0.0030 inches, for example.

Figure 10:
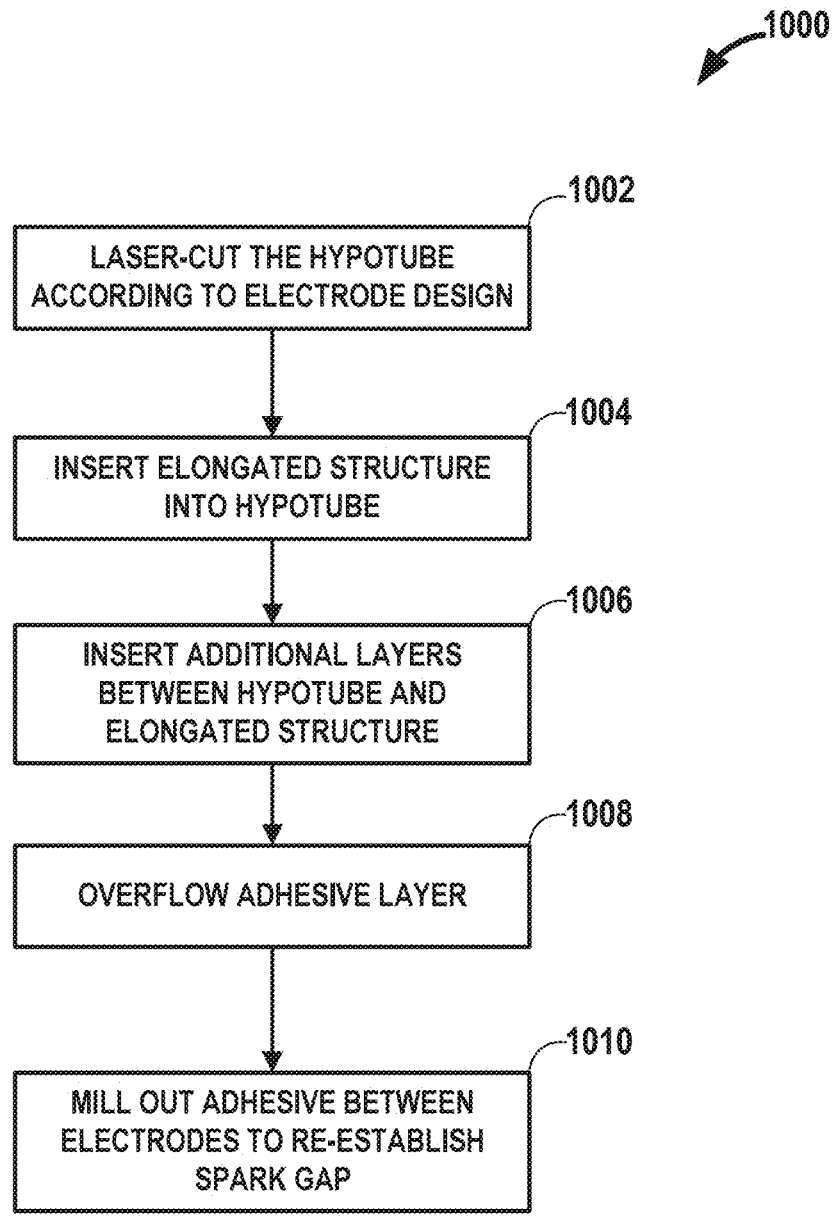
FIG. 10 is a flowchart illustrating an example technique for forming an emitter assembly for an IVL catheter.

FIG. 10 is a flowchart 1000 illustrating an example technique for forming an electronic emitter assembly for an IVL catheter, for instance, the emitter assembly 400 shown in FIG. 4A. The technique of FIG. 10 includes cutting a hypotube according to an electrode design, e.g., one of designs 700-900 of FIGS. 7A-9, respectively, so as to define one or more pairs of conductive electrodes aligned so as to define a respective spark gap therebetween (1002). The technique further includes inserting an elongated structure, such as inner elongated structure 318 of FIG. 4A, into the lumen of the cut hypotube (1004).

In some examples, but not all examples, additional layers may be inserted between hypotube 410 and the inner elongated structure 318 to help provide structural support, improve thermal conductance or increase energy efficiency, as illustrated in FIG. 4B. For instance, a pressure-reflective material, a thermoplastic elastomer 416, wire coils 418, or a polyimide layer 420 may be inserted, if not already present (1006). The technique of FIG. 10 further includes flowing a potting material 412 around the assembled components and causing or allowing the potting-material layer 412 to solidify so as to retain the assembled components in place relative to one another (1108).

In some examples, but not all examples, the technique of FIG. 10 includes removing a portion of the potting material 412 from between the conductive electrodes of the hypotube, so as to re-establish the spark gap(s) (1010). For instance, step 1010 may include milling out the potting material between electrodes or removing the potting material via laser ablation, variable-speed-rotary-tool removal, or other machine removal. In other examples, prior to flowing the potting layer (1008), the technique of FIG. 10 may further include filling the spark gap(s) with an easily removable material to block the potting material, and then subsequently removing the material. In other examples, the hypotube may be over-molded onto an existing potting layer, such that the spark gap is not filled-in in the first place.

In some examples, the technique of FIG. 10 further includes removing obsolete structural components from hypotube 410. For instance, as shown in FIG. 8A, temporary support structures 806 may be removed from between electrodes 802 once the electrodes 802 are secured in place.

FIGS. 11A and 11B illustrate an example flex circuit 1100 for an electronic emitter assembly 400 (FIG. 4) of an IVL catheter 104 (FIG. 1). For instance, conductive electrodes (e.g., copper strips) 1102A-1102C may be printed onto a flexible, planar substrate 1106 so as to define respective spark gaps 1104 therebetween. The flexible substrate 1106 may then be rolled into the tubular shape shown in FIG. 11B, and then wired to the rest of emitter assembly 400 (FIG. 4). Such techniques may significantly reduce the manufacturing time of an IVL catheter 104 including such circuits 1100.

For purposes of illustration, FIG. 11A includes some non-limiting example dimensions of flex circuit 1100. For instance, flex circuit 1100 may include a circumferential length 1110A of about 0.082 inches, and an axial length 1110B (e.g., parallel to longitudinal axis 116) of about 0.080 inches. The planar substrate may further define a primary rectangular body 1108 and two axial prongs 1112A, 1112B. Primary rectangular body 1108 may have dimensions of a circumferential length 1110A of about 0.082 inches by an axial length 1110C of about 0.060 inches. Axial prongs 1112 may similarly be substantially rectangular, defining circumferential widths 1110D of about 0.012 inches by axial lengths 1110E of about 0.020 inches. Axial prongs 1112A, 1112B may be circumferentially separated by a gap 1110F of about 0.046 inches.

Figure 12A:
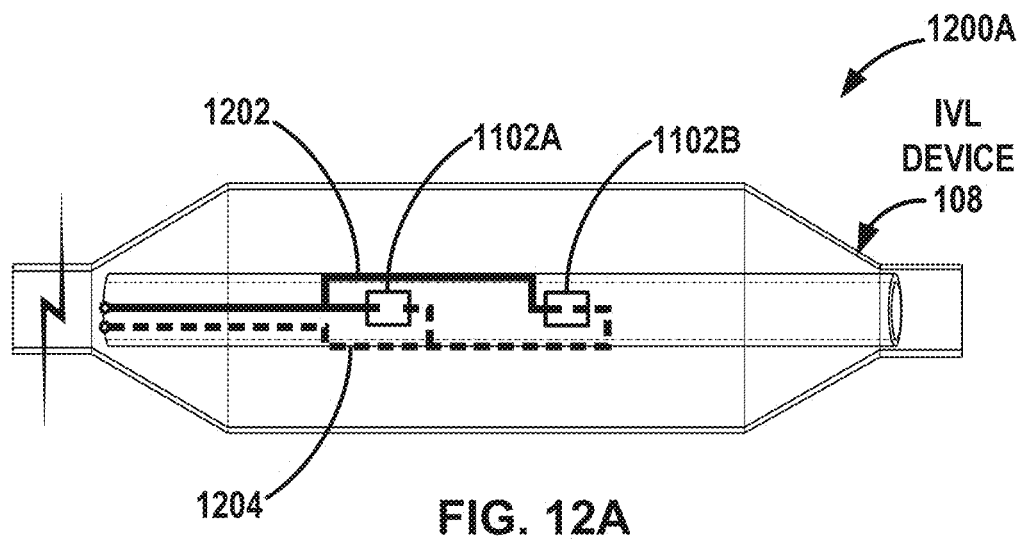
FIGS. 12A and 12B illustrate two example wiring configurations for the flex circuit of FIGS. 11A and 11B.
Figure 12B:
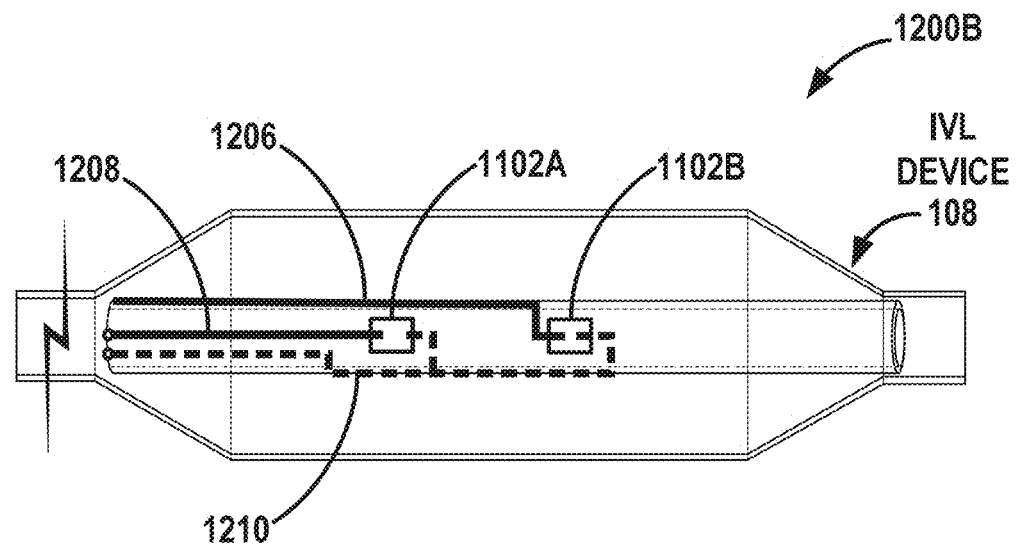

FIGS. 12A and 12B illustrate two example wiring configurations 1200A, 1200B, respectively, for an emitter array 112 (FIG. 1) of an IVL device 108 including two flex circuits 1100A, 1100B (e.g., flex circuit 1100 of FIGS. 11A and 11B). In particular, FIG. 12A shows an example wiring configuration 1200A in which the flex circuits 1102A, 1102B are wired in parallel. The top conductive wire 1202 (solid line) leads to a voltage input, and the bottom conductive wire 1204 (dashed line) leads to ground voltage.

FIG. 12B shows another example wiring configuration 1200B in which the flex circuits 1102A, 1102B are wired so as to be independently actuatable. For instance, the top conductive wire 1206 provides a connection between a voltage input and flex circuit 1102B, and the middle conductive wire 1208 (solid lines) provides a connection between the voltage input and flex circuit 1102A. The bottom conductive wire 1210 provides a common connection to ground voltage for both of flex circuits 1102.

FIGS. 13A and 13B illustrate two example wiring configurations 1300A, 1300B, respectively for conductively wiring an electronic emitter array 400 (FIG. 4). In the example 1300A shown in FIG. 13A, elongated body includes an inner elongated structure 1302 (e.g., polyimide inner layer 420 of FIG. 4), and an outer elongated structure 1304 having two nested layers: an inner layer 1306 and an outer layer 1308. A plurality of conductive wires 406, such as "flat" or "rectangular" wires, coil axially along an exterior surface of the inner layer 1306 of outer elongated structure 1304. The outer layer 1308 of outer elongated structure 1304, such as a heat-shrink tube, thermoplastic tube, or potting material 412 (FIG. 4) may then be reflowed overtop of the conductive wires 406, such that the conductive wires 406 are embedded in the outer layer 1308 of outer elongated structure 1304.

In some examples, outer layer 1308 of outer elongated structure 1304 may terminate a predetermined distance 1310 proximally from the distal end 1312 of inner layer 1306, such that distal portion of conductive wires 406 are exposed and may be adjusted underneath the interventional balloon 110 (FIG. 1). Conductive wires 406 may include flat wires, round wires, or a combination thereof. For instance, in some examples, conductive wires 406 include round wires with "flattened" portions near the emitters 114.

In wiring configuration 1300A, the adhesive outer layer 1308 is "tacked" to the inner layer 1306 to reinforce the structure of interventional balloon 110 (FIG. 1). This may help prevent the balloon 110 from "accordioning" during insertion or removal of the IVL device 108. The wires may also serve as a reinforcing member for the outer elongated structure 1304.

By comparison, FIG. 13B shows a different configuration 1300B, in which the conductive wires 406 are coiled directly around the inner elongated structure 1302. In some examples, the use of flat wires (e.g., round wires with flattened portions near the emitters) helps reduce the overall radial profile of the IVL device 108. In this configuration 1300B, conductive wires 406 could also serve as a reinforcing member for the inner elongated structure 1302 (e.g., coil layer 418 of FIG. 4B).

FIGS. 14A-14D are conceptual cross-sectional drawings illustrating four example wiring configurations 1400A-1400D, respectively, for an electronic emitter array 112 of catheter 104 of FIG. 1. In each of these four examples, conductive wires 406 run distally along an outer surface of inner elongated structure 318 but are not rigidly coupled to inner elongated structure 318.

Figure 14A:
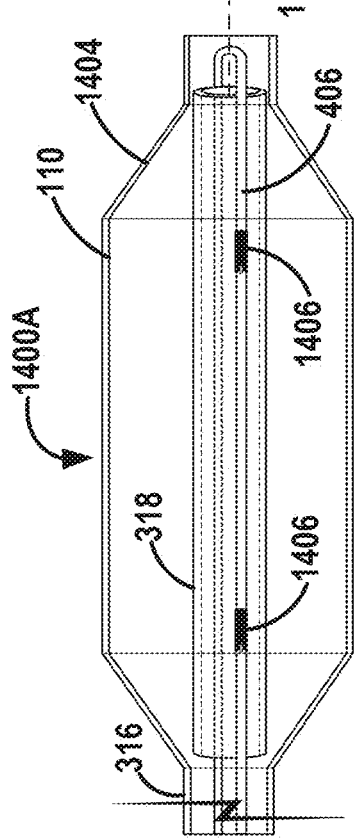
FIGS. 14A-14D are conceptual cross-sectional drawings illustrating four example wiring configurations for an electronic emitter array of the catheter of FIG. 1.

In the first example wiring configuration 1400A of FIG. 14A, conductive wire(s) 406 extend generally linearly along the distal direction, e.g., along to central longitudinal axis 116. In this configuration, the emitters 1406 may be wired in series, or in other examples, a combination of parallel and serial wiring.

Figure 14B:
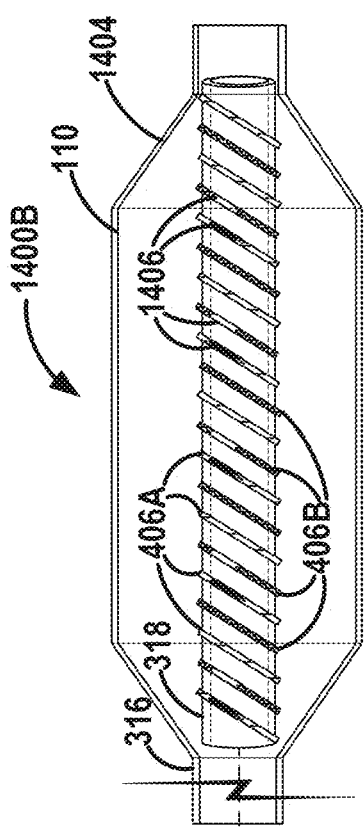

By comparison, in the second example wiring configuration 1400B of FIG. 14B, conductive wire(s) 406 coil helically around inner elongated structure 318 according to a "single wrap" configuration. In the single-wrap wiring configuration 1400B, two or more wires 406A, 406B are inter-coiled, with respective longitudinal spaces between adjacent coil turns. In these "coiled" configurations shown in FIGS. 14B, 14C, and 14D, the wire coils help provide structural support for inner elongated structure 318, e.g., by forming coil layer 418 of FIG. 4B. In some such examples, the emitter array may be wired according to an "n+1" configuration, in which the number of conductive wires 406 is one more than the number of emitters 1406, such that each emitter has a unique voltage-supply wire, but all share a common ground wire.

Figure 14C:
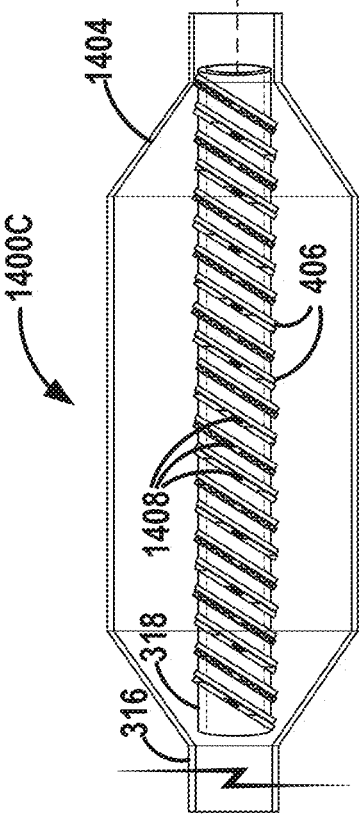

In the third example wiring configuration 1400C of FIG. 14C, conductive wire(s) 406 coil helically around inner elongated structure 318 according to a "double wrap" configuration. In the double-wrap wiring configuration 1400C, wires 406 are inter-coiled as wire pairs, with longitudinal spaces between adjacent pairs of coil turns. Wire-jacket portions 1408 may be removed (e.g., ablated) as necessary for conductively coupling wires 406 to electrode hypotube 410 (FIG. 4).

Figure 14D:
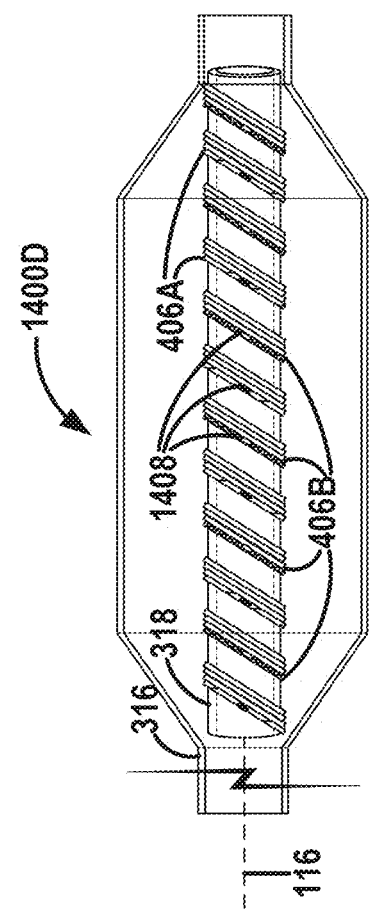

In the fourth example wiring configuration 1400D of FIG. 14D, conductive wires 406 coil helically around inner elongated structure 318 according to a "quadruple wrap" configuration. In the quadruple-wrap wiring configuration 1400D, wires 406 are inter-coiled as groups of four wires, with longitudinal spaces between adjacent groups of four coil turns. Wire-jacket portions 1408 may be removed (e.g., ablated) as necessary for conductively coupling wires 406 to electrode hypotube 410 (FIG. 4). In other examples, wires may be grouped and coiled in numbers greater than four.

FIG. 15A is a conceptual diagram illustrating an example wiring configuration 1500A for an electronic emitter array 1502A having four emitter units 1504A-1504D, and FIG. 15B is a conceptual diagram illustrating an example wiring configuration 1500B for an electronic emitter array 1502B having five emitters 1504A-1504E. While only four-emitter and five-emitter assemblies 1502 are shown, it is to be understood that any suitable and practical number of emitter units 1504 may be implemented within IVL device 108. As referenced above, both wiring configurations 1500A, 1500B are examples of an "n+1" configurations, in which the number of conductive wires is one more than the number of emitters 1504, such that each emitter 1504 has a unique voltage-supply wire, but all emitters 1504 share a common ground wire 1506. In such configurations, individual emitters 1504 are independently actuatable providing enhanced control over the IVL therapy for the clinician.

Figure 16A:
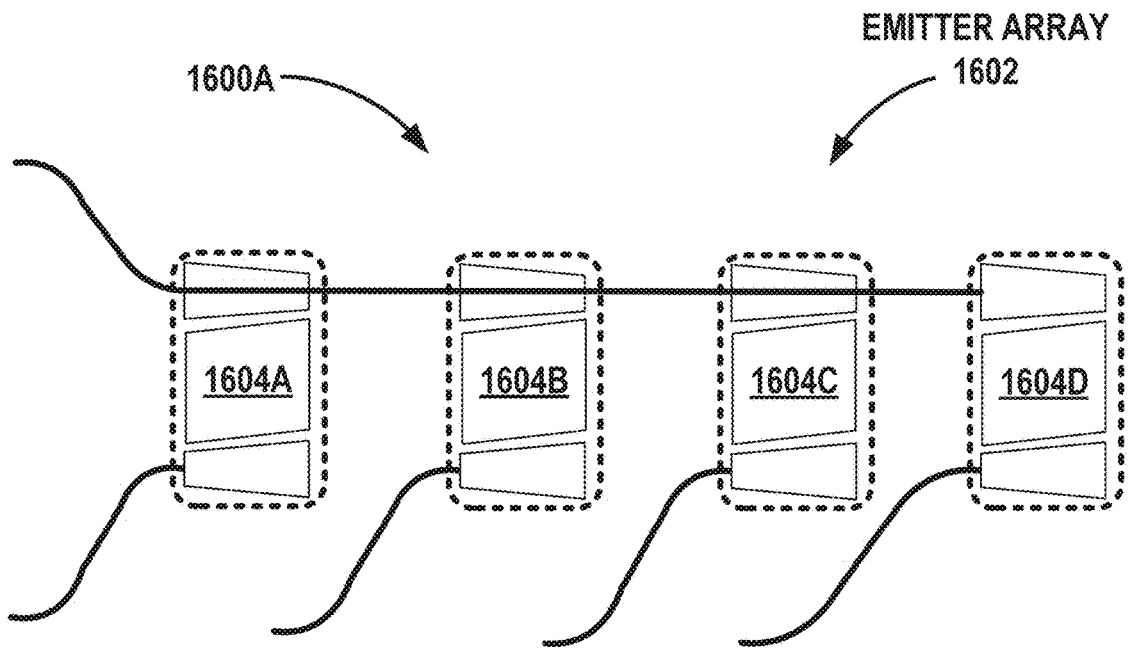
FIG. 16A is a conceptual diagram illustrating a first example wiring configuration.

FIG. 16A is a conceptual diagram illustrating a first example wiring configuration 1600A for an electronic emitter array 1602 having four emitter units 1604A-1604D. FIG. 16A, like FIGS. 15A and 15B, shows the emitter units 1604 wired according to the "n+1" configuration, and a configuration in which emitter assemblies 1604 wired in parallel.

Some example benefits of a parallel wiring configuration 1600A include the ability to transmit a higher electrical current across the emitter units 1604. A parallel wiring configuration 1600A also enables each individual emitter unit 1604 to be actuated (or "fired") independently of the other emitter units. Additionally, with a parallel wiring configuration 1600A, the total resistance of the IVL system 100 (FIG. 1) may be reduced. For instance, by individually powering a single emitter unit 1604, a greater electrical current may be generated across the spark gap 404 (FIG. 4), thereby reducing the necessary number of resistors in the corresponding electrical circuit.

Configuration 1600A may also allow for a reduction in the overall voltage through the system, e.g., translating to a reduction in energy consumption. The ability to individually power each emitter 1604, and the ability to choose a sequence of order of firing of each emitter unit 1604, allows for greater overall control of the IVL device 108, including how and where the applied energy is directed, as detailed further below.

Figure 16B:
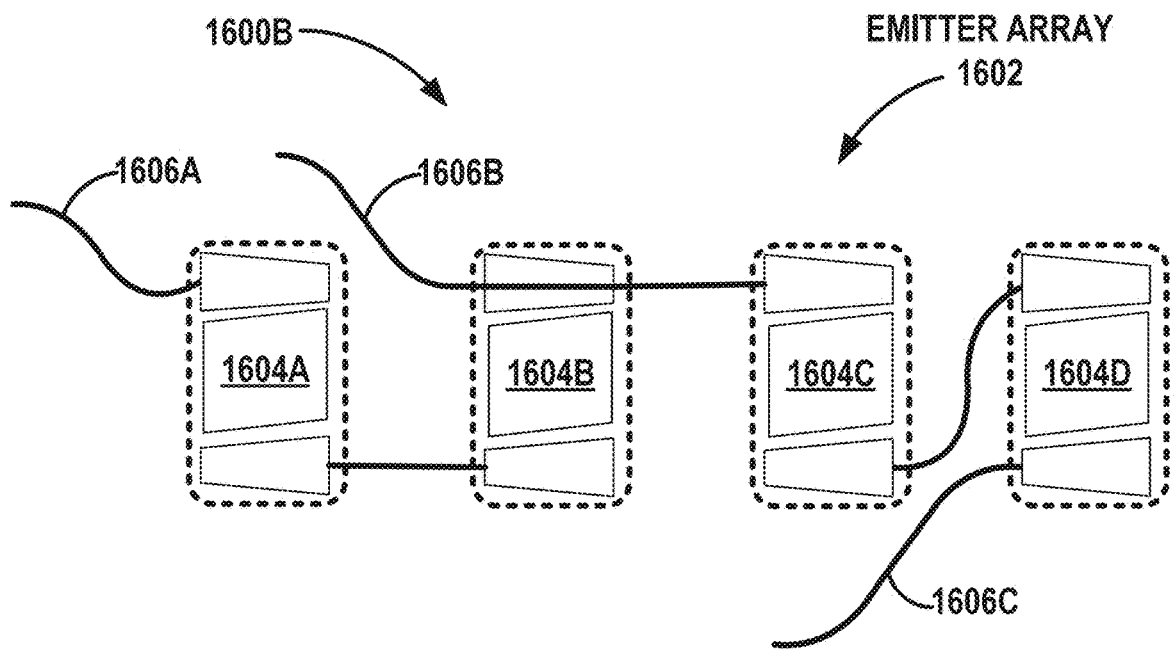
FIG. 16B is a conceptual diagram illustrating a second example wiring configuration.

FIG. 16B is a conceptual diagram illustrating a second example wiring configuration 1600B for the electronic emitter array 1602 of FIG. 16A. In wiring configuration 1600B, a combination of both parallel and serial wiring techniques may be implemented, enabling advantages of both configurations. For instance, emitters 1604A and 1604B are connected in series, whereas other emitters 1604 are connected in parallel. In particular, wiring configuration 1600B enables the clinician to simultaneously acuate: (1) emitters 1604A-1604D (e.g., using wires 1606A and 1606C); (2) emitters 1604C and 1604D (e.g., using wires 1606B and 1606C); or (3) emitters 1604A and 1604B (e.g., using wires 1606A and 1606B). However, FIG. 16B is not intended to be limiting-any suitable wiring combination for emitters 1604 is contemplated and encompassed herein.

FIG. 17A is a conceptual diagram, and FIG. 17B is a cross-sectional view, illustrating an IVL device 1700 having an array (e.g., emitter array 112 of FIG. 1) of optical-based pressure-wave emitters 1702A-1702C. As used herein, optical-based emitters 1702 can include the distal ends or distal portions of respective optical fibers or tubes 1704A-1704C, which IVL device 108 of FIG. 1 may include in addition to, or alternatively to, one or more electronic emitter units, as described above.

According to some non-limiting examples, optical fibers 1704 may deliver, e.g., about 20-100 millijoules of energy within about one millisecond into the inflation fluid 408, such as water, a saline/contrast-fluid mixture, another fluid, or a combination thereof, within interventional balloon 110 in order to generate and propagate high-energy pressure waves. However, these values are merely illustrative, and the amounts of energy and/or time may be adjusted for a particular clinical application. In some examples, an emitted optical pulse width (e.g., emitted-light duration) may be 5 nanoseconds or more.

Based on varying clinical needs, IVL device 1700 may include any suitable number of optical fibers 1704. In some examples, IVL device 1700 is configured to transmit a laser signal having a wavelength from about 1064 nanometers (nm) to about 1460 nm, though shorter wavelengths may be similarly effective. Example diameters for optical fibers 1704 can range from about 50 microns or less to about 200 microns or greater, depending on the particular clinical application.

As shown in FIG. 17A, in some examples, the distal emitter portion 1702A of optical fiber 1704A may be oriented at a predetermined angle "0" relative to central longitudinal axis 116. For instance, to protect inner elongated structure 318, distal emitter portion 1702A may be oriented at an angle θ of greater than 90 degrees, such as greater than about 114 degrees (e.g., greater than about 24 degrees from a vertical tangent. For optical fiber 1704A, only a distal-most surface or distal-most end of emitter portion 1702A is angled away from inner elongated structure 318. In other examples, such as the example of optical fiber 1704B, an entire distal portion 1702B may be bent or angled away from inner elongated structure 318. In some such examples, the optical fiber distal portion 1702B can diverge by an angle "q" from about 0 degrees to about 24 degrees.

Optical emitters 1702 of optical fibers 1704 may be positioned either circumferentially around inner elongated structure 318 (e.g., as shown in FIG. 17B), or in other examples, longitudinally along inner elongated structure 318, or in still other examples, a combination thereof to emit and deliver high-energy pressure waves. For instance, optical fibers 1704 may be adjacent to inner elongated structure 318 (e.g., 1704A) for circumferential lesion treatments, or radially off-centered (e.g., 1704B) for non-circumferential lesion treatments. Some example benefits of using more than one optical fiber 1704 include reducing the overall cross-sectional profile of IVL device 1700 by positioning optical fibers 1704 around the proximal portion of the catheter elongated body 106 (FIG. 1). Additionally, a greater number of optical fibers 1704 allows for a more controlled pressure wave. In addition to directing the energy based on where the optical fibers 1704 are placed about the IVL catheter 104, the size of the cavitation bubble may be controlled based on a selected diameter (e.g., cross-sectional area) of optical fibers 1704. These optical fibers 1704 may be individually or simultaneously actuated based on the needs of the treatment, e.g., allowing for a single IVL device 108 that can treat both circumferential calcified lesions as well as nodular calcified lesions.

Figure 18:
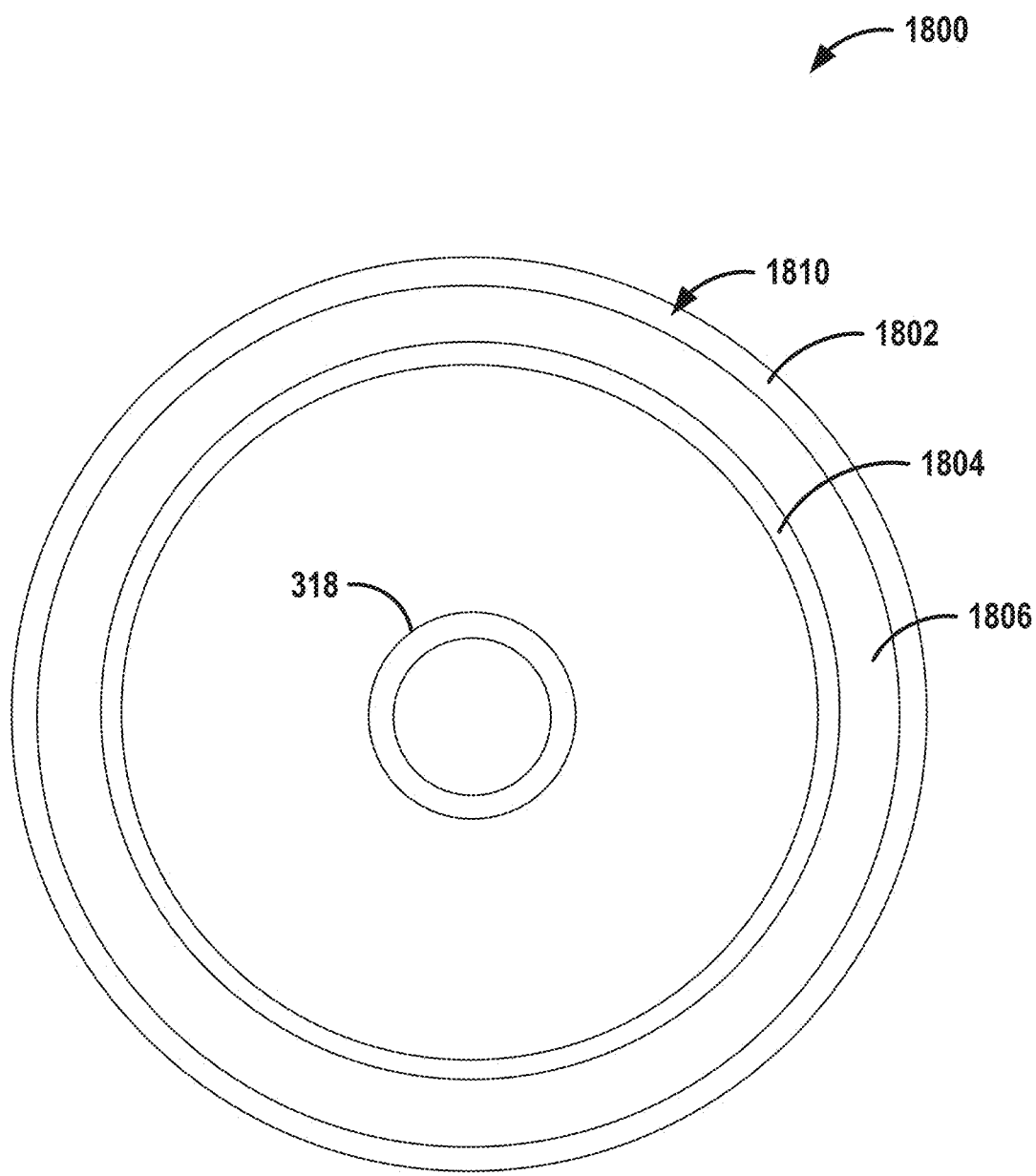
FIG. 18 is a cross-sectional diagram of an example IVL device having a multiple-layered interventional balloon.

FIG. 18 is a cross-sectional diagram of an example IVL device 1800 (e.g., IVL device 108 of FIG. 1) with an interventional balloon 1810 (e.g., balloon 110 of FIG. 1) having a multiple-layered construction for enhanced durability. As shown, balloon 1810 may have an outer layer 1802 and an inner layer 1804, for the purposes of reinforcement. Either or both of reinforcing layers 1802, 1804 may include a separate extrusion that goes over the top of the balloon 1810, with another layer over the top of this pressure-holding layer.

The example shown in FIG. 18 represents just one of multiple solutions to the potential risk of balloon rupture. For instance, balloon 1810 may be formed from a single multi-layered extrusion, wherein a thin, more-compliant layer 1802 on the outside of the balloon is softer and less prone to tearing than an inner, high-pressure, non-compliant (or "less compliant") holding layer 1804. For instance, one example structure could comprise a high-pressure inner holding layer 1804 that makes up, e.g., between 70% and 100% of the thickness of the balloon wall, such as Nylon-12, or Pebax-72D. The outside layer 1802 is made from a more-compliant substance such as urethane, Pebax, or any other suitable material with a medium-to-low durometer measurement, e.g., of about 63D or lower.

Another solution is to form the balloon from two separate extrusions 1802, 1804, e.g., a separate extrusion layer 1802 on the outside of the balloon placed upon the exterior surface of an inner non-compliant or semi-compliant balloon 1804. Another solution is to form the balloon 1810 from a thin polymer inner layer 1804 covered by reinforcing layers 1806 such as polymer fibers, like Aramid or UHMWPE, with a top coating 1802 for fiber encapsulation. The outer layer 1802 may be a plurality of reinforcing layers, for instance, a set of sixteen braided fibers, and four to eight (inclusive) longitudinal fibers, as one non-limiting example. Other variations of braid patterns are similarly viable, such as those including thirty-two fibers or forty-eight fibers. Additionally, the reinforcing fibers may be arranged in an orthogonal textile pattern, such as a mesh sheet cut into pieces, as opposed to (or in addition to) being braided directly onto the balloon 1810.

While not shown in FIG. 18, another solution against potential balloon rupture is to coat the balloon with an abrasion-resistant coating, such as exterior coating 326 of FIG. 3. This solution may be accomplished by applying the coating to the balloon 1800 through a dip, a spray, or a roll-cast. According to some examples, this coating may be or may include a polymer, such as urethane, parylene, silicone, or a thermoplastic polyurethane (TPU). These coatings may allow for a balloon 1810 that holds a high pressure while protecting the balloon structure from damage due to contact with the calcified lesions within the target vessel. Although not illustrated, another technique includes implementing a compliant balloon body to allow conformance to plaque and puncture resistance. In the example of this solution, non-compliant cones on either end of the balloon would be implemented to prevent the pressure wave from propagating proximal to, or distal from, the balloon 110.

Figure 19:
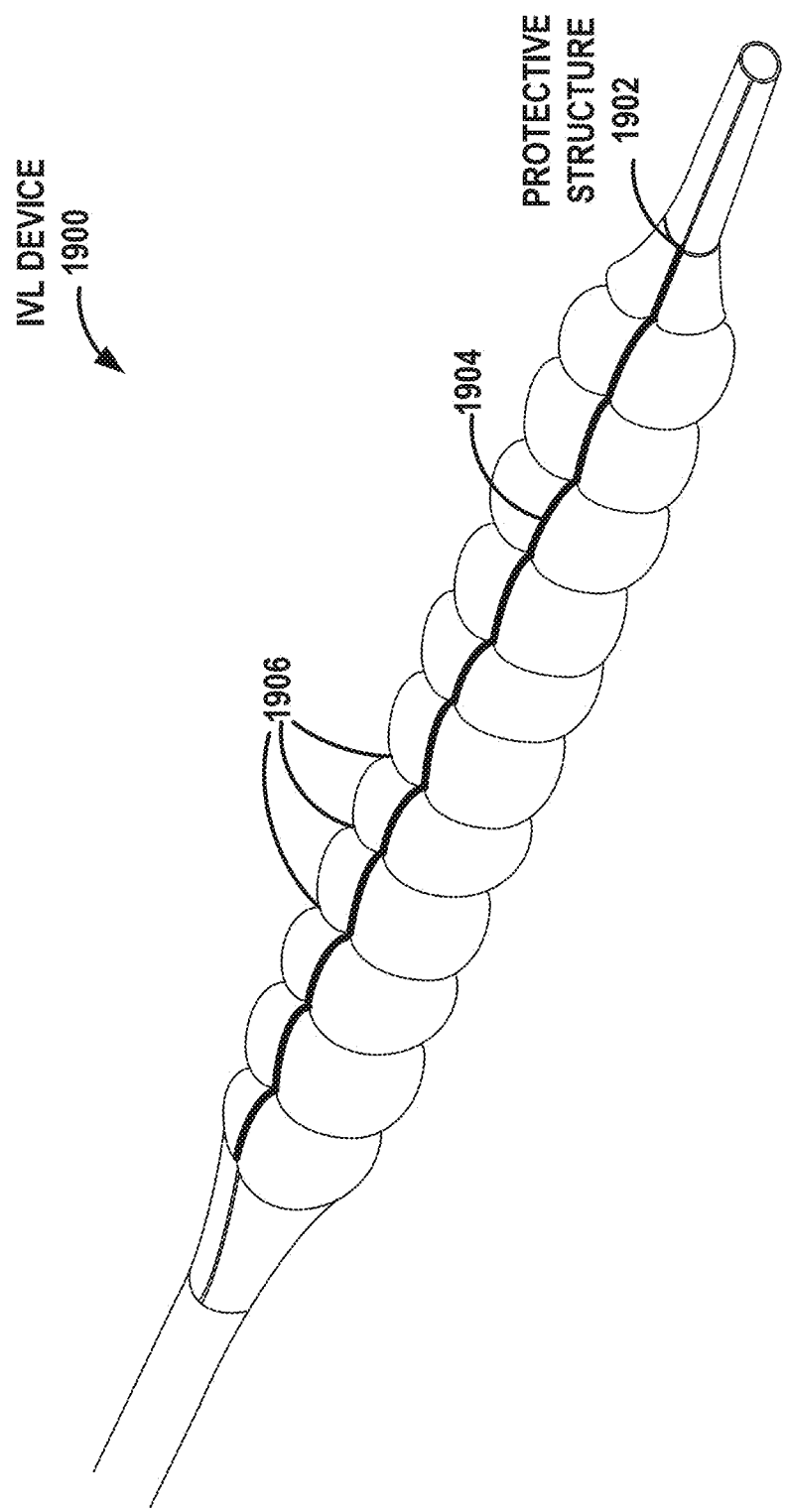
FIGS. 19 and 20 illustrate two example IVL devices having interventional balloons with protective structures.
Figure 20:
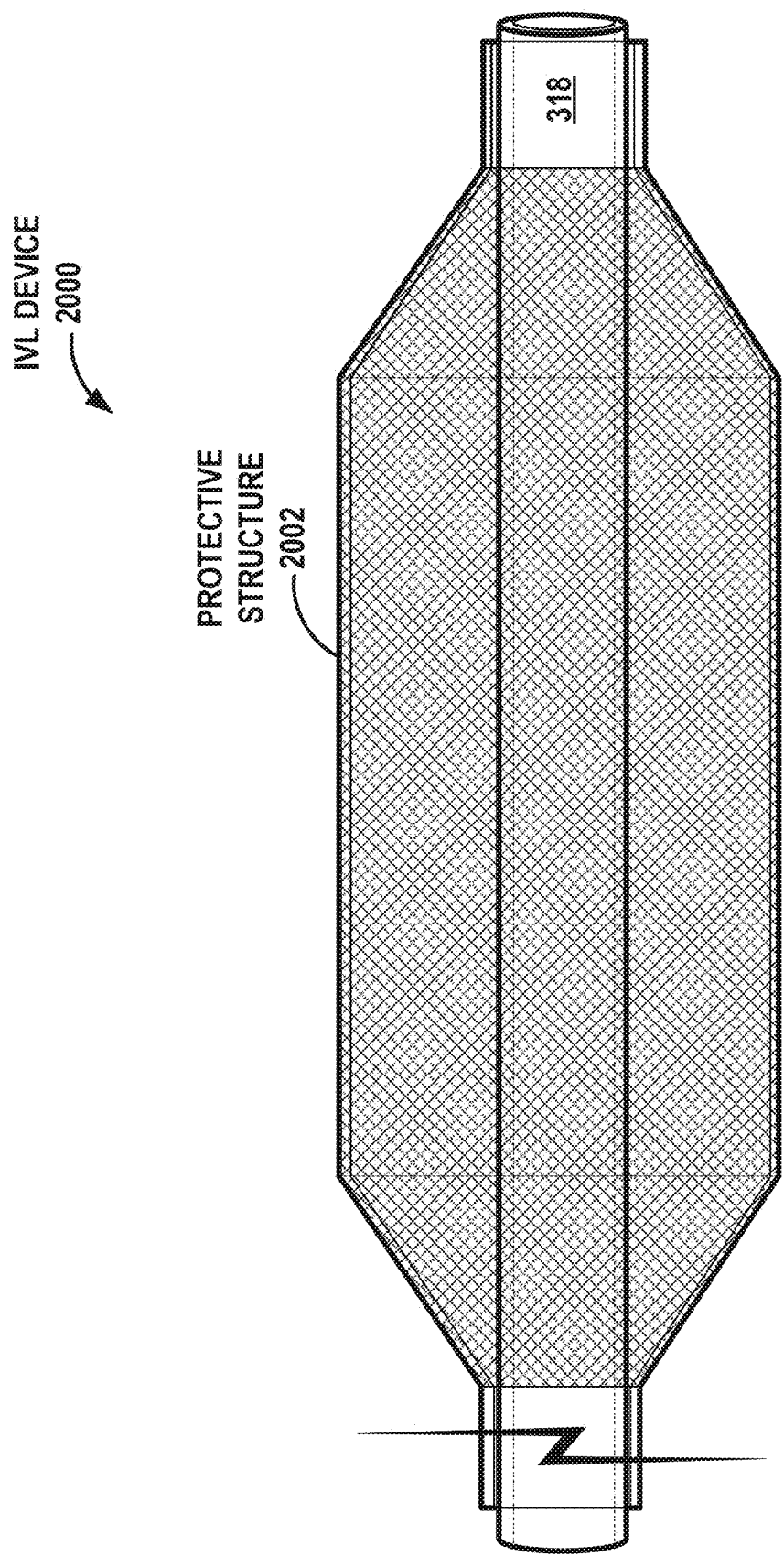

FIGS. 19 and 20 illustrate two example IVL devices 1900, 2000, respectively, having interventional balloons 110 with protective structures 1902, 2002, or "protective cages." Specifically, FIG. 19 is a profile view of a first example IVL device 1900 having a first-such protective structure 1902, and FIG. 20 is a side view of a second example IVL device 2000 having a second-such protective structure 2002.

These protective structures 1902, 2002 are configured to provide similar rupture-protection to the more-continuous balloon outer layer or coating 1802 described above with respect to FIG. 18. According to either of these examples, balloon 110 can have a cage-like structure overtop of it, thereby reducing direct physical contact (e.g., friction) between the exterior surface of the balloon and the calcified-plaque lesion appended to the vessel wall.

The cage-like structures 1902, 2002 may be or may include a metal, such as SST or nitinol, or a polymer. In a multi-nested-layer balloon (e.g., balloon 1800 of FIG. 18), the protective structure 1902, 2002 could be disposed between the outer and inner balloon layers 1802, 1804. In some examples, the cage-like structure 1902, 2002 includes multiple longitudinal members, e.g., extending parallel to central longitudinal axis 116. In some such examples, protective structure 1902, 2002 may be selected to include an odd number of longitudinal members, such as three longitudinal members or five longitudinal members, in order to promote re-wrap of the respective balloon prior to withdrawal of IVL device 108 from the patient's vasculature. These longitudinal members or bars may be interconnected as a stent-like structure, such that the structure has a predetermined size and shape that does not vary (or varies by a relatively small amount) during inflation of balloon 110.

According to some examples, the protective structure 1902, 2002 is rigidly coupled to the exterior surface of the balloon 110. In some such examples, the protective structure 1902, 2002 is rigidly coupled to the proximal and distal end portions of balloon 100, but not to a longitudinally central balloon portion.

The example of FIG. 19 shows a less-comprehensive protective structure 1902, as compared to the example protective structure 2002 of FIG. 20. For instance, protective structure 1902 includes, as non-limiting examples, two (top and bottom) longitudinal elements 1904, and about thirteen circumferential elements 1906. By comparison, protective structure 2002 is shown to include a more-continuous wire-mesh configuration or window-screen configuration having dozens or hundreds of interwoven longitudinal and circumferential elements.

Figure 21:
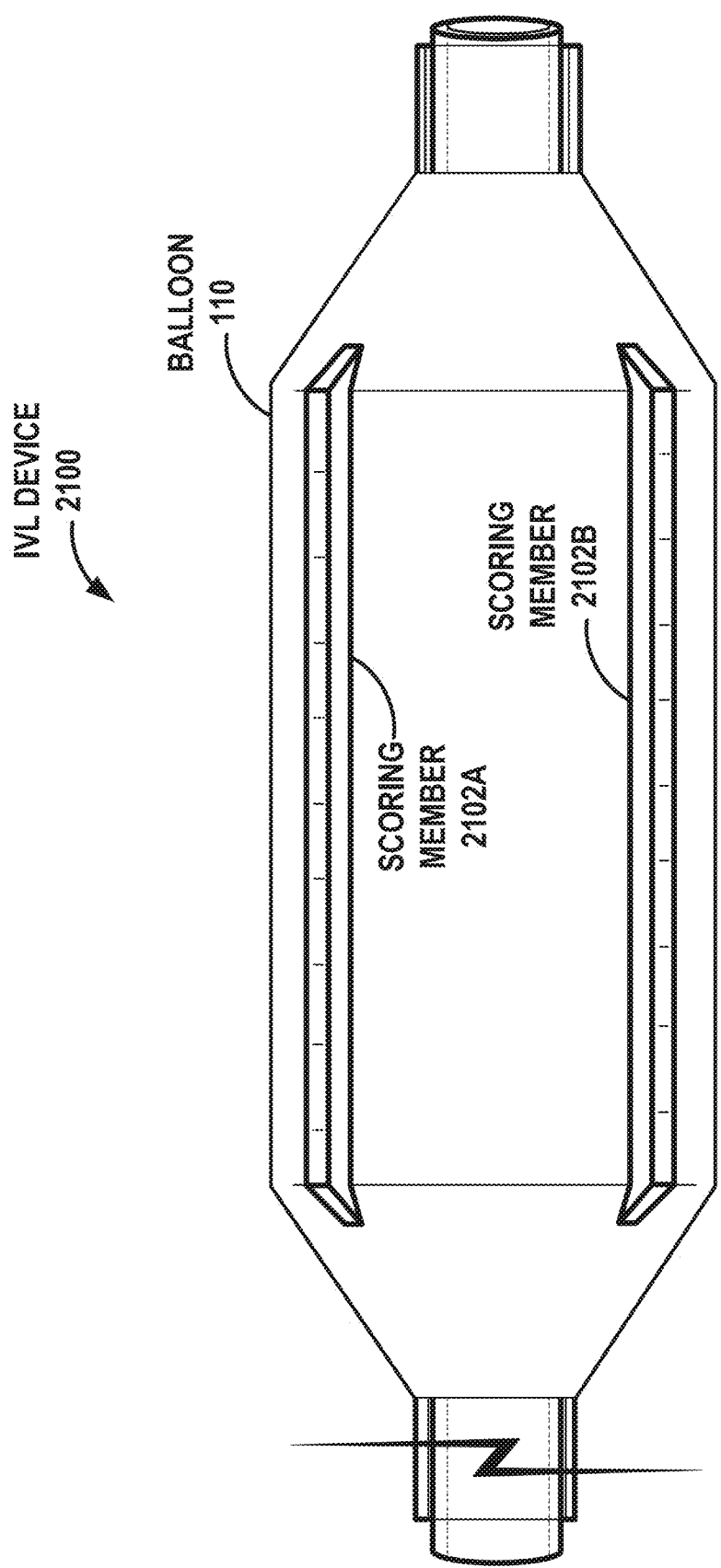
FIG. 21 illustrates an example IVL device having a pair of scoring members.

FIG. 21 illustrates an example IVL device 2100 (e.g., IVL device 108 of FIG. 1) including a pair of scoring members 2102A, 2102B. Scoring members 2102 are configured to physically contact and abrade (e.g., through friction applied across a substantially small surface area, corresponding to a substantially high stress-pressure at that point) an interior surface of a calcified-plaque lesion to help fragment and disintegrate the lesion.

In some examples, scoring members 2102 may be coupled to a protective structure (e.g., protective cages 1902, 2002 of FIGS. 19 and 20, respectively) within or over the balloon 110. In some examples, balloon 110 may include a single scoring member 2102. In other examples, multiple scoring members 2102 may be distributed, rotationally symmetrically or asymmetrically, about the circumference of balloon 110. During the IVL procedure, balloon 110 may be circumferentially rotated to apply a particular scoring member or members 2102 against the calcified lesion. In some examples, scoring members 2102 may be formed from a metal, such as an SST or a nickel-titanium alloy (e.g., Nitinol), a metal wire, a printed metal ink (which may contain a very small amount of polymer binder from processing), tungsten, or a polymer.

In some examples, such as the example shown in FIG. 21, scoring members 2102 may include generally flat or planar external surfaces. In other examples, scoring members 2102 may include toothed or serrated external surfaces, e.g., to increase kinetic friction when contacting the calcified-plaque lesion.

Figure 22:
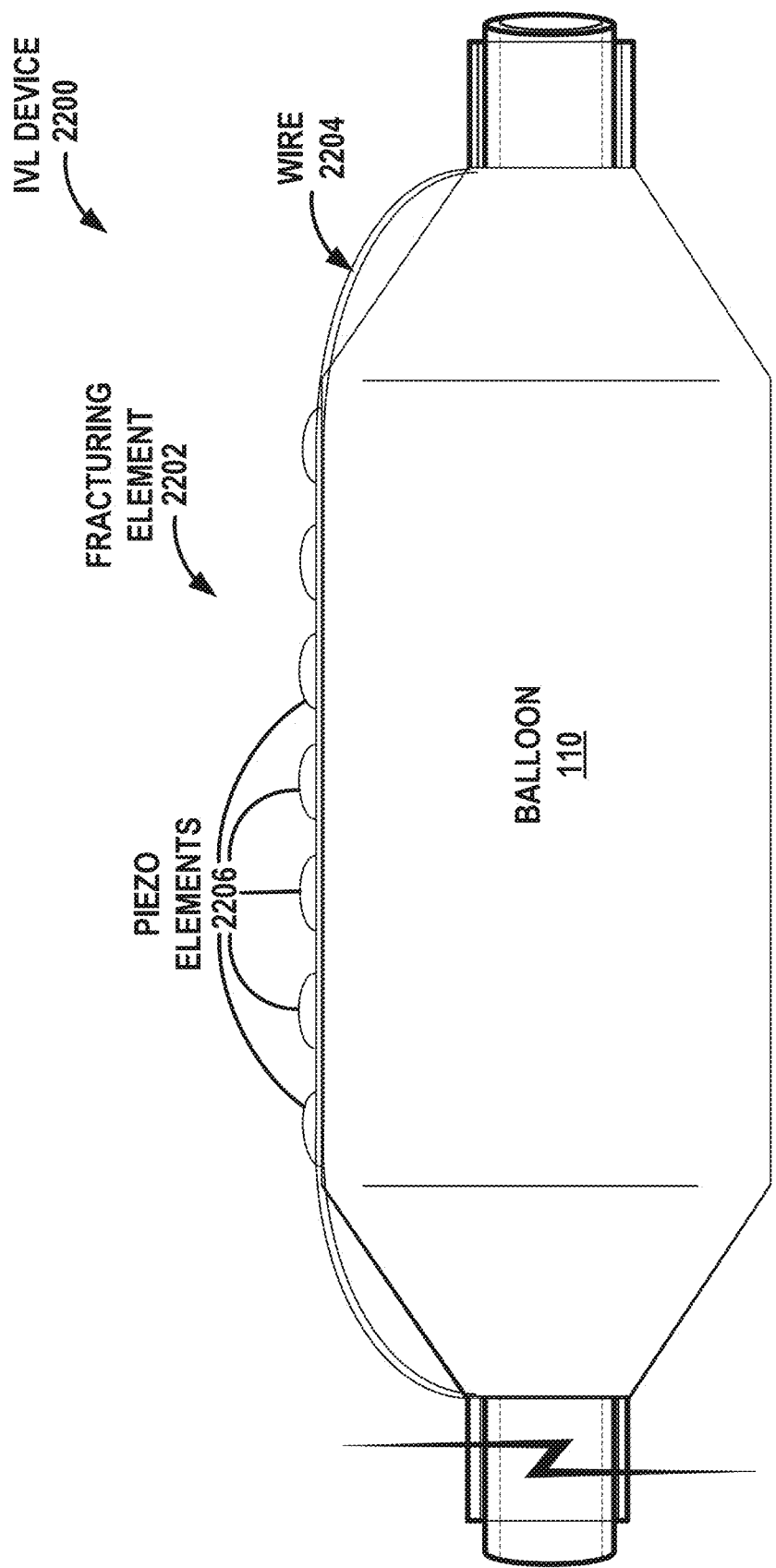
FIG. 22 illustrates an example IVL device having a fracturing element.

FIG. 22 illustrates an example IVL device 2200 (e.g., IVL device 108 of FIG. 1) including a fracturing element 2202 configured to help fragment the calcified-plaque lesion during the IVL procedure. As shown in FIG. 22, fracturing element 2202 includes an elongated conductive wire 2204, and a plurality of piezoelectric elements 2206 distributed longitudinally along the wire 2204.

Fracturing element 2202 provides at least two advantages. First, when conductive wire 2204 is aligned against the calcified-plaque lesion, the narrow-cross sectional area of conductive wire 2204 substantially increases a pressure applied to the lesion along the axis of the wire, enabling the clinician to control the particular location at which the lesion begins to fragment. Second, when an alternating current (AC) is applied through conductive wire 2204, piezoelectric elements 2206 are configured to rapidly expand and contract, thereby generating additional pressure waves that are focused directly against the exterior surface of the lesion.

In some examples, fracturing element 2200 includes a distal protective element, such as an embolic protection element, as described further below with respect to FIG. 24. For instance, the distal protective element may be coupled to a distal portion of conductive wire 2204. Additionally, or alternatively to wire 2204, fracturing element 2200 can include a braided layer, such as a Nitinol braid. Piezoelectric elements 2206 may be rigidly coupled to an exterior surface of the braid, and the braid may be coupled to the exterior surface of balloon 110. This braid may perform similar functions as those described above with respect to wire 2204.

Figure 23:
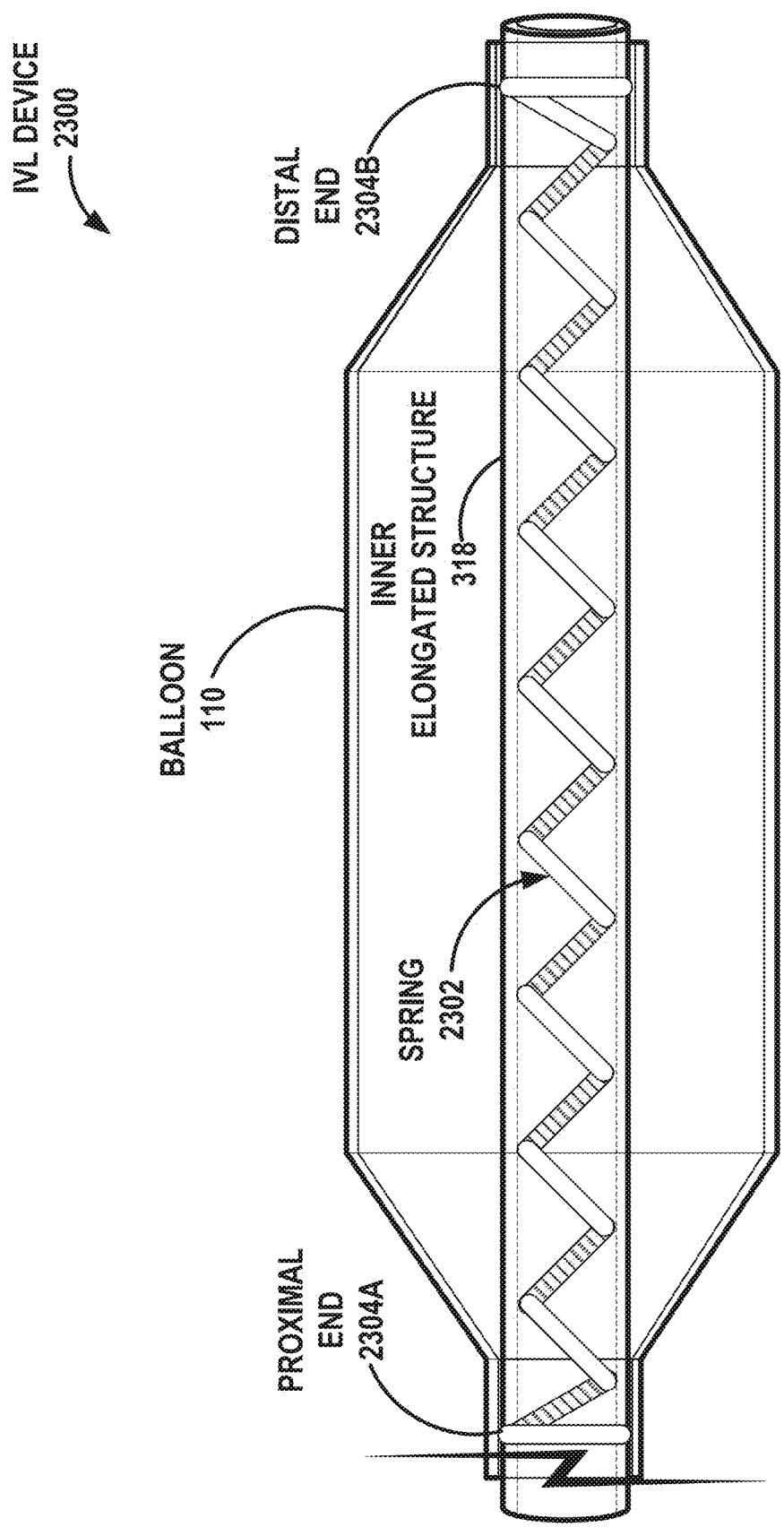
FIG. 23 illustrates an example IVL device having a spring mechanism.

FIG. 23 illustrates an IVL device 2300 (e.g., IVL device 108 of FIG. 1) with an example spring mechanism 2302. With some previous devices, the interventional balloon 110 can become difficult to insert into and remove from an introducer sheath (not shown) during an IVL procedure. This may be caused, for example, by excessively bulky proximal and/or distal balloon cones (as compared to, e.g., distal balloon cone 1404 of FIG. 14A), or a lack of effective folding or wrapping of balloon 110 during and/or after deflation. In some examples, this problem may be addressed by reducing the balloon's radial profile (e.g., cross-sectional area) while it is in an uninflated or deflated state. This could be accomplished by longitudinally stretching the balloon 110 while bonding the proximal and distal ends of the balloon to inner elongated structure 318.

Another technique for reducing the profile of balloon 110, which is illustrated in FIG. 23, is to incorporate a spring 2302 within inner elongated structure 318. The spring 2302 should be longitudinally compressed when bonded (e.g., at proximal end 2304A and distal end 2304B) to inner elongated structure 318. Balloon 110 may then be bonded to inner elongated structure 318 such that, when spring 2302 is allowed to expand back to its rest length, inner elongated structure 318 and balloon 110 similarly expand along the longitudinal direction 116 and compress radially inward. Balloon 110 may also be stretched longitudinally about the tube 318 (as described above) during the bonding process to further facilitate this technique. During inflation, balloon 110 will still expand to its pre-formed shape, while the inner elongated structure 318 will slightly compress along the longitudinal direction. That is, the proximal and distal points at which balloon 110 is bonded to inner elongated structure 318 may slightly compress toward one another as balloon 110 expands radially outward.

Another technique for reducing the cross-sectional profile of balloon 110 is to improve balloon re-wrap after deflation during a procedure. This can be accomplished in a number of ways, such as by incorporating or embedding a plurality of longitudinal wires into the balloon body. These longitudinal wires may help define pleats or pre-determined folding locations for balloon 110, rather than allowing the balloon material to "bunch up" in a disordered fashion. While any number of longitudinal wires may be incorporated, an odd number of longitudinal wires can help prevent the balloon from collapsing into a symmetrical plane, such as a "paddle" or "pancake" configuration of the balloon. Additionally, the longitudinal members may be radiopaque so that they can be used to visualize the inflated balloon 110 and its apposition relative to the vessel wall during the IVL procedure. Such configurations can obviate the use of a separate fluid contrast medium, thereby potentially reducing an overall duration of the IVL procedure. In some examples, these longitudinal wires could consist of metal wires (e.g., flat, round, or irregular-shaped, such as pentagonal), a printed ink (e.g., a metal or polymer ink), or a polymer structure.

Figure 24:
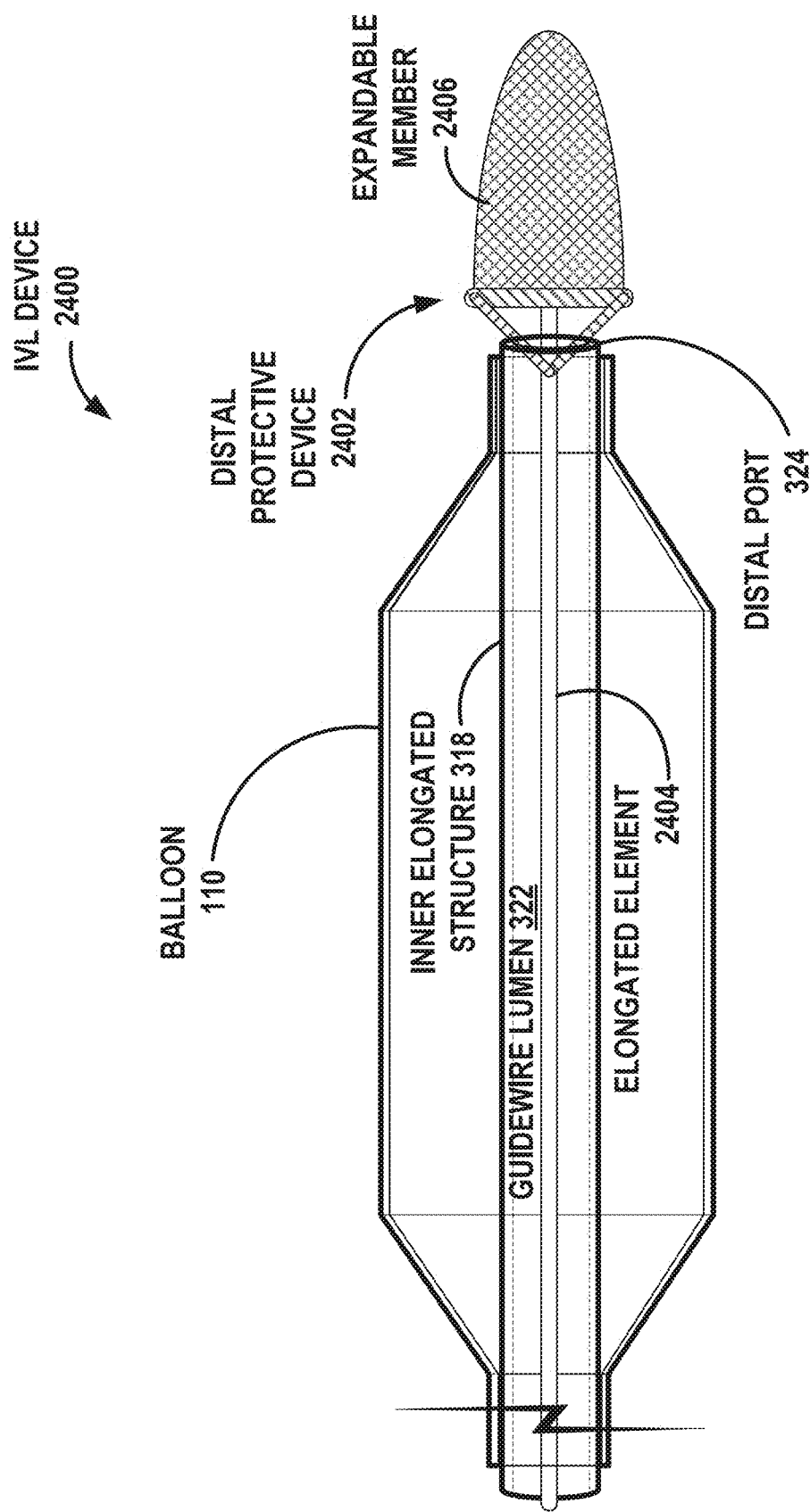
FIG. 24 illustrates an example IVL device having a distal protective member.

FIG. 24 illustrates an example IVL device 2400 (e.g., IVL device 108 of FIG. 1) including a distal protective device 2402. According to some examples, a distal protective device 2402 may be positioned at a distal end portion of IVL device 2400. In some examples (but not all examples), the distal protective device 2402 includes an elongated element 2404 (e.g., a guidewire) that extends, e.g., through guidewire lumen 322 of inner elongated structure 318, and a distal expandable member 2406. In some such examples, expandable member 2406 is configured to extend distally outward from distal port 324 and expand radially outward into the expanded configuration shown in FIG. 24. The inner lumen 322 of inner elongated structure 318 surrounding the extended distal protective device 2402 may be compatible for guidewires from 0.010" to 0.035". Therefore, the guidewire lumen size can range from 0.011" up to 0.038" to allow for free guidewire movement.

The distal protective device 2402 is configured to capture calcified particulates that are generated during the IVL procedure. Expandable member 2406 may include a basket-frame design, as shown in FIG. 24, but other suitable designs are contemplated as well. In some such examples, the basket frame 2406 may be or may include a Nitinol cut-tube (similar to a stent) or a Nitinol wireframe. The material that makes up the basket 2406 may be a thin polymer with ablated holes or a fiber mesh. According to some examples, the basket frame 2406 could be placed outside the balloon catheter 104 and is designed so that the distal protective member's shaft 2404 is compatible with the balloon dilation (wherein the balloon 110 presses up against the shaft 2404 of the filter device 2402).

Distal protective device 2402 could also be rapidly exchanged on the balloon catheter 104. A rapid exchange port may be proximal of the balloon 110 or distal of the balloon 110. The distal protective device 2402 may enter or exit the balloon catheter at the hub 306 (FIG. 3), proximal of the balloon 110, or distal of the balloon 110. This distal protective device 2402 may also be modular (e.g., removable) in nature, so that it is only present on the IVL device 2400 when needed for a procedure.

Figure 25:
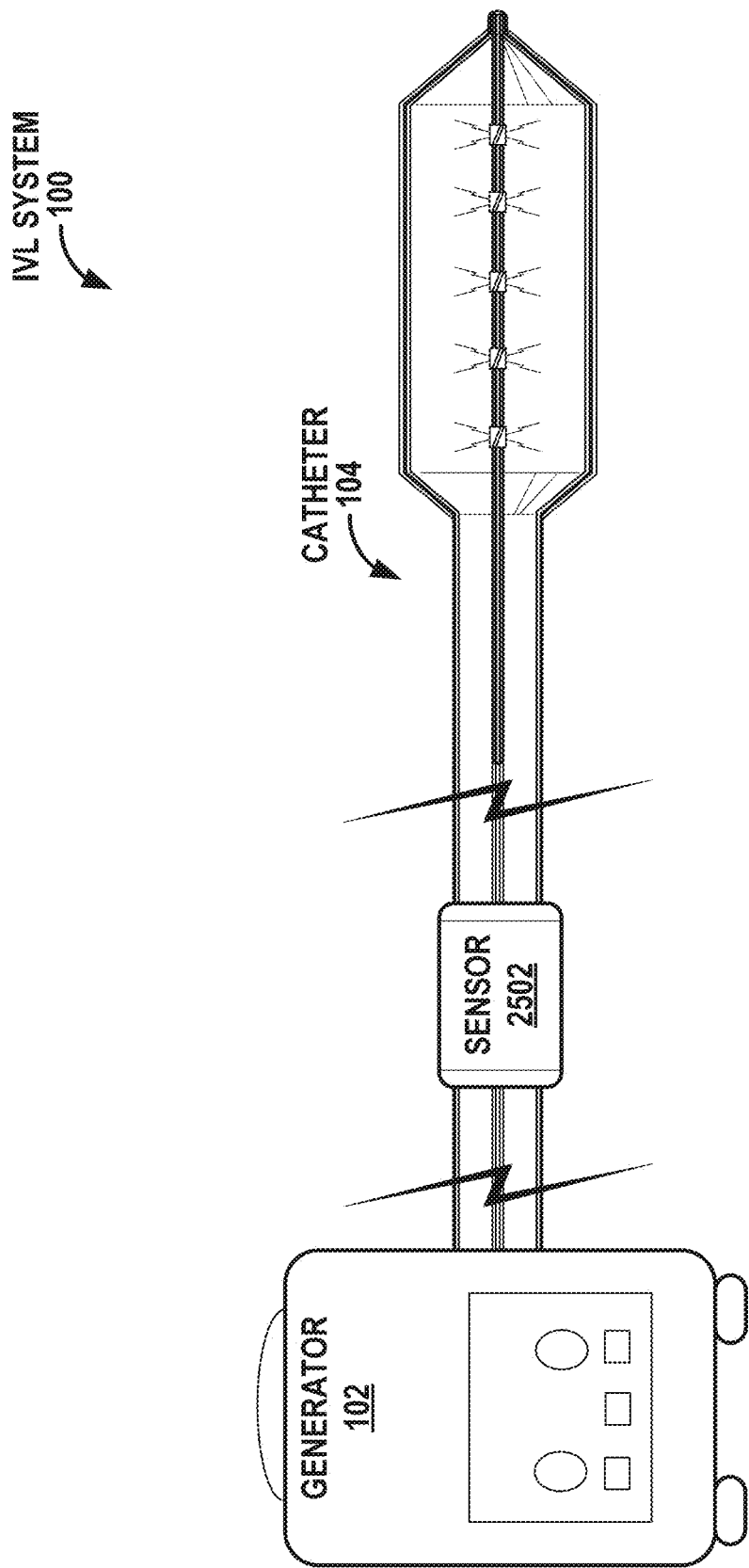
FIG. 25 illustrates the IVL system of FIG. 1 with an example closed-loop energy-delivery feedback mechanism.

FIG. 25 illustrates an example of IVL system 100 of FIG. 1, including a closed-loop energy-delivery feedback mechanism. In some current IVL systems, the amount of delivered energy is fixed and not tailored to the clinical need. This disclosure allows for the automatic delivery of energy based on the clinical scenario presented, in order to improve treatment efficacy and efficiency, via a sensor 2502 that measures, e.g., fluid pressure, fluid amount/rate, and/or temperature. Any combination or sole use of the monitoring provided by the controls as disclosed herein may provide input to determine a maximum pressure-wave intensity and/or heat level to be generated by the emitters.

According to some examples, system 100 may include one or more sensors 2502, e.g., incorporated within energy generator 102, catheter 104, or both. Based on data received from sensor 2502, system 100 (e.g., processing circuitry of generator 102, or a separate computing device associated with system 100) is configured to dynamically (e.g., in real-time) adjust energy levels output by generator 102.

For instance, sensor(s) 2502 may include as non-limiting examples: an inflation-fluid flow-rate monitor, an inflation-fluid pressure monitor, a vessel-wall surface monitor, a vessel-diameter monitor, a balloon-diameter monitor, a plaque-fragmentation monitor, or any other type of sensor configured to provide insight regarding a current progress of the IVL procedure. In some examples, sensor 2502 is configured to detect the resonant frequency (e.g., natural frequency or harmonic frequency) of the calcium in the lesion.

Based on real-time monitoring of the sensor data from sensor(s) 2502, system 100 may be configured to dynamically adjust one or more of: an electric-current level, a voltage level, an electric pulse duration or frequency, a light intensity, a light-pulse duration, a light-pulse frequency, or any other suitable parameter affecting an amount or rate of energy delivered via emitter array 112. For the specific example of plaque-lesion resonant frequency, system 100 may be configured to automatically adjust the emitter sonic frequency to match the detected resonant frequency of the lesion to more-effectively fragment the lesion.

In some examples additionally or alternatively to dynamically adjusting energy levels, system 100 is configured to automatically terminate an applied voltage in response to certain conditions being met, including (but not limited to) a threshold fragmentation of the calcified-plaque lesion being achieved or a detected system parameter being outside threshold levels (e.g., a suspected malfunction of balloon 110 or another component).

As one illustrative example, IVL system 100 may be configured to monitor a fluid pressure of balloon 110. For instance, sensor 2502 can include a pressure transducer configured to interact with the inflation lumen 320. Accordingly, system 100 can further include a three-way fluid connector (e.g., catheter hub 306 of FIG. 3) configured to fluidically couple an inflation syringe (e.g., inflation port 310), inflation lumen 320, and a pressure line running back to energy generator 102. The pressure transducer may be integrated into energy generator 102 and fluidically coupled along the pressure line. In some such examples, the fluid line may also include a transducer protector, such as a valve or membrane, configured to prevent the inflation fluid 408, e.g., a saline/contrast-fluid mixture, from entering components of energy generator 102.

As another illustrative example, IVL system 100 (e.g., processing circuitry of energy generator 102 or of another computing device associated with system 100) may be configured to monitor an electrical impedance of one or more components of system 100. When plasma is created within the spark gap 404 between the electrode pair 402 (FIG. 4), the local electrical impedance will drop, thus causing system 100 (upon detection) to terminate the applied voltage. Additionally, or alternatively, system 100 (e.g., measurement unit 216 of FIG. 2) may be configured to monitor an electrical-current level produced by generator 102 as it is output and automatically terminate the applied voltage in response to an above-threshold change in the monitored current.

In other examples, rather than dynamically modifying energy levels (e.g., applied voltage levels, or the like), system 100 may be configured to apply the energy level (e.g., voltage level) as an "all or nothing" (e.g., binary 0 or 1). For instance, system 100 may only transmit energy, at a predetermined level, through catheter 104 while certain conditions are determined to be met, as indicated by data from sensor 2502. Additionally, or alternatively, system 100 may be configured to adjust other parameters. For instance, system 100 may be configured to dynamically adjust a longitudinal length and/or an inflation diameter of balloon 110, as needed.

Figure 26:
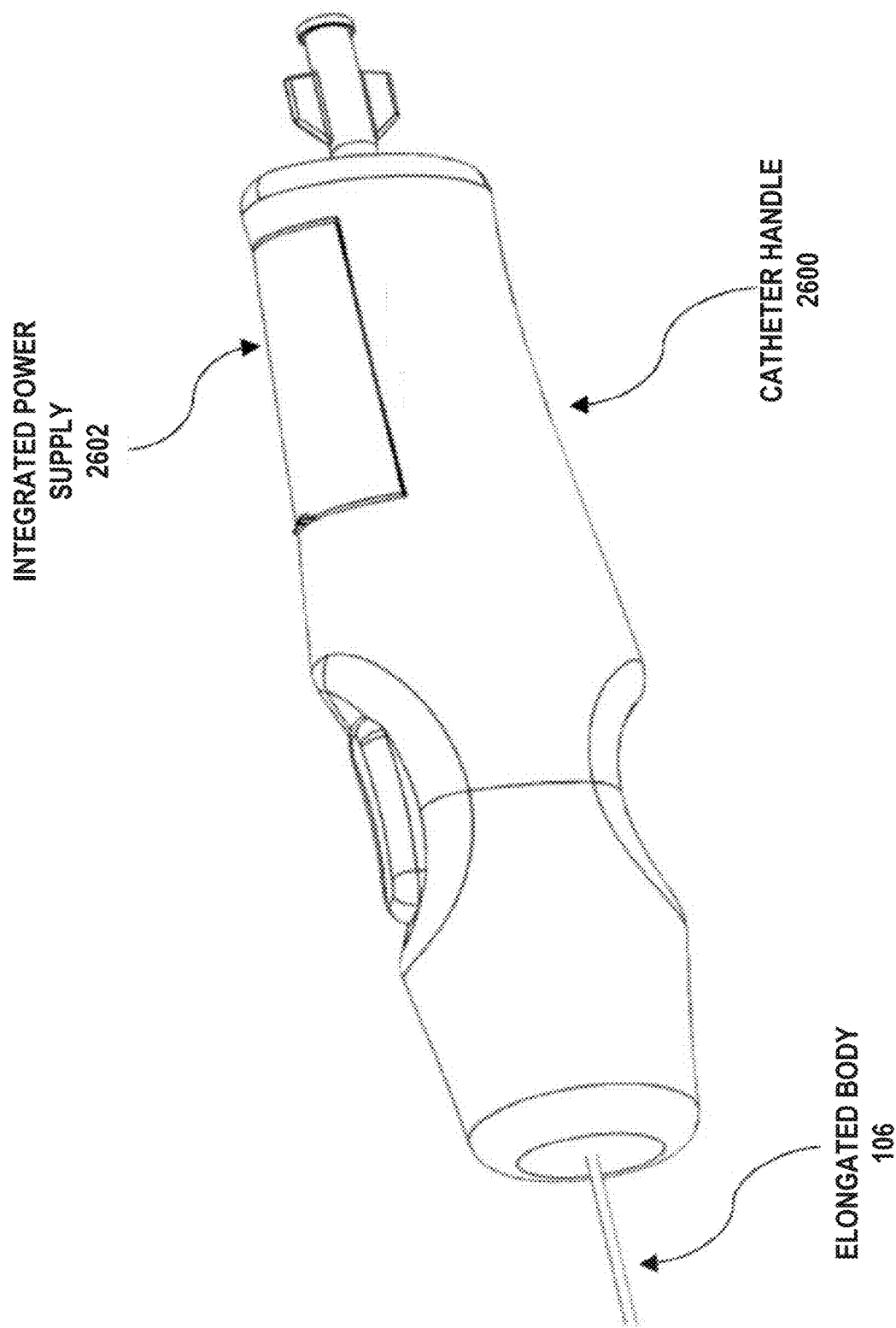
FIG. 26 illustrates an example handle for the IVL catheter of FIG. 1.

FIG. 26 illustrates an example handle 2600 that may be coupled at the proximal portion 302 (FIG. 3) of IVL catheter 104 of FIG. 1. Catheter 104 may include handle 2600 in addition to, or instead of, catheter hub 306 (FIG. 1). In instances in which both hub 306 and handle 2600 are present, handle 2600 may couple to a portion of elongated body 106 extending proximally through hub access port 308.

Existing IVL catheters require a costly generator to power the catheter. In the example shown in FIG. 26, catheter handle 2600 includes an integrated power supply 2602. Power supply 2602 may include a battery, capacitor, or any other suitable integrated power source configured to deliver sufficient power levels to actuate emitter array 112 (FIG. 1). That is, in some examples, system 100 (FIG. 1) may include handle 2600 in place of energy generator 102. In other examples, handle 2600 may be configured to supply supplemental or auxiliary power to emitter array 112. In some examples, catheter 104 may be configured to removably couple to energy generator 102 and function while either connected or disconnected, similar to a laptop or other mobile device.

Typical IVL systems and devices are configured to emit high-energy pressure waves that propagate across all spatial dimensions. This attribute may be relatively effective for ring-like calcified-plaque lesions, e.g., that appear around the entire inner circumference of the vessel wall. However, other lesion configurations are not as effectively treated, or alternatively may waste significant amounts of energy due to the inefficient application of the energy. Accordingly, a number of features and techniques are disclosed herein, enabling IVL device 108 (FIG. 1) to focus the emitted high-energy pressure waves in a particular spatial direction or limited range of directions.

For instance, FIG. 27 is a cross-sectional view of an IVL device 2700 (e.g., IVL device 108 of FIG. 1) having a first example wave director 2702. In some examples, wave director 2702 includes a layer of material oriented along just a portion of the inner circumference of balloon 110 and extending longitudinally (e.g., proximally and distally) through balloon 110. The material is configured to substantially absorb and/or reflect pressure waves that contact the material, thereby reducing energy that is wasted by being channeled in arbitrary directions. As described above, this acoustically opaque material can include, e.g., a ceramic, porcelain, diamond, polyimide, polyether ether ketone (PEEK), a similar material, or any suitable combination thereof.

In the example shown in FIG. 27, wave director 2702 is shown to have a half-moon-shape cross-sectional profile, although other configurations are contemplated. For instance, wave director 2702 may define a substantially semi-circular cross-sectional profile, or alternatively, include a relatively thin reflective layer coated onto the portion of the inner surface of balloon 110.

In some examples, wave director 2702 includes a distinct lumen "pocket" 2704 that can be inflated or deflated as needed with typical balloon angioplasty. In some examples, a fluid pocket 2704 separate from inflation lumen 320 (FIG. 3) is configured to deliver a gas to inflate the pocket 2704 so as not to interfere with inflation of the balloon 110 itself. During use of IVL device 2700, the pressure waves emitted from spark gap 404A will be unable to penetrate the fluid pocket 2704 and will therefore be absorbed and or reflected toward the opposite circumferential direction.

Additionally, or alternatively to an absorbent and/or reflective material, wave director 2702 of FIG. 27 may be or may include at least one of the pair of electrodes 402 (FIG. 4) of an electronic emitter unit 400. For instance, the half-moon-shaped director 2702 may include one or both of the electrodes 402 to directionally focus the emitted pressure waves to fragment a target calcification. In examples in which wave director 2702 includes both a reflective material as well as one or both electrodes 402, the electrode(s) 402 may be positioned radially inward from the reflective material, which may be adhered to the interior surface of balloon 110.

Additionally, or alternatively to the reflective material, in some examples, the compositional material of balloon 110 may be strategically varied to provide for directionally targeted wave emission. For instance, the material of balloon 110 may be configured to be thicker along some portions of the circumference than along other portions. In some examples, the balloon 110 may incorporate a more-transmissive material along a first portion of its circumference and a more-absorbent and/or more-reflective material along a second portion of its circumference.

In some examples, a fluoroscopic wire (e.g., conductive wire 2204, as described above with respect to FIG. 22) or other visual indicator 2704 may be positioned opposite wave director 2702. The visual indicator 2704 helps the clinician orient (e.g., rotate) IVL device 2700 toward the target calcification prior to beginning targeted fragmentation. Also, as described above with respect to FIG. 22, in some examples, piezo elements 2206 can be mounted or expanded to an off-center location (e.g., asymmetrically distributed) onto or within balloon 110, providing an increase in energy to that side. In such examples, the tissue region adjacent the piezo elements 2206 would receive a greater amount of energy, thus enabling directionally targeted lesion fragmentation.

Figure 28B:
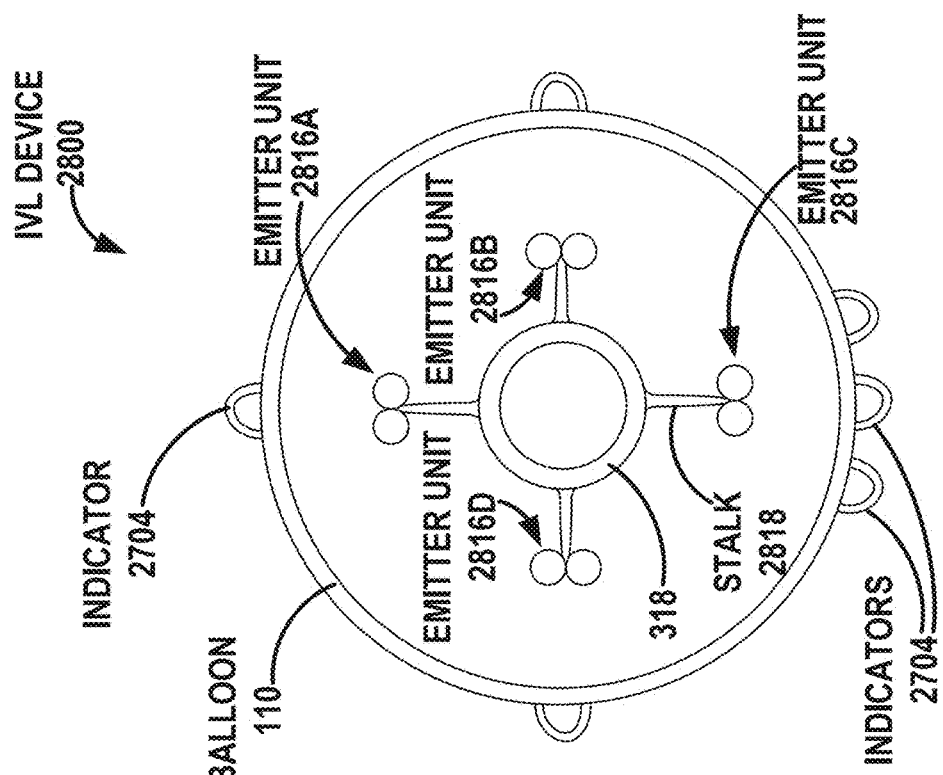
FIG. 28B is a cross-sectional view of a second example directionally focused IVL device.
Figure 28A:
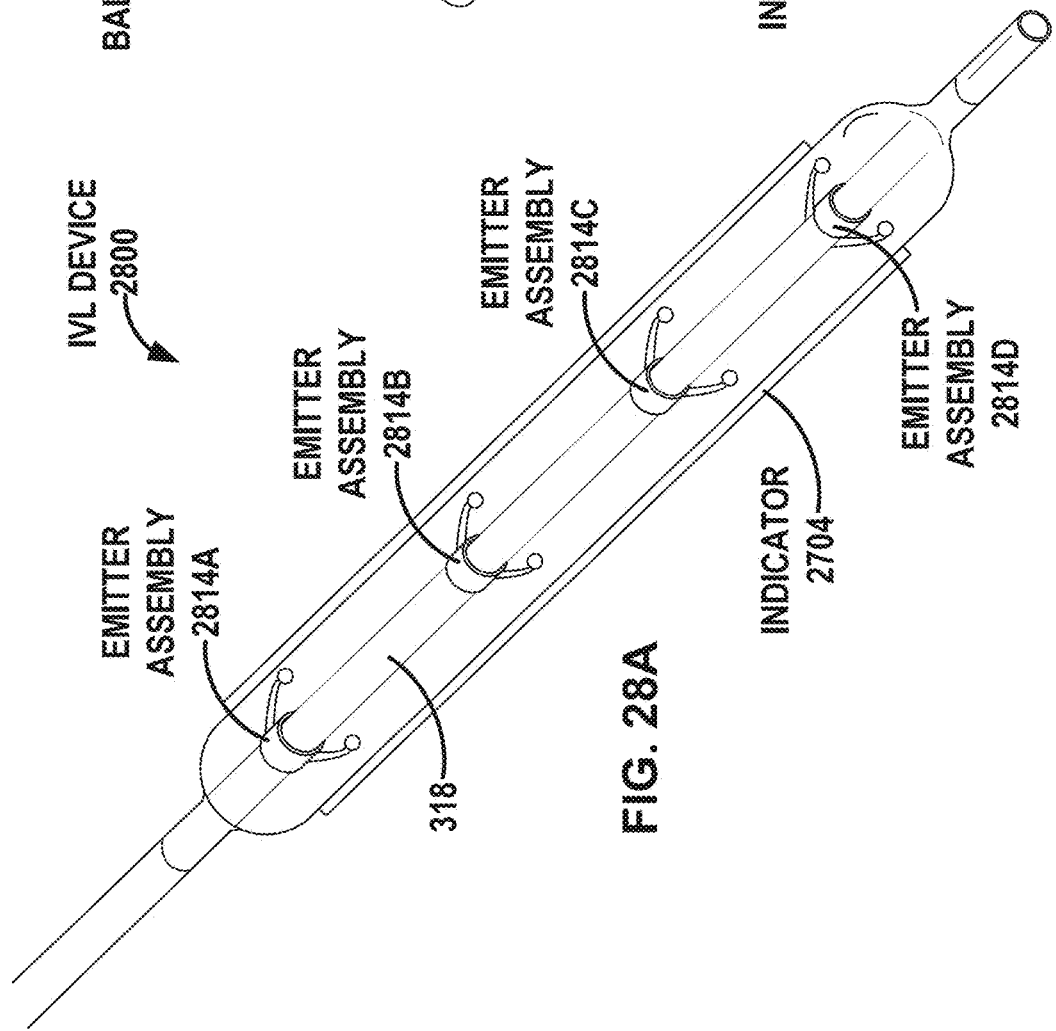
FIG. 28A is a perspective view.

FIG. 28A is a perspective view, and FIG. 28B is a cross-sectional view of a second example directionally focused IVL device 2800 (e.g., IVL device 108 of FIG. 1). IVL device 2800 includes an array of emitter assemblies 2814, wherein each emitter assembly 2814 includes two or more individual emitter units 2816 distributed circumferentially around inner elongated structure 318. Each individual emitter unit 2816 can include an electrode pair, a piezo element, or an optical emitter.

As shown in FIGS. 28A and 28B, emitter units 2816 may be configured to mount or expand to an off-center location within the cross-sectional area of balloon 110, thereby providing an increase in energy delivered to the respective side of balloon 110. In some examples, each individual emitter unit 2816 is configured to be independently actuatable. In other examples, all individual emitter units 2816 of different emitter assemblies 2814 that are aligned along a common longitudinal axis are configured to be commonly actuatable. Additionally, or alternatively, individual emitter units 2816, as mounted on stalks 2818, can be configured to tilt or angle toward and away from inner elongated structure 318, to further control directional energy transmission.

Also, as shown in FIGS. 28A and 28B, IVL device 2800 can include one or more radiopaque visual indicators 2704 to help with device orientation relative to the target treatment site. However, as shown in FIG. 28B, visual indicators 2704 should be asymmetrically distributed about the circumference of balloon 110 to prevent ambiguous balloon-orientation determinations.

FIG. 29A is a perspective view, and FIG. 29B is a cross-sectional view of a third example directionally focused IVL device 2900 (e.g., IVL device 108 of FIG. 1). IVL device 2900 is an example of IVL device 2800 of FIG. 28, except for the differences noted herein. In particular, interventional balloon 110 of IVL device 2900 includes two or more elongated sub-balloons 2902 distributed circumferentially around inner elongated structure 318. Each sub-balloon 2902 is configured to retain a subset of emitter units 2816 that are oriented along a common longitudinal axis. Each emitter-unit subset is configured to be independently actuatable from the other emitter-unit subsets, and the respective sub-balloon 2902 is configured to help apply the emitted pressure waves to a particular portion of the circumference of the interior surface of the target vessel.

In some examples, each sub-balloon 2902 is configured to be individually inflatable, e.g., according to a different inflation rate or amount than the other sub-balloons. In this way, IVL device may be positioned off-center toward a particular portion of the vessel wall (e.g., the calcified lesion). Such examples enable the respective subset of emitter units 2816, including a corresponding scoring member 2102 (FIG. 21), if present, to be positioned even closer to the target treatment site.

As described above, the emitters 2618 can tilt away from the inner elongated structure 318 to be closer to the inner diameter wall of the balloon 110 (e.g., instead of being adjacent to the inner elongated structure 318). Accordingly, the energy delivered by these emitters 2816 can be more focused on the wall of the vessel to which they are positioned closest. This, in combination with a cutting wire (e.g., conductive wire 2204 of fracturing element 2202 of FIG. 22), can create a high-stress focal point to more-efficiently and/or more-effectively break up a nodular calcified lesion.

Additionally, in the examples of FIGS. 28A and 29B, energy generator 102 (FIG. 1) may independently and selectively control the emitters 2816 that reside about the circumference of IVL device 2900. This means that, even without tilting or moving the emitters 2816 in any way, the energy delivery may be controlled by only firing the emitters 2816 closest to the calcified lesion. Additionally, if the treatment presented requires full-circumference energy delivery, all emitters 2816 may still be fired, allowing for a more traditional style of treatment to occur.

It should be noted that these emitters 2816 can all be located within the same balloon 110, as is shown in FIGS. 28A and 28B, or within their own, separate sub-balloons 2902, as shown in FIGS. 29A and 29B. Additionally, while the relative alignments shown in FIGS. 28B and 29B allow for just one array of emitter units, it should be noted that these emitters 2816 can be placed about the catheter throughout the balloon 110, and the quantity of possible emitters is only dictated by the length of the balloon 110 being used.

Figure 30:
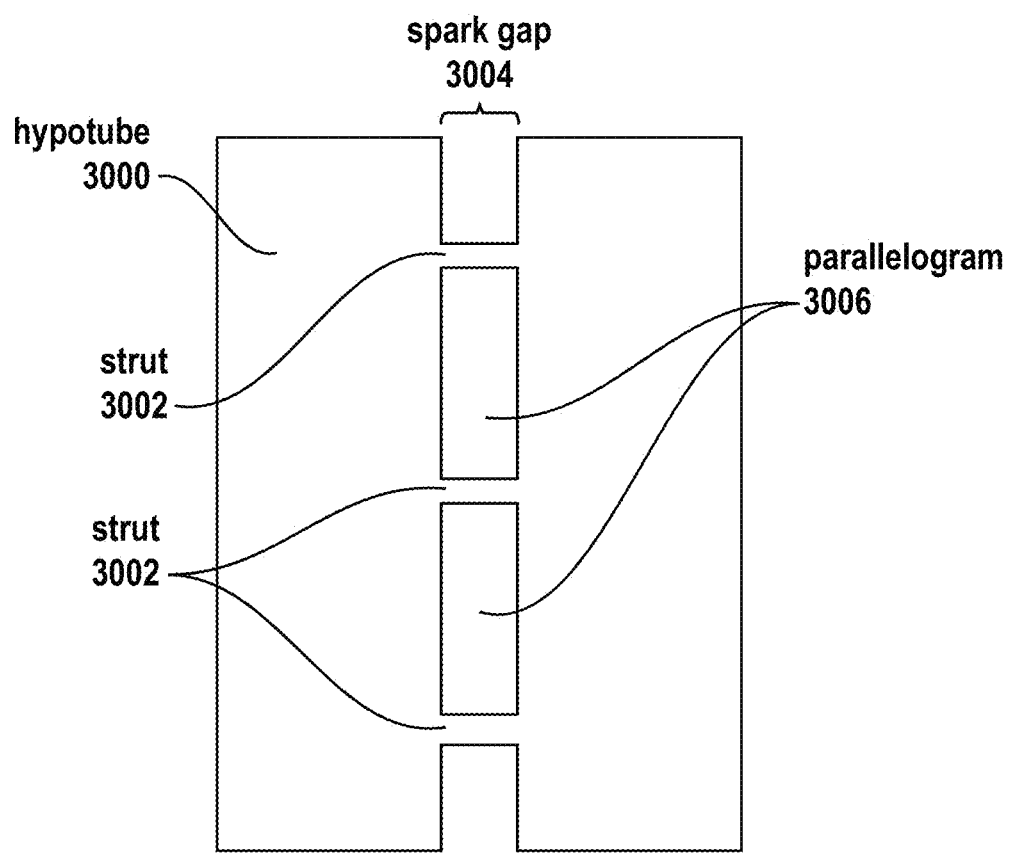
FIG. 30 is a front view of a flattened hypotube.

FIG. 30 illustrates a front view of a flattened hypotube 3000. While the hypotube 3000 may be cut in its elliptical form in practice, it is useful to see the hypotube 3000 in this flattened state to illustrate the geometry of the struts 3002 and cut-out portions. For example, in this view it is clear that the cut-out portions of the hypotube 3000 create parallelograms 3006. While the use of parallelograms 3006 is not necessary, it is a practical, and straightforward shape to cut from a three-dimensional object (such as the rolled hypotube). Additional shapes may also be considered, such as a chevron pattern. Cutting out these parallelograms 3006 creates struts 3002 between two distinct sections of the hypotube 3000 (which will become electrodes as described in FIGS. 33A, 33B, and 34). These struts 3002 bridge the gap between these sections of the hypotube 3000 to provide structure and keep the hypotube 3000 together during implementation onto an elongated body. The gap these struts 3002 bridge will become the spark gap 3004 once the struts 3002 are removed.

For the purposes of this disclosure, it is understood that, while hypotubes and spark gaps are referred to as elliptical, ellipses contain the subset of shapes known as circles. Ellipses are defined as having a major and minor axis, and circles are a special case where the major and minor axis are equal in length. Thus, any recitation of ellipses throughout this disclosure includes the recitation of a circle as well.

Figure 31:
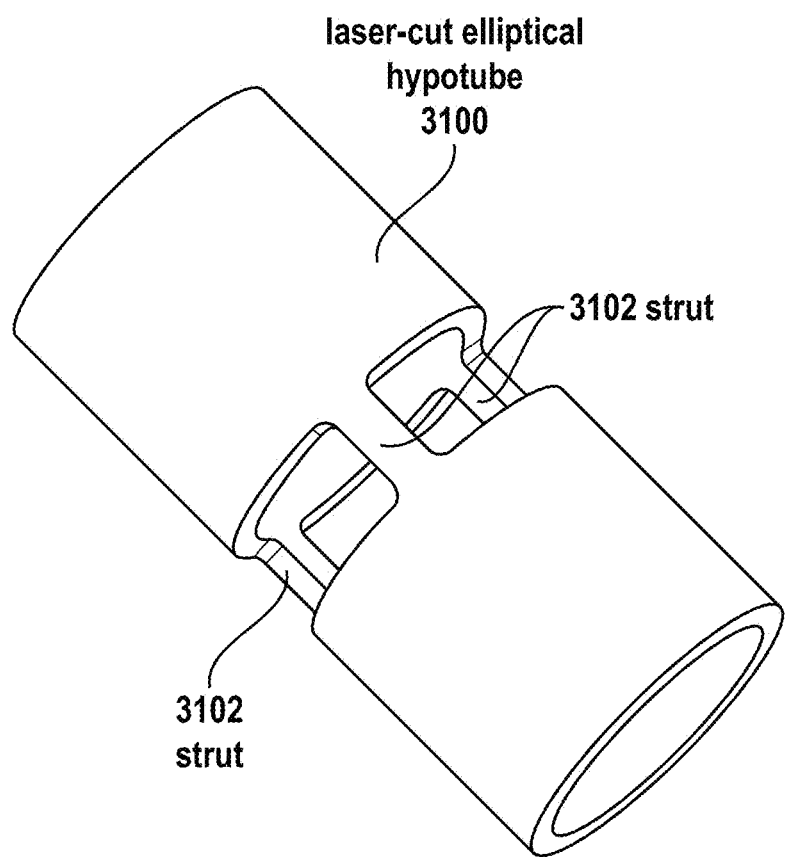
FIG. 31 is a perspective view of a laser-cut elliptical hypotube.

FIG. 31 is a perspective view of a laser-cut elliptical hypotube 3100. As can be seen here, the laser-cut elliptical hypotube 3100 may include struts 3102. FIG. 31 illustrates three struts 3102, similar to the flattened view of the hypotube 3000 in FIG. 30. It is noted, however, that as many struts 3102 as desired may be included without departing from this disclosure. According to some examples, the laser-cut elliptical hypotube 3100 is formed into its elliptical shape prior to the laser-cutting process. In this way, fewer cuts may be necessary in order to form the struts 3102.

Flat designs such as those in FIG. 30 represent cut patterns used by a laser on the hypotube. The hypotube is mounted within the laser cutter such that the laser points inward radially toward the center of the tube. The tube and laser are then rotated and translated relative to one another such that the pattern is wrapped around the tube circumference, thus forming the laser-cut hypotube 3100.

Figure 32A:
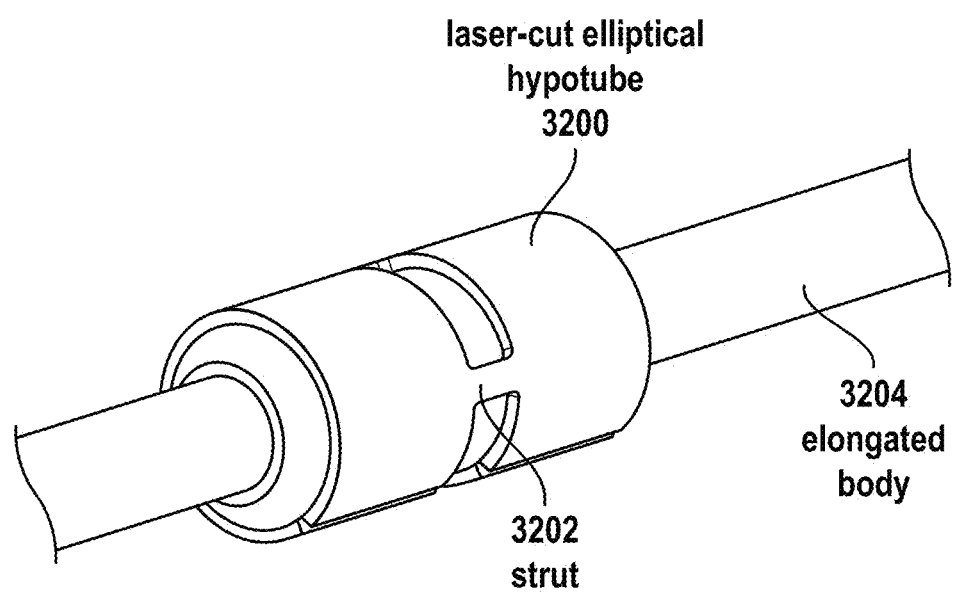
FIG. 32A is a perspective view.
Figure 32B:
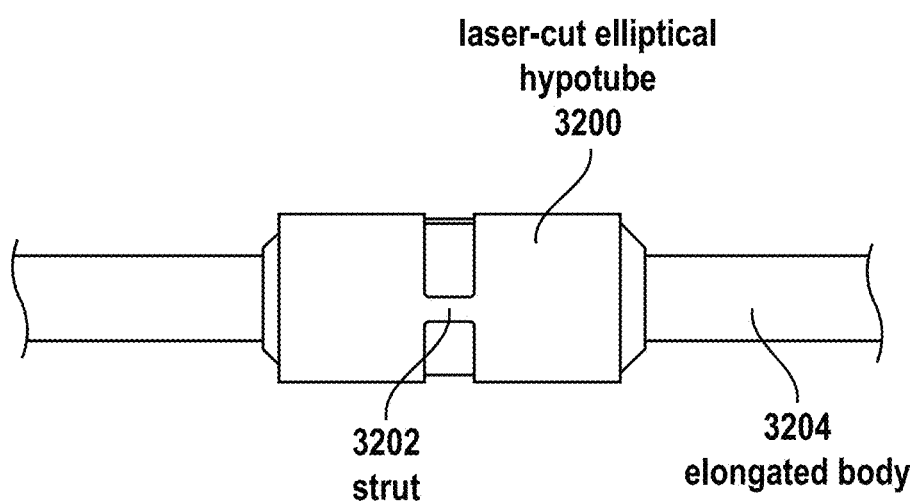
FIG. 32B is a side view of a laser-cut elliptical hypotube as it may appear in use.

FIG. 32A is a perspective view, and FIG. 32B is a side view of a laser-cut elliptical hypotube 3200 (perhaps the laser-cut elliptical hypotube 3100 of FIG. 31) as it may appear after being placed onto an elongated body 3204 (or, stated differently, after an elongated body 3204 has been inserted into the laser-cut elliptical hypotube 3200). Here, the struts 3202 (only one is shown in FIGS. 32A and 32B because the elongated body 3204 is blocking the view of any remaining struts) are still present in the laser-cut elliptical hypotube 3200, and, in some examples, will remain in place until the laser-cut elliptical hypotube 3200 has been adhered to the elongated body 3204.

Figure 33A:
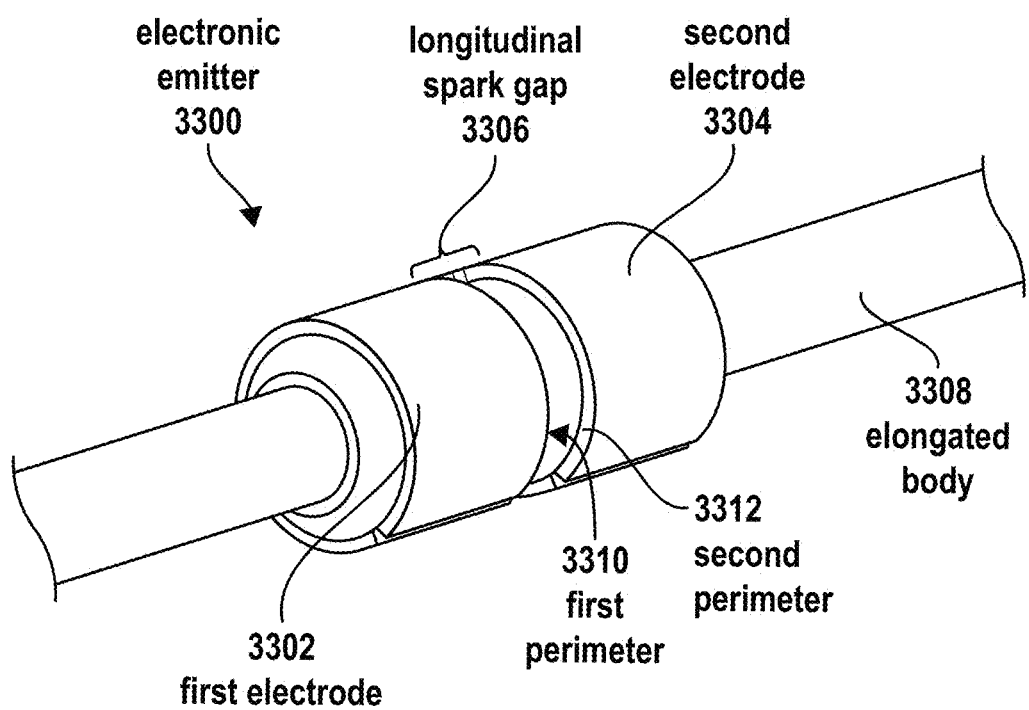
FIG. 33A is a perspective view.
Figure 33B:
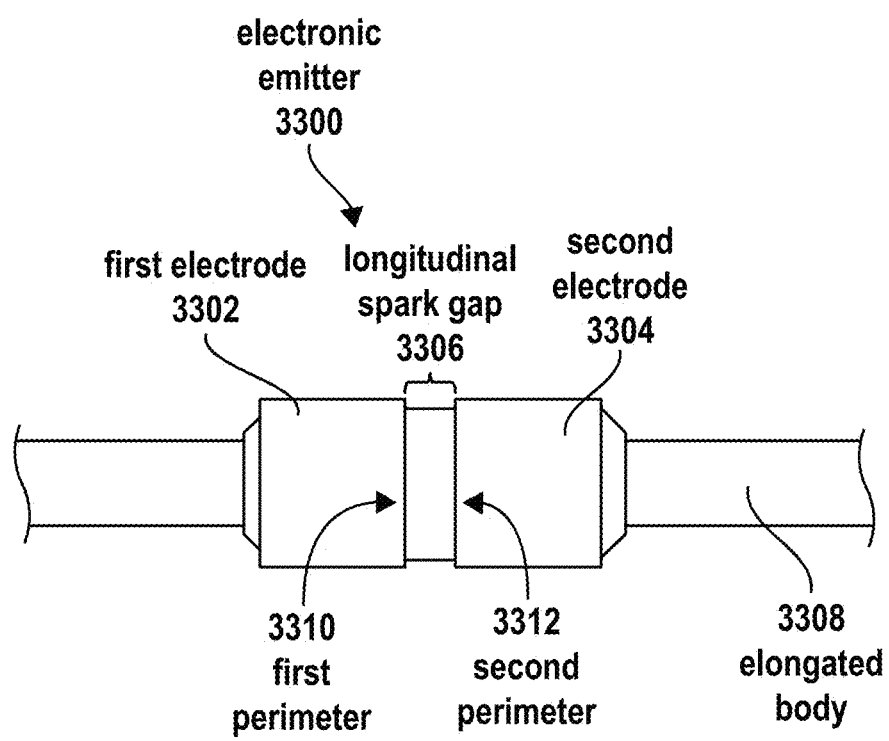
FIG. 33B is a side view of an electronic emitter as it may appear in use.

FIG. 33A is a perspective view, and FIG. 33B is a side view of an electronic emitter 3300 as it may appear after the removal of the struts of the hypotube. The electronic emitter 3300 may include a first electrode 3302 and a second electrode 3304 separated by a longitudinal spark gap 3306. The first electrode 3302 and the second electrode 3304 may lay upon the elongated body 3308, and the longitudinal spark gap 3306 may be longitudinal with respect to this elongated body 3308. In some examples, the first electrode 3302 includes a first perimeter 3310 facing the longitudinal spark gap 3306, and the second electrode 3304 includes a second perimeter 3312, also facing the longitudinal spark gap 3306. The first perimeter 3310 may be parallel to the second perimeter 3312, permitting the longitudinal spark gap 3306 to also be an elliptical spark gap. According to some examples, this allows the spark to arc from the first electrode 3302 randomly about the first perimeter 3310 to the second electrode 3304.

Figure 34:
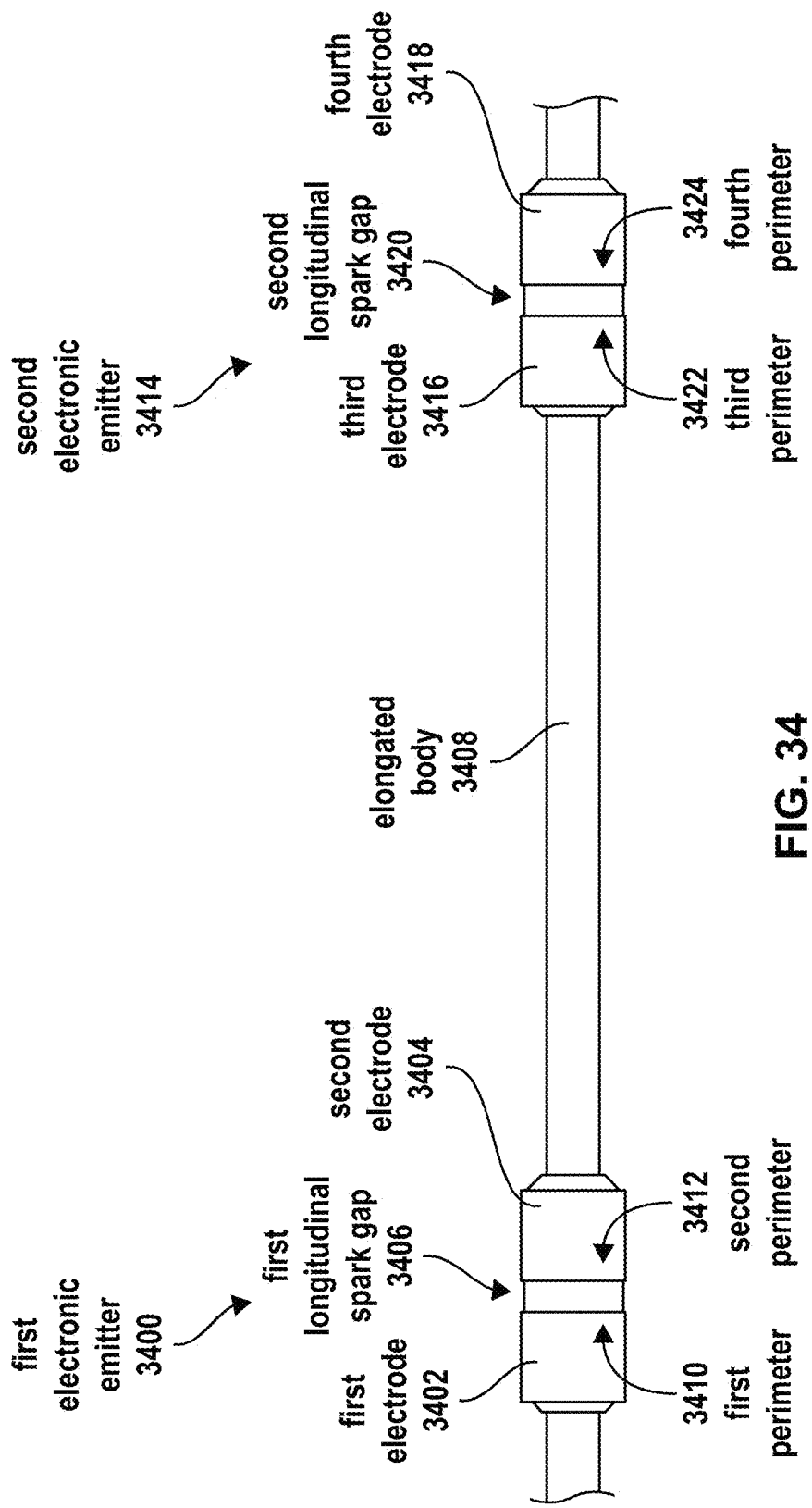
FIG. 34 is a side view of a pair of electronic emitters as they may appear in use.

FIG. 34 is a side view of a pair of electronic emitters as they may appear in use. As seen in FIG. 34, multiple electronic emitters may be used in conjunction in an IVL device, including a first electronic emitter 3400 and a second electronic emitter 3414. As was described previously in FIGS. 33A and 33B, the first electronic emitter 3400 may include a first electrode 3402 and a second electrode 3404 separated by a first longitudinal spark gap 3406. The first electrode 3402 and the second electrode 3404 may lay upon the elongated body 3408, and the first longitudinal spark gap 3406 may be longitudinal with respect to this elongated body 3408. It is understood for the purposes of this disclosure that longitudinal spark gap 3408 refers to the direction of traverse of the arc that is formed. The spark gap may also be considered an elliptical spark gap, or circumferential spark gap, as arcs may form at any point about the circumference of the electrodes. The first electrode 3402 may include a first perimeter 3410 facing the first longitudinal spark gap 3406 and the second electrode 3404 may include a second perimeter 3412, also facing the first longitudinal spark gap. In some examples, the first perimeter 3410 is parallel to the second perimeter 3412, permitting the first longitudinal spark gap 3406 to also be an elliptical spark gap. This may allow sparks to arc from the first electrode 3402 randomly about the first perimeter 3410 to the second electrode 3404.

Similarly, the second electronic emitter 3414 may include a third electrode 3416 and a fourth electrode 3418 separated by a second longitudinal spark gap 3420. The third electrode 3416 and the fourth electrode 3418 may lay upon the elongated body 3408, and the second longitudinal spark gap 3420 may be longitudinal with respect to this elongated body 3408. The third electrode 3416 may include a third perimeter 3422 facing the second longitudinal spark gap 3420 and the fourth electrode 3418 may include a fourth perimeter 3424, also facing the second longitudinal spark gap 3420. According to some examples, the third perimeter 3422 is parallel to the fourth perimeter 3424, permitting the second longitudinal spark gap 3420 to also be an elliptical spark gap. This may allow sparks to arc from the third electrode 3416 randomly about the third perimeter 3422 to the fourth electrode 3418.

The first perimeter 3410, the second perimeter 3412, the third perimeter 3422, and the fourth perimeter 3424 may all be parallel to one another, but this is not strictly necessary. Additionally, while only a first electronic emitter 3400 and a second electronic emitter 3414 are shown, it is understood that as many electronic emitters as are wanted and as can fit within the IVL device may be used.

Additionally, the electronic emitters may be wired separately. For example, a first ground wire may be welded to the first electrode 3402 and a second ground wire may be wired to the third electrode 3416. A common power wire may be wired to both the second electrode 3404 and the fourth electrode 3418. This configuration is similar to the multiple parallel wire configurations explored in FIGS. 15A, 15B, and 16A. In this way, the first electrode 3402 and the third electrode 3416 may be powered individually, permitting selective firing of the electronic emitters, while still limiting the necessary number of wires by grounding all electronic emitters together. As stated above, there may be more than two electronic emitters present in the invention, and this individual powering and group grounding of electronic emitters may still be utilized with as many electronic emitters as desired. It is understood that, due to the nature of parallel circuits, the described configuration may be achieved by reversing the power and ground wires, such that there are individual power wires for each electrode, and a common ground wire, as described in FIGS. 15A and 15B.

Figure 35A:
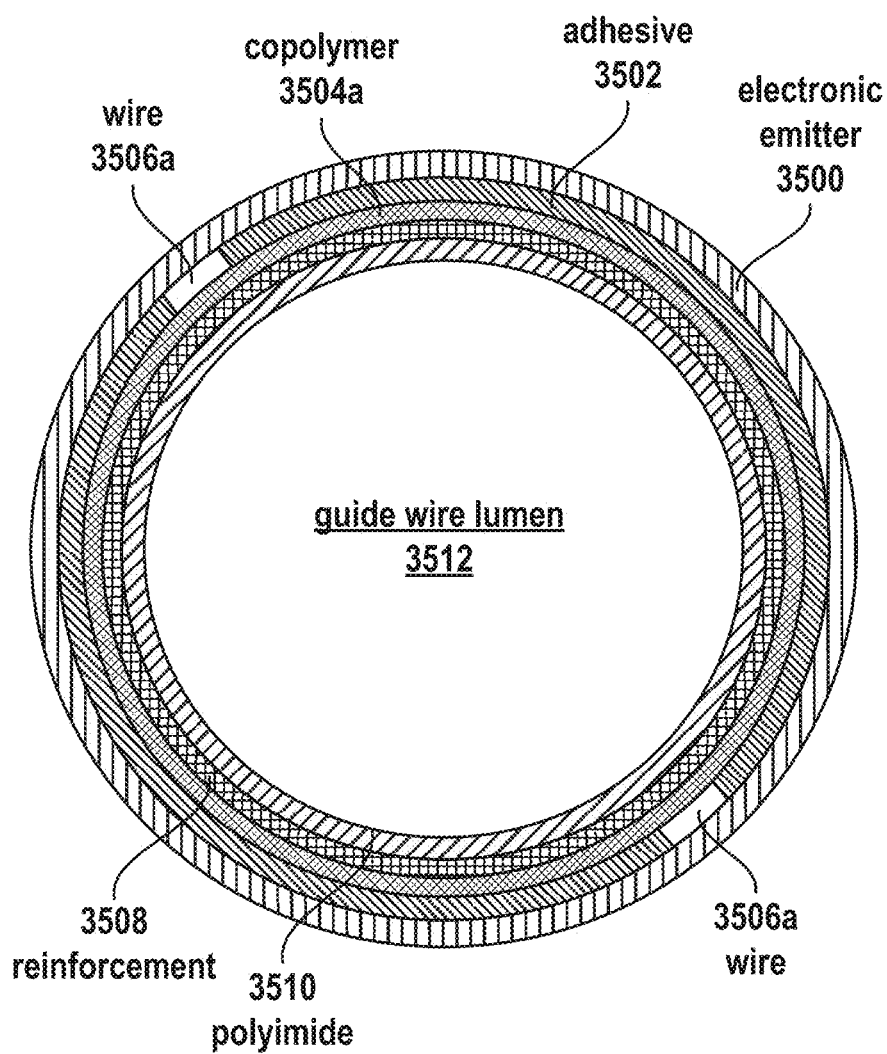
FIG. 35A is a cross-sectional diagram of an IVL device.

FIG. 35A is a cross-sectional diagram of an IVL device including an electronic emitter 3500. As is shown in FIG. 35A, the IVL device includes an "inner" portion, and an "outer" portion. The electronic emitter 3500 is part of the outer portion, and in non-adjacent relation to the guide wire lumen 3512. The electronic emitter 3500 may be welded to a wire 3506a (shown here as a flat, or rectangular wire), and this subassembly then adhered to the inner portion via a layer of adhesive 3502 (e.g., potting material). The inner portion may be a stack of copolymer 3504a, reinforcement 3508, and polyimide 3510, which form the elongated body of the catheter upon which the electronic emitters 3500 reside. While the inner portion is described as this stack of copolymer 3504a, reinforcement 3508, and polyimide 3510, it is understood that additional components may be used, or components left out. For instance, in some examples, the inner portion does not include reinforcement 3508, such as the example shown in FIG. 35B. In additional examples, the inner core includes a polyimide/polytetrafluoroethylene (ptfe) blend for improved lubricity in the inner diameter of the device.

In examples including a layer of reinforcement 3508, the reinforcement 3508 may be a nonmetallic material, such as polyetheretherketone (PEEK). In other examples, the reinforcement 3508 may be made from Kevlar fibers. In still other examples, the reinforcement 3508 may be made from high-density polyethylene fibers. These high-density polyethylene fibers may be either metallic or non-metallic. The reinforcement 3508 may further be an electrical conductor.

Figure 35B:
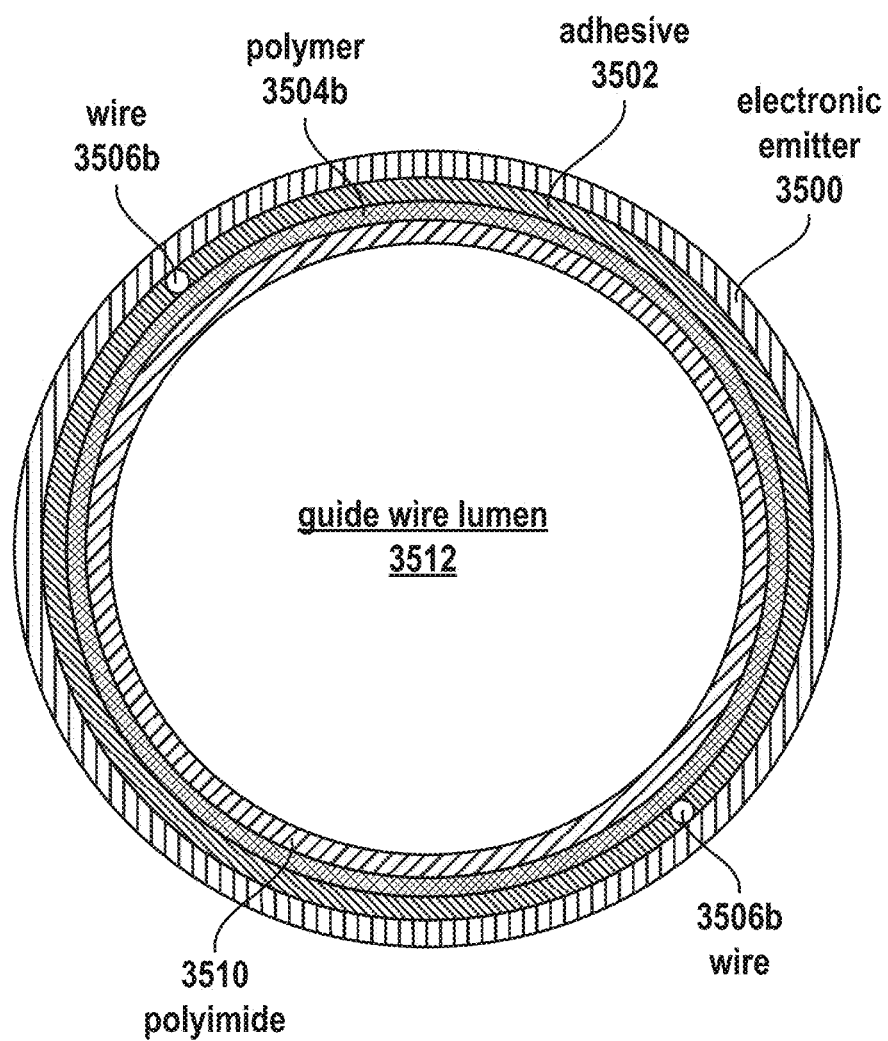
FIG. 35B is a cross-sectional diagram of another example IVL device.

FIG. 35B is an additional cross-sectional diagram of an electronic emitter 3500. The electronic emitter 3500 is a part of the outer portion and in non-adjacent relation the guide wire lumen 3512. Also, the electronic emitter 3500 can be welded to a wire 3506*b* (shown in FIG. 35B as a rounded wire as opposed to the flat wire illustrated by FIG. 35A), and is then adhered to the inner portion via a layer of adhesive 3502 (e.g., potting material). FIG. 35B illustrates an inner portion that is only made of a stack of polymer 3504*b* and polyimide 3510. It is additionally understood that copolymer 3504*a* and polymer 3504*b* are synonymous. In some examples, the polyimide 3510 is doped polyimide. This doped polyimide can be non-metallic.

Figure 36:
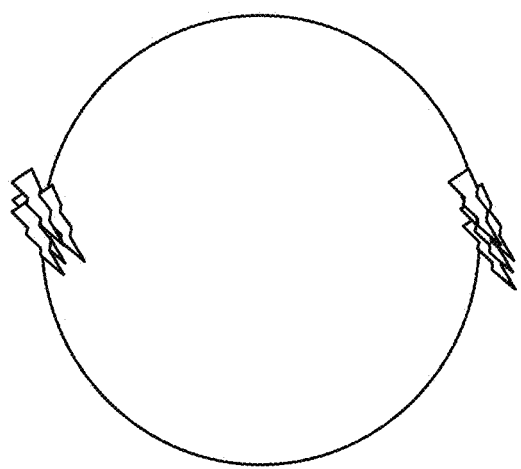
FIG. 36 is a cross-sectional illustration of a spark gap.

FIG. 36 is a cross-sectional illustration of a spark gap. Some IVL devices use two-point electrodes to create the arc that causes cavitation bubbles to occur. In these devices, the arc reoccurs between the same two points repetitively. Every time an arc occurs, degradation occurs at the location of the spark. Over time, this repeated degradation at a single location may lead to failure of the emitter, limiting the lifetime of the device.

Figure 37:
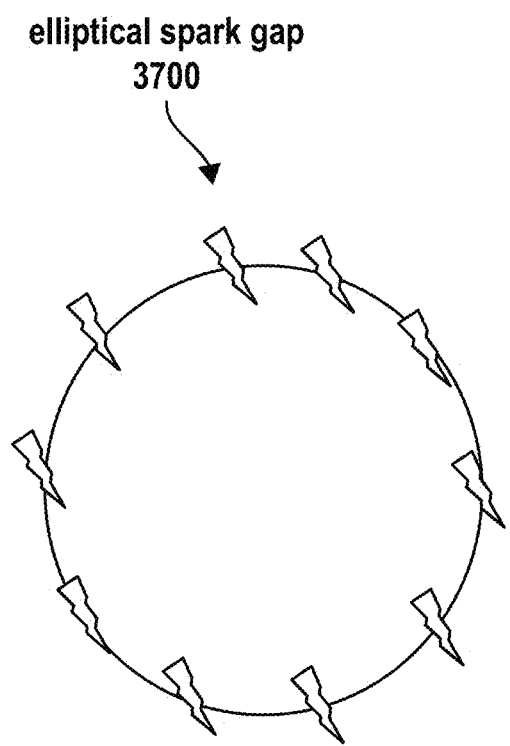
FIG. 37 is a cross-sectional illustration of an elliptical spark gap.

FIG. 37 is a cross-sectional illustration of an elliptical spark gap 3700, as disclosed in the present invention. This elliptical spark gap 3700 permits the arc to form anywhere around the perimeter of the electrode. This arc is perpetuated randomly about the electrode perimeter, and may tend to occur at portions of least degradation. Because the arc is not limited to specific points (both of creation and grounding), the associated degradation at any one location may accumulate more slowly, increasing the number of pulses before emitter failure. This may increase the life expectancy of an IVL device, and thus minimize the number of replacements needed. Additionally, this may increase the number of pulses a clinician is able to deliver. This random arc location may also provide for more consistent delivery of acoustic pressure over the course of delivery. The non-directional nature of cavitation means that this random firing may also provide for a more uniform field of treatment circumferentially.

Figure 38A:
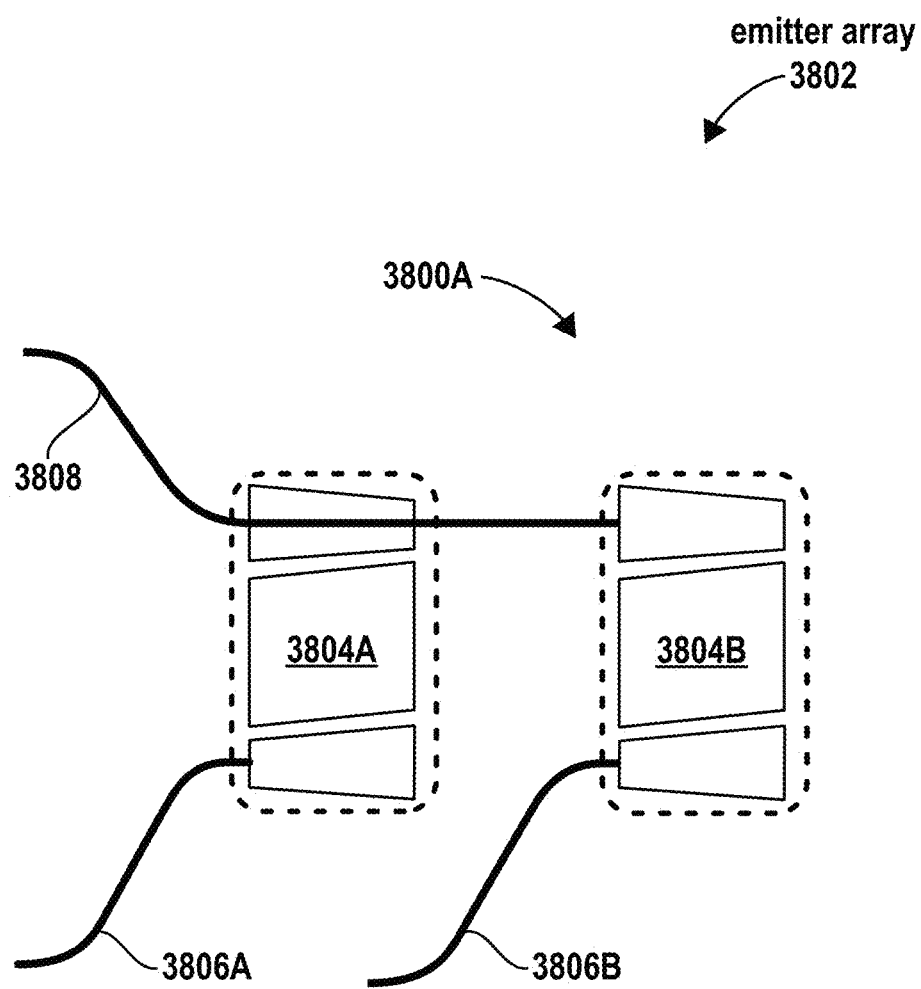
FIG. 38A is a conceptual diagram illustrating an example wiring configuration for an electronic-emitter array having two emitter units.

FIG. 38A is a conceptual diagram illustrating a first wiring configuration 3800A for an emitter array 3802 having two electrode pairs 3804, and goes into further detail about the parallel wiring configuration as shown in FIGS. 15A, 15B, and 16A. Like these preceding figures, FIG. 38A shows the electrode pairs 3804 wired according to the aforementioned "n+1" wiring configuration while wired in parallel. In some examples, such as in the schematic of FIG. 38A, the first electrode pair 3804A receives a first ground wire 3806A, and the second electrode pair 3804B receives a second ground wire 3806B. These power wires 3806 are coupled to their respective electrode pair 3804 through means such as welding. The first electrode pair 3804A and the second electrode pair 3804B are both coupled to the same power wire 3808. In this way, the first electrode pair 3804A and the second electrode pair 3804B may be provided power independently. Example benefits of this parallel wiring configuration include the ability to transmit a higher electrical current across each electrode pair 3804. Additionally, because each electrode pair 3804 is individually powered, each electrode pair 3804 may also be individually actuated (or "fired"). In some examples, a parallel wiring configuration reduces the total resistance of the IVL system, as individually powering one electrode pair 3804 may reduce the necessary number of resistors needed to generate an electrical current.

Figure 38B:
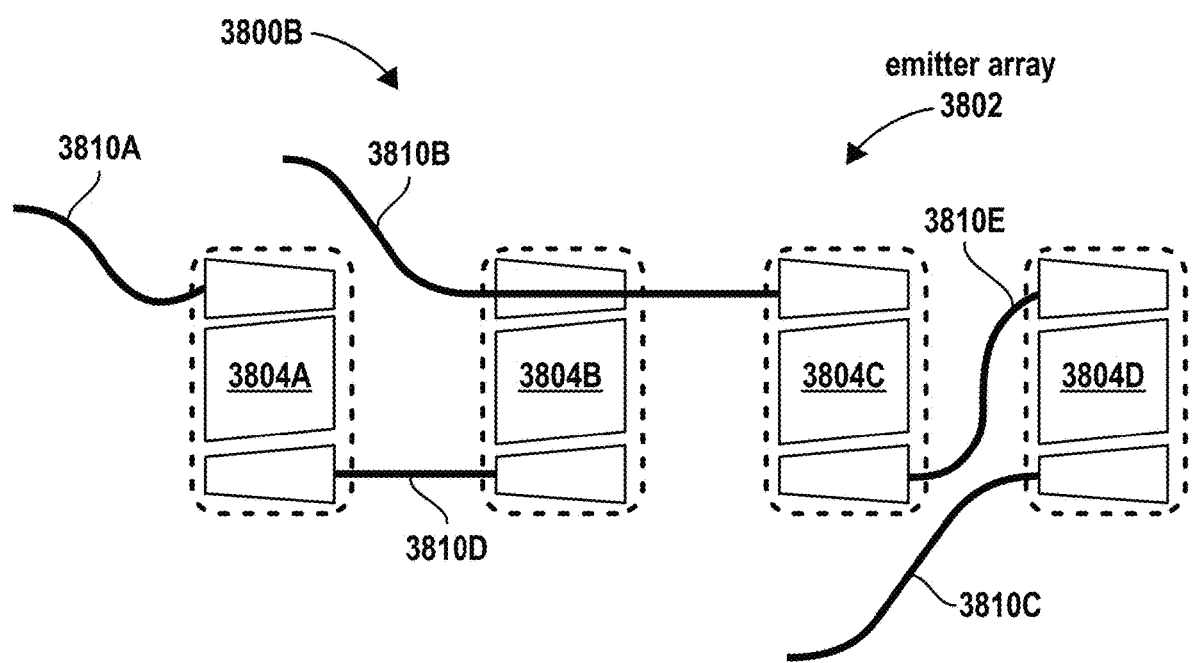
FIG. 38B is a conceptual diagram illustrating an example wiring configuration for an electronic-emitter array having four emitter units.

FIG. 38B is a conceptual diagram illustrating a second wiring configuration 3800B for an emitter array 3802 having four electrode pairs 3804, and goes into further detail about the wiring configuration as shown in FIG. 16B. In this second wiring configuration 3800B, a combination of both parallel and serial wiring techniques may be implemented, enabling advantages of both configurations. For instance, first electrode pair 3804A and second electrode pair 3804B are connected in series, whereas other electrode pairs 3804 are connected in parallel.

In particular, such a second wiring configuration 3800B enables the clinician to simultaneously acuate: (1) electrode pairs 3804A-3804D; (2) electrode pairs 3804C and 3804D; and (3) electrode pairs 3804A and 3804B. For the instance of these three examples, it is understood that any use of the term "ground wire" or "power wire" is not limiting, and those wires can be either not used in the circuit at all, or be used for purposes other than their descriptive name. As will be seen in example (1), a "ground wire" may also be a connecting wire and only serve as a conduit between electrode pairs.

For the case of example (1): power may come in through power wire 3810C, arc across fourth electrode pair 3804D, travel through second connecting wire 3810E to third electrode pair 3804C, arc across third electrode pair 3804C, traverse second ground wire 3810B which is not connected to ground for this example, arc across second electrode pair 3804B, cross first connecting wire 3810D, arc across first electrode pair 3804A, and then take the first ground wire 3810A to complete the circuit.

For example (2): power may come in through power wire 3810C, arc across fourth electrode pair 3804D, travel through second connecting wire 3810E to third electrode pair 3804C, arc across third electrode pair 3804C, and then take the second ground wire 3810B, bypassing the second electrode pair 3804B, in order to complete the circuit.

Finally, for example (3): power may come in through second ground wire 3810B (in this example, not a ground wire) arc across second electrode pair 3804B, traverse first connecting wire 3810D, arc across first electrode pair 3804A, and then take the first ground wire 3810A in order to complete the circuit.

FIG. 38B is not intended to be limiting-any suitable wiring combination for electrode pairs 3804 is contemplated and encompassed herein. Additionally, as seen in the above examples, electricity may be caused to flow in either direction through the circuit, as desired.

Figure 39:
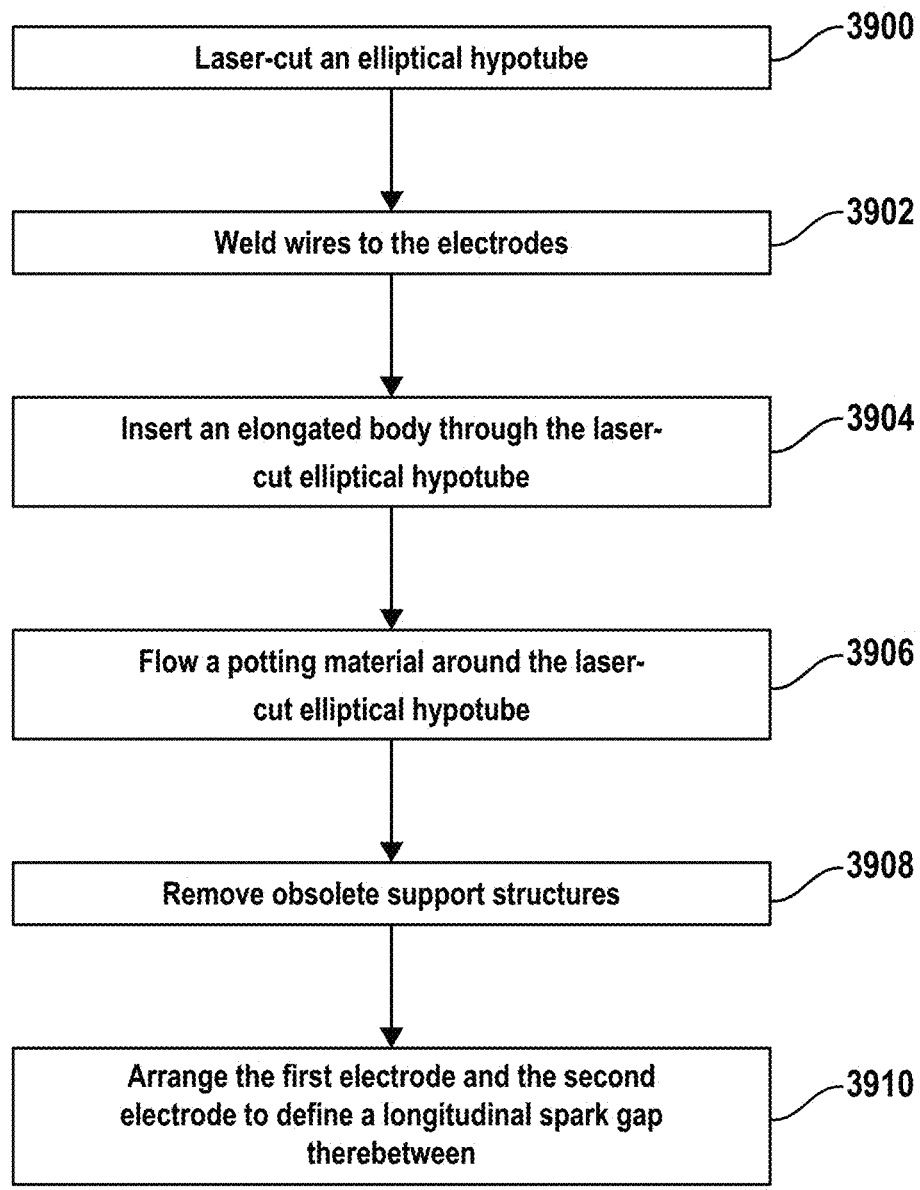
FIG. 39 is a flowchart illustrating an example technique for forming an emitter assembly for an IVL catheter.

FIG. 39 is a flowchart illustrating an example technique for forming an emitter assembly for an IVL catheter. Such a method may include laser-cutting an elliptical hypotube (at step 3900). This laser-cutting may create first and second electrodes separated by a longitudinal spark gap. Struts may be left in to support the hypotube until it is in the correct position, but these struts can be removed later on, as described below. It is also important to note, in this step, that the hypotube is in its elliptical form already, prior to being cut. According to some examples, the method includes welding wires to the electrodes (at step 3902). This allows the electrodes to receive a voltage (through a first wire), which causes the arc to form, and then return the voltage to ground (through a second wire).

In some examples, the method includes inserting an elongated body through the laser-cut elliptical hypotube (at step 3904). In this step, the elongated body (i.e., a catheter) is inserted into the hypotube, thus placing the hypotube into its correct position. While this step occurs prior to the removal of support structures (i.e., struts), this order is not necessary, and the removal of support structures may occur prior to the placement of the hypotube about the elongated body.

According to some examples, the method includes flowing a potting material around the laser-cut elliptical hypotube (at step 3906). This potting material may keep the hypotube in place with respect to the elongated body. The potting material may be an adhesive. The method may include removing obsolete support structures (at step 3908). As described above, the struts may be removed to create an elliptical spark gap around the entire perimeter of the electrodes. Additionally, this removal of obsolete support structures may separate the electrodes by a predetermined distance from one another.

In some examples, the method includes arranging the first electrode and the second electrode to define a longitudinal spark gap therebetween (at step 3910). While the spark gap was defined as elliptical in the preceding paragraph, it may also be longitudinal. The electrodes may be separated from one another longitudinally about the elongated body, thus creating a spark gap that is both longitudinal with respect to the elongated body, as well as elliptical around the perimeter of the electrode.

Figure 40:
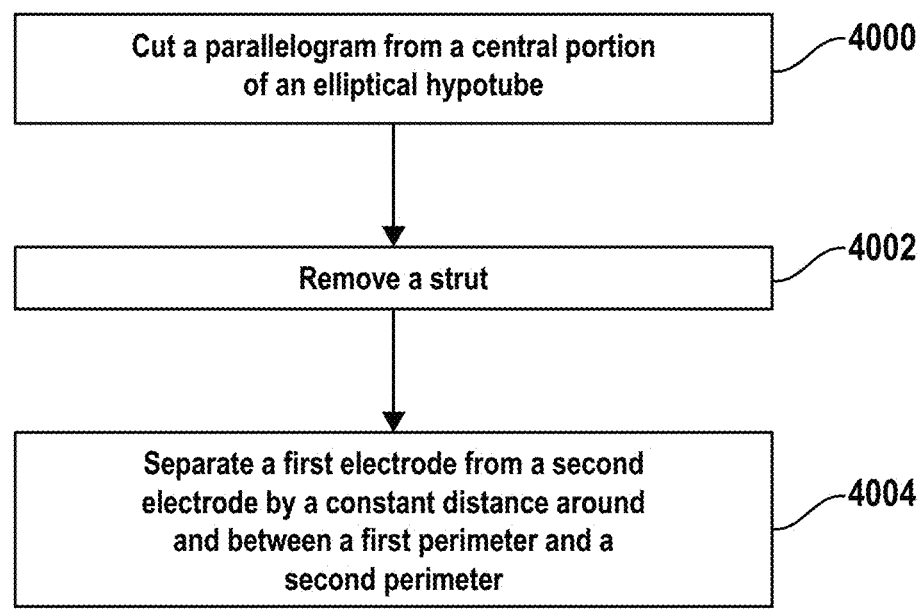
FIG. 40 is a flowchart illustrating an example technique for forming electrodes from a hypotube.

FIG. 40 is a flowchart illustrating another, or further example, technique for forming electrodes from a hypotube. In some examples, the method includes cutting a parallelogram from a central portion of an elliptical hypotube (at step 4000). While a parallelogram is not strictly necessary as the shape to be cut, it is a practical shape to use due to its symmetrical nature. According to some examples, the method may include removing a strut (at step 4002). As referred to above, the obsolete support structures may include struts, which, when removed, allow the two electrodes to be completely separated from one another, while maintaining a predetermined distance from one another.

The method may include separating a first electrode from a second electrode by a constant distance around and between a first perimeter and a second perimeter (at step 4004). By removing the strut(s) between the electrodes, the electrodes become separated. If the electrodes are already adhered in place (such as in FIG. 39 when the potting material was placed), the electrodes will maintain this constant distance from one another. Because the struts used may all be equal in length, the gap between the electrodes may also be equal about the entirety of the perimeter, thus maintaining a constant distance between the perimeters of each electrode.

Figure 41:
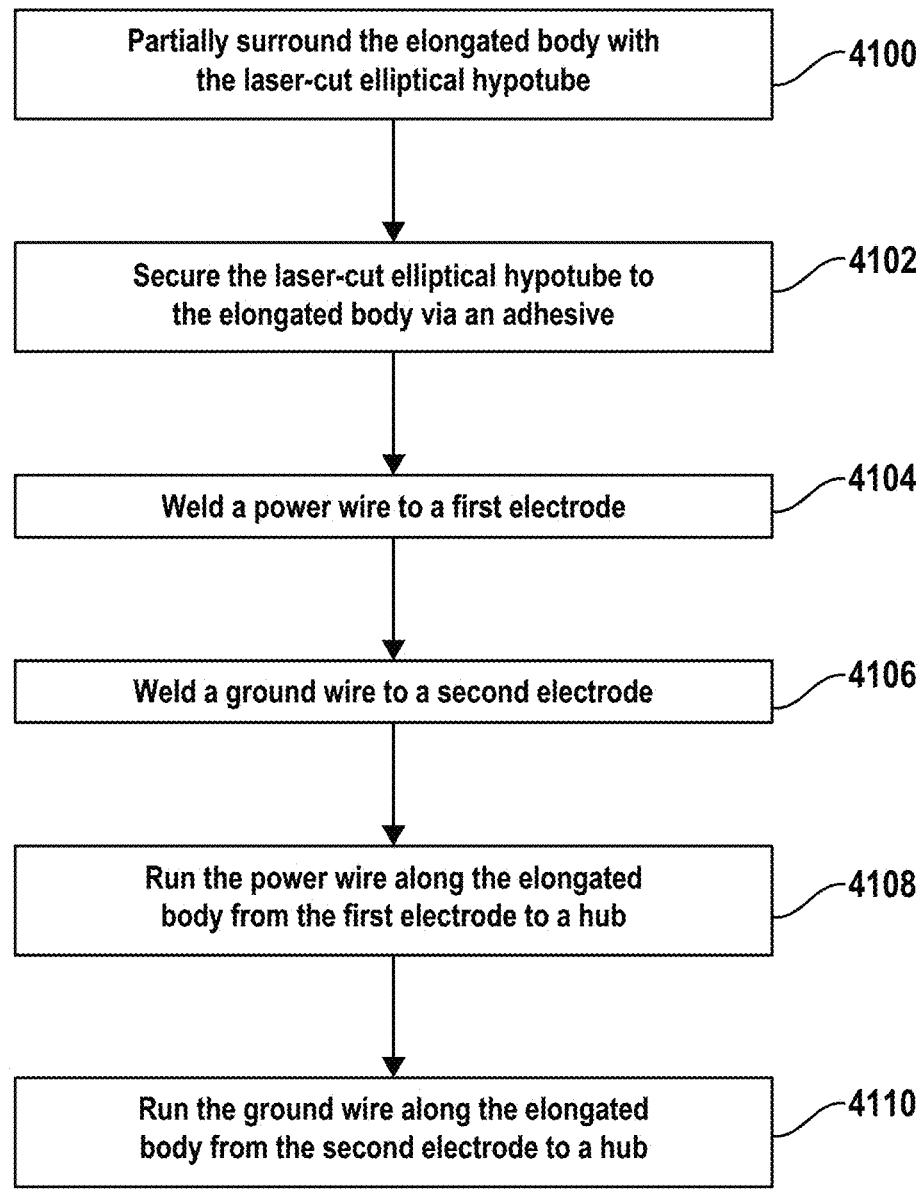
FIG. 41 is a flowchart illustrating an example technique for wiring electrodes in an IVL catheter.

FIG. 41 is a flowchart illustrating an example technique for wiring electrodes in an IVL catheter. In some examples, the method includes partially surrounding an elongated body with a laser-cut elliptical hypotube (at step 4100). While defined throughout as "circles" or "ellipses," it is understood that any shape hypotube that surrounds the elongated body to any extent, and thereby creates constant distance separation between electrodes, will create a spark gap that follows the perimeter of these electrodes. According to some examples, the method includes securing the laser-cut elliptical hypotube to the elongated body via an adhesive (at step 4102). The adhesive (or potting material as described above) may keep the hypotube in place with respect to the elongated body, thus preventing the electrodes, once formed, from moving with respect to one another.

The method may include welding a power wire to a first electrode (at step 4104). This power wire may be used to supply power to the first electrode, thus creating the spark that can arc to the second electrode, which creates the cavitation of the bubble. In some examples, the method includes welding a ground wire to a second electrode (at step 4106). This ground wire may complete the circuit, permitting the electricity provided by the power wire to return to the ground.

According to some examples, the method includes running the power wire along the elongated body from the first electrode to a hub (at step 4108). The power wire may also be secured in place along the elongated body to prevent movement. The method may include running the ground wire along the elongated body from the second electrode to a hub (at step 4110). Similarly, the ground wire may be secured in place along the elongated body to prevent movement. While only one power wire is described in this method, the use of more electronic emitters, and thus more electrodes, may either use one power wire (wired in series) or multiple power wires (wired in parallel to separate electrodes). The benefits of multiple power wires have been explored above and will be described again in the method of FIG. 43 below.

Figure 42:
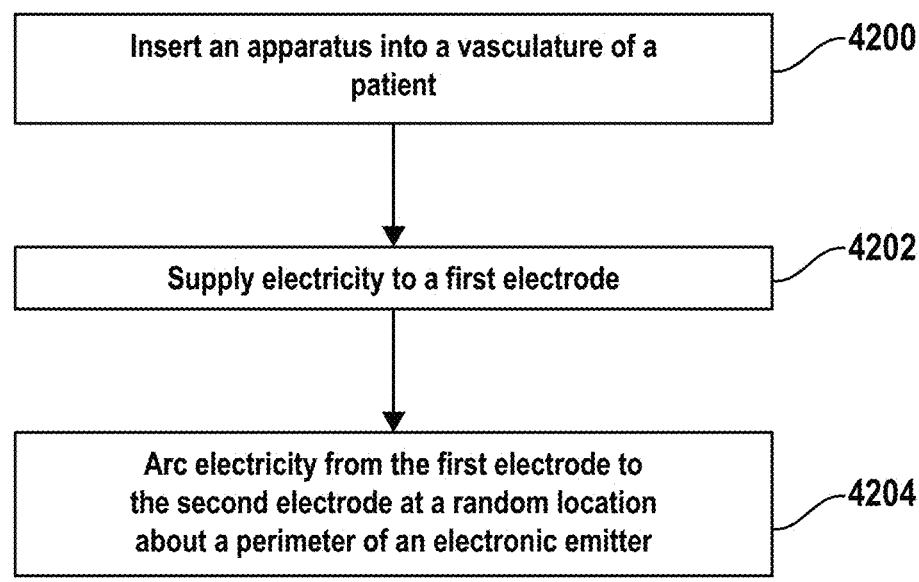
FIG. 42 is a flowchart illustrating an example method of using an IVL catheter.

FIG. 42 is a flowchart illustrating an example method of using an IVL catheter. In some examples, the method includes inserting an apparatus into a vasculature of a patient (at step 4200). Inserting the apparatus into the vasculature of the patient may also include locating the apparatus at a treatment site in which the apparatus is to be used. According to some examples, the method includes supplying electricity to a first electrode (at step 4202). As described previously, this electricity causes the arc across a spark gap which creates cavitation bubbles.

The method may include arcing electricity from the first electrode to a second electrode at a random location about a perimeter of an electronic emitter (at step 4204). Because the arcing occurs randomly about the perimeter, no single spot of the electrodes of the electronic emitter is subject to constant arcing, thus possibly reducing degradation of the device due to repeated arcs from a single point, and increasing the life expectancy of the apparatus as a whole.

Figure 43:
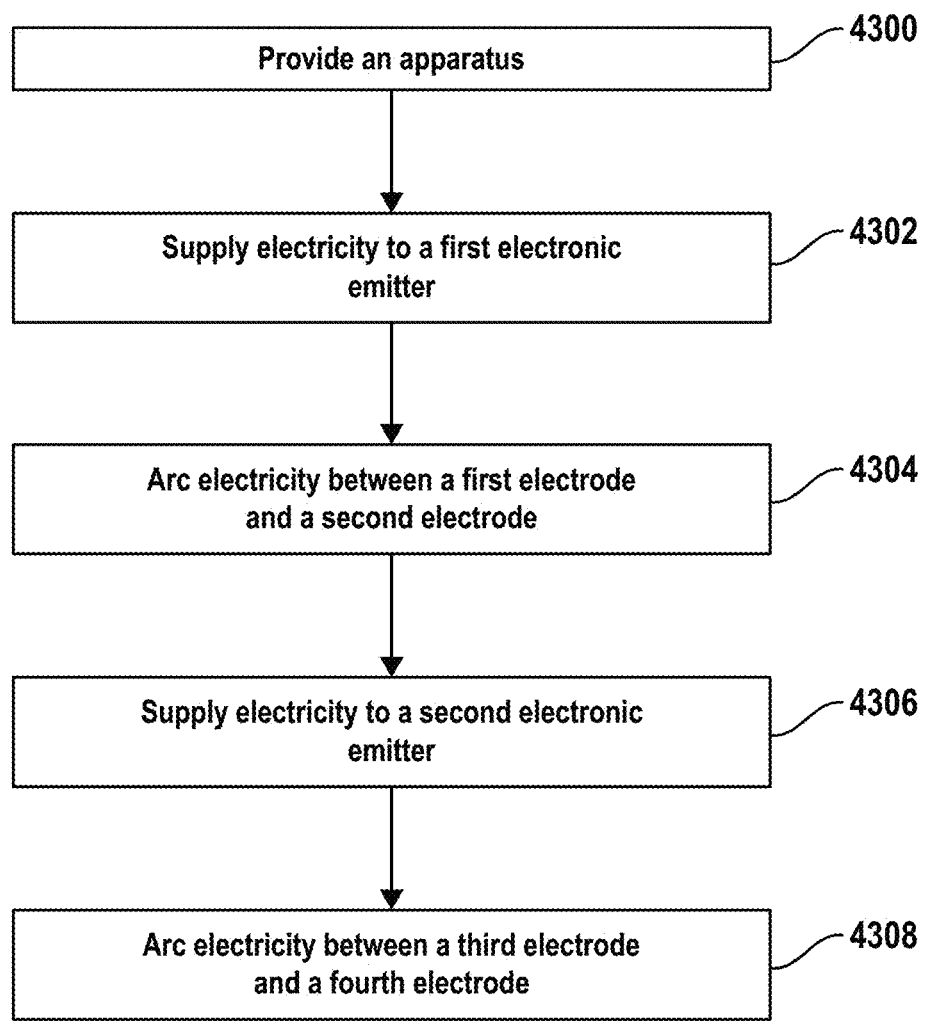
FIG. 43 is a flowchart illustrating an example method of using a multiple emitter IVL catheter.

FIG. 43 is a flowchart illustrating an example method of using a multiple emitter IVL catheter. In some examples, the method includes providing an apparatus (at step 4300). The apparatus may be any of the apparatuses described in this application, as well as any other apparatus that may be suited for IVL.

According to some examples, the method may include supplying electricity to a first electronic emitter (at step 4302). The electronic emitter may include first and second electrodes, across which the electricity can arc. The method may include arcing electricity between a first electrode and a second electrode (at step 4304). As previously described, the electricity is used to arc across a spark gap between the first electrode and the second electrode, thus creating cavitation bubbles.

In some examples, the method includes supplying electricity to a second electronic emitter (at step 4306). The second electronic emitter may be longitudinally separated from the first electronic emitter. Additionally, the second electronic emitter may be independently wired (by a power wire) from the first electronic emitter. This independent wiring may allow for selective powering of the electronic emitters, thus permitting the electronic emitters to arc and create cavitation bubbles in specific patterns, or as desired by a user, as described below in FIG. 44. According to some examples, the method includes arcing electricity between a third electrode and a fourth electrode (at step 4308). As with the first electrode and the second electrode, the electricity is used to arc across a spark gap between the third electrode and the fourth electrode, thus creating cavitation bubbles.

Figure 44:
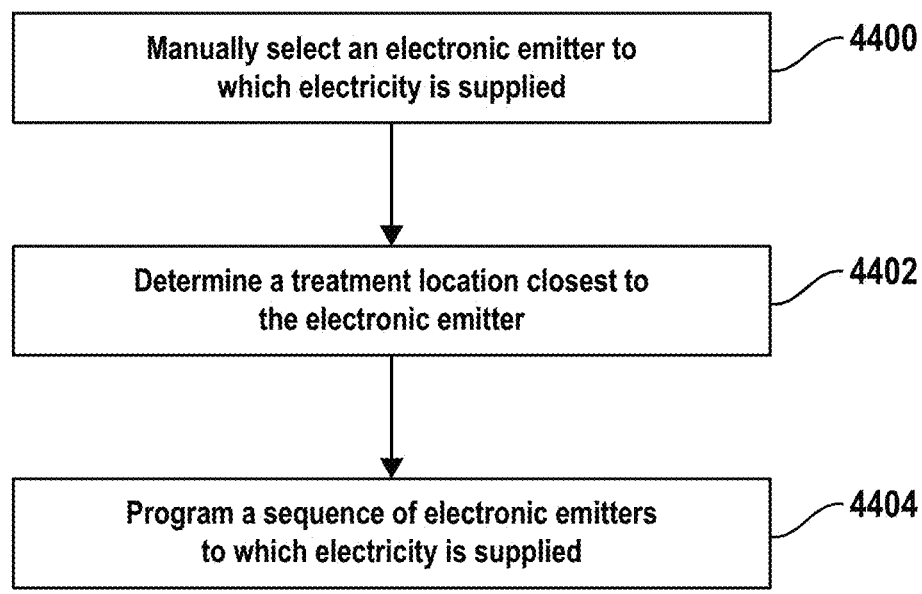
FIG. 44 is a flowchart illustrating an example method of controlling individual emitters in an IVL catheter.

FIG. 44 is a flowchart illustrating an example method of controlling individual emitters in an IVL catheter. The method may include manually selecting an electronic emitter to which electricity is supplied (at step 4400). When multiple electronic emitters are present, they may be powered by distinct power wires. This causes the electronic emitters to be wired in parallel (as seen in FIGS. 15A, 15B, 16A, and 38A). This independent wiring also allows for the electronic emitters to be powered individually, which means that a user may select which electronic emitter is to be fired, rather than firing all of the emitters at once.

In some examples, the method includes determining a treatment location closest to the electronic emitter (at step 4402). In a length of treatment area afflicted with calcified lesions, an operator may want to focus on a single spot for treatment. In some devices, because the entire device is powered at once, the entire length of the treatment area is treated, including areas that potentially do not need treatment. With a single emitter, treating the area could include repositioning the IVL device each time it is to be fired so that the cavitation bubbles are concentrated at the correct location. By wiring the electronic emitters in parallel, an operator may select the electronic emitter closest to the treatment location and individually fire that emitter, without the need for moving the device or firing other included emitters.

According to some examples, the method includes programming a sequence of electronic emitters to which electricity is supplied (at step 4404). Instead of needing manual selection of emitters by an operator, the device may include preprogrammed sequences. If an operator comes across a recognized pattern of calcified lesion(s), the operator can select the preprogrammed sequence to treat the recognized pattern. Additionally, if the operator wants to program a new pattern, i.e., a pattern they frequently see but has not been programmed already, the operator may program that specific sequence of emitters to be fired for future use.

FIGS. 45A-45D are perspective views of example emitters including various struts. In each of FIGS. 45A, 45B, 45C, and 45D, a first electrode 4502 and a second electrode 4504 are separated from one another by a strut 4506. In each figure, the strut 4506 is positioned and manufactured in such a way that the struts 4506 may be removed through mechanical means, such as via a laser, or by manual manipulation of the strut 4506 by an operator. The struts 4506 may be configured such that the first electrode 4502 and the second electrode 4504 are separated by a consistent distance about their respective perimeters, thereby permitting any arcs that form to arc randomly about these perimeters.

Also shown in each of FIGS. 45A, 45B, 45C, and 45D are recesses 4508 in the first electrode 4502 and the second electrode 4504 where the struts 4506 connect. These recesses 4508 may create a partial mechanical fragility, facilitating the manual removal of the struts 4506 by a manufacturer. In these examples, the area of the recesses 4508 would create minor gaps in the perimeter of the first electrode 4502 and the second electrode 4504 once the struts 4506 are removed, thereby creating a preferential location about the perimeters for the arc to occur. Because these recesses 4508 are small, the location of arcing will still occur about the majority of these perimeters. Additionally, while not shown in these figures, the struts 4506 may be perforated in addition to, or instead of these recesses 4508 to create this increased mechanical fragility.

Figure 45A:
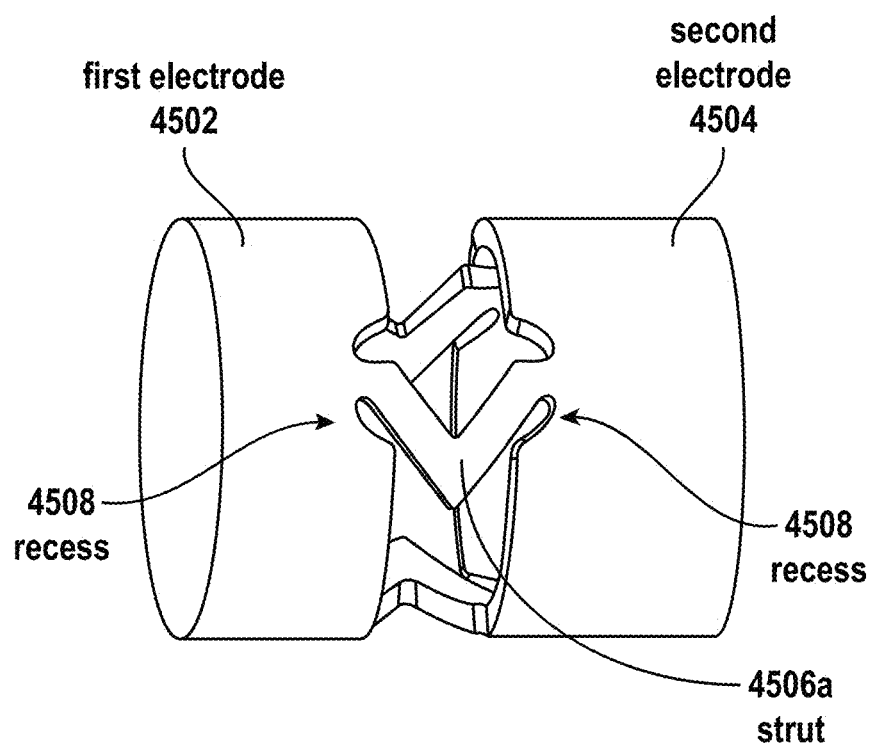
FIGS. 45A-45D are perspective views of example emitters including various struts.

FIG. 45A illustrates a "V-shaped" strut 4506a. In this figure, two small rectangular pieces extend at an angle from each of the first electrode 4502 and the second electrode 4504 before meeting in the middle, creating a vertex. A manufacturer can pull on or near this vertex in order to remove the strut 4506a.

Figure 45B:
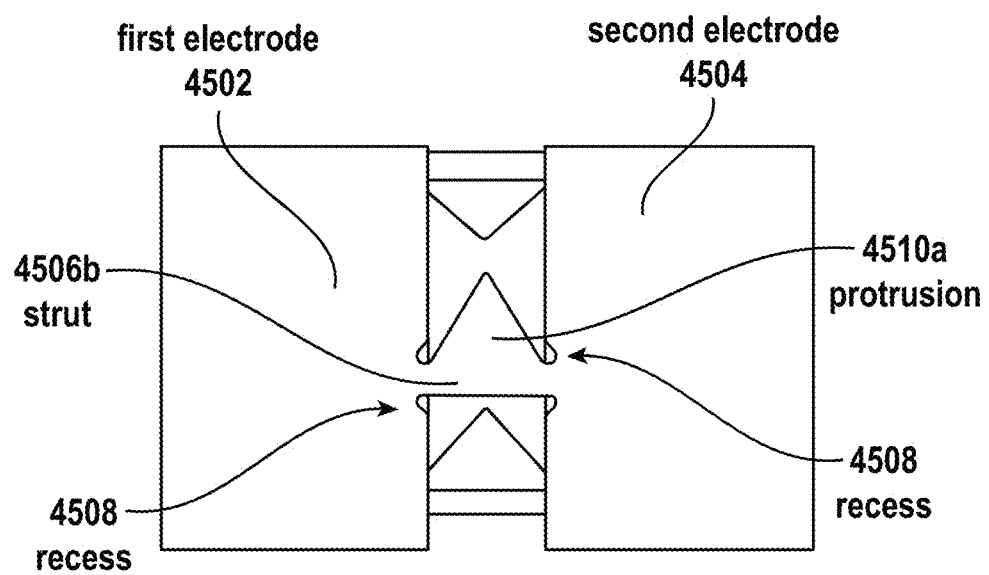

In FIG. 45B, the strut 4506b extends directly across the gap between the first electrode 4502 and the second electrode 4504. A triangular shaped protrusion 4510a is present across the middle of the strut 4506b. A manufacturer can pull on this protrusion 4510a in order to remove the strut 4506b.

Figure 45C:
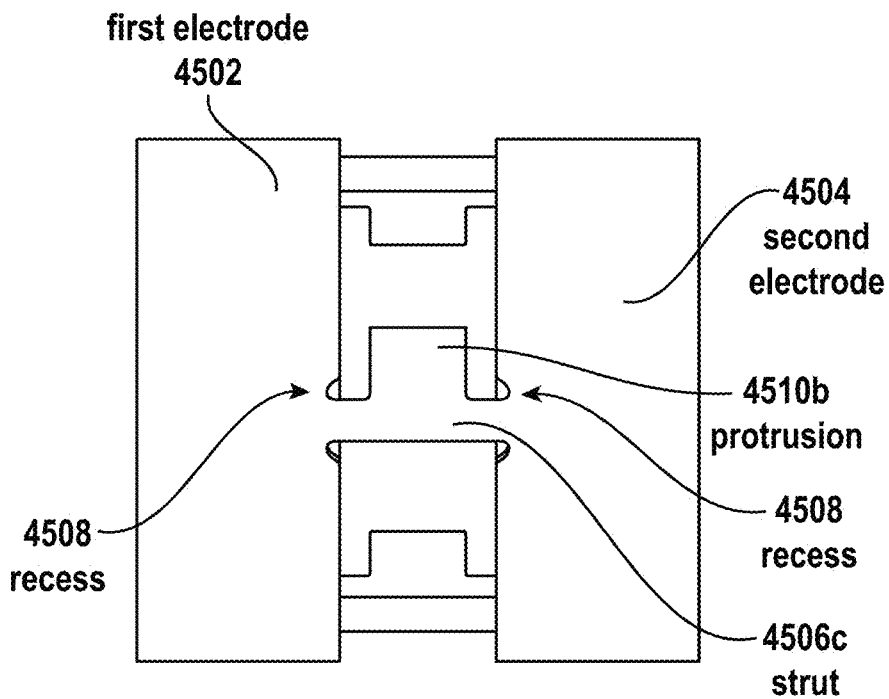

Similarly, in FIG. 45C, the strut 4506c extends directly across the gap between the first electrode 4502 and the second electrode 4504. A rectangular shaped protrusion 4510b is present across the middle of this strut 4506c. A manufacturer can pull on this protrusion 4510b in order to remove the strut 4506c.

Figure 45D:
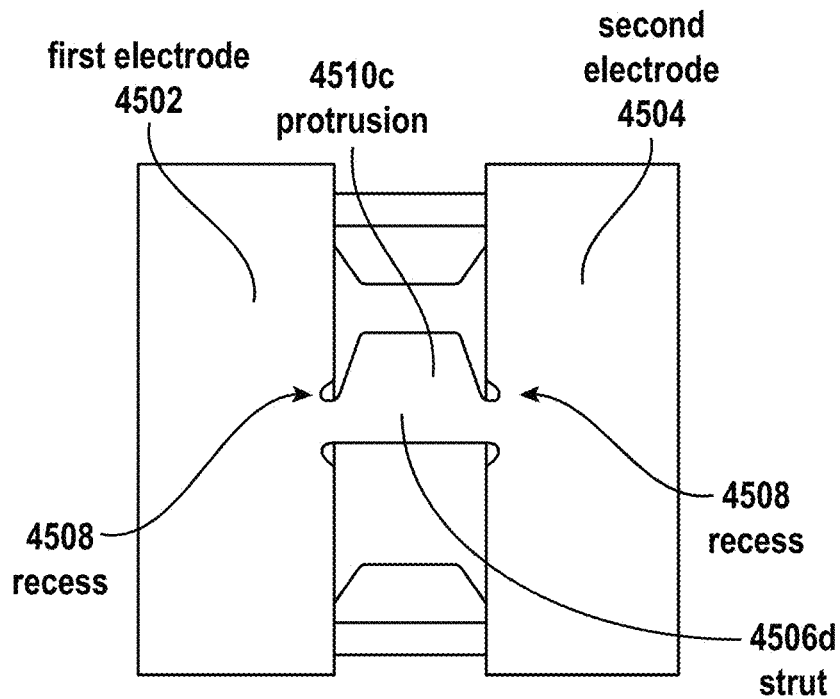

As a final example, in FIG. 45D, the strut 4506d extends directly across the gap between the first electrode 4502 and the second electrode 4504. A trapezoidal shaped protrusion 4510c is present across the middle of this strut 4506d. A manufacturer can pull on this protrusion 4510c in order to remove the strut 4506d.

Figure 46:
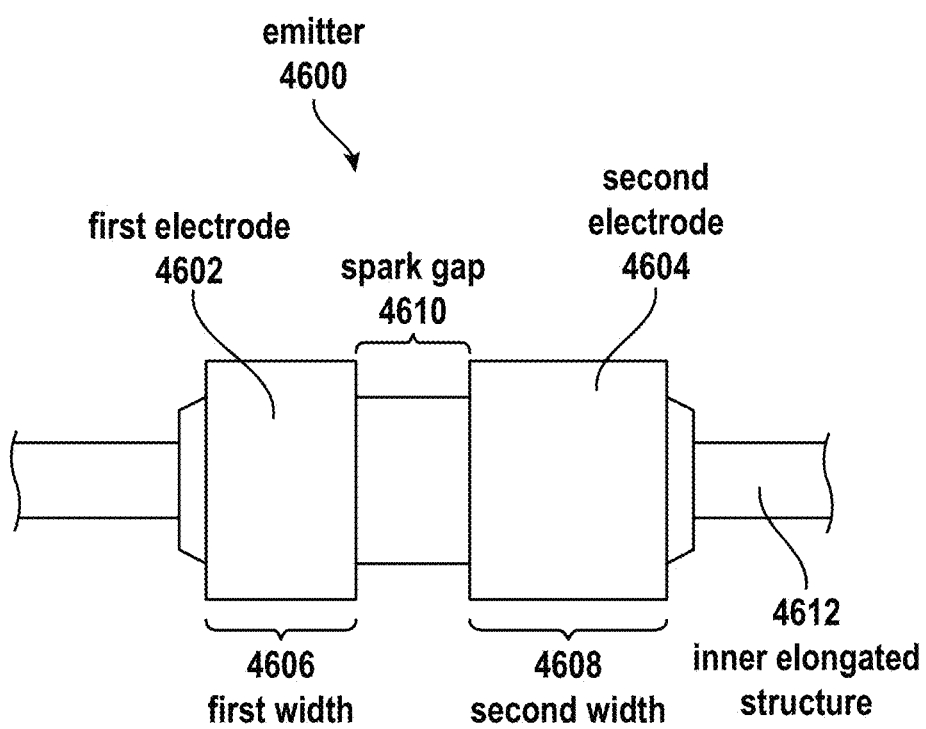
FIG. 46 is a side view of an example electronic emitter.
Figure 47:
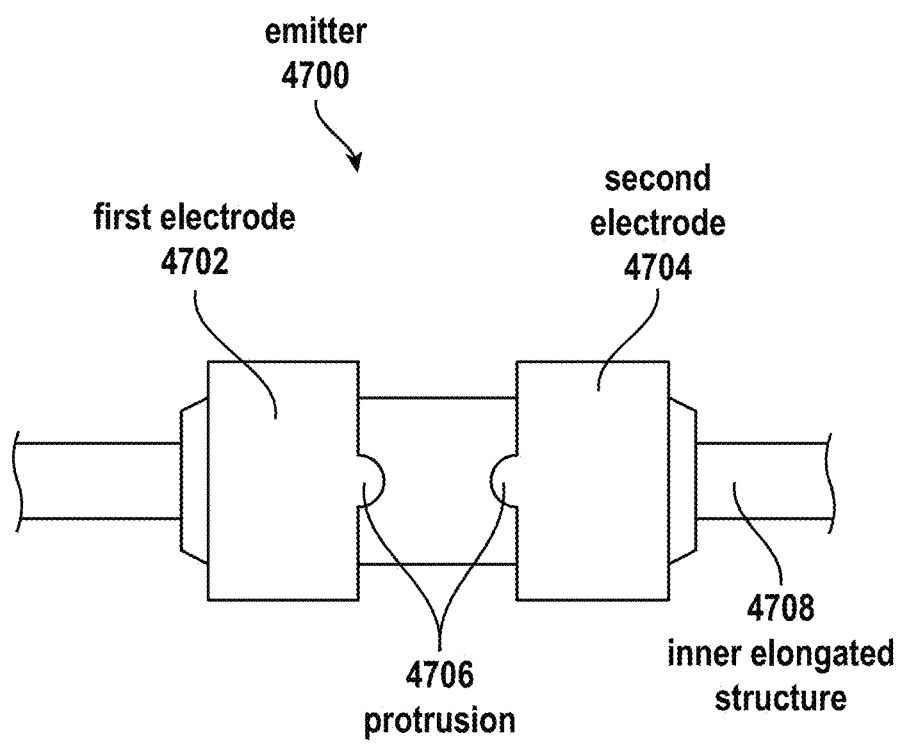
FIG. 47 is a side view of another example electronic emitter.
Figure 48:
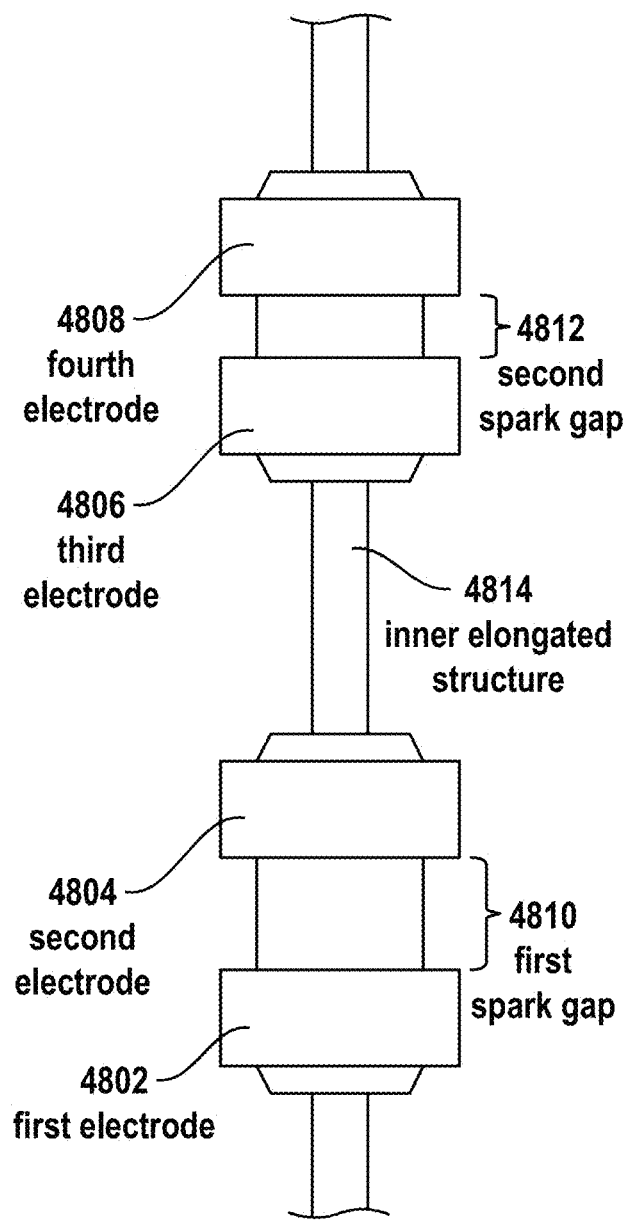
FIG. 48 is a side view of a pair of electronic emitters, according to some examples.

FIGS. 46 and 47 are side views of example emitters, and FIG. 48 is a side view of two pairs of these example emitters. Specifically, FIG. 46 illustrates an emitter 4600 including a first electrode 4602 having a first width 4606, and a second electrode 4604 having a second width 4608. A spark gap 4610 is present between the first electrode 4602 and the second electrode 4604. Additionally, both electrodes can be seen at least partially surrounding the inner elongated structure 4612.

By having the first width 4606 be narrower than the second width 4608, the resistance of each specific electrode can be better controlled. In this way, different voltages can produce different sized bubbles, and thus different sized pressure waves. Additionally, in systems with more than one emitter 4600, these different resistance electrodes could control the timing of the emitters 4600 firing, thereby creating specific sequences, or compound pressure waves.

FIG. 47 illustrates an emitter 4700 including a first electrode 4702 and a second electrode 4704. The first electrode 4702 and the second electrode 4704 can at least partially surround an inner elongated structure 4708. Also present in FIG. 47 are protrusions 4706 on each of the first electrode 4702 and the second electrode 4704. These protrusions 4706 can permit preferential arcing from the first electrode 4702 to the second electrode 4704. It is understood that there need only be a protrusion 4706 on the first electrode 4702, or only on the second electrode 4704, in order to create this preferential arcing. Additionally, these emitters 4700 can be rotatable, such that an operator can cause the protrusions 4706 to be facing the area of calcification to be treated, thus potentially improving the efficacy of the pressure wave treatment.

FIG. 48 illustrates two emitters, one having a first electrode 4802 and a second electrode 4804 separated by a first spark gap 4810, and the second emitter having a third electrode 4806 and a fourth electrode 4808 separated by a second spark gap 4812. Each of the first electrode 4802, the second electrode 4804, the third electrode 4806, and the fourth electrode 4808 can at least partially surround an inner elongated structure 4814.

As illustrated in FIG. 48, the first spark gap 4810 can be wider than the second spark gap 4812. These different width spark gaps can permit additional control over the pressure wave formed, and permit compound pressure wave profiles to be utilized.

While FIG. 48 only illustrates two emitters, it is understood that a greater number of emitters can be used in a device, so long as it remains capable of traversing the vasculature of a patient.

Figure 49:
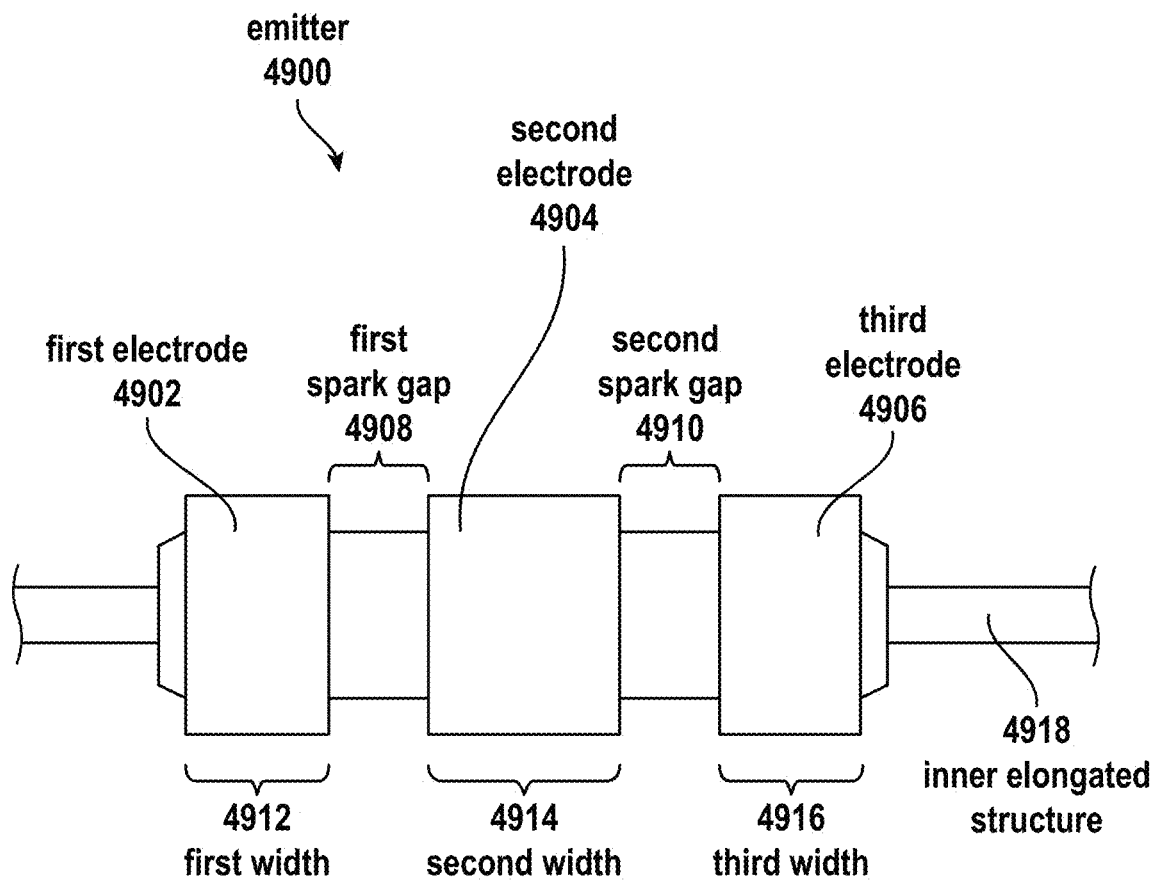
FIG. 49 is a side view of an example three-electrode electronic emitter.
Figure 51:
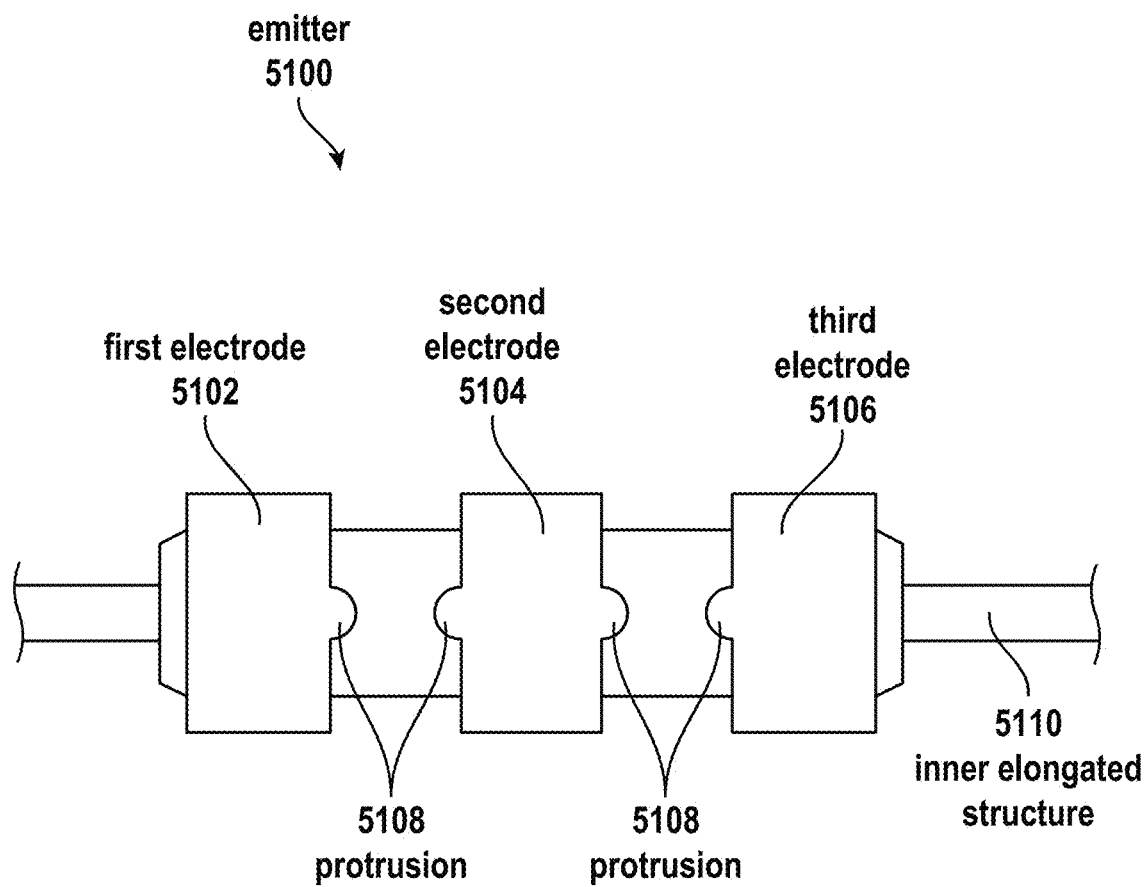
FIG. 51 is a side view of an additional three-electrode electronic emitter, according to some examples.
Figure 52:
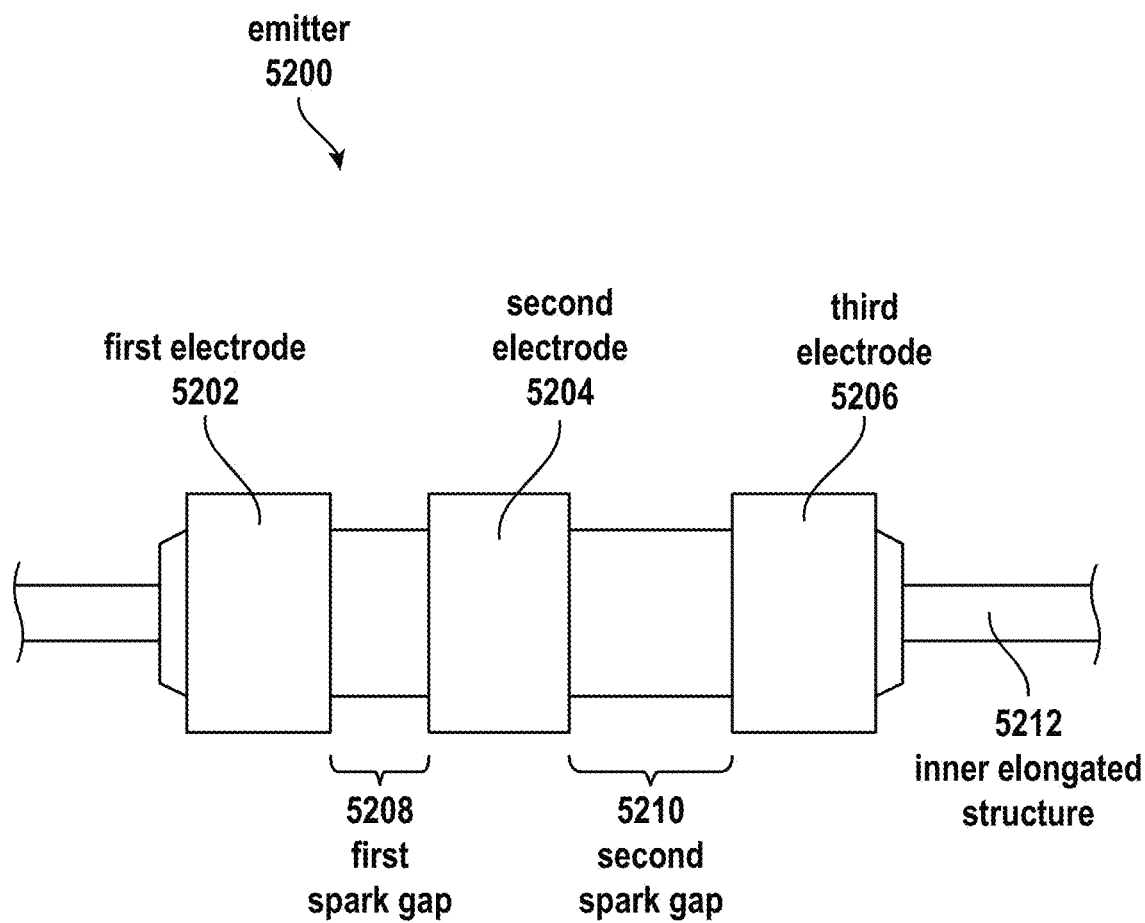
FIG. 52 is a side view of another example three-electrode electronic emitter.
Figure 53:
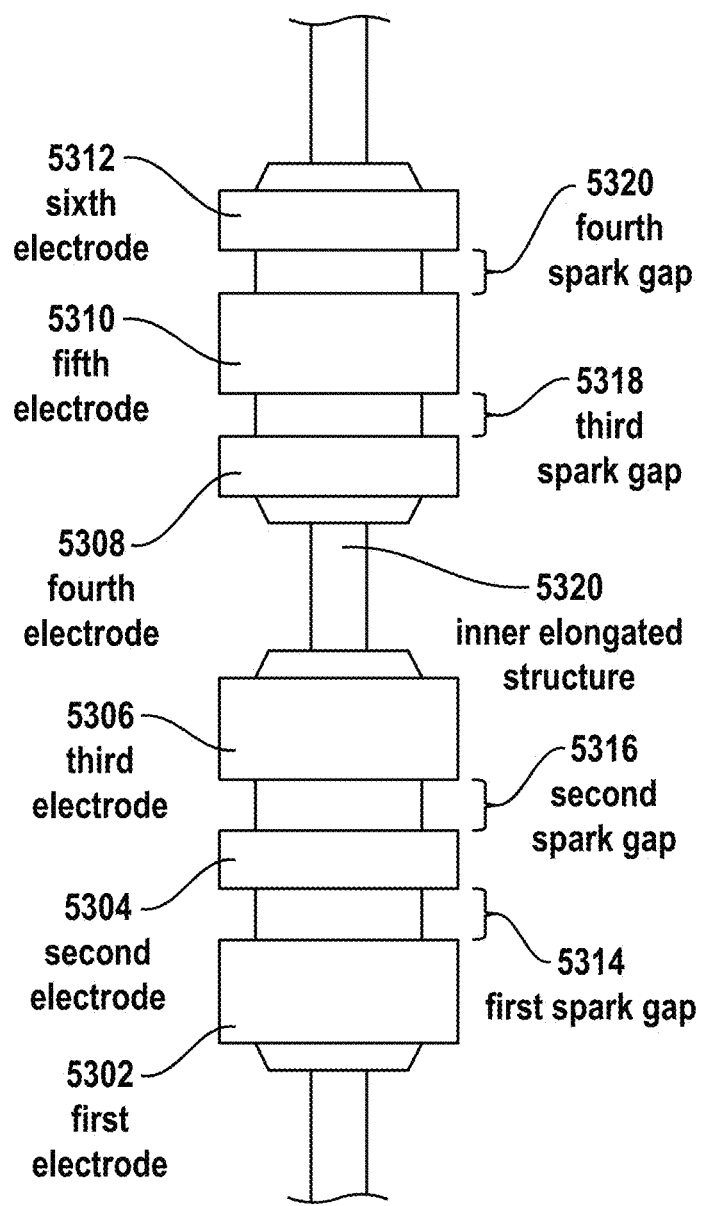
FIG. 53 is a side view of a pair of three-electrode electronic emitters, according to some examples.

FIGS. 49, 50, 51, and 52 are side views of an example emitter including three electrodes, and FIG. 53 is a side view of a pair of these example emitters. Specifically, FIG. 49 is a side view of an example three-electrode emitter 4900 including a first electrode 4902, a second electrode 4904, and a third electrode 4906, each of which at least partially surround an inner elongated structure 4918. The first electrode 4902 is seen separated from the second electrode 4904 by a first spark gap 4908, and the second electrode 4904 is shown as separated from the third electrode 4906 by a second spark gap.

The first electrode 4902 has a first width 4912, the second electrode 4904 has a second width 4914, and the third electrode 4906 has a third width 4916. As seen in FIG. 49, the second width 4914 is greater than that of the first width 4912 and the third width 4916. As illustrated in FIG. 49, the first width 4912 and the third width 4916 can be equal or approximately equal. However, this is not strictly necessary, as discussed previously, increasing any of these widths could change the resistance through the electrode thereby changing the spark created.

In some examples, the second electrode 4904 is grounded while the first electrode 4902 and the third electrode 4906 are powered-either in series or in parallel. In parallel, the first electrode 4902 and the third electrode 4906 can be individually selected for firing (i.e., arcing to the second electrode 4904). This configuration can permit a single grounded electrode to receive arcs from either side, thus potentially doubling the spark production from this emitter 4900. Additionally, because either side can be selectively activated in some examples, the life expectancy of the emitter 4900 can also potentially be doubled.

In other examples, the second electrode 4904 is powered while the first electrode 4902 and the third electrode 4906 are grounded-again, either in series or in parallel. In parallel, the first electrode 4902 and the third electrode 4906 can be individually selected to receive an arc from the second electrode 4904. The benefits of such a configuration are similar to those described above.

Figure 50:
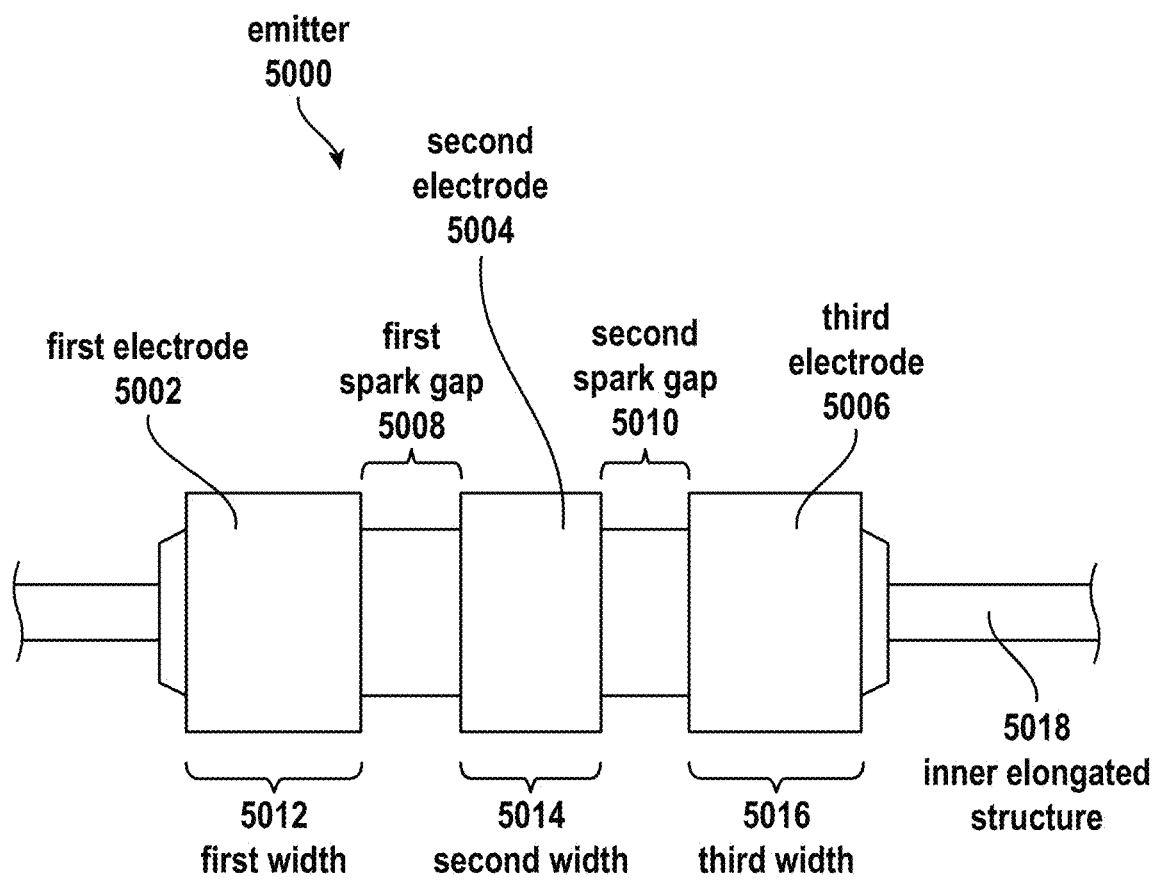
FIG. 50 is a side view of another example three-electrode electronic emitter.

FIG. 50 is a side view of another example three-electrode emitter 5000, and is similar to the emitter 4900 of FIG. 49 in many ways. Emitter 5000 is shown including a first electrode 5002, a second electrode 5004, and a third electrode 5006, each of which at least partially surround an inner elongated structure 5018. The first electrode 5002 is shown separated from the second electrode 5004 by a first spark gap 5008, and the second electrode 5004 is seen separated from the third electrode 5006 by a second spark gap 5010.

The first electrode 5002 has a first width 5012, the second electrode 5004 has a second width 5014, and the third electrode 5006 has a third width 5016. As illustrated in FIG. 50, the second width 5014 is narrower than that of the first width 5012 and the third width 5016. The first width 5012 and the third width 5016 can be equal or approximately equal, but this is not strictly necessary.

In some examples, the second electrode 5004 is grounded while the first electrode 5002 and the third electrode 5006 are powered-either in series or in parallel. In other examples, the second electrode 5004 is powered while the first electrode 5002 and the third electrode 5006 are grounded-either in series or in parallel. As the benefits of such configurations have been explored previously, they will not be reiterated here.

FIG. 51 is a side view of an additional three-electrode emitter 5100 including a first electrode 5102, a second electrode 5104, and a third electrode 5106, each of which at least partially surrounds an inner elongated structure 5110. The first electrode 5102, second electrode 5104, and third electrode 5106 are illustrated as being the same width, but it is understood that this example emitter 5100 could also work with other configurations. As shown in FIG. 51, the first electrode 5102 includes a protrusion 5108 facing the second electrode 5104, and the second electrode 5104 includes a protrusion 5108 facing the first electrode 5102. Similarly, the second electrode 5104 includes a protrusion 5108 facing the third electrode 5106, and the third electrode 5106 includes a protrusion 5108 facing the second electrode 5104.

These protrusions create a preferential spark gap location, such that the spark gap is no longer permitted to occur randomly about the perimeter of each electrode. Only one of these protrusions is needed to cause this preferential location of sparking. For example, maybe only the second electrode 5104 includes protrusions 5108 while the first electrode 5102 and the third electrode 5106 do not. Contra, perhaps the first electrode 5102 and the third electrode 5106 include protrusions 5108 while the second electrode 5104 does not. In some examples, if desired, perhaps only the first electrode 5102 includes a protrusion, thus making the spark gap between the first electrode 5102 and the second electrode 5104 preferential to the location of the protrusion 5108, while the spark gap between the second electrode 5104 and the third electrode 5106 remains random about the perimeter of these electrodes.

The benefits of wiring configurations will not be specifically reiterated here, but in some examples, the second electrode 5104 is grounded while the first electrode 5102 and the third electrode 5106 are powered-either in series or in parallel. In other examples, the second electrode 5104 is powered while the first electrode 5102 and the third electrode 5106 are grounded-either in series or in parallel.

FIG. 52 is a side view of another example three-electrode emitter 5200 including a first electrode 5202, a second electrode 5204, and a third electrode 5206, each of which at least partially surround an inner elongated structure 5212. The first electrode 5202, second electrode 5204, and the third electrode 5206 are illustrated as being the same width, but it is understood that this example emitter 5200 could work with those examples of FIGS. 49 and 50. As shown, the first electrode 5202 is separated from the second electrode 5204 by a first spark gap 5208, and the second electrode 5204 is separated from the third electrode 5206 by a second spark gap 5210.

The first spark gap 5208 is illustrated as narrower than the second spark gap 5210. Different lengths of these spark gaps can permit control over the pressure wave produced. This can be useful if a lower or higher-powered pressure wave is needed for a specific application. These pressure waves can also be combined, either through simultaneous firing or individual firing of the electrodes, in order to produce a compound pressure wave.

In some examples, the second electrode 5204 is grounded while the first electrode 5202 and the third electrode 5206 are powered-either in series or in parallel. In other examples, the second electrode 5204 is powered while the first electrode 5202 and the third electrode 5206 are grounded-either in series or in parallel.

Figure 54:
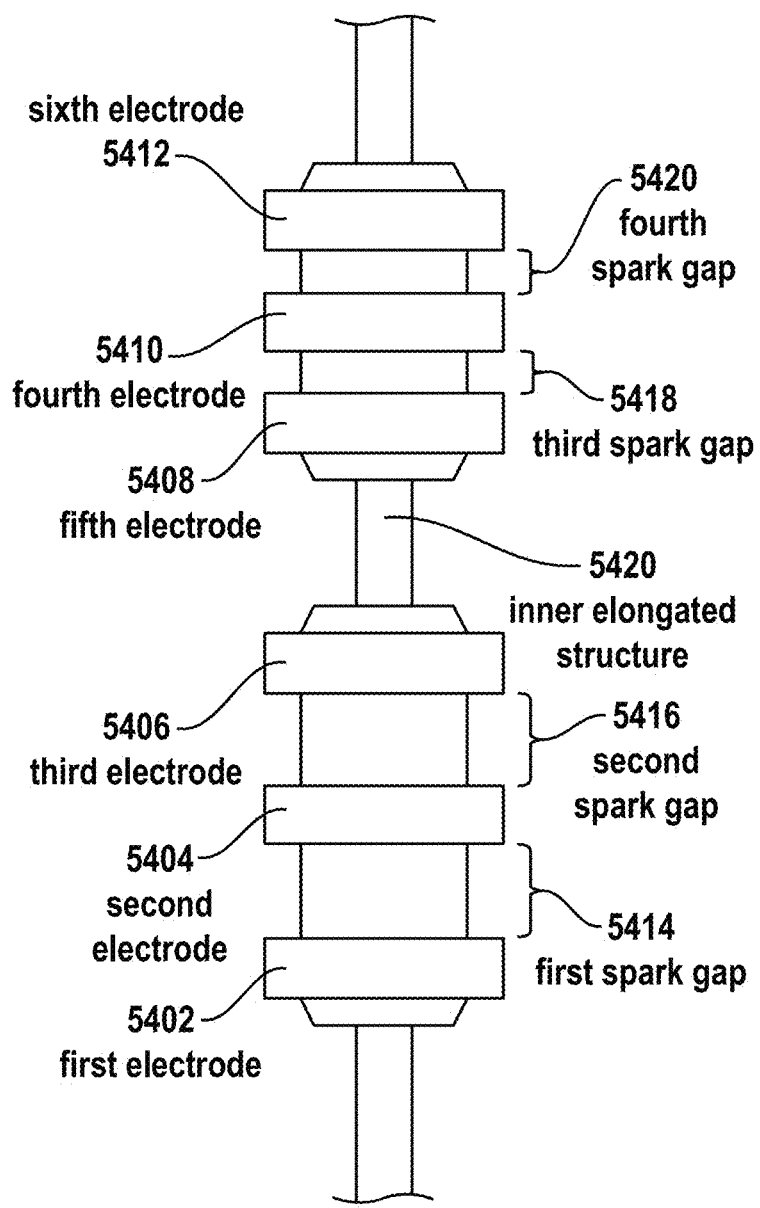
FIG. 54 is a side view of another example pair of three-electrode electronic emitters.

FIGS. 53 and 54 illustrate side views of example pairs of three-electrode emitters. Specifically, FIG. 53 shows a side view of a first emitter including a first electrode 5302, a second electrode 5304, and a third electrode 5306, and a second emitter including a fourth electrode 5308, a fifth electrode 5310, and a sixth electrode 5312. Each of the first electrode 5302, the second electrode 5304, the third electrode 5306, the fourth electrode 5308, the fifth electrode 5310, and the sixth electrode 5312 can at least partially surround an inner elongated structure 5322.

The first electrode 5302 is seen separated from the second electrode 5304 by a first spark gap 5314, and the second electrode 5304 is shown separated from the third electrode 5306 by a second spark gap 5316. Likewise, the fourth electrode 5308 is shown separated from the fifth electrode 5310 by a third spark gap 5318 and the fifth electrode 5310 is seen separated from the sixth electrode 5312 by a fourth spark gap 5320.

The first spark gap 5314, the second spark gap 5316, the third spark gap 5318, and the fourth spark gap 5320 are all shown as having the same width. However, this is not strictly necessary, and varying spark gap lengths can be implemented.

Additionally, the emitter including the first electrode 5302, the second electrode 5304, and the third electrode 5306 shows an emitter including two wider outer electrodes and a narrower inner electrode, while the emitter including the fourth electrode 5308, the fifth electrode 5310, and the sixth electrode 5312 shows an emitter including a wider inner electrode and two narrower outer electrodes. In fact, any emitter as described throughout the present disclosure can be used in conjunction with any other emitter within a same device, if desired.

The second electrode 5304, the fourth electrode 5308, and the sixth electrode 5312 all display approximately the same width, while the first electrode 5302, the third electrode 5306, and the fifth electrode 5310 all display approximately the same width—this width being greater than that of the second electrode 5304, the fourth electrode 5308, and the sixth electrode 5312. This is not strictly necessary, and in fact all of the electrodes could have varying widths from one another if desired.

FIG. 54 illustrates a side view of a first emitter including a first electrode 5402, a second electrode 5404, and a third electrode 5406, and a second emitter including a fourth electrode 5408, a fifth electrode 5410, and a sixth electrode 5412. Each of the first electrode 5402, the second electrode 5404, the third electrode 5406, the fourth electrode 5408, the fifth electrode 5410, and the sixth electrode 5412 can at least partially surround an inner elongated structure 5422.

In this figure, the first electrode 5402, the second electrode 5404, the third electrode 5406, the fourth electrode 5408, the fifth electrode 5410, and the sixth electrode 5412 all appear to have the same width. This is not strictly necessary, but this figure is illustrating the varying degree of widths of spark gaps between consecutive electrodes, and so for simplicity the electrodes are shown as the same size.

As seen in FIG. 54, the first electrode 5402 is seen separated from the second electrode 5404 by a first spark gap 5414, and the second electrode 5404 is shown separated from the third electrode 5406 by a second spark gap 5416. Likewise, the fourth electrode 5408 is shown separated from the fifth electrode 5410 by a third spark gap 5418 and the fifth electrode 5410 is seen separated from the sixth electrode 5412 by a fourth spark gap 5420.

The first spark gap 5414 and the second spark gap 5416 are illustrated as being approximately the same width, and the third spark gap 5418 and the fourth spark gap 5420 are shown as also being the same width, but narrower than that of the first spark gap 5414 and the second spark gap 5416.

In this way, the emitter including the first electrode 5402, the second electrode 5404, and the third electrode 5406 can produce pressure waves that differ in power from the emitter including the fourth electrode 5408, the fifth electrode 5410, and the sixth electrode 5412. Through either simultaneous, timed, or independently controlled firing of these electrodes, compound pressure waves can be produced.

Additionally, it is understood that, while the spark gaps of each emitter are shown to be the same size, further customization and control of the spark gap widths for specific compound pressure wave formation can be performed by using an example emitter as previously described.

In either of FIG. 53 and FIG. 54, multiple different wiring configurations can be constructed, depending on the needs of the user. For example, the second electrode 5304 and/or 5404 and the fifth electrode 5310 and/or 5410 can be wired in sequence to ground, while the first electrode 5302 and/or 5402, the third electrode 5306 and/or 5406, the fourth electrode 5308 and/or 5408, and the sixth electrode 5312 and/or 5412 are wired in sequence to power. The power and ground wires could also be flipped in this scenario. In this example, all of the electrodes would fire once power was provided.

In additional examples, the second electrode 5304 and/or 5404 and the fifth electrode 5310 and/or 5410 can receive their own independent wires, thus being wired in parallel. In this case, the emitters can be fired independent from one another, regardless of whether these wires return to ground or receive the voltage.

In still other examples, the first electrode 5302 and/or 5402, the third electrode 5306 and/or 5406, the fourth electrode 5308 and/or 5408, and the sixth electrode 5312 and/or 5412 can each receive their own independent wires, thus being wired in parallel. In this case, not only are the emitters capable of being fired independent from one another, but each of the first electrode 5302 and/or 5402, the third electrode 5306 and/or 5406, the fourth electrode 5308 and/or 5408, and the sixth electrode 5312 and/or 5412 can be fired independently, thus providing even greater control over which spark gap is utilized. This is regardless of whether these wires return to ground or receive the voltage. In this example, the second electrode 5304 and/or 5404 and the fifth electrode 5310 and/or 5410 can also receive their own independent wires, but this addition of wires would not have any impact on the parallel nature of this circuit.

Additionally, other wiring configurations can be used, such as wiring the second electrode 5304 and/or 5404, the fourth electrode 5308 and/or 5408, and the sixth electrode 5312 and/or 5412 in series. The practical effects of such a configuration would be the potential to enable individual electrode firing of one emitter, while the other emitter fires both electrodes at once.

While FIGS. 53 and 54 only illustrate two emitters, it is understood that a greater number of emitters can be used in a device, so long as it remains capable of traversing the vasculature of a patient.

Figure 55:
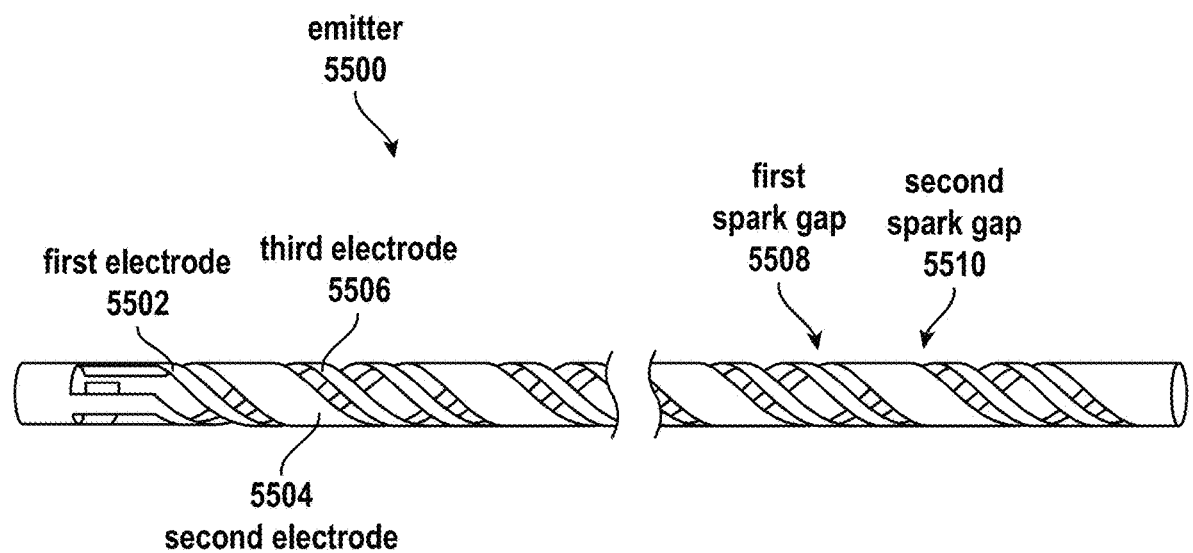
FIG. 55 is a side view of an example three-electrode spiraling electronic emitter.

FIG. 55 is a side view of an example three-electrode spiraling emitter 5500. As FIG. 55 illustrates, a first electrode 5502, a second electrode 5504, and a third electrode 5506 helically spiral about one another. The length of the emitter can be shorter or longer than that depicted, depending on the needs of the user. Additionally, while not shown in FIG. 55, the emitter 5500 can be placed on an internal elongated structure (and adhered, such as through potting material) for delivery to a target site.

As seen in this figure, the first electrode 5502 is separated from the second electrode 5504 by a first spark gap 5508, and the second electrode 5504 is separated from the third electrode 5506 by a second spark gap 5510. Because of the spiraling nature of each electrode, the first spark gap 5508 and the second spark gap 5510 also spiral. As shown in FIG. 55, the first spark gap 5508 and the second spark gap 5510 are approximately equal throughout the length of the emitter 5500. This can permit random spark formation about the perimeter, and throughout the length of the emitter 5500, thus further extending the life expectancy of the emitter 5500, as well as the number of sparks that can be formed before needing to pause to avoid overheating the emitter 5500.

While the second electrode 5504 is shown as wider than the first electrode 5502 and the third electrode 5506, it is understood that this is not strictly necessary. Additionally, the second electrode 5504 can receive power while the first electrode 5502 and the third electrode 5506 return to ground, or vice-versa.

Figure 56:
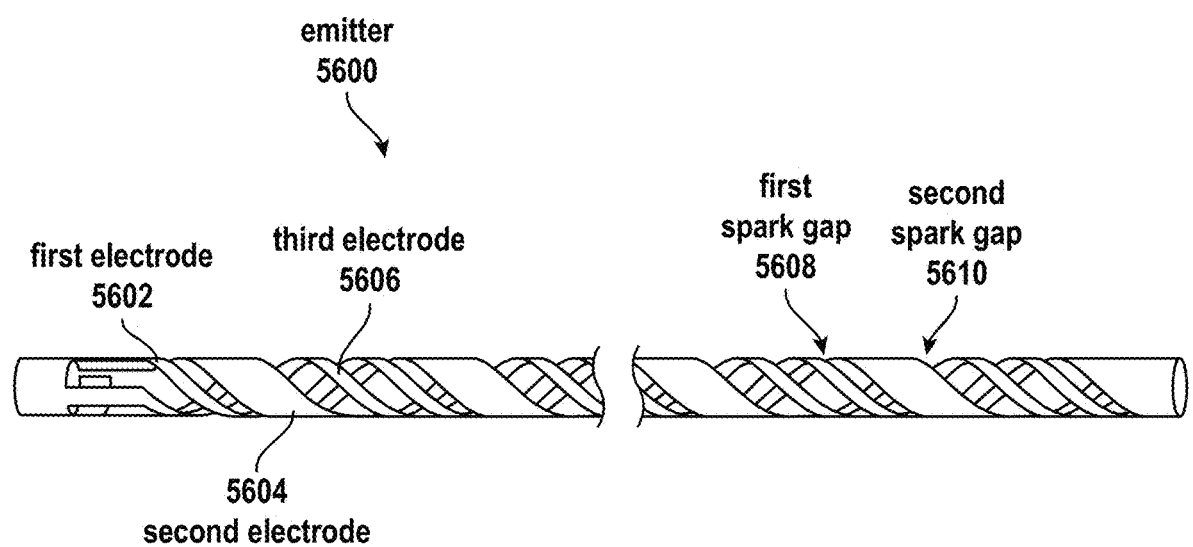
FIG. 56 is a side view of another three-electrode spiraling electronic emitter, according to some examples.

FIG. 56 is a side view of another three-electrode spiraling emitter 5600. Emitter 5600 includes a first electrode 5602 separated from a second electrode 5604 by a first spark gap 5608, and the second electrode 5504 is separated from a third electrode 5606 by a second spark gap 5610. In this example, the second spark gap 5610 is wider than the first spark gap, causing preferential sparking to occur between the first electrode 5602 and the second electrode 504. In some examples, where the first electrode 5602 and the third electrode 5606 are wired in parallel (either ground or power), the second spark gap 5610 can be used to generate sparks of a varying degree of energy to that of the first spark gap 5608. In this way, compound pressure waves can also be formed through sequential or simultaneous firing of the electrodes.

Figure 57:
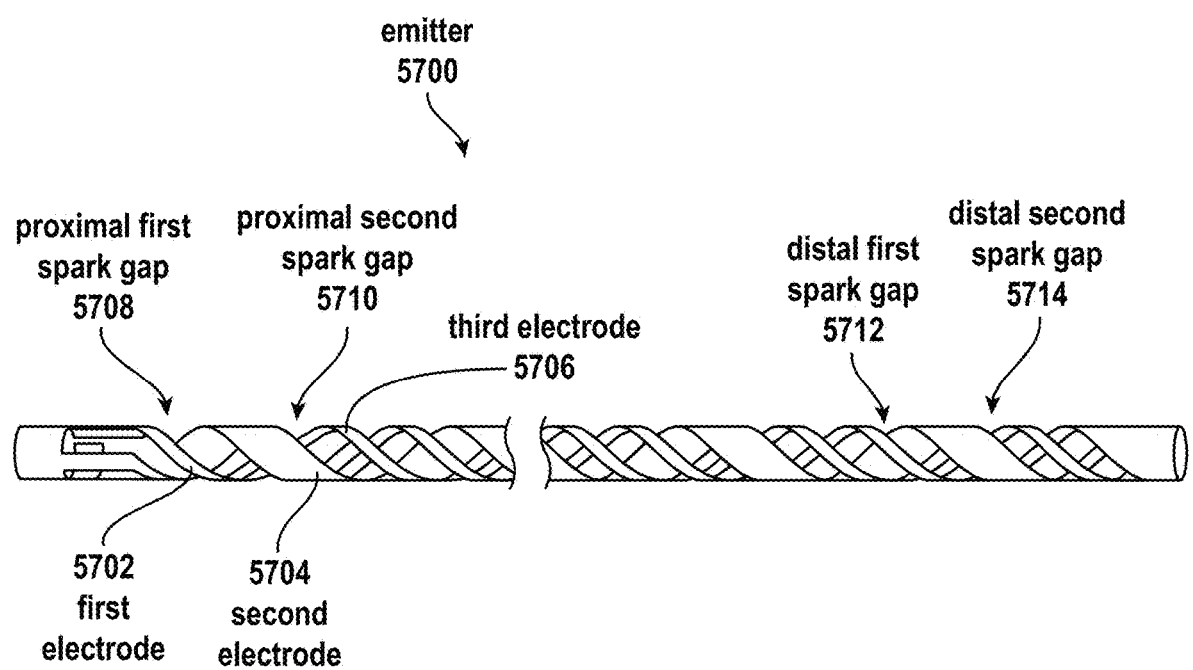
FIG. 57 is a side view of an additional three-electrode spiraling electronic emitter, according to some examples.

FIG. 57 is a side view of an additional three-electrode spiraling emitter 5700. Emitter 5700 includes a first electrode 5702 separated from a second electrode 5704 by a first spark gap, and the second electrode 5704 is separated from a third electrode 5706 by a second spark gap. In this example, the spark gaps decrease in width throughout the length of the emitter 5700.

As can be seen in FIG. 57, the proximal first spark gap 5708 (defined here as the spark gap closest to the proximal end of the emitter) and the proximal second spark gap 5710 are each wider than their distal counterparts, distal first spark gap 5712 and distal second spark gap 5714. In this example, should power be provided at the proximal end of the emitter 5700, any inherent resistance of the material that the emitter 5700 is made from can be overcome. By decreasing the width of the first and second spark gaps, the electricity will not find a preferential location to jump from one electrode to another, thus maintaining the truly random nature of spark formation locations.

Figure 58:
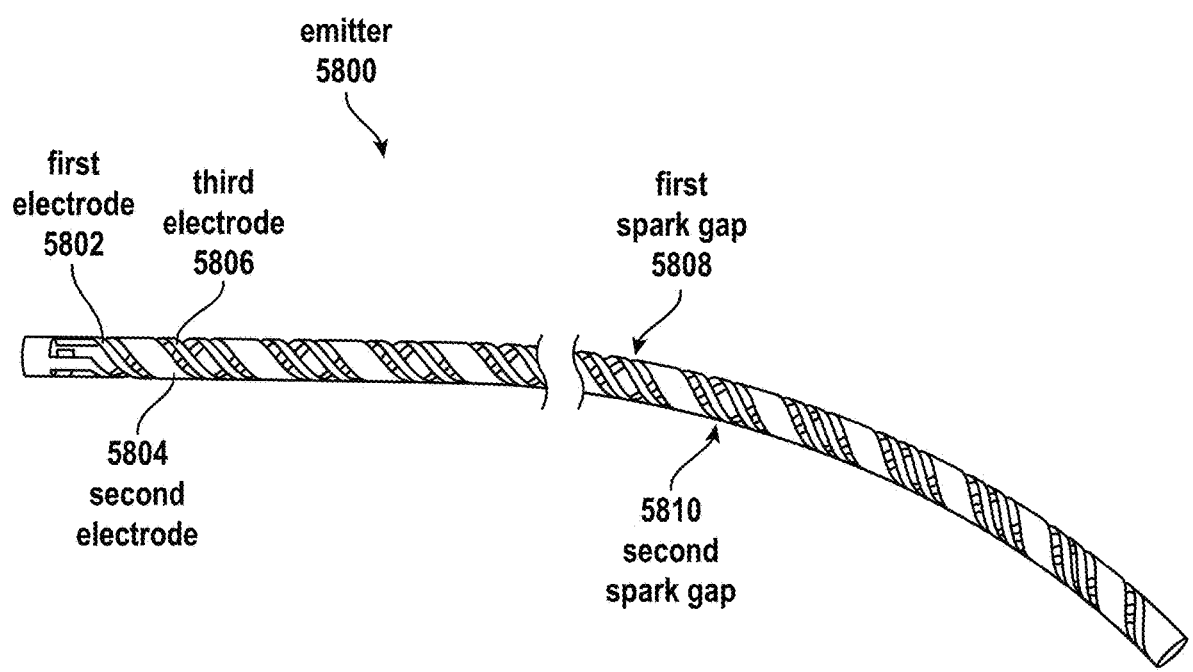
FIG. 58 is a side view of an example three-electrode spiraling electronic emitter as it may appear while articulated.

FIG. 58 is a side view of an example three-electrode spiraling emitter 5800 as it can appear while articulated. In this figure, emitter 5800 includes a first electrode 5802 separated from a second electrode 5804 by a first spark gap 5808, and the second electrode 5804 is separated from a third electrode 5806 by a second spark gap 5810. In this figure, the emitter 5800 is articulated, or bent, "downward" (downward in relation to the perspective being shown). This could be performed through manipulation of the emitter 5800 itself, or manipulation of the structure, such as an internal elongated structure, to which the emitter 5800 is attached.

By articulating the emitter 5800, the first spark gap 5808 and the second spark gap 5810 narrow on the side of the emitter 5800 that is being bent, and widen on the side of the emitter 5800 opposite the side being bent. In this way, even minor bending of the emitter 5800 can create preferential locations for the electricity to arc from one electrode to another, thereby permitting an operator to have some control over the direction of emission and pressure wave propagation.

Figure 59:
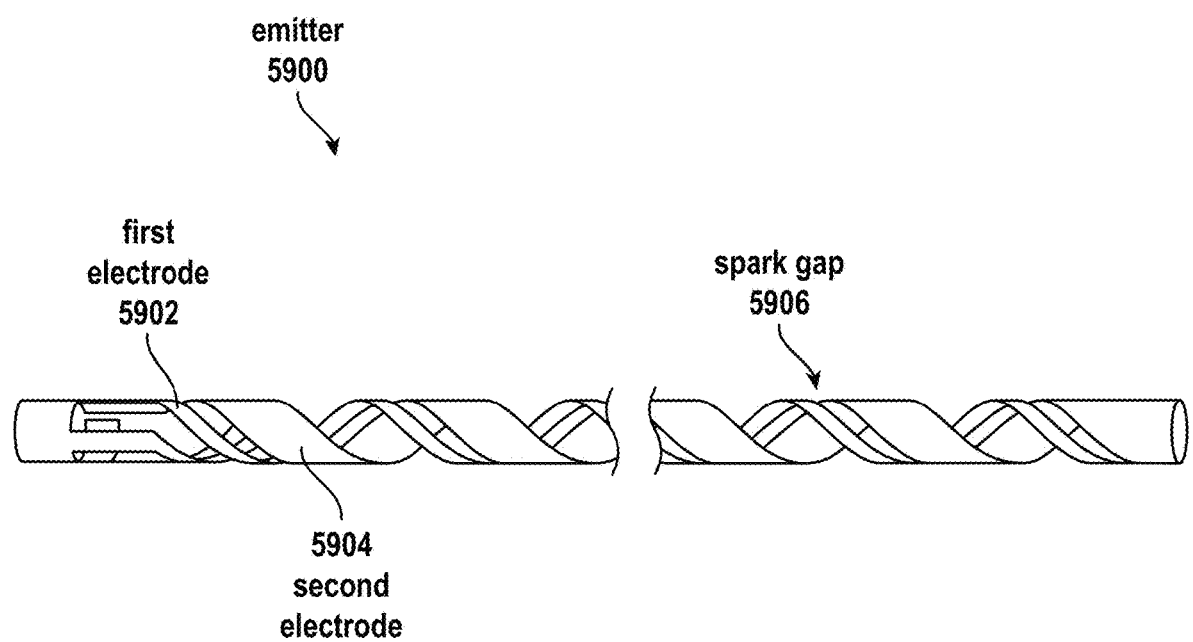
FIG. 59 is a side view of a two-electrode spiraling electronic emitter, according to some examples.

FIG. 59 is a side view of a two-electrode spiraling emitter 5900. Emitter 5900 includes a first electrode 5902 separated from a second electrode 5904 by a spark gap 5906. The use of only two electrodes, and thus only one spark gap 5906, can decrease the ability to create compound pressure waves while also decreasing the footprint of the emitter 5900, thus still enabling random spark formation and pressure wave propagation throughout the length of the emitter 5900 while decreasing material needs and potential size constraints.

A wider gap is shown between the second electrode 5904 and the first electrode 5902 opposite the spark gap 5906, in order to prevent spark formation from occurring on that side of the electrode. This is also not strictly necessary, and in fact the gap between the first electrode 5902 and the second electrode 5904 on either side of the first electrode 5902 can be the same width, thus permitting spark formation to occur in either of these gaps.

Figure 60:
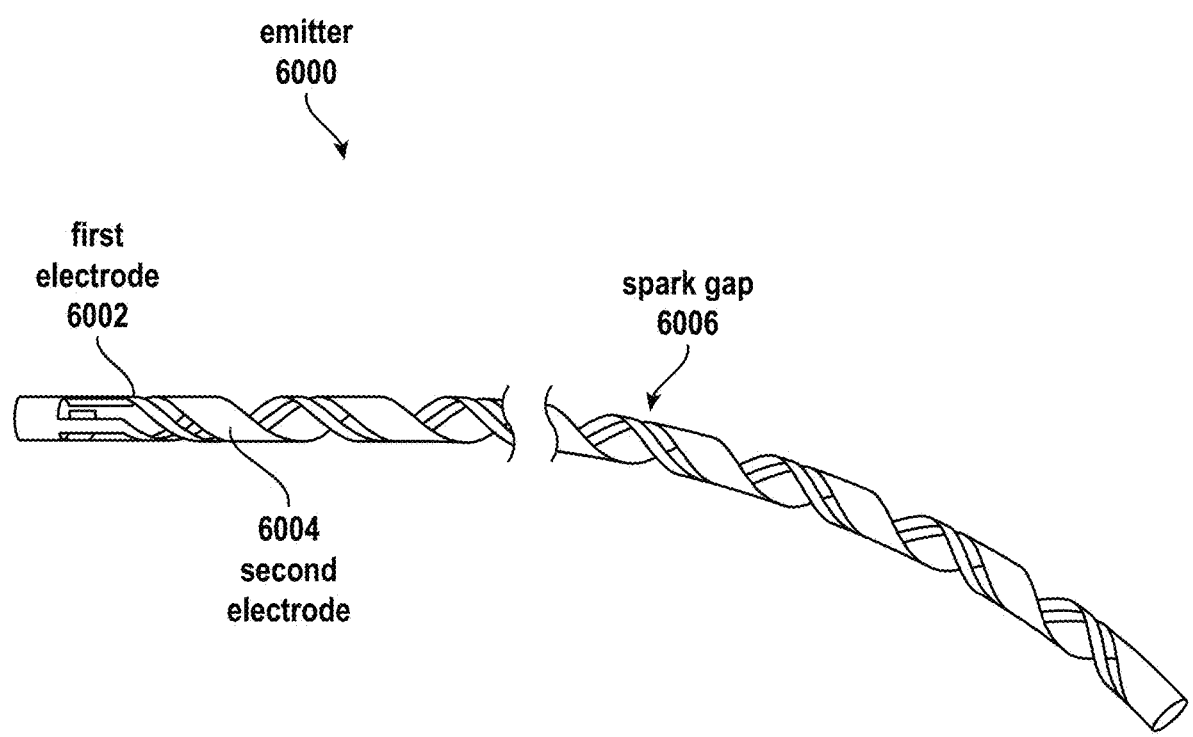
FIG. 60 is a side view of an example two-electrode spiraling electronic emitter as it may appear while articulated.

FIG. 60 is a side view of an example two-electrode spiraling emitter 6000 as it can appear while articulated. Emitter 6000 includes a first electrode 6002 separated from a second electrode 6004 by a spark gap 6006. The emitter 6000 can be articulated such that the spark gap 6006 becomes narrower on the side of the emitter 6000 that is being bent toward, and wider on the side of the emitter 6000 opposite this bend. In this manner, the side of the emitter 6000 being bent toward becomes a preferential side for sparks to occur, while still permitting the pressure waves to propagate randomly through the length of the emitter 6000.

Figure 61A:
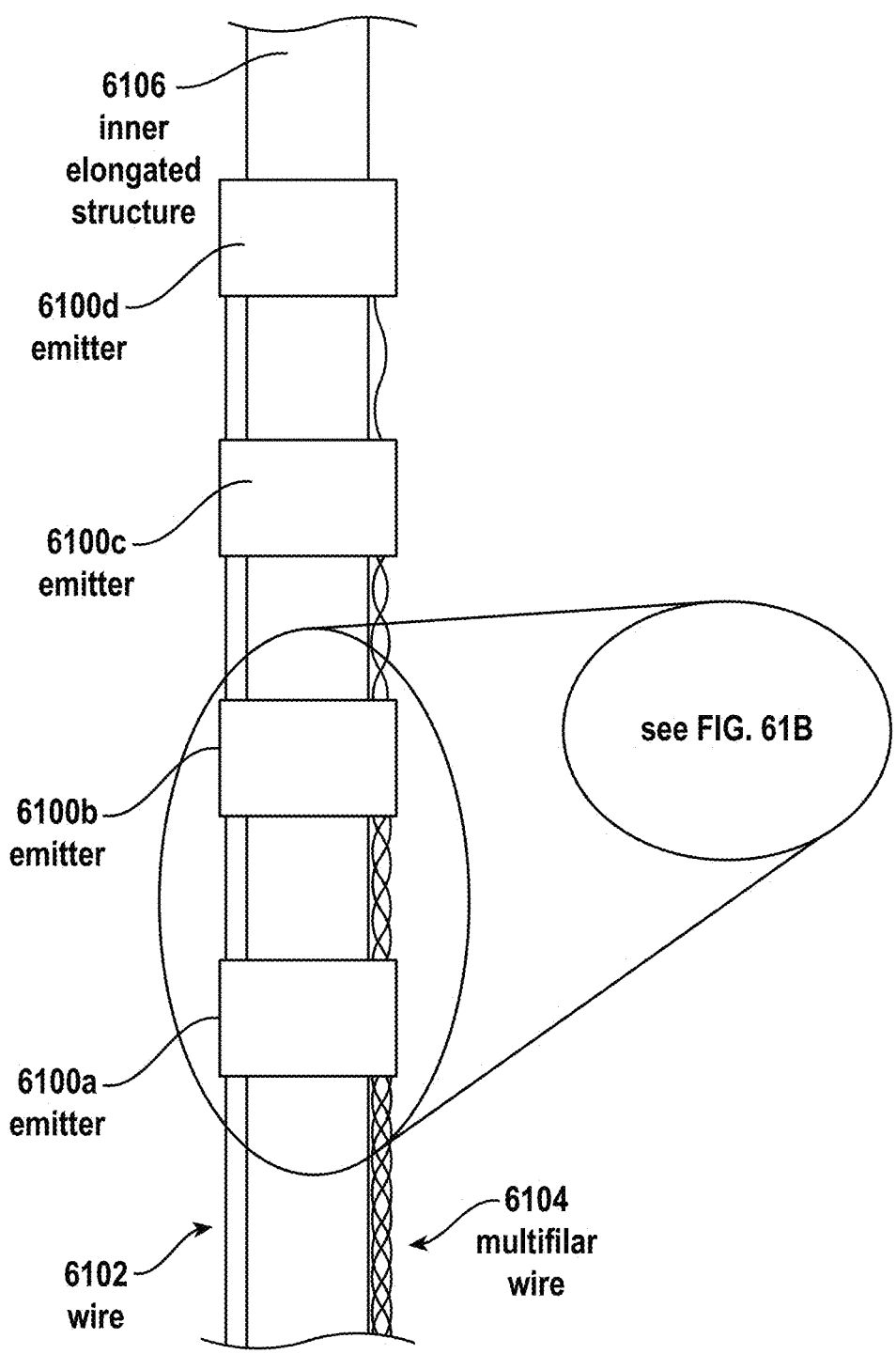
FIG. 61A is a side view of electronic emitters with an example wiring configuration.
Figure 61B:
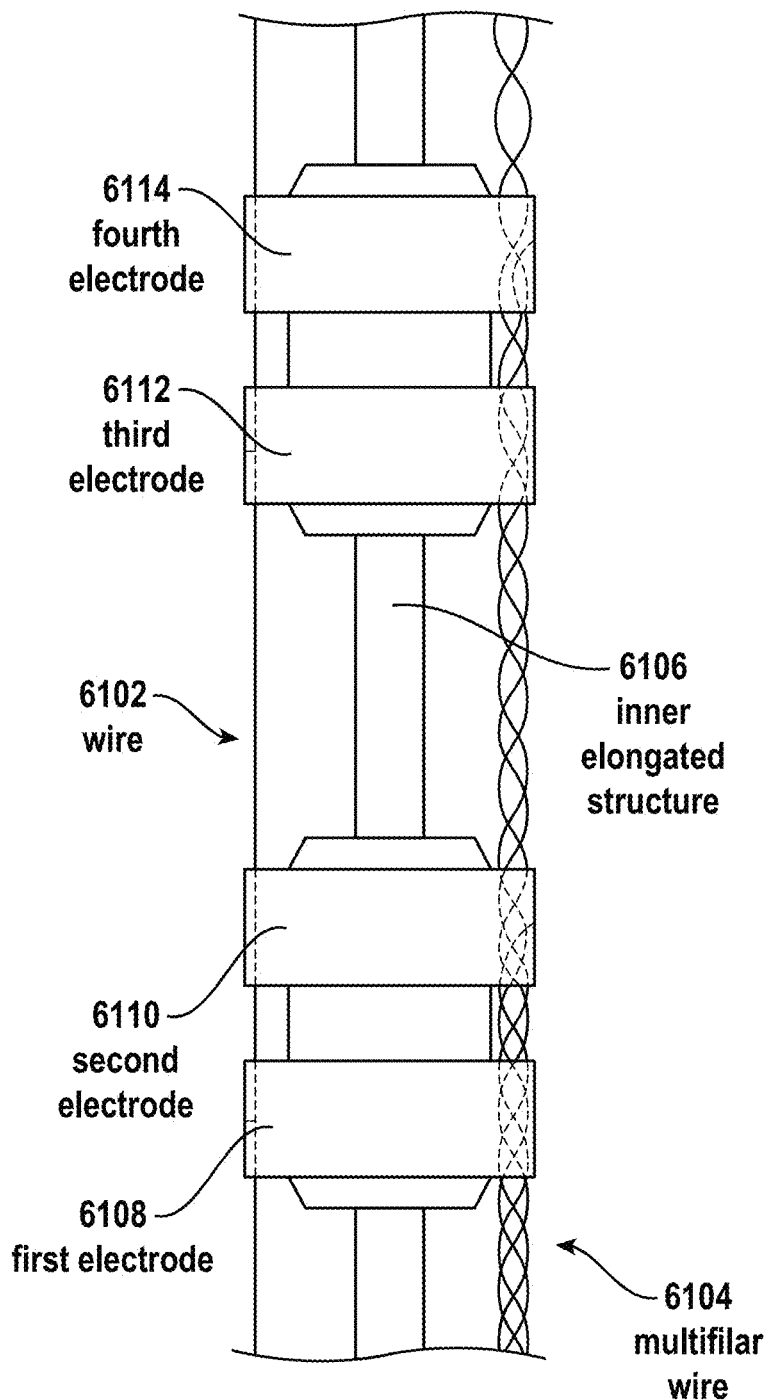
FIG. 61B is a side view of electrode pairs of two of the electronic emitters of FIG. 61A with an example wiring configuration.

FIG. 61A is a side view of emitters with an example wiring configuration, and FIG. 61B is a side view of electrode pairs of two of these emitters. Specifically, FIG. 61A illustrates a first emitter 6100*a*, a second emitter 6100*b*, a third emitter 6100*c*, and a fourth emitter 6100*d*, each of which can at least partially surround an inner elongated structure 6106.

A wire 6102 is shown connecting to each of the first emitter 6100*a*, the second emitter 6100*b*, the third emitter 6100*c*, and the fourth emitter 6100*d*, thus indicating that these emitters 6100 are wired sequentially through this single wire 6102. This wire 6102 can either ground each of the emitters 6100, or provide power to each of the emitters 6100, depending on the needs of the user.

On the opposite side of the inner elongated structure 6106, a multifilar wire 6104 can be present. This multifilar wire 6104 can be a collection of individual wires helically wrapped about one another. In other examples, the multifilar wire 6104 may be a ribbon wire. In still other examples, a multifilar wire 6104 may not be present at all, and instead individual wires may be present adjacent one another. At each emitter 6100, one of the wires of the multifilar wire 6104 can split from the rest of the wires and connect to the emitter 6100. Each of the wires of the multifilar wire 6104 can either ground or provide power to each emitter 6100, whichever is opposite that of wire 6102. This multifilar wire 6104 configuration permits parallel wiring of each of the emitters 6100 making a smaller footprint within the device.

It is understood that, while four emitters 6100 are illustrated in FIG. 61A, a greater number of emitters can be used in a device, so long as it remains capable of traversing the vasculature of a patient.

FIG. 61B illustrates a side view of what can be occurring within each emitter 6100, along with hidden lines. For the purposes of simplicity, two-electrode emitters are shown in FIG. 61B, but it is understood that other emitters, such as three-electrode emitters, can also be implemented in this device. As illustrated, the first emitter 6100a includes a first electrode 6108 and a second electrode 6110, and the second emitter includes a third electrode 6112 and a fourth electrode 6114.

In FIG. 61B, it can be seen that wires of the multifilar wire 6104 are splitting away from the multifilar wire 6104, one for each emitter. A first wire of the multifilar wire 6104 splits off and makes connection with the second electrode 6110. A second wire of the multifilar wire 6104 splits off and makes connection with the fourth electrode 6114. On the opposite side, wire 6102 is shown extending through each of the electrodes, and it is understood that this is because this wire 6102 connects the electrodes sequentially, and only makes electrical connection with those electrodes not being powered (or grounded, in other examples) by the multifilar wire 6104. Therefore, wire 6102 is electrically connected to the first electrode 6108 and the third electrode 6112, in this example.

Included in this disclosure is an apparatus, including an elongated body. In some examples, the apparatus includes a balloon positioned at a distal portion of the elongated body, whereby the balloon is configured to receive a fluid that inflates the balloon such that an exterior surface of the balloon contacts an interior surface of a target treatment site within a vasculature of a patient. According to some examples, the apparatus includes an electronic emitter positioned along a central longitudinal axis of the elongated body within the balloon, the electronic emitter is configured to propagate pressure waves radially outward through the fluid to fragment a calcified lesion at the target treatment site. The electronic emitter may include a first electrode and a second electrode. In some examples, the first electrode is longitudinally spaced from the second electrode such that the longitudinal spacing forms a spark gap between the first electrode and the second electrode. According to some examples, the first electrode and the second electrode at least partially surround the elongated body.

The first electrode and the second electrode may define circles. In some examples, the first electrode defines a first perimeter facing the spark gap, the second electrode defines a second perimeter facing the spark gap, the first perimeter facing the second perimeter. According to some examples, the electronic emitter is configured to create a spark at a random location about the first perimeter and thereby arc to the second perimeter.

The first electrode may define a first perimeter facing the spark gap, and the second electrode may define a second perimeter facing the spark gap, the first perimeter facing the second perimeter. In some examples, the first perimeter is parallel to the second perimeter. According to some examples, the apparatus further includes a power wire electrically coupled to the first electrode. The apparatus may further include a ground wire electrically coupled to the second electrode.

In some examples, the electronic emitter that includes the first electrode and the second electrode is a first electronic emitter and the spark gap is a first spark gap. According to some examples, the second electronic emitter including a third electrode and a fourth electrode. The second electronic emitter may be longitudinally spaced from the first electronic emitter. In some examples, the third electrode is longitudinally spaced from the fourth electrode such that the longitudinal spacing forms a second spark gap between the third electrode and the fourth electrode. According to some examples, the third electrode and the fourth electrode at least partially surround the elongated body.

The first electrode, the second electrode, the third electrode, and the fourth electrode may define circles. In some examples, the first electrode defines a first perimeter facing the first spark gap, and the second electrode defines a second perimeter facing the first spark gap, the first perimeter facing the second perimeter. According to some examples, the third electrode defines a third perimeter facing the second spark gap, and the fourth electrode defines a fourth perimeter facing the second spark gap, the third perimeter facing the fourth perimeter. The first perimeter may be parallel to the second perimeter. In some examples, the third perimeter is parallel to the fourth perimeter.

According to some examples, the apparatus further includes a first power wire electrically coupled to the first electrode. The apparatus may further include a second power wire electrically coupled to the third electrode. In some examples, the apparatus further includes a ground wire electrically coupled to the second electrode and the fourth electrode. According to some examples, when the first electrode receives electricity, the electricity arcs to the second electrode. When the third electrode receives electricity, the electricity may arc to the fourth electrode.

In some examples, the first power wire is configured to provide electricity separately from the second power wire. According to some examples, the first electronic emitter is configured to propagate pressure waves independently from the second electronic emitter.

Also included in this disclosure is an apparatus including an elongated body. The apparatus may include a first electronic emitter positioned along a central longitudinal axis of the elongated body. In some examples, the apparatus includes a second electronic emitter positioned along a central longitudinal axis of the elongated body, the second electronic emitter longitudinally spaced from the first electronic emitter. According to some examples, the apparatus includes a first power wire electrically coupled to the first electronic emitter. The apparatus may include a second power wire electrically coupled to the second electronic emitter. In some examples, the first electronic emitter and the second electronic emitter at least partially surround the elongated body. According to some examples, the first power wire is configured to provide electricity separately from the second power wire.

The apparatus may further include a balloon positioned at a distal portion of the elongated body, the balloon configured to receive a fluid to inflate such that an exterior surface of the balloon contacts an interior surface of a target treatment site within a vasculature of a patient. In some examples, the first electronic emitter and the second electronic emitter are located within the balloon. According to some examples, the first electronic emitter and the second electronic emitter are configured to propagate pressure waves radially outward through the fluid to fragment a calcified lesion at the target treatment site.

The apparatus may further include a ground wire electrically coupled to the first electronic emitter and the second electronic emitter. In some examples, the first electronic emitter includes a first electrode and a second electrode, the first power wire is electrically coupled to the first electrode, and when the first electrode receives electricity, the electricity arcs to the second electrode. According to some examples, the second electronic emitter includes a third electrode and a fourth electrode, the second power wire is electrically coupled to the third electrode, and when the third electrode receives electricity, the electricity arcs to the fourth electrode. The first electronic emitter may be configured to propagate pressure waves independently from the second electronic emitter.

Also included in this disclosure is an apparatus including an elongated body. In some examples, the apparatus includes a balloon positioned at a distal portion of the elongated body, the balloon configured to receive a fluid to inflate such that an exterior surface of the balloon contacts an interior surface of a target treatment site within a vasculature of a patient. According to some examples, the apparatus includes a first electronic emitter positioned along a central longitudinal axis of the elongated body within the balloon. The first electronic emitter may include a first electrode and a second electrode. In some examples, the first electrode is longitudinally spaced from the second electrode such that the longitudinal spacing forms a spark gap between the first electrode and the second electrode. According to some examples, the apparatus includes a second electronic emitter positioned along a central longitudinal axis of the elongated body within the balloon, the second electronic emitter longitudinally spaced from the first electronic emitter. The second electronic emitter may include a third electrode and a fourth electrode. In some examples, the third electrode is longitudinally spaced from the fourth electrode such that the longitudinal spacing forms a spark gap between the third electrode and the fourth electrode. According to some examples, the first electrode, the second electrode, the third electrode, and the fourth electrode at least partially surround the elongated body. The first electronic emitter and the second electronic emitter may be configured to propagate pressure waves radially outward through the fluid to fragment a calcified lesion at the target treatment site.

In some examples, the first electrode defines a first perimeter facing the first spark gap, and the second electrode defines a second perimeter facing the first spark gap, the first perimeter facing the second perimeter. According to some examples, the third electrode defines a third perimeter facing the second spark gap, the fourth electrode defines a fourth perimeter facing the second spark gap, the third perimeter facing the fourth perimeter. The first perimeter may be parallel to the second perimeter. In some examples, the third perimeter is parallel to the fourth perimeter. According to some examples, the first perimeter is parallel to the third perimeter.

The apparatus may further include a first power wire electrically coupled to the first electrode. In some examples, the apparatus further includes a second power wire electrically coupled to the third electrode. According to some examples, the apparatus further includes a ground wire electrically coupled to the second electrode and the fourth electrode. When the first electrode receives electricity, the electricity may arc to the second electrode. In some examples, when the third electrode receives electricity, the electricity arcs to the fourth electrode. According to some examples, the first power wire is configured to provide electricity separately from the second power wire.

Also included in this disclosure is a method, including laser-cutting an elliptical hypotube to define a first electrode and a second electrode arranged to define a longitudinal spark gap therebetween. In some examples, the method includes inserting an elongated body through the laser-cut elliptical hypotube. According to some examples, the method includes flowing a potting material around the laser-cut elliptical hypotube. The method may include removing obsolete support structures from the laser-cut elliptical hypotube. In some examples, the method includes arranging the first electrode and the second electrode to define the longitudinal spark gap therebetween. In alternative examples, the step of inserting an elongated body occurs through the first electrode and the second electrode after the obsolete support structures have been removed.

In some examples, laser-cutting the elliptical hypotube includes laser-cutting a parallelogram from a central portion of the elliptical hypotube, such that the first electrode and the second electrode are separated by a strut. In additional or alternative examples, the shape that is cut is other than that of a parallelogram, such as a chevron pattern. According to some examples, removing obsolete support structures from the elliptical hypotube includes removing the strut. Removing the strut may be performed via laser-cutting the strut out of the hypotube. In additional or alternative examples, removing the strut may be performed through using a cutting tool, a mechanical tab-break design, or a wheel type cutting tool. In some examples, the first electrode defines a first perimeter. According to some examples, the second electrode defines a second perimeter. Removing the strut may include separating the first electrode from the second electrode by a constant distance around and between the first perimeter and the second perimeter.

In some examples, in response to removing the strut, the first electrode and the second electrode are separated by a predetermined distance. According to some examples, when the first electrode and the second electrode are separated by the predetermined distance around the first perimeter and the second perimeter. In some examples, in response to removing the strut, the first perimeter and the second perimeter are parallel.

According to some examples, laser-cutting the elliptical hypotube includes laser cutting three parallelograms from a central portion of the elliptical hypotube, such that the first electrode and the second electrode are separated by three struts. Removing obsolete support structures from the elliptical hypotube may include removing the three struts. In some examples, the first electrode defines a first perimeter. According to some examples, the second electrode defines a second perimeter. Removing the three struts may include separating the first electrode from the second electrode by a constant distance around and between the first perimeter and the second perimeter.

In some examples, inserting the elongated body through the laser-cut elliptical hypotube includes at least partially surrounding the elongated body with the laser-cut elliptical hypotube. According to some examples, flowing potting material around the laser-cut elliptical hypotube includes securing the laser-cut elliptical hypotube to the elongated body via an adhesive.

The method may further include welding a power wire to the first electrode. In some examples, welding the power wire to the first electrode occurs prior to inserting the elongated body through the laser-cut elliptical hypotube. According to some examples, the method further includes running the power wire along the elongated body from the first electrode to a hub. Described differently, the method may further include locating the power wire along the elongated body from the first electrode to a hub.

In some examples, the method further includes welding a ground wire to the second electrode. According to some examples, welding the ground wire to the second electrode occurs prior to inserting the elongated body through the laser-cut elliptical hypotube. The method may further include running the ground wire along the elongated body from the second electrode to a hub. Described differently, the method may further include locating the ground wire along the elongated body from the second electrode to a hub.

In some examples, the laser-cut elliptical hypotube is a first laser-cut elliptical hypotube and wherein the elliptical spark gap is a first elliptical spark gap. According to some examples, the method further includes laser-cutting a second hypotube to define a third electrode and a fourth electrode to define a second elliptical spark gap therebetween. The method may further include inserting the elongated body through the second laser-cut elliptical hypotube. In some examples, the method further includes flowing the potting material around the second laser-cut elliptical hypotube. According to some examples, the method further includes removing obsolete support structures from the second laser-cut elliptical hypotube.

The method may further include welding a first power wire to the first electrode. In some examples, the method further includes welding a second power wire to the third electrode. According to some examples, the method further includes welding a ground wire to the second electrode. The method may further include welding the ground wire to the fourth electrode.

In some examples, welding the first power wire to the first electrode, welding the second power wire to the third electrode, welding the ground wire to the second electrode, and welding the ground wire to the fourth electrode occur prior to inserting the elongated body through the first laser-cut elliptical hypotube and the second laser-cut elliptical hypotube.

The method may further include running the first power wire along the elongated body from the first electrode to a hub. In some examples, the method further includes running the second power wire along the elongated body from the third electrode to a hub. According to some examples, the method further includes running the ground wire along the elongated body from the fourth electrode to the second electrode. The method may further include running the ground wire along the elongated body from the second electrode to the hub.

As pertaining to the preceding paragraph, described differently, the method may further include locating the first power wire along the elongated body from the first electrode to a hub. In some examples, the method further includes locating the second power wire along the elongated body from the third electrode to a hub. According to some examples, the method further includes locating the ground wire along the elongated body from the fourth electrode to the second electrode. The method may further include locating the ground wire along the elongated body from the second electrode to the hub.

Also included in this disclosure is a method, including inserting an apparatus into a vasculature of a patient. The apparatus may include an elongated body. In some examples, the apparatus includes one or more electronic emitters positioned along a central longitudinal axis of the elongated body. According to some examples, at least one of the one or more electronic emitters includes a first electrode and a second electrode. The first electrode may be longitudinally spaced from the second electrode such that the longitudinal spacing defines a spark gap between the first electrode and the second electrode. In some examples, the first electrode and the second electrode at least partially surround the elongated body. According to some examples, the method includes supplying electricity to the first electrode. The method may include arcing the electricity from the first electrode to the second electrode at a random location about a perimeter of the electronic emitter (i.e., about a perimeter of the first electrode and the second electrode).

Also included in this disclosure is a method, including providing an apparatus. The apparatus may include an elongated body. In some examples, the apparatus includes a first electronic emitter positioned along a central longitudinal axis of the elongated body. According to some examples, the first electronic emitter includes a first electrode and a second electrode arranged to define a first spark gap. The apparatus may include a second electronic emitter positioned along the central longitudinal axis of the elongated body and longitudinally spaced from the first electronic emitter. In some examples, the second electronic emitter includes a third electrode and a fourth electrode arranged to define a second spark gap. According to some examples, the apparatus includes a first power wire configured to provide electricity to the first electrode. The apparatus may include a second power wire configured to provide electricity to the third electrode. In some examples, the apparatus includes a ground wire configured to ground the second electrode and the fourth electrode. According to some examples, the method includes supplying electricity to the first electronic emitter. The method may include arcing the electricity between the first electrode and the second electrode. In some examples, the method includes supplying electricity to the second electronic emitter. According to some examples, the method includes arcing the electricity between the third electrode and the fourth electrode.

Supplying electricity to the first electronic emitter and supplying electricity to the second electronic emitter may include manually selecting, via a user, an electronic emitter to which electricity is supplied. In some examples, manually selecting the electronic emitter to which electricity is supplied includes determining a treatment location closest to the electronic emitter. According to some examples, supplying electricity to the first electronic emitter and supplying electricity to the second electronic emitter includes programming a sequence of electronic emitters to which electricity is supplied.

Also included in the present disclosure is a system, including an inner elongated structure defining a guidewire lumen. In some examples, the system includes a balloon positioned at a distal portion of an elongated body, the elongated body including the inner elongated structure, the balloon configured to be inflated. According to some examples, the system includes an emitter 3500 positioned along the elongated body and within the balloon, the emitter 3500 configured to emit pressure waves to fragment a buildup in an organ. The emitter 3500 can include a first electrode and a second electrode arranged to form a spark gap between the first electrode and the second electrode.

In some examples, the inner elongated structure includes a layer of polyimide 3510. According to some examples, the inner elongated structure further includes a layer of polymer 3504*b*. The layer of polymer 3504*b* can at least partially surround the layer of polyimide 3510. In some examples, the layer of polymer 3504*b* includes a single polymer. According to some examples, the layer of polymer 3504*b* includes a copolymer. The layer of polyimide 3510 can include a doped polyimide. In some examples, the doped polyimide is non-metallic.

According to some examples, the system further includes a layer of reinforcement 3508. The layer of polymer 3504*b* can at least partially surround the layer of reinforcement 3508. In some examples, the layer of reinforcement 3508 at least partially surrounds the layer of polyimide 3510.

According to some examples, the layer of reinforcement 3508 includes a braid. The layer of reinforcement 3508 can include a nonmetallic material. In some examples, the nonmetallic material is polyetheretherketone (PEEK). According to some examples, the layer of reinforcement 3508 includes Kevlar fibers.

The layer of reinforcement 3508 can include high-density polyethylene fibers. In some examples, the high-density polyethylene fibers are metallic. According to some examples, the high-density polyethylene fibers are non-metallic. The layer of reinforcement 3508 can be an electrical conductor.

In some examples, the layer of reinforcement 3508 includes a multifilar wire 6104 helically wrapped about the layer of polymer 3504*b*. According to some examples, the multifilar wire 6104 includes a power wire for providing power to the first electrode or the second electrode. The system can further include a layer of adhesive 3502 at least partially surrounding the layer of reinforcement 3508. In some examples, material is removed from the layer of adhesive 3502 to permit the multifilar wire 6104 to electrically couple to the first electrode or the second electrode.

Also included in the present disclosure is a system, including an inner elongated structure defining a guidewire lumen. In some examples, the system includes a balloon positioned at a distal portion of an elongated body, the elongated body including the inner elongated structure, the balloon configured to be inflated. According to some examples, the system includes an emitter positioned along the elongated body and within the balloon, and the emitter configured to emit pressure waves to fragment a buildup in an organ. The emitter can include a first electrode 4502 and a second electrode 4504. In some examples, the first electrode 4502 is spaced from the second electrode 4504 such that the spacing forms a spark gap between the first electrode 4502 and the second electrode 4504.

According to some examples, the emitter further includes a strut 4506 mechanically coupled to each of the first electrode 4502 and the second electrode 4504. The strut 4506 can include less material than each of the first electrode 4502 and the second electrode 4504. In some examples, a location of coupling between the strut 4506 and the first electrode 4502 includes a recess 4508 in the first electrode 4502. According to some examples, a location of coupling between the strut 4506 and the second electrode 4504 includes a recess 4508 in the second electrode 4504. The strut 4506*b*, 4506*c*, and/or 4506*d* can be transverse to each of the first electrode 4502 and the second electrode 4504.

In some examples, the strut 4506*b*, 4506*c*, and/or 4506*d* includes a protrusion 4510. According to some examples, the protrusion 4510 is transverse to the 4506*b*, 4506*c*, and/or 4506*d*. The protrusion 4510*a* can be triangular. In some examples, the protrusion 4510*b* is rectangular. According to some examples, the protrusion 4510*c* is trapezoidal.

The strut 4506*a* can extend at a non-perpendicular angle from each of the first electrode 4502 and the second electrode 4504. In some examples, the strut 4506 is configured to be removed. According to some examples, the strut 4506 is configured to keep an entirety of a perimeter of the first electrode 4502 a constant distance away from an entirety of a perimeter of the second electrode 4504.

Also included in the present disclosure is a system, including an inner elongated structure 4612, 4708, and/or 4814 including a guidewire lumen. In some examples, the system includes an outer elongated structure defining an inflation lumen. According to some examples, the system includes a balloon positioned at a distal portion of an elongated body, the elongated body including the inner elongated structure and the outer elongated structure, the balloon configured to receive a fluid via the inflation lumen to be inflated. The system can include an emitter 4600 and/or 4700 positioned along the elongated body and within the balloon, the emitter 4600 and/or 4700 configured to emit pressure waves to fragment a buildup in an organ. In some examples, the emitter 4600 and/or 4700 includes a first electrode 4602, 4702, and/or 4802 and a second electrode 4604, 4704, and/or 4804. According to some examples, the first electrode 4602, 4702, and/or 4802 is spaced from the second electrode 4604, 4704, and/or 4804 to form a spark gap 4610 between the first electrode 4602, 4702, and/or 4802 and the second electrode 4604, 4704, and/or 4804. The first electrode 4602, 4702, and/or 4802 and the second electrode 4604, 4704, and/or 4804 can each at least partially surround the inner elongated structure 4612, 4708, and/or 4814.

In some examples, the system further includes a power conductor electrically coupled to the first electrode 4602, 4702, and/or 4802. According to some examples, the system further includes a grounded conductor electrically coupled to the second electrode 4604, 4704, and/or 4804. The second electrode 4604, 4704, and/or 4804 can be narrower than the first electrode 4602, 4702, and/or 4802. In some examples, the first electrode 4602, 4702, and/or 4802 is narrower than the second electrode 4604, 4704, and/or 4804.

According to some examples, the system further includes a protrusion 4706 on a side of the second electrode 4604, 4704, and/or 4804, wherein the protrusion faces the first electrode 4602, 4702, and/or 4802. The emitter 4600 and/or 4700 can be rotatable. In some examples, the system further includes a protrusion 4706 on a side of the first electrode 4602, 4702, and/or 4802, wherein the protrusion faces the second electrode 4604, 4704, and/or 4804. According to some examples, the emitter 4600 and/or 4700 is rotatable.

The emitter 4600 and/or 4700 can be a first emitter 4600 and/or 4700 and the spark gap 4610 can be a first spark gap 4810, wherein the system further includes a second emitter 4600 and/or 4700 having a third electrode 4806 and a fourth electrode 4808. In some examples, the third electrode 4806 is spaced from the fourth electrode 4808 to form a second spark gap 4812 between the third electrode 4806 and the fourth electrode 4808. According to some examples, the third electrode 4806 and the fourth electrode 4808 each at least partially surround the inner elongated structure 4612, 4708, and/or 4814. The first spark gap 4810 can be wider than the second spark gap 4812.

In some examples, the power conductor is a first power conductor, wherein the system further includes a second power conductor electrically coupled to the third electrode 4806, wherein the grounded conductor is electrically coupled to the fourth electrode 4808. According to some examples, the fourth electrode 4808 is narrower than the third electrode 4806. The third electrode 4806 can be narrower than the fourth electrode 4808.

In some examples, the system further includes a protrusion 4706 on a side of the fourth electrode 4808, wherein the protrusion faces the third electrode 4806. According to some examples, the second emitter 4600 and/or 4700 is rotatable. The system can further include a protrusion 4706 on a side of the third electrode 4806, wherein the protrusion faces the fourth electrode 4808. In some examples, the second emitter 4600 and/or 4700 is rotatable.

According to some examples, the first emitter 4600 and/or 4700 and the second emitter 4600 and/or 4700 are configured to propagate pressure waves independently of one another. The first emitter 4600 and/or 4700 and the second emitter 4600 and/or 4700 can be configured to create a compound pressure wave from sequential firing of the first emitter 4600 and/or 4700 and the second emitter 4600 and/or 4700. In some examples, the first emitter 4600 and/or 4700 and the second emitter 4600 and/or 4700 are configured to create a compound pressure wave from timed firing of the first emitter 4600 and/or 4700 and the second emitter 4600 and/or 4700.

According to some examples, the grounded conductor is a first grounded conductor, wherein the system further includes a second grounded conductor electrically coupled to the fourth electrode 4808, wherein the power conductor is electrically coupled to the third electrode 4806. The fourth electrode 4808 can be narrower than the third electrode 4806. In some examples, the third electrode 4806 is narrower than the fourth electrode 4808.

According to some examples, the system further includes a protrusion 4706 on a side of the fourth electrode 4808, wherein the protrusion faces the third electrode 4806. The second emitter 4600 and/or 4700 can be rotatable. In some examples, the system further includes a protrusion 4706 on a side of the third electrode 4806, wherein the protrusion faces the fourth electrode 4808. According to some examples, the emitter 4600 and/or 4700 is rotatable.

The first emitter 4600 and/or 4700 and the second emitter 4600 and/or 4700 can be configured to propagate pressure waves independently of one another. In some examples, the first emitter 4600 and/or 4700 and the second emitter 4600 and/or 4700 are configured to create a compound pressure wave from sequential firing of the first emitter 4600 and/or 4700 and the second emitter 4600 and/or 4700. According to some examples, the first emitter 4600 and/or 4700 and the second emitter 4600 and/or 4700 are configured to create a compound pressure wave from timed firing of the first emitter 4600 and/or 4700 and the second emitter 4600 and/or 4700.

Also included in the present disclosure is a system, including an inner elongated structure 4918, 5018, 5110, 5212, 5322, and/or 5422 defining a guidewire lumen. In some examples, the system includes an outer elongated structure including an inflation lumen. According to some examples, the system includes a balloon positioned at a distal portion of an elongated body, the elongated body including the inner elongated structure and the outer elongated structure, the balloon configured to receive a fluid via the inflation lumen to be inflated. The system can include an emitter 4900, 5000, 5100, and/or 5200 positioned along the elongated body and within the balloon, the emitter configured to emit pressure waves to fragment a buildup in an organ. In some examples, the emitter includes a first electrode 4902, 5002, 5102, 5202, 5302, and/or 5402, a second electrode 4904, 5004, 5104, 5204, 5304, and/or 5404, and a third electrode 4906, 5006, 5106, 5206, 5306, and/or 5406. According to some examples, the first electrode 4902, 5002, 5102, 5202, 5302, and/or 5402 is spaced from the second electrode 4904, 5004, 5104, 5204, 5304, and/or 5404 to form a first spark gap 4908, 5008, 5208, 5314, and/or 5414 between the first electrode 4902, 5002, 5102, 5202, 5302, and/or 5402 and the second electrode 4904, 5004, 5104, 5204, 5304, and/or 5404. The second electrode 4904, 5004, 5104, 5204, 5304, and/or 5404 can be spaced from the third electrode 4906, 5006, 5106, 5206, 5306, and/or 5406 to form a second spark gap 4910, 5010, 5210, 5316, and/or 5416 between the second electrode 4904, 5004, 5104, 5204, 5304, and/or 5404 and the third electrode 4906, 5006, 5106, 5206, 5306, and/or 5406. In some examples, the first electrode 4902, 5002, 5102, 5202, 5302, and/or 5402, the second electrode 4904, 5004, 5105, 5204, 5204, and/or 5404, and the third electrode 4906, 5006, 5106, 5206, 5306, and/or 5406 each at least partially surround the inner elongated structure 4918, 5018, 5110, 5212, 5322, and/or 5422.

According to some examples, the system further includes a power conductor electrically coupled to the second electrode 4904, 5004, 5104, 5204, 5304, and/or 5404. The system can include a first grounded conductor electrically coupled to the first electrode 4902, 5002, 5102, 5202, 5302, and/or 5402. In some examples, the system includes a second grounded conductor electrically coupled to the third electrode 4906, 5006, 5106, 5206, 5306, and/or 5406.

According to some examples, the second electrode 4904 is wider than the first electrode 4902 and the third electrode 4906. A width of the first electrode 4902 and a width of the third electrode 4906 can be the same. In some examples, the second electrode 5004 is narrower than the first electrode 5002 and the third electrode 5006. According to some examples, a width of the first electrode 5002 and a width of the third electrode 5006 are the same.

The system can further include a protrusion 5108 on a side of the second electrode 5104, wherein the protrusion faces the first electrode 5102. In some examples, the emitter 5100 is rotatable. According to some examples, the system further includes a protrusion 5108 on a side of the first electrode 5102, wherein the protrusion faces the second electrode 5104. The emitter 5100 can be rotatable. In some examples, the system further includes a protrusion 5108 on a side of the second electrode 5104, wherein the protrusion faces the third electrode 5106. According to some examples, the emitter 5100 is rotatable. The system can include a protrusion 5108 on a side of the third electrode 5106, wherein the protrusion faces the second electrode 5104. In some examples, the emitter 5100 is rotatable. According to some examples, the second spark gap 5210 is wider than the first spark gap 5208.

The emitter 4900, 5000, 5100, and/or 5200 can be a first emitter, wherein the system can further includes a second emitter including a fourth electrode 5308 and/or 5408, a fifth electrode 5310 and/or 5410, and a sixth electrode 5312 and/or 5412. In some examples, the fourth electrode 5308 and/or 5408 is spaced from the fifth electrode 5310 and/or 5410 to form a third spark gap 5318 and/or 5418 between the fourth electrode 5308 and/or 5408 and the fifth electrode 5310 and/or 5410. According to some examples, the fifth electrode 5310 and/or 5410 is spaced from the sixth electrode 5312 and/or 5412 to form a fourth spark gap 5320 and/or 5420 between the fifth electrode 5310 and/or 5410 and the sixth electrode 5312 and/or 5412.

The system can further include a third grounded conductor electrically coupled to the fourth electrode 5308 and/or 5408. In some examples, the system further includes a fourth grounded conductor electrically coupled to the sixth electrode 5312 and/or 5412. According to some examples, the power conductor is electrically coupled to the fifth electrode 5310 and/or 5410.

The fifth electrode 5310 can be wider than the fourth electrode 5308 and the sixth electrode 5312. In some examples, a width of the fifth electrode 5310 and a width of the second electrode are the same. According to some examples, a width of the fourth electrode 5308 and a width of the sixth electrode 5312 are the same. A width of the first electrode, a width of the third electrode, the width of the fourth electrode 5308, and the width of the sixth electrode 5312 can be the same.

In some examples, the fifth electrode is narrower than the fourth electrode and the sixth electrode. According to some examples, a width of the fifth electrode and a width of the second electrode are the same. A width of the fourth electrode and a width of the sixth electrode are the same. In some examples, a width of the first electrode, a width of the third electrode, the width of the fourth electrode, and the width of the sixth electrode are the same.

According to some examples, the system further includes a protrusion on a side of the fifth electrode 5310 and/or 5410, wherein the protrusion faces the fourth electrode 5308 and/or 5408. The second emitter can be rotatable. In some examples, the system further includes a protrusion on a side of the fourth electrode 5308 and/or 5408, wherein the protrusion faces the fifth electrode 5310 and/or 5410. According to some examples, the second emitter is rotatable. The system can further include a protrusion on a side of the fifth electrode 5310 and/or 5410, wherein the protrusion faces the sixth electrode 5312 and/or 5412. In some examples, the second emitter is rotatable. According to some examples, the system further includes a protrusion on a side of the sixth electrode 5312 and/or 5412, wherein the protrusion faces the fifth electrode 5310 and/or 5410. The second emitter can be rotatable.

In some examples, the first emitter and the second emitter are configured to propagate pressure waves independently of one another. According to some examples, the first emitter and the second emitter are configured to create a compound pressure wave from sequential firing of the first emitter and the second emitter. The first emitter and the second emitter can be configured to create a compound pressure wave from timed firing of the first emitter and the second emitter.

In some examples, the third spark gap is wider than the fourth spark gap. According to some examples, a width of the first spark gap and a width of the third spark gap are the same. A width of the second spark gap and a width of the fourth spark gap are the same.

In some examples, the power conductor is a first power conductor, wherein the system further includes a second power conductor electrically coupled to the fifth electrode 5310 and/or 5410. According to some examples, the system further includes a third grounded conductor electrically coupled to the fourth electrode 5308 and/or 5408. The system can further include a fourth grounded conductor electrically coupled to the sixth electrode 5312 and/or 5412.

In some examples, the fifth electrode 5310 is wider than the fourth electrode 5308 and the sixth electrode 5312. According to some examples, a width of the fifth electrode 5310 and a width of the second electrode are the same. A width of the fourth electrode 5308 and a width of the sixth electrode 5312 can be the same. In some examples, a width of the first electrode, a width of the third electrode, the width of the fourth electrode 5308, and the width of the sixth electrode 5312 are the same.

According to some examples, the fifth electrode is narrower than the fourth electrode and the sixth electrode. A width of the fifth electrode and a width of the second electrode can be the same. In some examples, a width of the fourth electrode and a width of the sixth electrode are the same. According to some examples, a width of the first electrode, a width of the third electrode, the width of the fourth electrode, and the width of the sixth electrode are the same.

The system can further include a protrusion on a side of the fifth electrode 5310 and/or 5410, wherein the protrusion faces the fourth electrode 5308 and/or 5408. In some examples, the second emitter is rotatable. According to some examples, the system further includes a protrusion on a side of the fourth electrode 5308 and/or 5408, wherein the protrusion faces the fifth electrode 5310 and/or 5410. The second emitter can be rotatable. In some examples, the system further includes a protrusion on a side of the fifth electrode 5310 and/or 5410, wherein the protrusion faces the sixth electrode 5312 and/or 5412. According to some examples, the second emitter is rotatable. The system can further include a protrusion on a side of the sixth electrode 5312 and/or 5412, wherein the protrusion faces the fifth electrode 5310 and/or 5410. In some examples, the second emitter is rotatable.

According to some examples, the first emitter and the second emitter are configured to propagate pressure waves independently of one another. The first emitter and the second emitter can be configured to create a compound pressure wave from sequential firing of the first emitter and the second emitter. In some examples, the first emitter and the second emitter are configured to create a compound pressure wave from timed firing of the first emitter and the second emitter.

According to some examples, the third spark gap is wider than the fourth spark gap. A width of the first spark gap and a width of the third spark gap can be the same. In some examples, a width of the second spark gap and a width of the fourth spark gap are the same.

According to some examples, the system further includes a grounded conductor electrically coupled to the second electrode 4904, 5004, 5104, 5204, 5304, and/or 5404. The system can further include a first power conductor electrically coupled to the first electrode 4902, 5002, 5102, 5202, 5302, and/or 5402. In some examples, the system further includes a second power conductor electrically coupled to the third electrode 4906, 5006, 5106, 5206, 5306, and/or 5406.

According to some examples, the second electrode 4904 is wider than the first electrode 4902 and the third electrode 4906. A width of the first electrode 4902 and a width of the third electrode 4906 can be the same. In some examples, the second electrode 5004 is narrower than the first electrode 5002 and the third electrode 5006. According to some examples, a width of the first electrode 5002 and a width of the third electrode 5006 are the same.

The system can further include a protrusion 5108 on a side of the second electrode 5104, wherein the protrusion faces the first electrode 5102. In some examples, the emitter 5100 is rotatable. According to some examples, the system further includes a protrusion 5108 on a side of the first electrode 5102, wherein the protrusion faces the second electrode 5104. The emitter can be rotatable. In some examples, the system further includes a protrusion 5108 on a side of the second electrode 5104, wherein the protrusion faces the third electrode 5106. According to some examples, the emitter 5100 is rotatable. The system can further include a protrusion 5108 on a side of the third electrode 5106, wherein the protrusion faces the second electrode 5104. In some examples, the emitter 5100 is rotatable. According to some examples, the second spark gap 5210 is wider than the first spark gap 5208.

The emitter 4900, 5000, 5100, and/or 5200 can be a first emitter, wherein the system can further include a second emitter including a fourth electrode 5308 and/or 5408, a fifth electrode 5310 and/or 5410, and a sixth electrode 5312 and/or 5412. In some examples, the fourth electrode 5308 and/or 5408 is spaced from the fifth electrode 5310 and/or 5410 such that the spacing forms a third spark gap 5318 and/or 5418 between the fourth electrode 5308 and/or 5408 and the fifth electrode 5310 and/or 5410. According to some examples, the fifth electrode 5310 and/or 5410 is spaced from the sixth electrode 5312 and/or 5412 to form a fourth spark gap 5320 and/or 5420 between the fifth electrode 5310 and/or 5410 and the sixth electrode 5312 and/or 5412.

The system can further include a third power conductor electrically coupled to the fourth electrode 5308 and/or 5408. In some examples, the system further includes a fourth power conductor electrically coupled to the sixth electrode 5312 and/or 5412. According to some examples, the grounded conductor is electrically coupled to the fifth electrode 5310 and/or 5410.

The fifth electrode 5310 can be wider than the fourth electrode and the sixth electrode. In some examples, a width of the fifth electrode 5310 and a width of the second electrode are the same. According to some examples, a width of the fourth electrode 5308 and a width of the sixth electrode 5312 are the same.

A width of the first electrode, a width of the third electrode, the width of the fourth electrode 5308, and the width of the sixth electrode 5312 can be the same. In some examples, the fifth electrode is narrower than the fourth electrode and the sixth electrode. According to some examples, a width of the fifth electrode and a width of the second electrode are the same. A width of the fourth electrode and a width of the sixth electrode are the same. In some examples, a width of the first, a width of the third electrode 4906, the width of the fourth electrode, and the width of the sixth electrode are the same.

According to some examples, the system further includes a protrusion on a side of the fifth electrode 5310 and/or 5410, wherein the protrusion faces the fourth electrode 5308 and/or 5408. The second emitter can be rotatable. In some examples, the system further includes a protrusion on a side of the fourth electrode 5308 and/or 5408, wherein the protrusion faces the fifth electrode 5310 and/or 5410. According to some examples, the second emitter is rotatable. The system can further include a protrusion on a side of the fifth electrode 5310 and/or 5410, wherein the protrusion faces the sixth electrode 5312 and/or 5412. In some examples, the second emitter is rotatable. According to some examples, the system further includes a protrusion on a side of the sixth electrode 5312 and/or 5412, wherein the protrusion faces the fifth electrode 5310 and/or 5410. The second emitter can be rotatable.

In some examples, the first emitter and the second emitter are configured to propagate pressure waves independently of one another. According to some examples, the first emitter and the second emitter are configured to create a compound pressure wave from sequential firing of the first emitter and the second emitter. The first emitter and the second emitter can be configured to create a compound pressure wave from timed firing of the first emitter and the second emitter.

In some examples, the third spark gap is wider than the fourth spark gap. According to some examples, a width of the first spark gap and a width of the third spark gap are the same. A width of the second spark gap and a width of the fourth spark gap can be the same.

In some examples, the grounded conductor is a first grounded conductor, wherein the system further includes a second grounded conductor electrically coupled to the fifth electrode 5310 and/or 5410. According to some examples, the system further includes a third power conductor electrically coupled to the fourth electrode 5308 and/or 5408. The system can further include a fourth power conductor electrically coupled to the sixth electrode 5312 and/or 5412.

In some examples, the fifth electrode 5310 is wider than the fourth electrode 5308 and the sixth electrode 5312. According to some examples, a width of the fifth electrode 5310 and a width of the second electrode are the same. A width of the fourth electrode 5308 and a width of the sixth electrode 5312 can be the same. In some examples, a width of the first electrode, a width of the third electrode, the width of the fourth electrode 5308, and the width of the sixth electrode 5312 are the same.

According to some examples, the fifth electrode is narrower than the fourth electrode and the sixth electrode. A width of the fifth electrode and a width of the second electrode can be the same. In some examples, a width of the fourth electrode and a width of the sixth electrode are the same. According to some examples, a width of the first electrode, a width of the third electrode, the width of the fourth electrode, and the width of the sixth electrode are the same.

The system can further include a protrusion on a side of the fifth electrode 5310 and/or 5410, wherein the protrusion faces the fourth electrode 5308 and/or 5408. In some examples, the second emitter is rotatable. According to some examples, the system further includes a protrusion on a side of the fourth electrode 5308 and/or 5408, wherein the protrusion faces the fifth electrode 5310 and/or 5410. The second emitter can be rotatable. In some examples, the system further includes a protrusion on a side of the fifth electrode 5310 and/or 5410, wherein the protrusion faces the sixth electrode 5312 and/or 5412. According to some examples, the second emitter is rotatable. The system can further include a protrusion on a side of the sixth electrode 5312 and/or 5412, wherein the protrusion faces the fifth electrode 5310 and/or 5410. In some examples, the second emitter is rotatable.

According to some examples, the first emitter and the second emitter are configured to propagate pressure waves independently of one another. The first emitter and the second emitter can be configured to create a compound pressure wave from sequential firing of the first emitter and the second emitter. In some examples, the first emitter and the second emitter are configured to create a compound pressure wave from timed firing of the first emitter and the second emitter.

According to some examples, the third spark gap is wider than the fourth spark gap. A width of the first spark gap and a width of the third spark gap can be the same. In some examples, a width of the second spark gap and a width of the fourth spark gap are the same.

Also included in the present disclosure is a system, including an inner elongated structure including a guidewire lumen. In some examples, the system includes a balloon positioned at or near a distal portion of the inner elongated structure, the balloon configured to be inflated. According to some examples, the system includes an emitter 5500, 5600, 5700, and/or 5800 positioned along the inner elongated structure and within the balloon, the emitter 5500, 5600, 5700, and/or 5800 configured to emit pressure waves to fragment a buildup in an organ. The emitter 5500, 5600, 5700, and/or 5800 can include a first electrode 5502, 5602, 5702, and/or 5802, a second electrode 5504, 5604, 5704, and/or 5804, and a third electrode 5506, 5606, 5706, and/or 5806, as well as a first spark gap 5508, 5608, and/or 5808 between the first electrode 5502, 5602, 5702, and/or 5802 and the second electrode 5504, 5604, 5704, and/or 5804, and a second spark gap 5510, 5610, and/or 5810 between the second electrode 5504, 5604, 5704, and/or 5804 and the third electrode 5506, 5606, 5706, and/or 5806.

In some examples, the first electrode 5502, 6602, 5702, and/or 5802, the second electrode 5504, 5604, 5704, and/or 5804, and the third electrode 5506, 5606, 5706, and/or 5806 each at least partially surround the inner elongated structure. According to some examples, the first electrode 5502, 6602, 5702, and/or 5802, the second electrode 5504, 5604, 5704, and/or 5804, and the third electrode 5506, 5606, 5706, and/or 5806 each wrap around the inner elongated structure.

A distance between the first electrode 5502, 6602, and/or 5802 and the second electrode 5504, 5604, and/or 5804 can be equal throughout a wrapping around of the inner elongate structure. In some examples, a distance between the second electrode 5504, 5604, and/or 5804 and the third electrode 5506, 5606, and/or 5806 is equal throughout a wrapping around of the inner elongate structure. According to some examples, the distance between the second electrode 5604, 5704, and/or 5804 and the third electrode 5606, 5706, and/or 5806 is less than the distance between the first electrode 5602, 5702, and/or 5802 and the second electrode 5604, 5704, and/or 5804.

The first electrode 5502, 6602, 5702, and/or 5802, the second electrode 5504, 5604, 5704, and/or 5804, and the third electrode 5506, 5606, 5706, and/or 5806 can each wrap around the inner elongated structure, helically. In some examples, a distance between the first electrode 5502, 6602, and/or 5802 and the second electrode 5504, 5604, and/or 5804 is equal throughout a wrapping around of the inner elongate structure. According to some examples, a distance between the second electrode 5504, 5604, and/or 5804 and the third electrode 5506, 5606, and/or 5806 is equal throughout a wrapping around of the inner elongate structure.

A distance between the first electrode 5702, and/or 5802 and the second electrode 5704, and/or 5804 can decrease throughout a wrapping around of the inner elongate structure. In some examples, a distance between the second electrode 5704, and/or 5804 and the third electrode 5706, and/or 5806 decreases throughout a wrapping around of the inner elongate structure. According to some examples, the first spark gap 5608, and/or 5808 is shorter than the second spark gap 5610, and/or 5810.

The system can further include a power conductor electrically coupled to the second electrode 5504, 5604, 5704, and/or 5804. In some examples, the system further includes a grounded conductor electrically coupled to the first electrode 5502, 6602, 5702, and/or 5802 and the third electrode 5506, 5606, 5706, and/or 5806. According to some examples, the second electrode is narrower than the first electrode and the third electrode. A width of the first electrode and a width of the third electrode can be the same.

In some examples, the second electrode 5504, 5604, 5704, and/or 5804 is wider than the first electrode 5502, 6602, 5702, and/or 5802 and the third electrode 5506, 5606, 5706, and/or 5806. According to some examples, a width of the first electrode 5502, 6602, 5702, and/or 5802 and a width of the third electrode 5506, 5606, 5706, and/or 5806 are the same.

The system can include a protrusion on a side of the second electrode 5504, 5604, 5704, and/or 5804, wherein the protrusion faces the first electrode 5502, 6602, 5702, and/or 5802. In some examples, the system includes a protrusion on a side of the second electrode 5504, 5604, 5704, and/or 5804, wherein the protrusion faces the third electrode 5506, 5606, 5706, and/or 5806. According to some examples, the system further includes a protrusion on the first electrode 5502, 6602, 5702, and/or 5802, wherein the protrusion faces the second electrode 5504, 5604, 5704, and/or 5804. The system can further include a protrusion on the third electrode 5506, 5606, 5706, and/or 5806, wherein the protrusion faces the second electrode 5504, 5604, 5704, and/or 5804.

In some examples, the inner elongated structure is pliable. According to some examples, the emitter 5500, 5600, 5700, and/or 5800 is configured to articulate from inner elongated structure bending, thereby causing the first spark gap 5508, 5608, and/or 5808 and the second spark gap 5510, 5610, and/or 5810 to decrease.

The system can further include a power conductor coupled to the first electrode 5502, 6602, 5702, and/or 5802 and the third electrode 5506, 5606, 5706, and/or 5806. In some examples, the system further includes a grounded conductor electrically coupled to the second electrode 5504, 5604, 5704, and/or 5804. According to some examples, the second electrode is narrower than the first electrode and the third electrode. A width of the first electrode and a width of the third electrode are the same.

In some examples, the second electrode 5504, 5604, 5704, and/or 5804 is wider than the first electrode 5502, 6602, 5702, and/or 5802 and the third electrode 5506, 5606, 5706, and/or 5806. According to some examples, a width of the first electrode 5502, 6602, 5702, and/or 5802 and a width of the third electrode 5506, 5606, 5706, and/or 5806 are the same.

The system can further include a protrusion on a side of the second electrode 5504, 5604, 5704, and/or 5804, wherein the protrusion faces the first electrode 5502, 6602, 5702, and/or 5802. In some examples, the system further includes a protrusion on a side of the second electrode 5504, 5604, 5704, and/or 5804, wherein the protrusion faces the third electrode 5506, 5606, 5706, and/or 5806. According to some examples, the system further includes a protrusion on the first electrode 5502, 6602, 5702, and/or 5802, wherein the protrusion faces the second electrode 5504, 5604, 5704, and/or 5804. The system can further include a protrusion on the third electrode 5506, 5606, 5706, and/or 5806, wherein the protrusion faces the second electrode 5504, 5604, 5704, and/or 5804.

In some examples, the inner elongated structure is pliable. According to some examples, the emitter 5500, 5600, 5700, and/or 5800 is configured to articulate from the inner elongated structure bending, thereby causing the first spark gap 5508, 5608, and/or 5808 and the second spark gap 5510, 5610, and/or 5810 to decrease in width.

Also included in the present disclosure is a system, including an inner elongated structure including a guidewire lumen. In some examples, the system includes a balloon positioned at or near a distal portion of the inner elongated structure, the balloon configured to be inflated. According to some examples, the system includes an emitter 5900 and/or 6000 positioned along the inner elongated structure and within the balloon, the emitter 5900 and/or 6000 configured to emit pressure waves to fragment a buildup in an organ. The emitter 5900 and/or 6000 can include a first electrode 5902 and/or 6002 and a second electrode 5904 and/or 6004 arranged to define a spark gap 5906 and/or 6006 between the first electrode 5902 and/or 6002 and the second electrode 5904 and/or 6004.

In some examples, the first electrode 5902 and/or 6002 and the second electrode 5904 and/or 6004 each at least partially surround the inner elongated structure. According to some examples, the first electrode 5902 and/or 6002 and the second electrode 5904 and/or 6004 wrap around the inner elongate structure. A distance between the first electrode 5902 and/or 6002 and the second electrode 5904 and/or 6004 can be equal throughout a wrapping around of the inner elongate structure.

In some examples, the first electrode 5902 and/or 6002 and the second electrode 5904 and/or 6004 wrap around the inner elongate structure, helically. According to some examples, a distance between the first electrode 5902 and/or 6002 and the second electrode 5904 and/or 6004 is equal throughout a wrapping around of the inner elongate structure. A distance between the first electrode 5902 and/or 6002 and the second electrode 5904 and/or 6004 decreases throughout a wrapping around of the inner elongate structure.

In some examples, the system further includes a power conductor electrically coupled to the first electrode 5902 and/or 6002. According to some examples, the system further includes a grounded conductor coupled to the second electrode 5904 and/or 6004. The first electrode 5902 and/or 6002 can be wider than the second electrode 5904 and/or 6004. In some examples, the second electrode 5904 and/or 6004 is wider than the first electrode 5902 and/or 6002.

According to some examples, the system further includes a protrusion on the first electrode 5902 and/or 6002. The system can further include a protrusion on the second electrode 5904 and/or 6004.

In some examples, the inner elongated structure is pliable. According to some examples, the emitter 5900 and/or 6000 is configured to articulate from the inner elongated structure bending, thereby causing a spark gap 5906 and/or 6006 between the first electrode 5902 and/or 6002 and the second electrode 5904 and/or 6004 to decrease.

Also included in the present disclosure is a system, including an inner elongated structure 6106 defining a guidewire lumen. In some examples, the system includes a balloon positioned at a distal portion of an elongated body, the elongated body including the inner elongate structure 6106, the balloon configured to be inflated. According to some examples, the system includes an emitter 6100 positioned along the elongated body and within the balloon, the emitter 6100 configured to emit pressure waves to fragment a buildup in an organ. The emitter 6100 can include a first electrode 6108 and a second electrode 6110 arranged to form a spark gap between the first electrode 6108 and the second electrode 6110.

In some examples, the emitter 6100 that includes the first electrode 6108 and the second electrode 6110 is a first emitter 6100*a* and the spark gap is a first spark gap. According to some examples, the system further includes a second emitter 6100*b*. The second emitter 6100*b* can include a third electrode 6112 and a fourth electrode 6114 arranged to define a second spark gap between the third electrode 6112 and the fourth electrode 6114.

In some examples, the system further includes a first grounded conductor electrically coupled to the second electrode 6110. According to some examples, the system further includes a second grounded conductor electrically coupled to the fourth electrode 6114. The system can further include a power conductor electrically coupled to the first electrode 6108 and the third electrode 6112. In some examples, the first grounded conductor is configured to ground the second electrode 6110 separately from the fourth electrode 6114. According to some examples, the first emitter 6100*a* is configured to propagate pressure waves independently from the second emitter 6100*b*.

The system can further include a multifilar wire 6104, wherein the multifilar wire 6104 includes the first grounded conductor and the second grounded conductor coupled to one another in a helical twist. According to some examples, the multifilar wire 6104 is a multifilar ribbon wire. The multifilar wire 6104 may be replaced by individual, non-coupled wires adjacent one another. In some examples, the first grounded conductor is configured to removably couple from the second grounded conductor when the multifilar wire 6104 is near the second electrode 6110. According to some examples, the first electrode 6108 and the second electrode 6110 surround the inner elongated structure 6106. The first grounded conductor and the second grounded conductor can be located on opposite sides of the inner elongated structure 6106 than the power conductor.

In some examples, the system further includes a first power conductor electrically coupled to the second electrode 6110. According to some examples, the system further includes a second power conductor electrically coupled to the fourth electrode 6114. The system can further include a grounded conductor electrically coupled to the first electrode 6108 and the third electrode 6112.

In some examples, the first power conductor is configured to power the second electrode 6110 separately from the fourth electrode 6114. According to some examples, the first emitter 6100*a* is configured to propagate pressure waves independently from the second emitter 6100*b*.

The system can further include a multifilar wire 6104. In some examples, the multifilar wire 6104 includes the first power conductor and the second power conductor coupled to one another in a helical twist. According to some examples, the first power conductor is configured to removably couple from the second power conductor when the multifilar wire 6104 is near the second electrode 6110.

The first electrode 6108 and the second electrode 6110 can surround the inner elongated structure 6106. In some examples, the first power conductor and the second power conductor are located on opposite sides of the inner elongated structure 6106 than the grounded conductor.

The section headings and subheadings provided herein are nonlimiting. The section headings and subheadings do not represent or limit the full scope of the embodiments described in the sections to which the headings and subheadings pertain. For example, a section titled "Topic 1" may include embodiments that do not pertain to Topic 1 and embodiments described in other sections may apply to and be combined with embodiments described within the "Topic 1" section.

The various features and processes described above may be used independently of one another, or may be combined in various ways. All possible combinations and subcombinations are intended to fall within the scope of this disclosure. In addition, certain method, event, state, or process blocks may be omitted in some implementations. The methods, steps, and processes described herein are also not limited to any particular sequence, and the blocks, steps, or states relating thereto can be performed in other sequences that are appropriate. For example, described tasks or events may be performed in an order other than the order specifically disclosed. Multiple steps may be combined in a single block or state. The example tasks or events may be performed in serial, in parallel, or in some other manner. Tasks or events may be added to or removed from the disclosed example embodiments. The example systems and components described herein may be configured differently than described. For example, elements may be added to, removed from, or rearranged compared to the disclosed example embodiments.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require at least one of X, at least one of Y, and at least one of Z to each be present.

The term "and/or" means that "and" applies to some embodiments and "or" applies to some embodiments. Thus, A, B, and/or C can be replaced with A, B, and C written in one sentence and A, B, or C written in another sentence. A, B, and/or C means that some embodiments can include A and B, some embodiments can include A and C, some embodiments can include B and C, some embodiments can only include A, some embodiments can include only B, some embodiments can include only C, and some embodiments can include A, B, and C. The term "and/or" is used to avoid unnecessary redundancy.

We claim:

1. An apparatus, comprising:
   an elongated body comprising a guidewire lumen and a pressure wave emitter, the pressure wave emitter configured to emit a pressure wave,
   the pressure wave emitter comprising a first electrode and a second electrode each at least partially surrounding the guidewire lumen, the first electrode distal in its entirety to and longitudinally spaced from the second electrode such that the longitudinal spacing forms a spark gap between the first electrode and the second electrode,
   the first electrode and the second electrode fixed with respect to one another such that the spark gap between the first electrode and the second electrode remain a consistent distance from one another, the first electrode and the second electrode configured to remain fixed in orientation with respect to one another,
   wherein the first electrode and the second electrode are parallel to one another, and
   wherein the first electrode is configured to spark at a random location about the first electrode and thereby arc to the second electrode.

2. The apparatus of claim 1, wherein the first electrode and the second electrode each comprise an elliptical cross-section.

3. The apparatus of claim 1, further comprising:
   an inflation lumen extending through the elongated body, and
   a balloon positioned at a distal portion of the elongated body, the balloon configured to receive a fluid via the inflation lumen.

4. The apparatus of claim 1, further comprising:
   a power conductor electrically coupled to the first electrode; and
   a grounded conductor electrically coupled to the second electrode.

5. The apparatus of claim 1, further comprising a protrusion located along a portion of the first electrode and facing the second electrode, thereby forming a preferential location for electricity to arc from the first electrode to the second electrode.

6. The apparatus of claim 5, wherein the pressure wave emitter is rotatable such that the protrusion is configured to be positioned nearest a treatment site.

7. An apparatus, comprising:
   an elongated body comprising a guidewire lumen;
   a pressure wave emitter positioned along the elongated body and configured to emit a pressure wave, the pressure wave emitter comprising a first electrode, a second electrode, and a third electrode,
     wherein the first electrode is spaced from the second electrode to thereby form a first spark gap therebetween,
     wherein the second electrode is spaced from the third electrode to thereby form a second spark gap therebetween,
     wherein the first electrode, the second electrode, and the third electrode each at least partially surround the guidewire lumen,
     wherein a distal face of the first electrode is parallel to a proximal face of the second electrode,
     wherein a distal face of the second electrode is parallel to a proximal face of the third electrode,
       the first spark gap forming between the parallel portions of the first electrode and the second electrode, and the second spark gap forming between the parallel portions of the second electrode and the third electrode,
     wherein the first electrode and the second electrode are parallel to one another, and
     wherein the second electrode and the third electrode are parallel to one another;
   a power conductor electrically coupled to the second electrode;
   a first grounded conductor electrically coupled to the first electrode; and
   a second grounded conductor electrically coupled to the third electrode,
     wherein electricity is configured to spark at a random location about the second electrode and thereby arc to the first electrode along the first spark gap, and
     wherein electricity is configured to spark at a random location about the second electrode and thereby arc to the third electrode along the second spark gap.

8. The apparatus of claim 7, wherein the first electrode, the second electrode, and the third electrode each comprise an elliptical cross-section.

9. The apparatus of claim 7, further comprising a protrusion located along a portion of the first electrode, a portion of the third electrode, or both, the protrusion facing the second electrode, thereby forming a preferential location for electricity to arc along the first spark gap, the second spark gap, or both.

10. The apparatus of claim 9, wherein the pressure wave emitter is rotatable such that the protrusion is configured to be positioned nearest a treatment site.

11. The apparatus of claim 7, further comprising:
an inflation lumen extending through the elongated body, and
a balloon positioned at a distal portion of the elongated body, the balloon configured to receive a fluid via the inflation lumen.

12. The apparatus of claim 7, wherein the second electrode defines a width that is different from a width of the first electrode and a width of the third electrode.

13. The apparatus of claim 12, wherein the width of the first electrode and the width of the third electrode are about the same.

14. The apparatus of claim 7, wherein the first spark gap defines a width that is different from a width of the second spark gap.

15. An apparatus, comprising:
an elongated body comprising a guidewire lumen;
a pressure wave emitter positioned along the elongated body and configured to emit a pressure wave, the pressure wave emitter comprising a first electrode, a second electrode, and a third electrode,
wherein the first electrode is spaced from the second electrode to thereby form a first spark gap therebetween,
wherein the second electrode is spaced from the third electrode to thereby form a second spark gap therebetween,
wherein the first electrode, the second electrode, and the third electrode each at least partially surround the guidewire lumen,
wherein a distal face of the first electrode is parallel to a proximal face of the second electrode,
wherein a distal face of the second electrode is parallel to a proximal face of the third electrode,
the first spark gap forming between the parallel portions of the first electrode and the second electrode, and the second spark gap forming between the parallel portions of the second electrode and the third electrode,
wherein the first electrode and the second electrode are parallel to one another, and
wherein the second electrode and the third electrode are parallel to one another;
a grounded conductor electrically coupled to the second electrode;
a first power conductor electrically coupled to the first electrode; and
a second power conductor electrically coupled to the third electrode,
wherein electricity is configured to spark at a random location about the first electrode and thereby arc to the second electrode along the first spark gap, and
wherein electricity is configured to spark at a random location about the third electrode and thereby arc to the second electrode along the second spark gap.

16. The apparatus of claim 15, wherein the first electrode, the second electrode, and the third electrode each comprise an elliptical cross-section.

17. The apparatus of claim 15, further comprising a protrusion located along a portion of the first electrode, a portion of the third electrode, or both, the protrusion facing the second electrode, thereby forming a preferential location for electricity to arc along the first spark gap, the second spark gap, or both.

18. The apparatus of claim 15, further comprising:
an inflation lumen extending through the elongated body, and
a balloon positioned at a distal portion of the elongated body, the balloon configured to receive a fluid via the inflation lumen.

19. The apparatus of claim 15, wherein the second electrode defines a width that is different from a width of the first electrode and a width of the third electrode.

20. The apparatus of claim 15, wherein the first spark gap defines a width that is different from a width of the second spark gap.

* * * * *